US012202828B2

(12) United States Patent
Chessari et al.

(10) Patent No.: US 12,202,828 B2
(45) Date of Patent: *Jan. 21, 2025

(54) BICYCLIC HETEROCYCLE COMPOUNDS AND THEIR USES IN THERAPY

(71) Applicant: ASTEX THERAPEUTICS LIMITED, Cambridge (GB)

(72) Inventors: Gianni Chessari, Cambridge (GB); Christopher Norbert Johnson, Saffron Walden (GB); Steven Howard, Cambridge (GB); James Edward Harvey Day, Cambridge (GB); Ildiko Maria Buck, London (GB); Charlotte Mary Griffiths-Jones, Cambridge (GB); Gordon Saxty, Zagreb (HR); Emiliano Tamanini, Cambridge (GB); Nicola Elizabeth Wilsher, Newmarket (GB)

(73) Assignee: ASTEX THERAPEUTICS LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,571

(22) Filed: Dec. 21, 2022

(65) Prior Publication Data

US 2023/0227450 A1 Jul. 20, 2023

Related U.S. Application Data

(60) Continuation of application No. 17/643,083, filed on Dec. 7, 2021, now Pat. No. 11,643,410, which is a division of application No. 16/795,117, filed on Feb. 19, 2020, now Pat. No. 11,225,476, which is a division of application No. 15/675,052, filed on Aug. 11, 2017, now Pat. No. 10,618,895, which is a continuation of application No. 15/105,360, filed as application No. PCT/GB2014/053778 on Dec. 19, 2014, now Pat. No. 9,783,538.

(30) Foreign Application Priority Data

Dec. 20, 2013 (GB) ..................... 1322755
Apr. 17, 2014 (GB) ..................... 1406986

(51) Int. Cl.
C07D 471/04 (2006.01)
A61K 31/5377 (2006.01)

(52) U.S. Cl.
CPC ........ C07D 471/04 (2013.01); A61K 31/5377 (2013.01)

(58) Field of Classification Search
CPC ................... C07D 471/04; A61K 31/5377
See application file for complete search history.

(56) References Cited

U.S. PATENT DOCUMENTS

| | | |
|---|---|---|
| 4,080,330 A | 3/1978 | Kubela et al. |
| 4,138,494 A | 2/1979 | Kubela et al. |
| 4,153,789 A | 5/1979 | Kubela et al. |
| 6,084,098 A | 7/2000 | Kover et al. |
| 7,935,819 B2 | 5/2011 | Halley et al. |
| 7,977,477 B2 | 7/2011 | Berdini et al. |
| 8,044,206 B2 | 10/2011 | Kikuchi et al. |
| 8,415,486 B2 | 4/2013 | Condon et al. |
| 9,018,214 B2 | 4/2015 | Woolford et al. |
| 9,155,743 B2 | 10/2015 | Buck et al. |
| 9,458,158 B2 | 10/2016 | Buck et al. |
| 9,617,248 B2 | 4/2017 | Chessari et al. |
| 9,617,283 B2 | 4/2017 | Chessari et al. |
| 9,663,512 B2 | 5/2017 | Chessari et al. |
| 9,676,768 B2 | 6/2017 | Woolford et al. |
| 9,783,538 B2 | 10/2017 | Chessari et al. |
| 9,980,973 B2 | 5/2018 | Chessari et al. |
| 10,618,895 B2 | 4/2020 | Chessari et al. |
| 11,225,476 B2 | 1/2022 | Chessari et al. |
| 11,643,410 B2 | 5/2023 | Chessari et al. |
| 11,866,428 B2 | 1/2024 | Woolford |
| 2005/0245537 A1 | 11/2005 | Tsuchimori et al. |
| 2008/0021066 A1 | 1/2008 | Condon et al. |
| 2011/0230471 A1 | 9/2011 | Staehle et al. |
| 2012/0157390 A1 | 6/2012 | Condon et al. |
| 2014/0045831 A1 | 2/2014 | Buck et al. |
| 2014/0179666 A1 | 6/2014 | Woolford et al. |
| 2015/0259359 A1 | 9/2015 | Chessari et al. |
| 2015/0266873 A1 | 9/2015 | Chessari et al. |
| 2015/0291586 A1 | 10/2015 | Woolford et al. |
| 2015/0353537 A1 | 12/2015 | Chessari et al. |
| 2016/0083377 A1 | 3/2016 | Buck et al. |
| 2017/0029419 A1 | 2/2017 | Chessari et al. |

(Continued)

FOREIGN PATENT DOCUMENTS

CA 2433090 A1 7/2002
EP 302008 A2 2/1989

(Continued)

OTHER PUBLICATIONS

Chessari, Gianni et al., "Bicyclic Heterocycle Compounds and Their Uses in Therapy", U.S. Appl. No. 18/499,940, filed Nov. 1, 2023.
Flygare, J., et al., "Small-molecule pan-IAP antagonists: a patent review", Expert Opinion on Therapeutic Patents, Informa Healthcare, GB, vol. 20 (2), pp. 251-267 (2010).
Eckelman, B.P., et al "The mechanism of peptide-binding specificity of IAP-BIR domains", Cell Death and Differentiation, Nature Publishing Group, GB, vol. 15(5), pp. 920-928 (2008).
Ashton, K., et al., "Small Molecule Disruptors of the Glucokinase-Glucokinase Regulatory Protein Interaction: 1. Discovery of a Novel Tool Compound for in Vivo Proof-of-Concept", Journal of Medicinal Chemistry, vol. 57(2), pp. 309-324 (2014).

(Continued)

*Primary Examiner* — Rebecca L Anderson
(74) *Attorney, Agent, or Firm* — HESLIN ROTHENBERG FARLEY & MESITI P.C.

(57) ABSTRACT

The invention relates to new bicyclic heterocycle compounds, to pharmaceutical compositions comprising the compounds and to the use of the compounds in the treatment of diseases, e.g. cancer.

48 Claims, 17 Drawing Sheets

(56) References Cited

U.S. PATENT DOCUMENTS

| | | |
|---|---|---|
| 2017/0224705 A1 | 8/2017 | Chessari et al. |
| 2017/0334907 A1 | 11/2017 | Woolford et al. |
| 2018/0065959 A1 | 3/2018 | Chessari et al. |
| 2019/0375748 A1 | 12/2019 | Woolford et al. |
| 2020/0325134 A1 | 10/2020 | Chessari et al. |
| 2021/0122749 A1 | 4/2021 | Woolford et al. |
| 2022/0204503 A1 | 6/2022 | Chessari et al. |
| 2023/0183234 A1 | 6/2023 | Bodhuri et al. |
| 2023/0348352 A1 | 11/2023 | Bodhuri et al. |
| 2024/0082286 A1 | 3/2024 | Sims et al. |
| 2024/0199607 A1 | 6/2024 | Woolford et al. |

FOREIGN PATENT DOCUMENTS

| | | |
|---|---|---|
| EP | 560235 A1 | 9/1993 |
| EP | 778277 A1 | 6/1997 |
| GB | 1550230 | 8/1979 |
| JP | S52-012162 A | 1/1977 |
| WO | 97/16440 A1 | 5/1997 |
| WO | 97/30971 A1 | 8/1997 |
| WO | 97/38665 A2 | 10/1997 |
| WO | 98/00401 A1 | 1/1998 |
| WO | 98/50346 A1 | 11/1998 |
| WO | 98/50358 A1 | 11/1998 |
| WO | 99/28313 A1 | 6/1999 |
| WO | 99/43670 A1 | 9/1999 |
| WO | 99/50247 A1 | 10/1999 |
| WO | 00/15612 A1 | 3/2000 |
| WO | 00/51984 A1 | 9/2000 |
| WO | 00/55143 A1 | 9/2000 |
| WO | 01/05763 A2 | 1/2001 |
| WO | 01/12600 A1 | 2/2001 |
| WO | 01/17942 A1 | 3/2001 |
| WO | 01/44226 A1 | 6/2001 |
| WO | 02/50061 A1 | 6/2002 |
| WO | 02/080853 A2 | 10/2002 |
| WO | 02/088101 A2 | 11/2002 |
| WO | 2004/000832 A1 | 12/2003 |
| WO | 2004/087714 A1 | 10/2004 |
| WO | 2005/019167 A2 | 3/2005 |
| WO | 2005/039572 A1 | 5/2005 |
| WO | 2005/097791 A1 | 10/2005 |
| WO | 2006/010118 A2 | 1/2006 |
| WO | 2006/014361 A1 | 2/2006 |
| WO | 2006/032987 A1 | 3/2006 |
| WO | 2006/069063 A1 | 6/2006 |
| WO | 2006/091972 A1 | 8/2006 |
| WO | 2007/054453 A1 | 5/2007 |
| WO | 2007/073405 A1 | 6/2007 |
| WO | 2007/090617 A2 | 8/2007 |
| WO | 2007/106192 A2 | 9/2007 |
| WO | 2007/125325 A1 | 11/2007 |
| WO | 2008/045905 A1 | 4/2008 |
| WO | 2008/073305 A1 | 6/2008 |
| WO | 2008/109181 A2 | 9/2008 |
| WO | 2008/116107 A2 | 9/2008 |
| WO | 2009/020990 A1 | 2/2009 |
| WO | 2009/067233 A1 | 5/2009 |
| WO | 2009/094287 A1 | 7/2009 |
| WO | 2009/147476 A1 | 12/2009 |
| WO | 2009/150240 A1 | 12/2009 |
| WO | 2010/011666 A2 | 1/2010 |
| WO | 2010/048149 A2 | 4/2010 |
| WO | 2010/060532 A1 | 6/2010 |
| WO | 2010/099527 A1 | 9/2010 |
| WO | 2010/121212 A2 | 10/2010 |
| WO | 2010/129467 A1 | 11/2010 |
| WO | 2012/080271 A1 | 6/2012 |
| WO | 2012/143725 A1 | 10/2012 |
| WO | 2012/143726 A1 | 10/2012 |
| WO | 2013/052110 A1 | 4/2013 |
| WO | 2013/102242 A1 | 7/2013 |
| WO | 2014/060767 A1 | 4/2014 |
| WO | 2014/060768 A1 | 4/2014 |
| WO | 2014/060770 A1 | 4/2014 |
| WO | 2015/092420 A1 | 6/2015 |
| WO | 2015/106025 A1 | 7/2015 |
| WO | 2021/225955 A1 | 11/2021 |
| WO | 2021/225956 A1 | 11/2021 |
| WO | 2023/168394 A1 | 9/2023 |
| WO | 2024/047394 A1 | 3/2024 |

OTHER PUBLICATIONS

Moore, C., et al., "Structural and Biophysical Characterization of Xiap BIR3 G306E Mutant: Insights in Protein Dynamics and Application for Fragment-Based Drug Design", Chem. Biol. Drug Design, vol. 74(3), pp. 212-223 (2009).

Zhao, H., et al., "Indoline and Piperazine Containing Derivatives as a Novel Class of Mixed D2/D4 Receptor Antagonists. Part 1: Identification and Structure-Activity Relationships" Bioorganic & Medicinal Chemistry Letters, vol. 12, pp. 3105-3109 (2002).

International Search Report for PCT/ PCT/GB2014/053778 dated Feb. 17, 2015.

Vippagunta, S.R. et al., Crystalline Solids, *Advanced Drug Delivery Reviews*, vol. 48, pp. 3-26 (2001).

GB Search Report for GB1322755.8 dated Jul. 21, 2014.

GB Search Report for GB1406986.8 dated Nov. 19, 2014.

Tamanini et al., Discovery of a Potent Nonpeptidomimetic, Small-Molecule Antagonist of Cellular Inhibitor of Apoptosis Protein 1 (cIAP1) and X-Linked Inhibitor of Apoptosis Protein (XIAP), Journal of Medicinal Chemistry 2017 60 (11), 4611-4625.

Curran P. et al., "Loss of the tert-butyloxycarbonyl (Boc) protecting group under basic conditions." *Tetrahedron Letters* 35 (1994): 5409-5412.

George, et al., "Mild deprotection of the N-tert-butyloxycarbonyl (N-Boc) group using oxalyl chloride", *Royal Society of Chemistry, RSC Adv.*, 2020, 10, pp. 24017-24026 (2020).

Lu Dayong, et al., Effect of three piperazine diketones on pulmonary metastasis of Lewis carcinoma in vivo; 540-541, 1-14, Chinese Pharmacological Bulletin; Dec. 31, 2000.

BICYCLIC HETEROCYCLE COMPOUNDS AND THEIR USES IN THERAPY

CROSS REFERENCE TO RELATED APPLICATIONS

This application is continuation of U.S. patent application Ser. No. 17/643,083, filed on Dec. 7, 2021 (and published as US 2022-0204503 A1), which is a divisional of U.S. patent application Ser. No. 16/795,117, filed on Feb. 19, 2020 (and published as US 2020-0325134 A1), which is a divisional of U.S. patent application Ser. No. 15/675,052, filed on Aug. 11, 2017 (and published as US 2018-0065959 A1), which is a continuation of U.S. patent application Ser. No. 15/105,360, filed on Jun. 16, 2016 (and published as US 2017-0029419 A1), which is a § 371 National Phase Application based on International Application No. PCT/GB2014/053778, filed on Dec. 19, 2014 and published as WO 2015/092420 on Jun. 25, 2015, which claims priority to Great Britain Patent Application No. 1406986.8, filed on Apr. 17, 2014, and to Great Britain Patent Application No. 1322755.8, filed on Dec. 20, 2013. The entire contents of US 2018-0065959 A1 are hereby incorporated herein by reference.

FIELD OF THE INVENTION

The invention relates to new bicyclic heterocycle compounds, to pharmaceutical compositions comprising said compounds and to the use of said compounds in the treatment of diseases, e.g. cancer.

BACKGROUND OF THE INVENTION

IAP Family

The family of inhibitor of apoptosis (IAP) proteins comprises 8 members, XIAP, cIAP1, cIAP2, NAIP, ILP2, ML-IAP, survivin and BRUCE (also known as apollon). Members of the IAP family have been shown to inhibit programmed cell death through their ability to directly inhibit members of the caspase family of apoptotic enzymes, although the precise role of all 8 members is yet to be fully defined. The common structural feature of all IAP family members is a ~70 amino acid zinc-binding fold termed the baculovirus IAP repeat (BIR) domain, which is present in one to three copies.

Many interactions between IAPs and other proteins are mediated via a surface groove on the BIR domain. BIR domains may be classified by their peptide-binding specificity. There are three types of BIR domains; type III domains (capable of binding caspase (and caspase-like) peptides with a specificity for proline in the third (P3) position (e.g. XIAP BIR3), type II domains (like type III domains but lacking the proline requirement e.g. XIAP BIR2) and type I domains (which do not bind caspases or similar peptides, e.g. XIAP BIR1) (Eckelman et al. Cell Death and Differentiation 2008; 15: 920-928). BIRs are small (~70 amino acids) Zn-coordinated domains and a variety of proteins use their N-terminal to interact with the BIR domains grooves. BIR antagonists prevent caspases binding to BIRs and hence result in increased caspase activity thereby inducing auto-ubiquitination and proteasomal degradation of IAPs.

IAPs are overexpressed in many cancers including renal, melanoma, colon, lung, breast, ovarian and prostate cancers (Tamm et al., Clin. Cancer Research 2000; 6(5): 1796-803), and have been implicated in tumour growth, pathogenesis and resistance to chemo- and radio-therapy (Tamm 2000).

XIAP

XIAP is a 57 kDa protein with three BIR domains, the second and third of which bind caspases and a RING-type zinc finger (E3 ligase). XIAP binds several proteins in addition to caspases, including ligation substrates such as TAK1 and cofactor TAB1, MURR1 involved in copper homeostasis (Burstein et al., EMBO 2004; 23: 244-254), endogenous inhibitors such as second mitochondria-derived activator of caspases (SMAC), and those of less clear function such as MAGE-D1, NRAGE (Jordan et al., J. Biol. Chem. 2001; 276: 39985-39989).

The BI R3 domain binds and inhibits caspase-9, an apical caspase in the mitochondrial pathway of caspase activation. A groove on the surface of the BI R3 domain interacts with the N-terminus of the small subunit of caspase-9, locking capsase-9 in its inactive monomeric form with an incompetent catalytic site (Shiozaki et al., Mol. Cell 2003; 11: 519-527).

In addition to caspase-binding, XIAP also inhibits apoptosis through other mechanisms. XIAP forms a complex with TAK1 kinase and its cofactor TAB1 that leads to activation of JNK and MAPK signal transduction pathways, in turn leading to activation of NF-κB (Sanna et al., Mol Cell Biol 2002; 22: 1754-1766). XIAP also activates NF-κB by promoting NF-κB translocation to the nucleus and degradation of IκB (Hofer-Warbinek et al., J. Biol. Chem. 2000; 275: 22064-22068, Levkau et al., Circ. Res. 2001; 88: 282-290).

Cells transfected with XIAP are able to block programmed cell death in response to a variety of apoptotic stimuli (Duckett et al., EMBO 1996; 15: 2685-2694, Duckett et al., MCB 1998; 18: 608-615, Bratton, Lewis, Butterworth, Duckett and Cohen, Cell Death and Differentiation 2002; 9: 881-892).

XIAP is ubiquitously expressed in all normal tissues, but it is pathologically elevated in many acute and chronic leukaemias, prostate, lung, renal, and other types of tumours (Byrd et al., 2002; Ferreira et al., 2001; Hofmann et al., 2002; Krajewska et al., 2003; Schimmer et al., 2003; Tamm et al., 2000). In de novo acute myeloid leukaemia (AML), XIAP expression correlates with myelomonocytic French-American-British (FAB) subtypes M4/M5 (P<0.05) and expression of monocytic markers in AML blasts. In addition, XIAP was found to be overexpressed in normal monocytes but undetectable in granulocytes. In AML, XIAP expression was significantly lower in patients with favourable rather than intermediate or poor cytogenetics (n=74; P<0.05) (Tamm et al., Hematol. J. 2004; 5(6): 489-95).

Overexpression renders cells resistant to multi-agent therapy and is associated with poor clinical outcome in disease including AML, renal cancer, melanoma (Tamm et al., Clin. Cancer Research 2000; 6: 1796-1803) and lung cancer (Hofmann et al., J. Cancer Res. Clin. Oncology 2002; 128(10): 554-60).

XIAP is translated by a cap-independent mechanism of translation initiation that is mediated by a unique internal ribosome entry site (IRES) sequence element located in its 5' untranslated region. This allows XIAP mRNA to be actively translated during conditions of cellular stress when the majority of cellular protein synthesis is inhibited. Translational upregulation of XIAP in response to stress increases resistance to radiation induced cell death (Holcik et al., Oncogene 2000; 19: 4174-4177).

XIAP inhibition has been investigated in vitro via several techniques including RNA silencing, gene knockout, peptidic ligand mimetics and small molecule antagonists, and has been shown to promote apoptosis as a monotherapy and to sensitise many tumour types to chemotherapy, including bladder (Kunze et al., 2008; 28(4B): 2259-63). XIAP knockout mice are born at the expected Mendelian frequency, with no obvious physical or histological defects, and normal life spans (Harlin et al., Mol. Cell Biol. 2001; 21(10): 3604-3608). This indicates that lacking XIAP activity is not toxic in normal tissues and suggests a therapeutic window over tumour cells. Further studies have shown XIAP is a critical discriminator between apoptosis in type 1 and type 2 cells including hepatocytes and therefore should be used with caution in patients with underlying liver conditions (Jost et al., Nature, 2009, 460, 1035-1041). It was noted that the cIAP1 and cIAP2 levels are upregulated in the XIAP knockout mouse and may protect from pathology via a compensatory mechanism, suggesting pan-inhibition may be required for functional knockout. Similarly, cIAP1 and cIAP2 knockout mice are also asympotomatic (Conze et al., Mol. Biol. Cell 2005; 25(8): 3348-56). While lack of any one of the IAPs produced no overt phenotype in mice, deletion of cIAP1 with cIAP2 or XIAP resulted in mid embryonic lethality (Moulin, EMBO J., 2012).

Endogenous IAP antagonists such as SMAC have been used to validate members of this family as targets for therapeutic agents. SMAC peptides chemosensitise tumour cells, and in combination with platins and Tumour Necrosis Factor α-related apoptosis inducing ligand (TRAIL) in xenografts, results in tumour growth delay (Fulda et al., Nat. Med. 2002; 808-815; Yang et al., Cancer Res. 2003; 63: 831-837).

A natural product, embellin, was identified as binding at the surface groove of the BI R3 domain of XIAP with similar affinity to the natural SMAC peptide. Embellin induces apoptosis in cell lines in vitro and results in tumour growth delay in xenografts (Nikolovska-Coleska et al., J. Med. Chem. 2004; 47(10): 2430-2440; Chitra et al., Chemotherapy 1994; 40: 109-113).

XIAP antisense oligonucleotides have been developed as therapeutic agents for solid tumour and haematological malignancies. In vitro these antisense oligonucleotides have been shown to knockdown protein expression levels by ~70%, induce apoptosis and sensitise cells to chemotherapy and delay tumour growth in vivo. One of these agents, AEG351156, has been studied in clinical trials (Hu et al., Clin. Cancer Res. 2003; 9: 2826-2836; Cummings et al., Br. J. Cancer 2005; 92: 532-538).

Small molecule antagonists of XIAP developed include peptidomimetics as well as synthetic agents. The peptidomimetics target the BI R3 domain, mimicking SMAC disruption of caspase-9 binding to XIAP, have shown induction of apoptosis in a variety of tumour cell lines as a single agent, as well as chemosensitisers and are being further investigated clinically (Oost et al., J. Med. Chem. 2004; 47: 4417-4426; Sun et al., Bioorg. Med. Chem. Lett. 2005; 15: 793-797).

Synthetic small molecule antagonists of BI R3 and BI R2 domains also demonstrate anti-tumour activity in several different models, including induction of apoptosis by annexin-V staining and IC50s of <10 μM against over one-third of the NC160 cell line panel. XIAP antagonists also induced dose-dependent cell death of primary-cultured leukaemia cells in 5 out of 5 chronic lymphocytic leukaemia cell lines and 4 out of 5 acute myeloid leukaemia cell lines (Schimmer et al., Cancer Cell 2004; 5: 25-35; Berezovskaya et al., Cancer Res. 2005; 65(6): 2378-86).

High levels of XIAP protein in tumour cell lines were inversely correlated with sensitivity to some anti-cancer drugs, particularly cytarabine and other nucleosides (Tamm et al., Clin. Cancer Research 2000; 6: 1796-1803). XIAP inhibition potentiates TRAIL-induced antitumor activity in two preclinical models of pancreatic cancer in vivo (Vogler 2008). Gene expression and transfection studies suggest that the increased expression of apoptosis suppressor XIAP plays an important role in anoikis resistance and in the survival of circulating human prostate carcinoma cells, thereby promoting metastasis. Small molecule antagonists were found to be anti-metastatic in these models (Berezovskaya et al., Cancer Res. 2005; 65(6): 2378-86).

XIAP has also been found to be involved in other pathways associated with cancer and other diseases and these may also benefit from XIAP targeted agents. The E3 ligase activity of the RING finger domain of XIAP is able to bind both to TAB1 and to an upstream BM P receptor (type 1), suggesting that XIAP may signal in a TGF-β-mediated pathway (Yamaguchi et al., EMBO 1999; 179-187). Focal adhesion kinase (FAK) overexpression has been shown to result in upregulated XIAP expression (Sonoda et al., J. Biol. Chem. 2000; 275: 16309-16315). E3 ligases are attractive therapeutic targets and molecules which target this activity in other proteins such as MDM2 are being developed (Vassilev et al., Science 2004; 303: 844-848). Direct or indirect inhibition of the XIAP ligase activity may also be useful in the treatment of cancer and other diseases. Dysregulated apoptotic signalling, which would result from inhibition of IAP function in controlling programmed cell death, has also been implicated in many diseases, including disorders associated with cell accumulation (e.g. cancer, autoimmunity, inflammation and restenosis) or disorders where excessive apoptosis results in cell loss (e.g. stroke, heart failure, neurodegeneration such as Alzheimer's disease, Parkinson's disease, Huntington's disease, amyotrophic lateral sclerosis, AIDS, ischaemia (stroke, myocardial infarction) and osteoporosis).

XIAP is an important apoptotic regulator in experimental autoimmune encephalomyelitis and a potential pharmacological target for treating autoimmune diseases such as multiple sclerosis (MS) (Moore et al., 2004; 203(1): 79-93). Antisense-mediated knockdown of XIAP reverses paralysis in an animal model of MS suggesting that treatments targeting XIAP, and perhaps other IAPs, may have utility in the treatment of MS (Hebb et al., Curr. Drug Disc. Tech. 2008; 5(1): 75-7).

cIAP1, cIAP-2, XIAP and survivin are overexpressed in malignant pleural mesothelioma and are responsible for a large degree of the resistance of cultured mesothelioma cells to cisplatin. Levels of circulating TNF-α are significantly higher in mesothelioma patients prior to surgical tumor debulking compared with those after surgery. TNF-α increases mRNA and protein levels of IAP-1, IAP-2 and XIAP (Gordon et al., 2007). NF-κB upregulation plays an important survival role in mesotheliomas in response to the inflammatory effects of exposure to asbestos fibres (Sartore-Bianchi et al., 2007). IAP antagonists have the potential to reverse the pro-survival effect of TNF-α.

The ability of cell lines to upregulate TNF-alpha expression sufficiently to act in an autocrine fashion and kill the cells, once cIAP1 & 2 are depleted, is believed to be important for IAP activity (Nature Reviews Cancer (2010), 10(8), 561-74, Gryd-Hansen, M). In vivo, however, certain tumour types are surrounded by a pro-inflammatory cytokine network and hence the tumour cells which, on depletion of cIAP1/2 are switched towards cell killing by apoptosis, may be triggered to apoptose by TNF-alpha (or other Death Receptor cytokine agonists) already being produced by surrounding cells in the tumour microenvironment, such as tumour-associated macrophages, or indeed by the tumour cells themselves. Certain tumour types such as breast, ovarian and melanoma display this "inflammatory phenotype" which could potentially be targeted by IAP antagonists.

cIAP1 and cIAP2

Cellular IAP (cIAP) 1 and 2 are closely related members of the IAP family with three BIR domains, a RING domain and a caspase-recruitment (CARD) domain. A functional nuclear export signal exists within the CARD domain of cIAP1 which appears to be important for cell differentiation (Plenchette et al., Blood 2004; 104: 2035-2043). The presence of this CARD domain is unique to cIAP1 and cIAP2 within the IAP family of proteins. These two genes reside in tandem on chromosome 11q22 and given their high degree of similarity are thought to have arisen via gene duplication.

cIAP1, like XIAP and survivin, is widely expressed in tumour cell lines, and has been found to be expressed at high levels in colorectal cancers in particular, as well as lung, ovarian, renal, CNS and breast cancers (Tamm et al., Clin. Cancer Res. 2000; 6: 1796-1803). cIAP2 expression is generally more restricted and is thought to be regulated though constitutive ubiquitination and degradation by cIAP1 (Conze et al., Mol. Biol. Cell 2005; 25(8): 3348-56; Mahoney et al., PNAS 2008; 105: 11778-11783). Immunohistochemistry and western blot analysis identified cIAP1 and cIAP2 as potential oncogenes as both are overexpressed in multiple lung cancers with or without higher copy numbers (Dia et al., Human Mol. Genetics 2003; 12(7): 791-801). cIAP1 expression level preferentially seems to play an important role in low-stage adenocarcinoma (Hofmann et al., J. Cancer Res. Clin. Oncology 2002; 128(10): 554-60).

Increased levels of cIAP1 and cIAP2 and reduced levels of endogenous inhibitors are associated with chemoresistance as has been seen for XIAP. cIAP overexpression has been found to correlate in vitro to resistance to DNA alkylating agents such as carboplatin, cisplatin and topoisomerase inhibitor VP-16 (Tamm et al., Clin. Cancer Res. 2000; 6: 1796-1803). Levels of cIAP1 and survivin were found to be high in thyroid cancer cells after cisplatin and doxorubicin treatment. Cells resistant to chemotherapy such as taxol showed reduced expression of SMAC and released minimal amounts of this protein from the mitochondria. Down-regulation of cIAP1 and survivin has been found to increase the cytotoxicity of cisplatin and doxorubicin, whereas overexpression of SMAC improved the efficacy of taxol. However, silencing of cIAP1 and survivin by RNA interference restored sensitivity to doxorubicin and cisplatin (Tirro et al.; Cancer Res. 2006; 66(8): 4263-72).

SMAC mimetics such as LBW242 were originally thought to primarily target XIAP. However studies have shown that cIAP1 was targeted for degradation by autoubiquitination in cells (Yang et al., J. Biol. Chem. 2004; 279(17): 16963-16970) and may have contributed to the apoptotic effects that resulted. SiRNA of cIAP1 and Tumour Necrosis Factor (TNF)-alpha induction (or stimulation) were found to combine synergistically and render cell lines more sensitive (Gaither et al. Cancer Res. 2007; 67 (24): 11493-11498).

cIAP1 and cIAP2 have been demonstrated to be critical regulators of the NF-κB signalling pathway which is involved in a diverse range of biological processes, particularly in innate and adaptive immunity as well as in proliferation and survival. NF-κB pathway deregulation is associated with inflammation and cancers including hepatitis and ulcerative colitis, gastritis, hepatocellular carcinoma colorectal cancer and gastric cancers, as well as angiogenesis and metastasis (Shen et al., Apoptosis 2009; 14: 348-363).

On ligand binding, the TNF Receptor (TNF-R) recruits TNFR-associated Death Domain (TRADD) and receptor-interacting protein (RIP) 1. TRAF2 and cIAP1/cIAP2 are then recruited to form a large membrane complex. RIP1 is ubiquitinated and these polyubiquitin chains serve as a docking site for downstream kinases, resulting in NF-κB pathway signalling effects (Ea et al., Mol. Cell 2006; 22: 245-257; Wu et al., Nat. Cell Biol. 2006; 8: 398-406). The extended roles are complex and yet to be fully defined but cIAP1 and cIAP2 are identified as key components of TNF-alpha mediated NF-κB signalling regulation as well as constitutive (ligand-independent/classical) NF-κB signalling (Varfolomeev et al., Cell 2007; 131(4): 669-81). cIAP1 and cIAP2 have been shown to bind TRAF2, an adapter protein that functions in both the classical and alternative NF-κB pathways as well as MAPK pathway signalling pathway (Rothe et al., Cell 2005; 83: 1243-1252). cIAP1 and cIAP2 directly target RIP1 for ubiquitination in vitro (Betrand et al., Mol. Cell 2008; 30: 689-700).

TNF-alpha regulates many cellular functions, including apoptosis, inflammation, immune response, and cell growth and differentiation (Trace et al., Annu. Rev. Med. 1994; 45: 491-503) and therapeutic IAP antagonists may be of benefit in conditions where these functions are affected.

Production of TNF-alpha is seen in many malignant tumours, and is one of the key drivers of cancer-related inflammation that drives tumour development and/or progression. cIAPs protect cancer cells from the lethal effects of TNF-alpha.

NAIP

NAIP was the first IAP to be discovered (Roy et al., Cell 1995; 80: 167-178). NAIP is unique among the IAPs in that it possesses a nucleotide-binding and oligomerisation domain, as well as leucine rich repeats which are similar to those contained in proteins normally involved in innate immunity. There are indications that NAIP may also be over expressed in some cancers including breast and oesophageal cancer (Nemoto et al., Exp. Mol. Pathol. 2004; 76(3): 253-9) as well as MS (Choi et al., J. Korean Med. 2007; 22 Suppl: S17-23; Hebb et al., Mult. Sclerosis 2008; 14(5): 577-94).

ML-IAP

Melanoma inhibitor of apoptosis protein (ML-IAP) contains a single BIR and RING finger motif. ML-IAP is a powerful inhibitor of apoptosis induced by death receptors and chemotherapeutic agents, probably functioning as a direct inhibitor of downstream effector caspases (Vucic et al., Curr. Biol. 2000; 10(21): 1359-66). ML-IAP is also known as Baculoviral IAP repeat-containing protein 7 (BIRC7), Kidney inhibitor of apoptosis protein (KIAP), RING finger protein 50 (RNF50) and Livin. The BIR domain of ML-IAP possesses an evolutionarily conserved fold that is necessary for anti-apoptotic activity. It has been found that the majority of melanoma cell lines express high levels of ML-IAP in contrast to primary melanocytes, which expressed undetectable levels. These melanoma cells were significantly more resistant to drug-induced apoptosis. Elevated expression of ML-IAP renders melanoma cells resistant to apoptotic stimuli and thereby potentially contributes to the pathogenesis of this malignancy.

ILP-2

ILP-2, also known as BIRC8, has a single BIR domain and a RING domain. ILP-2 is expressed only in testis in normal cells, and binds to caspase 9 (Richter et al, Mol. Cell. Biol. 2001; 21: 4292-301).

Survivin

Survivin, also known as BIRC5, inhibits both caspase 3 and caspase 7, but its primary function is mitotic progression regulation, rather than the regulation of apoptosis. Survivin promotes formation of microtubules in the mitotic spindle, counteracting apoptosis during cell cycle. Apoptosis inhibition by survivin is predictive of poor outcome in colorectal cancer (Kawasaki et al., Cancer Res. 1998; 58(22): 5071-5074) and stage III gastric cancer (Song et al., Japanese J. Clin. Oncol. 2009; 39(5): 290-296).

BRUCE

BRUCE (BIR repeat-containing ubiquitin-conjugating enzyme) is a peripheral membrane protein in the trans-Golgi network with a single BIR domain, most similar to that of survivin. BRUCE is inhibited via three mechanisms: (i) SMAC binding, (ii) HtrA2 protease and (iii) caspase-mediated cleavage. In addition, BRUCE acts as a E2/E3 ubiquitin ligase via ubiquitin-conjugating (UBC) domain.

SUMMARY OF THE INVENTION

The present invention provides compounds of formula (I). The present invention provides compounds which are useful in therapy, in particular in the treatment of cancer. The compounds of formula (I) may be antagonists of the IAP family of proteins (IAP), and especially XIAP, and/or cIAP (such as cIAP1 and/or cIAP2) and may be useful in the treatment of IAP-mediated conditions.

According to a first aspect of the invention, there is provided a compound of formula (I):

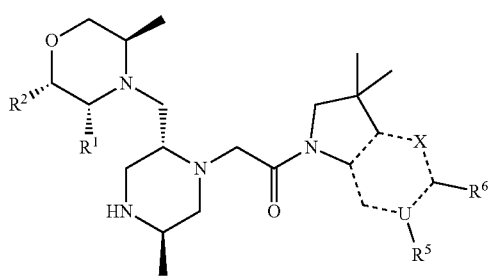

(I)

or a tautomeric or a stereochemically isomeric form, a pharmaceutically acceptable salt or a solvate thereof;
wherein
X is $CR^4$, N or $NR^3$;
wherein
when X is $CR^4$, then U represents nitrogen and $R^6$ represents oxo; or
when X is N, then U represents carbon and $R^6$ represents hydroxymethyl or $-CH(OR^x)CH_2OR^z$; or
when X is $NR^3$, then U represents carbon and $R^6$ represents oxo;
dashed bond (-------) represents a single or double bond wherein at least two of said dashed bonds represent a double bond;
$R^1$ and $R^2$ independently represent hydrogen or methyl;
$R^3$ represents hydrogen, methyl or $-NH_2$;
$R^4$ represents hydrogen, methyl, hydroxymethyl, $-NH_2$ or fluorine;
$R^5$ represents unsubstituted n-butyl or benzyl substituted on the phenyl group by one or two fluorines; and
$R^x$ and $R^z$ independently represent hydrogen or methyl.

In a further aspect of the invention there is provided a compound of formula (I) for use in the prophylaxis or treatment of a disease or condition as described herein, pharmaceutical compositions comprising a compound of formula (I) and processes for the synthesis of compound of formula (I).

DEFINITIONS

Figure 1:
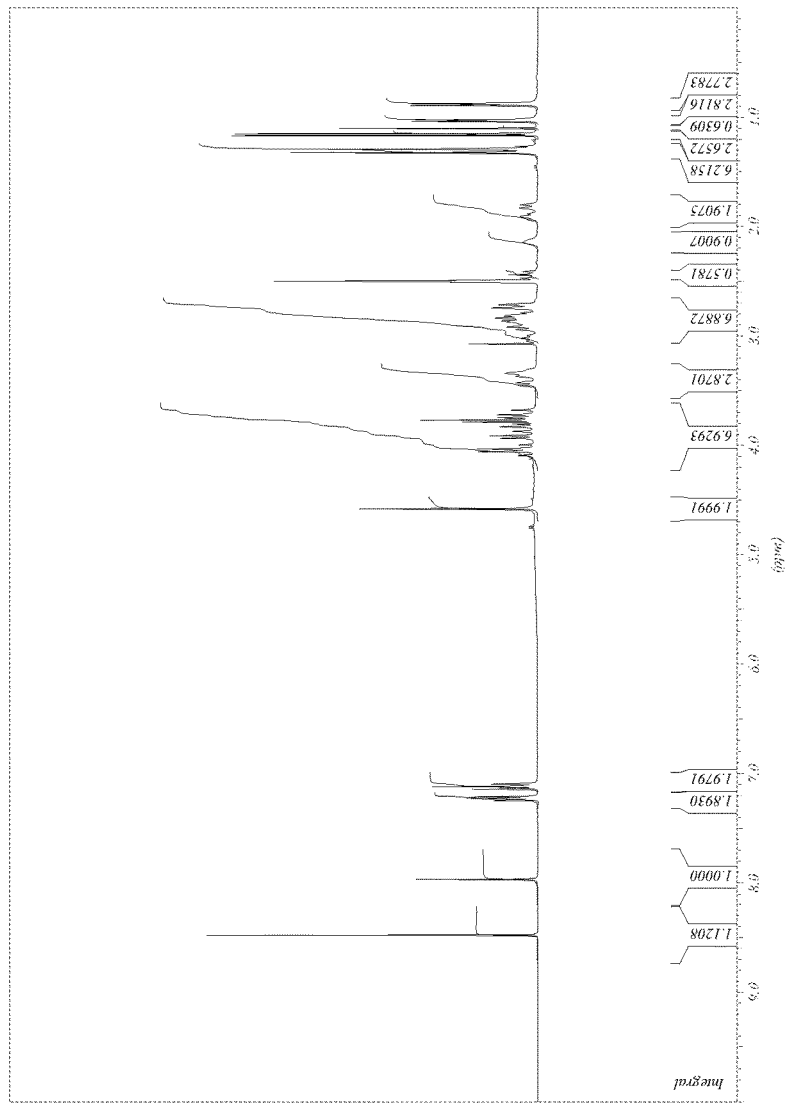
FIG. 1: $^1$H NMR of Example 39. Sample acquired in DMSO-$D_6$ and calibrated to the non-deuterated solvent residual of DMSO at δ=2.50 ppm. Contained an internal reference standard (TCNB) present as a singlet at δ=8.5 ppm.

Unless the context indicates otherwise, references to formula (I) in all sections of this document (including the uses, methods and other aspects of the invention) include references to all other sub-formula, sub-groups, preferences, embodiments and examples as defined herein.

By "IAP" we mean any of the IAP family members XIAP, cIAP (cIAP1 and/or cIAP2), NAIP, ILP2, ML-IAP, survivin and/or BRUCE, in particular XIAP, cIAP1, cIAP2, ML-IAP, more particularly XIAP, cIAP1 and/or cIAP2, most particularly XIAP and/or cIAP1. In particular we mean the BIR domains of IAP, in particular the BIR domains of XIAP, cIAP1, or cIAP2.

By "one or more IAP family members" we mean any of the IAP family members in particular XIAP, cIAP1 and/or cIAP2, more particularly XIAP and/or cIAP1.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "antagonist" refers to a type of receptor ligand or drug that blocks or dampens agonist-mediated biological responses. Antagonists have affinity but no agonistic efficacy for their cognate receptors, and binding will disrupt the interaction and inhibit the function of any ligand (e.g. endogenous ligands or substrates, an agonist or inverse agonist) at receptors. The antagonism may arise directly or indirectly, and may be mediated by any mechanism and at any physiological level. An example of indirect antagonism, would be the indirect antagonism of cIAP as a consequence of ubiquination of cIAP resulting in its degradation. As a result, antagonism of ligands may under different circumstances manifest itself in functionally different ways. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist—receptor complex, which, in turn, depends on the nature of antagonist receptor binding.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence of cancer.

As used herein, the term "mediated", as used e.g. in conjunction with IAP as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The combinations of the invention may produce a therapeutically efficacious effect relative to the therapeutic effect of the individual compounds/agents when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. A "synergistic" effect in the present context refers to a therapeutic effect produced by the combination which is larger than the sum of the therapeutic effects of the agents of the combination when presented individually. An "additive" effect in the present context refers to a therapeutic effect produced by the combination which is larger than the therapeutic effect of any of the agents of the combination when presented individually. The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term "combination", as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include:

- compositions (e.g. unitary formulations) comprising the two or more compounds/agents in admixture (for example within the same unit dose);
- compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses).

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may be unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may be unitary or non-unitary formulations. The unit dose(s) may be contained within a blister pack. The pharmaceutical pack may optionally further comprise instructions for use.

The term 'n-butyl' as used herein refers to a linear alkyl group containing 4 carbon atoms.

The term 'oxo' as used herein refers to the group =O.

Dashed bond (------) represents a single or double bond as required to complete the valencies of the atoms being linked by the bond. It will be understood that in some instances the bond has aromatic character. Dashed bond (------) represents a single or double bond such that the ring containing X and U contains at least two double bonds.

DETAILED DESCRIPTION OF THE INVENTION

It will be understood from formula (I) that the compounds of the invention can be represented as follows:

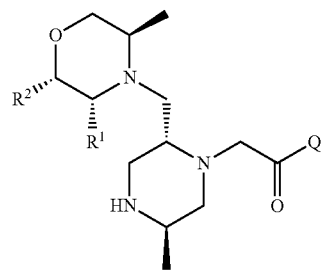

wherein Q represents any of A, B or C below:

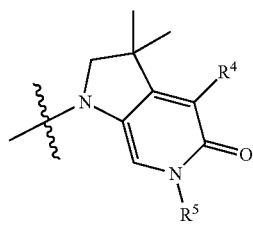

A

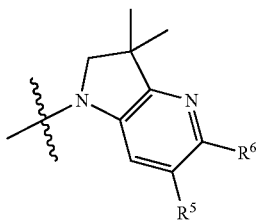

B

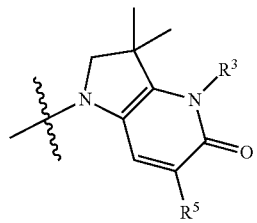

C

In one embodiment Q represents A. In one embodiment Q represents B. In one embodiment Q represents C.

In one embodiment, X represents $CR^4$ or N. In an alternative embodiment, X represents $CR^4$ or $NR^3$. In an alternative embodiment, X represents N or NR³. In a further embodiment, X represents CR⁴. In a further alternative embodiment, X represents N. In a yet further alternative embodiment, X represents NR³.

In one embodiment, one of R¹ and R² represents hydrogen and the other represents methyl, or R¹ and R² both represent hydrogen. In one embodiment, one of R¹ and R² represents hydrogen and the other represents methyl. In a further embodiment, R¹ represents methyl and R² represents hydrogen. In an alternative embodiment, R¹ represents hydrogen and R² represents methyl. In a further alternative embodiment, R¹ and R² both represent hydrogen.

In one embodiment, R³ represents hydrogen or methyl. In an alternative embodiment, R³ represents hydrogen or —NH₂. In a further alternative embodiment, R³ represents methyl or —NH₂. In a further embodiment, R³ represents hydrogen. In a further alternative embodiment, R³ represents methyl. In a yet further alternative embodiment, R³ represents —NH₂.

In one embodiment, R⁴ represents hydrogen or methyl. In a further embodiment, R⁴ represents hydrogen. In an alternative embodiment, R⁴ represents methyl.

In one embodiment, R⁵ represents unsubstituted n-butyl or benzyl substituted by one or two fluorines on the 2, 3 and/or 4 positions of the phenyl group. In one embodiment, R⁵ represents unsubstituted n-butyl. In an alternative embodiment, R⁵ represents benzyl substituted on the phenyl group by one or two fluorines. In a further embodiment, R⁵ represents benzyl substituted by one or two fluorines on the 2, 3 and/or 4 positions of the phenyl group. In a further embodiment, R⁵ represents benzyl substituted by one fluorine on the 2, 3 or 4 position of the phenyl group (i.e. R⁵ represents 2-fluorobenzyl, 3-fluorobenzyl or 4-fluorobenzyl). In a further embodiment, R⁵ represents benzyl substituted by one fluorine on the 4 position of the phenyl group (i.e. R⁵ represents 4-fluorobenzyl). In a further embodiment, R⁵ represents benzyl substituted by two fluorines on the 2,3, 3,4 or 2,4 positions of the phenyl group (i.e. R⁵ represents 2,3-difluorobenzyl, 3,4-difluorobenzyl or 2,4-difluorobenzyl). In a yet further embodiment, R⁵ represents benzyl substituted by two fluorines on the 2,4 positions of the phenyl group (i.e. R⁵ represents 2,4-difluorobenzyl).

In a further embodiment, R⁵ represents unsubstituted n-butyl, 4-fluorophenyl or 2,4-difluorophenyl. In a yet further embodiment, R⁵ represents 4-fluorophenyl.

In one embodiment R⁶ represents hydroxymethyl or —CH(ORˣ)CH₂ORᶻ. In one embodiment R⁶ represents hydroxymethyl.

In one embodiment R⁶ represents —CH(ORˣ)CH₂ORᶻ. In one embodiment, one of Rˣ and Rᶻ represents hydrogen and the other represents methyl or Rˣ and Rᶻ both represent hydrogen. In a further embodiment, Rˣ represents methyl and Rᶻ represents hydrogen. In an alternative embodiment, Rˣ represents hydrogen and Rᶻ represents methyl. In a further alternative embodiment, Rˣ and Rᶻ both represent hydrogen. In a further embodiment, Rˣ represents hydrogen or methyl and Rᶻ represents hydrogen. In a further alternative embodiment, Rˣ and Rᶻ both represent methyl.

In one embodiment, R⁶ represents hydroxymethyl, —CH(OH)CH₂OH, —CH(OMe)CH₂OH or —CH(OH)CH₂OMe. In a further embodiment, R⁶ represents hydroxymethyl, —CH(OH)CH₂OH or —CH(OMe)CH₂OH. In a yet further embodiment, R⁶ represents hydroxymethyl.

In one embodiment R⁶ represents oxo (i.e. =O).

Sub-Formulae

In one embodiment the compound of formula (I) is wherein:
X is CR⁴, N or NR³;
wherein
when X is CR⁴, then U represents nitrogen and R⁶ represents oxo; or
when X is N, then U represents carbon and R⁶ represents hydroxymethyl or —CH(ORˣ)CH₂ORᶻ; or
when X is NR³, then U represents carbon and R⁶ represents oxo;
dashed bond ( ------- ) represents a single or double bond wherein at least two of said dashed bonds represent a double bond;
one of R¹ and R² represents hydrogen and the other represents methyl or R¹ and R² both represent hydrogen;
R³ represents hydrogen, methyl or —NH₂;
R⁴ represents hydrogen or methyl;
R⁵ represents unsubstituted n-butyl or benzyl substituted by one or two fluorines on the 2, 3 and/or 4 positions of the phenyl group; and
one of Rˣ and Rᶻ represents hydrogen and the other represents methyl or Rˣ and Rᶻ both represent hydrogen.

In a further embodiment the compound of formula (I) is wherein:
X is CR⁴, N or NR³;
wherein
when X is CR⁴, then U represents nitrogen and R⁶ represents oxo; or
when X is N, then U represents carbon and R⁶ represents hydroxymethyl or —CH(ORˣ)CH₂ORᶻ; or
when X is NR³, then U represents carbon and R⁶ represents oxo;
dashed bond ( ------- ) represents a single or double bond wherein at least two of said dashed bonds represent a double bond;
one of R¹ and R² represents hydrogen and the other represents methyl or R¹ and R² both represent hydrogen;
R³ represents hydrogen, methyl or —NH₂;
R⁴ represents hydrogen or methyl;
R⁵ represents unsubstituted n-butyl, 4-fluorobenzyl or 2,4-fluorobenzyl;
Rˣ represents hydrogen or methyl; and
Rᶻ represents hydrogen.

In one embodiment, the compound of formula (I) is a compound of formula (Ia):

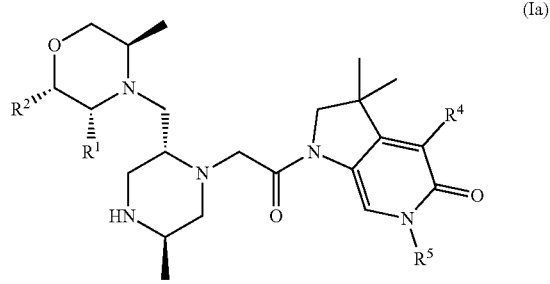

(Ia)

or a tautomeric or a stereochemically isomeric form, a pharmaceutically acceptable salt or a solvate thereof; wherein R¹, R², R⁴ and R⁵ are as defined in any of the embodiments.

In one embodiment of the compound of formula (Ia), one of R¹ and R² represents hydrogen and the other represents methyl or $R^1$ and $R^2$ both represent hydrogen. In a further embodiment of the compound of formula (Ia), $R^1$ represents hydrogen and $R^2$ represents methyl or $R^1$ and $R^2$ both represent hydrogen.

In a further embodiment of the compound of formula (Ia), $R^1$ represents methyl and $R^2$ represents hydrogen. In an alternative embodiment of the compound of formula (Ia), $R^1$ represents hydrogen and $R^2$ represents methyl.

In one embodiment of the compound of formula (Ia), $R^4$ represents hydrogen or methyl.

In one embodiment of the compound of formula (Ia), $R^5$ represents unsubstituted n-butyl or benzyl substituted by one or two fluorines on the 2, 3 and/or 4 positions of the phenyl group. In one embodiment of the compound of formula (Ia), $R^5$ represents unsubstituted n-butyl. In an alternative embodiment of the compound of formula (Ia), $R^5$ represents benzyl substituted on the phenyl group by one or two fluorines. In a further embodiment of the compound of formula (Ia), $R^5$ represents benzyl substituted by one or two fluorines on the 2, 3 and/or 4 positions of the phenyl group. In a further embodiment of the compound of formula (Ia), $R^5$ represents benzyl substituted by one fluorine on the 4 position of the phenyl group (i.e. $R^5$ represents 4-fluorobenzyl). In a further embodiment of the compound of formula (Ia), $R^5$ represents benzyl substituted by two fluorines on the 2,4 positions of the phenyl group (i.e. $R^5$ represents 2,4-difluorobenzyl).

In one embodiment, the compound of formula (I) is a compound of formula (Ib):

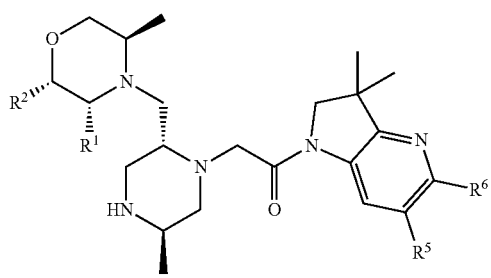

(Ib)

or a tautomeric or a stereochemically isomeric form, a pharmaceutically acceptable salt or a solvate thereof; wherein $R^1$, $R^2$, $R^5$, $R^6$, $R^x$ and $R^z$ are as defined in any of the embodiments. In one embodiment $R^6$ represents hydroxymethyl or —CH(OR$^x$)CH$_2$OR$^z$.

In one embodiment of the compound of formula (Ib), $R^1$ represents methyl and $R^2$ represents hydrogen or $R^1$ and $R^2$ both represent hydrogen.

In a further embodiment of the compound of formula (Ib), $R^1$ and $R^2$ both represent hydrogen.

In one embodiment of the compound of formula (Ib), $R^5$ represents unsubstituted n-butyl or benzyl substituted by one or two fluorines on the 2, 3 and/or 4 positions of the phenyl group. In one embodiment of the compound of formula (Ib), $R^5$ represents unsubstituted n-butyl. In an alternative embodiment of the compound of formula (Ib), $R^5$ represents benzyl substituted on the phenyl group by one or two fluorines. In a further embodiment of the compound of formula (Ib), $R^5$ represents benzyl substituted by one or two fluorines on the 2, 3 and/or 4 positions of the phenyl group. In a further embodiment of the compound of formula (Ib), $R^5$ represents benzyl substituted by one fluorine on the 2, 3 or 4 position of the phenyl group (i.e. $R^5$ represents 2-fluorobenzyl, 3-fluorobenzyl or 4-fluorobenzyl). In a further embodiment of the compound of formula (Ib), $R^5$ represents benzyl substituted by two fluorines on the 2,4 positions of the phenyl group (i.e. $R^5$ represents 2,4-difluorobenzyl). In a yet further embodiment of the compound of formula (Ib), $R^5$ represents benzyl substituted by one fluorine on the 4 position of the phenyl group (i.e. $R^5$ represents 4-fluorobenzyl).

In one embodiment of the compound of formula (Ib), $R^6$ represents hydroxymethyl, —CH(OH)CH$_2$OH, —CH(OMe)CH$_2$OH or —CH(OH)CH$_2$OMe.

In a further embodiment of the compound of formula (Ib), $R^6$ represents hydroxymethyl, —CH(OH)CH$_2$OH or —CH(OMe)CH$_2$OH.

In a yet further embodiment of the compound of formula (Ib), $R^6$ represents hydroxymethyl.

In one embodiment, the compound of formula (I) is a compound of formula (Ic):

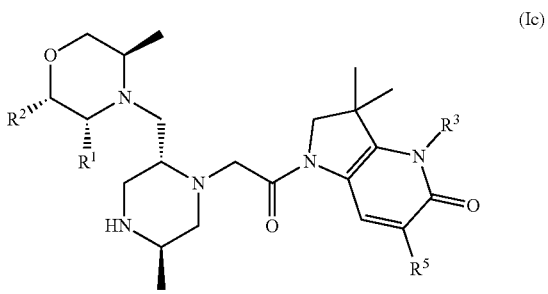

(Ic)

or a tautomeric or a stereochemically isomeric form, a pharmaceutically acceptable salt or a solvate thereof; wherein $R^1$, $R^2$, $R^3$ and $R^5$ are as defined in any of the embodiments.

In one embodiment of the compound of formula (Ic), one of $R^1$ and $R^2$ represents hydrogen and the other represents methyl or $R^1$ and $R^2$ both represent hydrogen. In a further embodiment of the compound of formula (Ic), $R^1$ represents methyl and $R^2$ represents hydrogen or $R^1$ and $R^2$ both represent hydrogen.

In one embodiment of the compound of formula (Ic), $R^3$ represents hydrogen or methyl. In an alternative embodiment of the compound of formula (Ic), $R^3$ represents hydrogen or —NH$_2$. In a further alternative embodiment of the compound of formula (Ic), $R^3$ represents methyl or —NH$_2$. In a further embodiment of the compound of formula (Ic), $R^3$ represents hydrogen. In a further alternative embodiment of the compound of formula (Ic), $R^3$ represents methyl. In a yet further alternative embodiment of the compound of formula (Ic), $R^3$ represents —NH$_2$.

In one embodiment of the compound of formula (Ic), $R^5$ represents unsubstituted n-butyl or benzyl substituted by one or two fluorines on the 2, 3 and/or 4 positions of the phenyl group. In one embodiment of the compound of formula (Ic), $R^5$ represents unsubstituted n-butyl. In an alternative embodiment of the compound of formula (Ic), $R^5$ represents benzyl substituted on the phenyl group by one or two fluorines. In a further embodiment of the compound of formula (Ic), $R^5$ represents benzyl substituted by one or two fluorines on the 2, 3 and/or 4 positions of the phenyl group. In a further embodiment of the compound of formula (Ic), $R^5$ represents benzyl substituted by one fluorine on the 2 or 4 position of the phenyl group (i.e. $R^5$ represents 2-fluorobenzyl or 4-fluorobenzyl). In a further embodiment of the compound of formula (Ic), $R^5$ represents benzyl substituted by one fluorine on the 4 position of the phenyl group (i.e. $R^5$ represents 4-fluorobenzyl). In a further embodiment of the compound of formula (Ic), $R^5$ represents benzyl substituted by two fluorines on the 2,4 positions of the phenyl group (i.e. $R^5$ represents 2,4-difluorobenzyl).

In one embodiment, the compound of formula (I) is a compound of formula (Id):

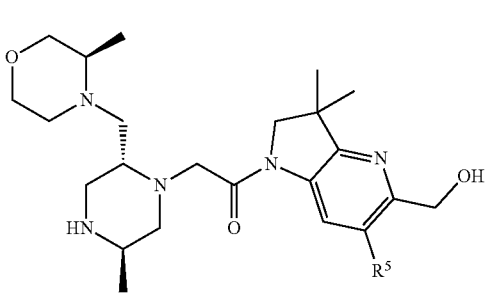

(Id)

or a tautomeric or a stereochemically isomeric form, a pharmaceutically acceptable salt or a solvate thereof; wherein $R^5$ is as defined in any of the embodiments.

In one embodiment of the compound of formula (Id), $R^5$ represents unsubstituted n-butyl or benzyl substituted by one or two fluorines on the 2, 3 and/or 4 positions of the phenyl group. In one embodiment of the compound of formula (Id), $R^5$ represents unsubstituted n-butyl. In an alternative embodiment of the compound of formula (Id), $R^5$ represents benzyl substituted on the phenyl group by one or two fluorines. In a further embodiment of the compound of formula (Id), $R^5$ represents benzyl substituted by one or two fluorines on the 2, 3 and/or 4 positions of the phenyl group. In a further embodiment of the compound of formula (Id), $R^5$ represents benzyl substituted by one fluorine on the 2, 3 or 4 position of the phenyl group (i.e. $R^5$ represents 2-fluorobenzyl, 3-fluorobenzyl or 4-fluorobenzyl). In a further embodiment of the compound of formula (Id), $R^5$ represents benzyl substituted by two fluorines on the 2,4 positions of the phenyl group (i.e. $R^5$ represents 2,4-difluorobenzyl). In a yet further embodiment of the compound of formula (Id), $R^5$ represents benzyl substituted by one fluorine on the 4 position of the phenyl group (i.e. $R^5$ represents 4-fluorobenzyl).

In one embodiment, the compound of formula (I) is a compound of formula (I), (Ia), (Ib) or (Ic) wherein $R^1$ represents methyl and $R^2$ represents hydrogen.

In one embodiment, the compound of formula (I) is a compound of formula (I), (Ia), (Ib) or (Ic) wherein $R^1$ and $R^2$ both represent hydrogen.

In one embodiment, the compound of formula (I) is a compound of formula (I), (Ia), (Ib) or (Ic) wherein $R^1$ represents hydrogen and $R^2$ represents methyl.

In one embodiment, the compound of formula (I) is a compound of formula (I), (Ia), (Ib), (Ic) or (Id) wherein $R^5$ represents unsubstituted n-butyl.

In one embodiment, the compound of formula (I) is a compound of formula (I), (Ia), (Ib), (Ic) or (Id) wherein $R^5$ represents benzyl substituted by one or two fluorines on the 2, 3 and/or 4 positions of the phenyl group.

In one embodiment, the compound of formula (I) is a compound of formula (I), (Ia), (Ib), (Ic) or (Id) wherein $R^5$ represents benzyl substituted on the phenyl group by one or two fluorines.

In one embodiment, the compound of formula (I) is a compound of formula (I), (Ia), (Ib), (Ic) or (Id) wherein $R^5$ represents benzyl substituted on the phenyl group by two fluorines, e.g. 2,3 disubstituted, 2,4 disubstituted, 2,5 disubstituted, 3,5 disubstituted, 2,6 disubstituted or 3,4 disubstituted.

In one embodiment, the compound of formula (I) is a compound of formula (I), (Ia), (Ib), (Ic) or (Id) wherein $R^5$ represents benzyl substituted by one or two fluorines on the 2, 3 and/or 4 positions of the phenyl group.

In one embodiment, the compound of formula (I) is a compound of formula (I), (Ia), (Ib), (Ic) or (Id) wherein $R^5$ represents benzyl substituted by one fluorine on the 2, 3 or 4 position of the phenyl group (i.e. $R^5$ represents 2-fluorobenzyl, 3-fluorobenzyl or 4-fluorobenzyl).

In one embodiment, the compound of formula (I) is a compound of formula (I), (Ia), (Ib), (Ic) or (Id) wherein $R^5$ represents benzyl substituted by two fluorines on the 2,3, 3,4 or 2,4 positions of the phenyl group (i.e. $R^5$ represents 2,3-difluorobenzyl, 3,4-difluorobenzyl or 2,4-difluorobenzyl).

In one embodiment, the compound of formula (I) is a compound of formula (I), (Ia), (Ib), (Ic) or (Id) wherein $R^5$ represents benzyl substituted by two fluorines on the 2,4 positions of the phenyl group (i.e. $R^5$ represents 2,4-difluorobenzyl).

In one embodiment, the compound of formula (I) is a compound of formula (I), (Ia), (Ib), (Ic) or (Id) wherein $R^5$ represents 2,4-difluorobenzyl or 4-fluorobenzyl.

In one embodiment, the invention provides a compound of formula (I) which comprises the free base of a compound of Examples 1-37 or a tautomeric or a stereochemically isomeric form, a pharmaceutically acceptable salt or a solvate thereof.

In one embodiment, the invention provides a compound of formula (I) which is the free base of a compound of Examples 1-37 or a tautomeric or a stereochemically isomeric form, a pharmaceutically acceptable salt or a solvate thereof.

In one embodiment, the invention provides a compound of formula (I) which comprises a compound of Examples 1-37 or a tautomeric or a stereochemically isomeric form or a solvate thereof.

In a further embodiment, the compound is selected from the free base of Examples 1 to 34 or a tautomeric or a stereochemically isomeric form, a pharmaceutically acceptable salt or a solvate thereof.

In a further embodiment, the invention provides a compound of formula (I) which comprises a compound selected from:
1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one;
6-[(4-Fluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one;
6-[(2,4-Difluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one;
6-[(2,4-Difluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one;

1-[5-((R or S)-1,2-Dihydroxyethyl)-6-[(4-fluorophenyl)methyl]-3,3-dimethyl-1H,2H,3H-pyrrolo[3,2-b]pyridin-1-yl]-2-[(2R,5R)-2-{[(3R,5R)-3,5-dimethylmorpholin-4-yl]methyl}-5-methylpiperazin yl]ethan-1-one;

6-[(2,4-Difluorophenyl)methyl]-1-{2-[(2R,5R)-2-{[(2S,5R)-2,5-dimethylmorpholin-4-yl]methyl}-5-methylpiperazin-1-yl]acetyl}-3,3-dimethyl-1H,2H,3H,5H,6H-pyrrolo[2,3-c]pyridin-5-one;

4-Amino-6-[(4-fluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one;

1-{6-[(4-Fluorophenyl)methyl]-5-((R or S)-2-hydroxy-1-methoxyethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one;

4-Amino-6-butyl-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one;

6-[(2,4-Difluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,5H,6H-pyrrolo[2,3-c]pyridin-5-one;

6-Butyl-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one; and 6-Butyl-1-{2-[(2R,5R)-2-{[(2S,5R)-2,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one;

or a tautomeric or a stereochemically isomeric form, a pharmaceutically acceptable salt or a solvate thereof.

In a further embodiment, the invention provides a compound selected from:

1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one dihydrochloride (E2);

6-[(4-Fluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride (E6);

6-[(2,4-Difluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride (E8);

6-[(2,4-Difluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride (E19);

1-[5-((R or S)-1,2-Dihydroxyethyl)-6-[(4-fluorophenyl)methyl]-3,3-dimethyl-1H,2H,3H-pyrrolo[3,2-b]pyridin-1-yl]-2-[(2R,5R)-2-{[(3R,5R)-3,5-dimethylmorpholin-4-yl]methyl}-5-methylpiperazin-1-yl]ethan-1-one dihydrochloride (E21);

6-[(2,4-Difluorophenyl)methyl]-1-{2-[(2R,5R)-2-{[(2S,5R)-2,5-dimethylmorpholin-4-yl]methyl}-5-methylpiperazin-1-yl]acetyl}-3,3-dimethyl-1H,2H,3H,5H,6H-pyrrolo[2,3-c]pyridin-5-one dihydrochloride (E22);

4-Amino-6-[(4-fluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride (E24);

1-{6-[(4-Fluorophenyl)methyl]-5-((R or S)-2-hydroxy-1-methoxyethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one trihydrochloride (E27);

4-Amino-6-butyl-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one dihydrochloride (E30);

6-[(2,4-Difluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,5H,6H-pyrrolo[2,3-c]pyridin-5-one dihydrochloride (E31);

6-Butyl-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one dihydrochloride (E32) and 6-Butyl-1-{2-[(2R,5R)-2-{[(2S,5R)-2,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one dihydrochloride (E37)

or a tautomeric or a stereochemically isomeric form, or a solvate thereof.

In a further embodiment, the compound is selected from the free base of Examples 2, 6, 19, 21, 22, 24, 27, 30, 31 and 32, or a tautomeric or a stereochemically isomeric form, a pharmaceutically acceptable salt or a solvate thereof.

In a yet further embodiment, the invention provides a compound of formula (I) which comprises 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one or a tautomeric or a stereochemically isomeric form, a pharmaceutically acceptable salt or a solvate thereof.

In a yet further embodiment, the invention provides a compound of formula (I) which comprises 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one hydrochloride salt or a tautomeric or a stereochemically isomeric form, or a solvate thereof.

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one dihydrochloride (E2).

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one lactate salt or a tautomeric or a stereochemically isomeric form, or a solvate thereof.

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate salt or a tautomeric or a stereochemically isomeric form, or a solvate thereof.

In a yet further embodiment, the compound is selected from Examples 38-42.

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate (Form A) (E39).

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate (Form B) (E40).

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate (Form C) (E43).

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate salt or a tautomeric or a stereochemically isomeric form, or a solvate thereof.

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate (Form F) (E41).

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate salt or a tautomeric or a stereochemically isomeric form, or a solvate thereof.

In a yet further embodiment, the invention provides 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate (Form B) (E42).

In a further embodiment, the compound selected is other than Example 35, or a tautomeric or a stereochemically isomeric form, a pharmaceutically acceptable salt or a solvate thereof.

In a further embodiment, the compound selected is other than Example 2, or a tautomeric or a stereochemically isomeric form, a pharmaceutically acceptable salt or a solvate thereof.

For the avoidance of doubt, it is to be understood that each general and specific preference, embodiment and example for one substituent may be combined with each general and specific preference, embodiment and example for one or more, particularly, all other substituents as defined herein and that all such embodiments are embraced by this application.

Salts, Solvates, Tautomers, Isomers, N-Oxides, Esters, Prodrugs and Isotopes

A reference to a compound of the formula (I) and subgroups thereof also includes ionic forms, salts, solvates, isomers (including geometric and stereochemical isomers), tautomers, N-oxides, esters, prodrugs, isotopes and protected forms thereof, for example, as discussed below; particularly, the salts or tautomers or isomers or N-oxides or solvates thereof; and more particularly, the salts or tautomers or N-oxides or solvates thereof, even more particularly the salts or tautomers or solvates thereof.

Salts

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular, sub group of salts consists of salts formed from hydrochloric, lactic (e.g. (+)-L-lactic, (−)-D-lactic or (±)-DL-lactic), sulfuric and methanesulfonic (mesylate) acids. One particular, further sub group of salts consists of salts formed from lactic (e.g. (+)-L-lactic, (−)-D-lactic or (±)-DL-lactic), sulfuric and methanesulfonic (mesylate) acids. One particular, further sub group of salts consists of salts formed from lactic (e.g. (+)-L-lactic, (−)-D-lactic or (±)-DL-lactic) and sulfuric acids. One particular salt is the hydrochloride salt. One further particular salt is the lactate salt (such as the compound of Examples 39, 40 and 43). One further particular salt is the sulfate salt (such as the compound of Example 41). One further particular salt is the mesylate salt (such as the compound of Example 42). One particular salt is the lactate salt (such as the compound of Examples 39, 40 and 43, in particular the compound of Example 43), e.g. the L-(+)-lactate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono-, di- or tri-salts, in particular mono- or di-salts, depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/mL, typically greater than 15 mg/mL and particularly greater than 20 mg/mL.

N-Oxides

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I), the phenyl ring of compounds when X represents NH and U represents carbon can exist in a tautomeric form as illustrated below. For simplicity, the general formula (I) illustrates one form 1 but the formula is to be taken as embracing both tautomeric forms (1 and 2).

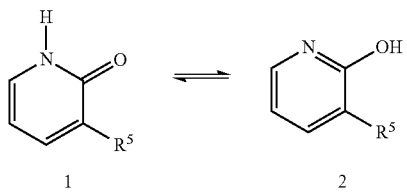

1                    2

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

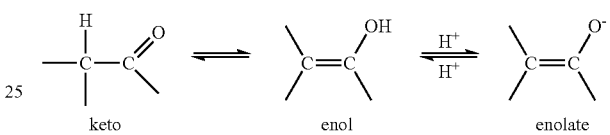

keto            enol            enolate

Stereoisomers

Unless otherwise mentioned or indicated, the chemical designation of compounds denotes the mixture of all possible stereochemically isomeric forms.

Stereocentres are illustrated in the usual fashion, using 'hashed' or 'wedged' lines. e.g.

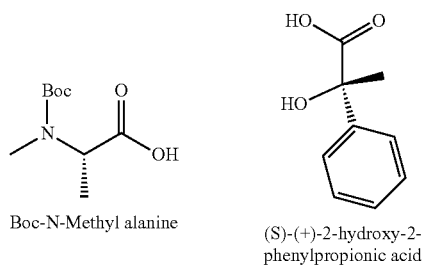

Boc-N-Methyl alanine        (S)-(+)-2-hydroxy-2-
                             phenylpropionic acid Where a compound is described as a mixture of two diastereoisomers/epimers, the configuration of the stereo-centre is not specified and is represented by straight lines.

Unless otherwise mentioned or indicated, where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be used in some circumstances. Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-12}$ heterocyclyl group, or a $C_{5-12}$ aryl group, particularly a $O_{1-6}$ alkyl group. Particular examples of ester groups include, but are not limited to —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $O_{1-6}$ alkyl group, a $C_{3-12}$ heterocyclyl group, or a $C_{5-12}$ aryl group, particularly a $O_{1-6}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph. Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described above, can be used to establish whether solvates had formed.

In one embodiment the salt of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one has <10% solvates present (such as no more than any one of the following amounts 9, 8, 7, 6, 5, 4, 3, 2, 1, 0.5, 0.1, 0.05 or 0.01%), e.g. hydrates, alcoholates, isopropylacetate, methyl acetate or alkanes, such as heptanes.

In one embodiment the salt of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one is anhydrous. In a further embodiment, the anhydrous salt of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one contains no more than 5% (such as no more than any one of the following amounts 4, 3, 2, 1, 0.5, 0.1, 0.05 or 0.01%) by weight of water.

In one embodiment the salt of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin yl]methyl}piperazin-1-yl]ethan-1-one contains a single crystalline form and no more than 5% (such as no more than any one of the following amounts 4, 3, 2, 1, 0.5, 0.1, 0.05 or 0.01%) by weight of other crystalline forms.

In one embodiment the salt of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one is crystalline.

In one embodiment the salt of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one is amorphous.

Furthermore, the compounds of the present invention may have one or more polymorph or amorphous crystalline forms and as such are intended to be included in the scope of the invention.

References herein to "polymorph" refer to the existence of more than one crystal structure of a compound of formula (I). The ability of a chemical compound to crystallize in more than one crystal modification can have an effect upon the properties of said compound, such as physicochemical properties, shelf life, solubility, formulation properties, toxicity, bioavailability, hygroscopicity and processing properties. In addition, the therapeutic action of a pharmaceutical compound can be affected by the polymorphism of the drug molecule.

In one embodiment, the compound of formula (I) comprises a polymorphic form of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one or salt thereof.

In a further embodiment, the compound of formula (I) comprises a polymorphic form of a salt of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one.

In a further embodiment, the compound of formula (I) comprises the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate. This compound may be prepared as defined herein in Example 39.

In a yet further embodiment, 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin yl]methyl}piperazin-1-yl]ethan-1-one L-(+)-lactate is characterised by the $^1$H NMR spectrum depicted in FIG. 1.

A compound's X-ray powder pattern is characterised by the diffraction angle (2θ) and interplanar spacing (d) parameters of an X-ray diffraction spectrum. These are related by Bragg's equation, nλ=2d Sin θ, (where n=1; λ=wavelength of the cathode used; d=interplanar spacing; and θ=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean ones which coincide in the range of 2θ±0.2°. The peaks mean main peaks and include peaks not larger than medium at diffraction angles other than those stated above.

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern having peaks at 6.5±0.5°, 7.1±0.5°, 7.9±0.5°, 9.3±0.5°, 10.2±0.5°, 11.0±0.5°, 11.6±0.5°, 13.3±0.5°, 14.4±0.5°, 15.0±0.5°, 16.7±0.5°, 18.0±0.5°, 18.4±0.5°, 20.0±0.5°, 21.0±0.5°, 23.4±0.5°, 25.2±0.5° and 26.1±0.5° (2θ, 1d.p).

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5- methyl-2-{[(3R)-3-methylmorpholin-4-yl]methyl}piperazin-1-yl]ethan-1-one L-(+)-lactate is characterised by an XRPD pattern having peaks at 6.5±0.2°, 7.1±0.2°, 7.9±0.2°, 9.3±0.2°, 10.2±0.2°, 11.0±0.2°, 11.6±0.2°, 13.3±0.2°, 14.4±0.2°, 15.0±0.2°, 16.7±0.2°, 18.0±0.2°, 18.4±0.2°, 20.0±0.2°, 21.0±0.2°, 23.4±0.2°, 25.2±0.2° and 26.1±0.2° (2θ, 1d.p).

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern having peaks at 6.5±0.1°, 7.1±0.1°, 7.9±0.1°, 9.3±0.1°, 10.2±0.1°, 11.0±0.1°, 11.6±0.1°, 13.3±0.1°, 14.4±0.1°, 15.0±0.1°, 16.7±0.1°, 18.0±0.1°, 18.4±0.1°, 20.0±0.1°, 21.0±0.1°, 23.4±0.1°, 25.2±0.1° and 26.1±0.1° (2θ, 1d.p).

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern having peaks at 6.5°, 7.1°, 7.9°, 9.3°, 10.2°, 11.0°, 11.6°, 13.3°, 14.4°, 15.0°, 16.7°, 18.0°, 18.4°, 20.0°, 21.0°, 23.4°, 25.2° and 26.1° (2θ, 1d.p).

Figure 2:
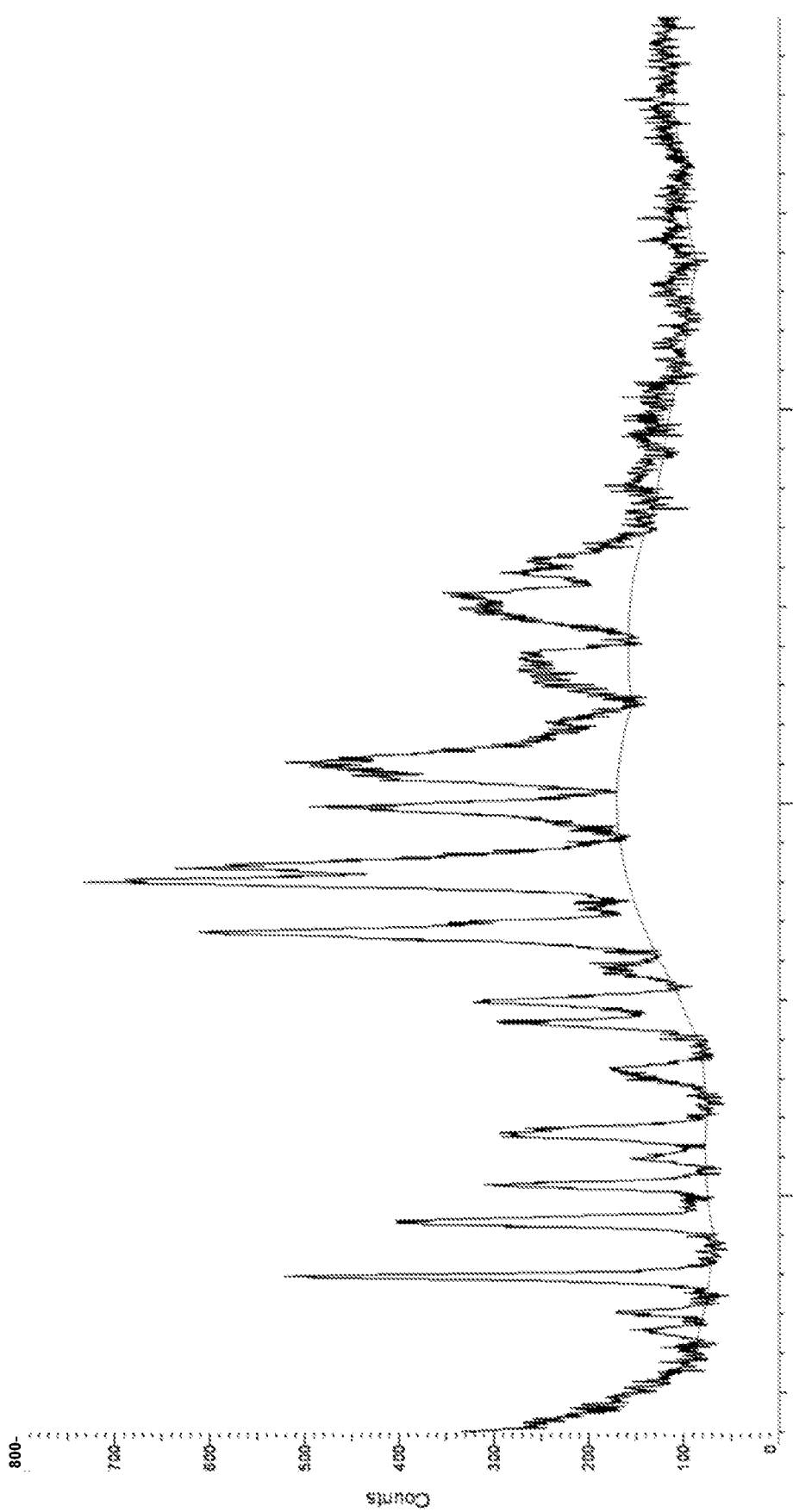
FIG. 2: XRPD of Example 39.

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern substantially as shown in FIG. 2.

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by having peaks at the same diffraction angles (2θ) of the XRPD pattern shown in FIG. 2 and optionally wherein the peaks have the same relative intensity as the peaks shown in FIG. 2.

It will be appreciated by the skilled person that references herein to "intensity" of peaks with respect to XRPD refer to relative intensities which have taken into account normalisation of background noise and other such parameters.

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by having major peaks at diffraction angles (2θ) and intensities as those shown in the XRPD pattern in FIG. 2.

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 13.59±0.5 Å, 12.44±0.5 Å, 11.19±0.5 Å, 9.50±0.5 Å, 8.67±0.5 Å, 8.04±0.5 Å, 7.62±0.5 Å, 6.65±0.5 Å, 6.15±0.5 Å, 5.90±0.5 Å, 5.31±0.5 Å, 4.93±0.5 Å, 4.82±0.5 Å, 4.44±0.5 Å, 4.23±0.5 Å, 3.80±0.5 Å, 3.53±0.5 Å and 3.41±0.5 Å (d, 2d.p.).

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 13.59±0.2 Å, 12.44±0.2 Å, 11.19±0.2 Å, 9.50±0.2 Å, 8.67±0.2 Å, 8.04±0.2 Å, 7.62±0.2 Å, 6.65±0.2 Å, 6.15±0.2 Å, 5.90±0.2 Å, 5.31±0.2 Å, 4.93±0.2 Å, 4.82±0.2 Å, 4.44±0.2 Å, 4.23±0.2 Å, 3.80±0.2 Å, 3.53±0.2 Å and 3.41±0.2 Å (d, 2d.p.).

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 13.59±0.1 Å, 12.44±0.1 Å, 11.19±0.1 Å, 9.50±0.1 Å, 8.67±0.1 Å, 8.04±0.1 Å, 7.62±0.1 Å, 6.65±0.1 Å, 6.15±0.1 Å, 5.90±0.1 Å, 5.31±0.1 Å, 4.93±0.1 Å, 4.82±0.1 Å, 4.44±0.1 Å, 4.23±0.1 Å, 3.80±0.1 Å, 3.53±0.1 Å and 3.41±0.1 Å (d, 2d.p.).

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 13.59 Å, 12.44 Å, 11.19 Å, 9.50 Å, 8.67 Å, 8.04 Å, 7.62 Å, 6.65 Å, 6.15 Å, 5.90 Å, 5.31 Å, 4.93 Å, 4.82 Å, 4.44 Å, 4.23 Å, 3.80 Å, 3.53 Å and 3.41 Å (d, 2d.p.).

In a further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by DSC peak temperatures of 78.69° C.±0.5° C. and/or 113.91° C.±0.5° C. (such as 78.69° C.±0.2° C. and/or 113.91° C.±0.2° C., in particular 78.69° C.±0.1° C. and/or 113.91° C.±0.1° C., more particularly 78.69° C. and/or 113.91° C.).

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by DSC onset temperatures of 72.3° C.±0.5° C. (endotherm, broad) and/or 102° C.±0.5° C. (endotherm, broad) (such as 72.3° C.±0.2° C. and/or 102° C.±0.2° C., in particular 72.3° C.±0.1° C. and/or 102° C.±0.1° C., more particularly 72.3° C. and/or 102° C.).

Figure 3:
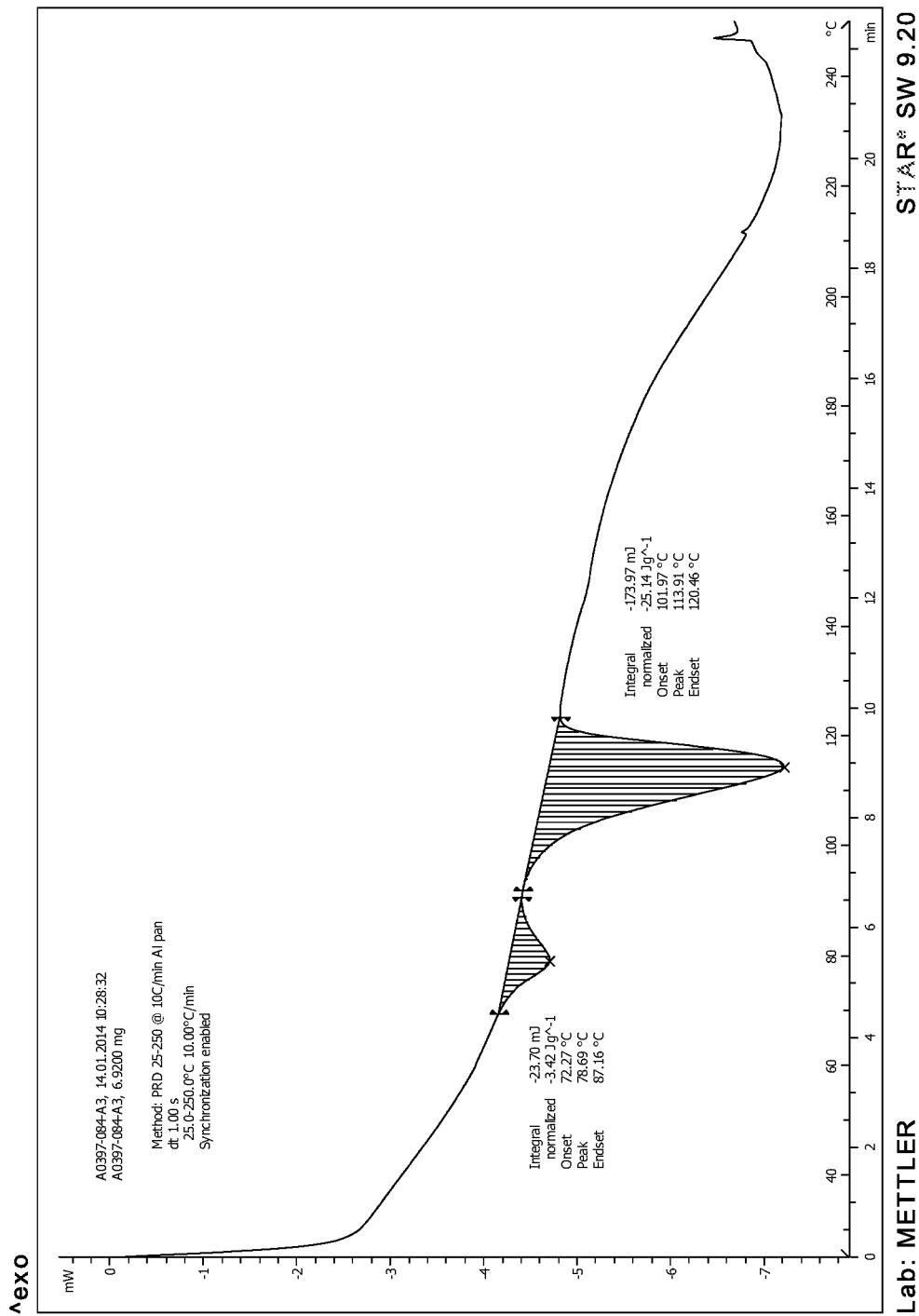
FIG. 3: DSC of Example 39.

In a yet further embodiment, the Form A polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by a DSC thermogram as depicted in FIG. 3.

In a further embodiment, the compound of formula (I) comprises the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate. This compound may be prepared as defined herein in Example 40.

Figure 4:
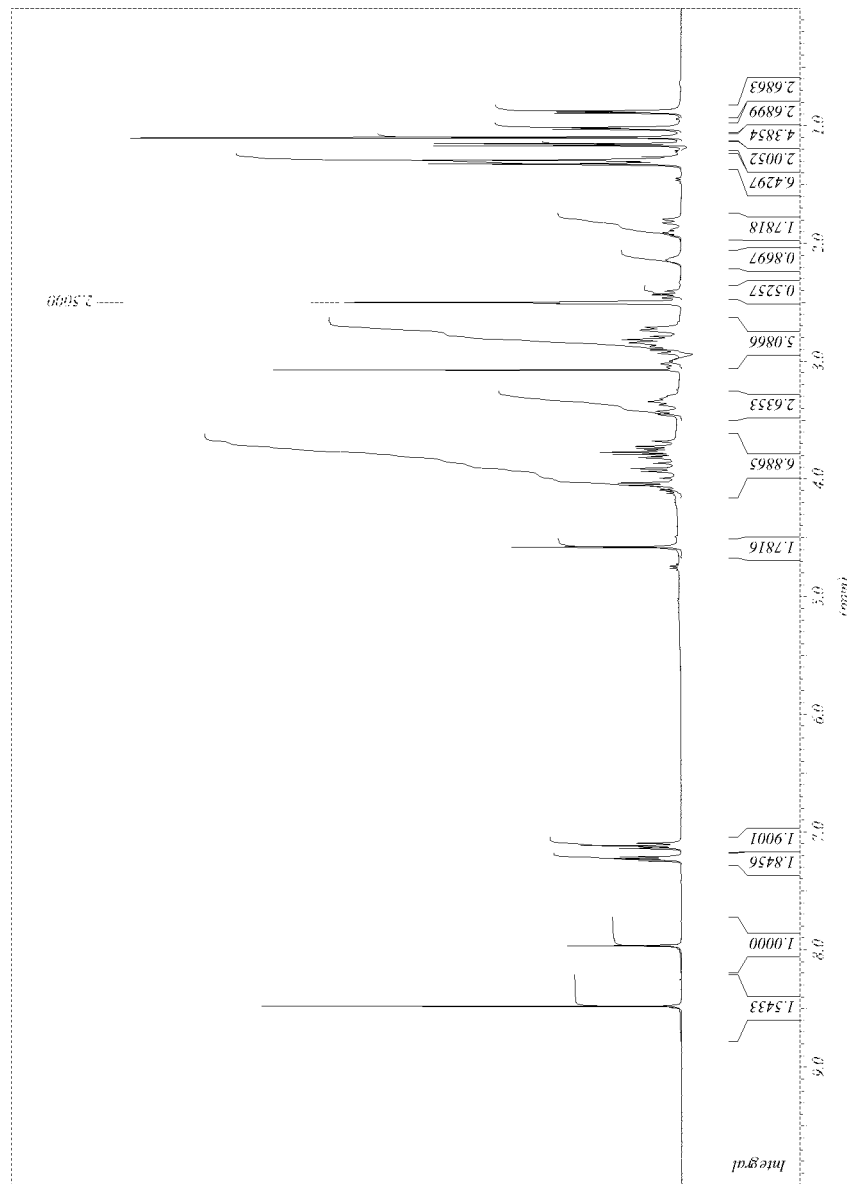
FIG. 4: $^1$H NMR of Example 40. Sample acquired in DMSO-$D_6$ and calibrated to the non-deuterated solvent residual of DMSO at δ=2.50 ppm. Contained an internal reference standard (TCNB) present as a singlet at δ=8.5 ppm.

In a yet further embodiment, 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by the $^1$H NMR spectrum depicted in FIG. 4.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern having peaks at 6.6±0.5°, 9.4±0.5°, 11.0±0.5°, 13.2±0.5°, 14.3±0.5°, 15.8±0.5°, 17.4±0.5°, 18.4±0.5°, 19.1±0.5°, 20.9±0.5°, 21.8±0.5°, 23.1±0.5°, 24.9±0.5°, 26.7±0.5° and 27.8±0.5° (2θ, 1d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern having peaks at 6.6±0.2°, 9.4±0.2°, 11.0±0.2°, 13.2±0.2°, 14.3±0.2°, 15.8±0.2°, 17.4±0.2°, 18.4±0.2°, 19.1±0.2°, 20.9±0.2°, 21.8±0.2°, 23.1±0.2°, 24.9±0.2°, 26.7±0.2° and 27.8±0.2° (2θ, 1d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern having peaks at 6.6±0.1°, 9.4±0.1°, 11.0±0.1°, 13.2±0.1°, 14.3±0.1°, 15.8±0.1°, 17.4±0.1°, 18.4±0.1°, 19.1±0.1°, 20.9±0.1°, 21.8±0.1°, 23.1±0.1°, 24.9±0.1°, 26.7±0.1° and 27.8±0.1° (2θ, 1d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern having peaks at 6.6°, 9.4°, 11.0°, 13.2°, 14.3°, 15.8°, 17.4°, 18.4°, 19.1°, 20.9°, 21.8°, 23.1°, 24.9°, 26.7° and 27.8° (2θ, 1d.p.).

Figure 5:
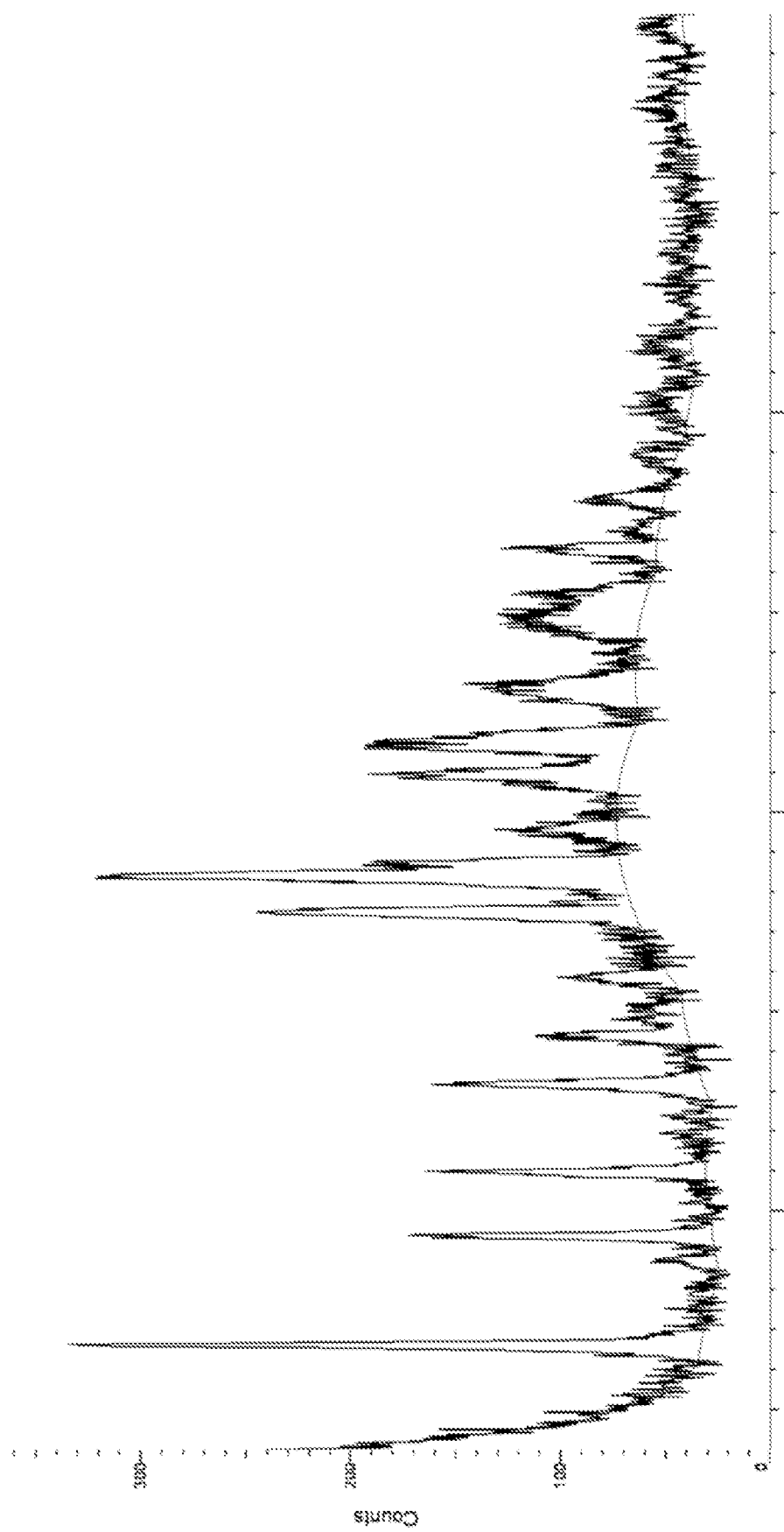
FIG. 5: XRPD of Example 40.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by an XRPD pattern substantially as shown in FIG. 5.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by having peaks at the same diffraction angles (2θ) of the XRPD pattern shown in FIG. 5 and optionally wherein the peaks have the same relative intensity as the peaks shown in FIG. 5.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by having major peaks at diffraction angles (2θ) and intensities as those shown in the XRPD pattern in FIG. 5.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 13.39±0.5 Å, 9.40±0.5 Å, 8.04±0.5 Å, 6.70±0.5 Å, 6.19±0.5 Å, 5.61±0.5 Å, 5.09±0.5 Å, 4.82±0.5 Å, 4.64±0.5 Å, 4.25±0.5 Å, 4.07±0.5 Å, 3.85±0.5 Å, 3.57±0.5 Å, 3.34±0.5 Å and 3.21±0.5 Å (d, 2d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 13.39±0.2 Å, 9.40±0.2 Å, 8.04±0.2 Å, 6.70±0.2 Å, 6.19±0.2 Å, 5.61±0.2 Å, 5.09±0.2 Å, 4.82±0.2 Å, 4.64±0.2 Å, 4.25±0.2 Å, 4.07±0.2 Å, 3.85±0.2 Å, 3.57±0.2 Å, 3.34±0.2 Å and 3.21±0.2 Å (d, 2d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 13.39±0.1 Å, 9.40±0.1 Å, 8.04±0.1 Å, 6.70±0.1 Å, 6.19±0.1 Å, 5.61±0.1 Å, 5.09±0.1 Å, 4.82±0.1 Å, 4.64±0.1 Å, 4.25±0.1 Å, 4.07±0.1 Å, 3.85±0.1 Å, 3.57±0.1 Å, 3.34±0.1 Å and 3.21±0.1 Å (d, 2d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 13.39 Å, 9.40 Å, 8.04 Å, 6.70 Å, 6.19 Å, 5.61 Å, 5.09 Å, 4.82 Å, 4.64 Å, 4.25 Å, 4.07 Å, 3.85 Å, 3.57 Å, 3.34 Å and 3.21 Å (d, 2d.p.).

In a further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by DSC peak temperatures of 85.25° C.±0.5° C. and/or 106.72° C.±0.5° C. (such as 85.25° C.±0.2° C. and/or 106.72° C.±0.2° C., in particular 85.25° C.±0.1° C. and/or 106.72° C.±0.1° C., more particularly 85.25° C. and/or 106.72° C.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by DSC onset temperatures of 68° C.±0.5° C. (large endotherm, broad) and/or 102° C.±0.5° C. (very small endotherm, broad) (such as 68° C.±0.2° C. and/or 102° C.±0.2° C., in particular 68° C.±0.1° C. and/or 102° C.±0.1° C., more particularly 68° C. and/or 102° C.).

Figure 6:
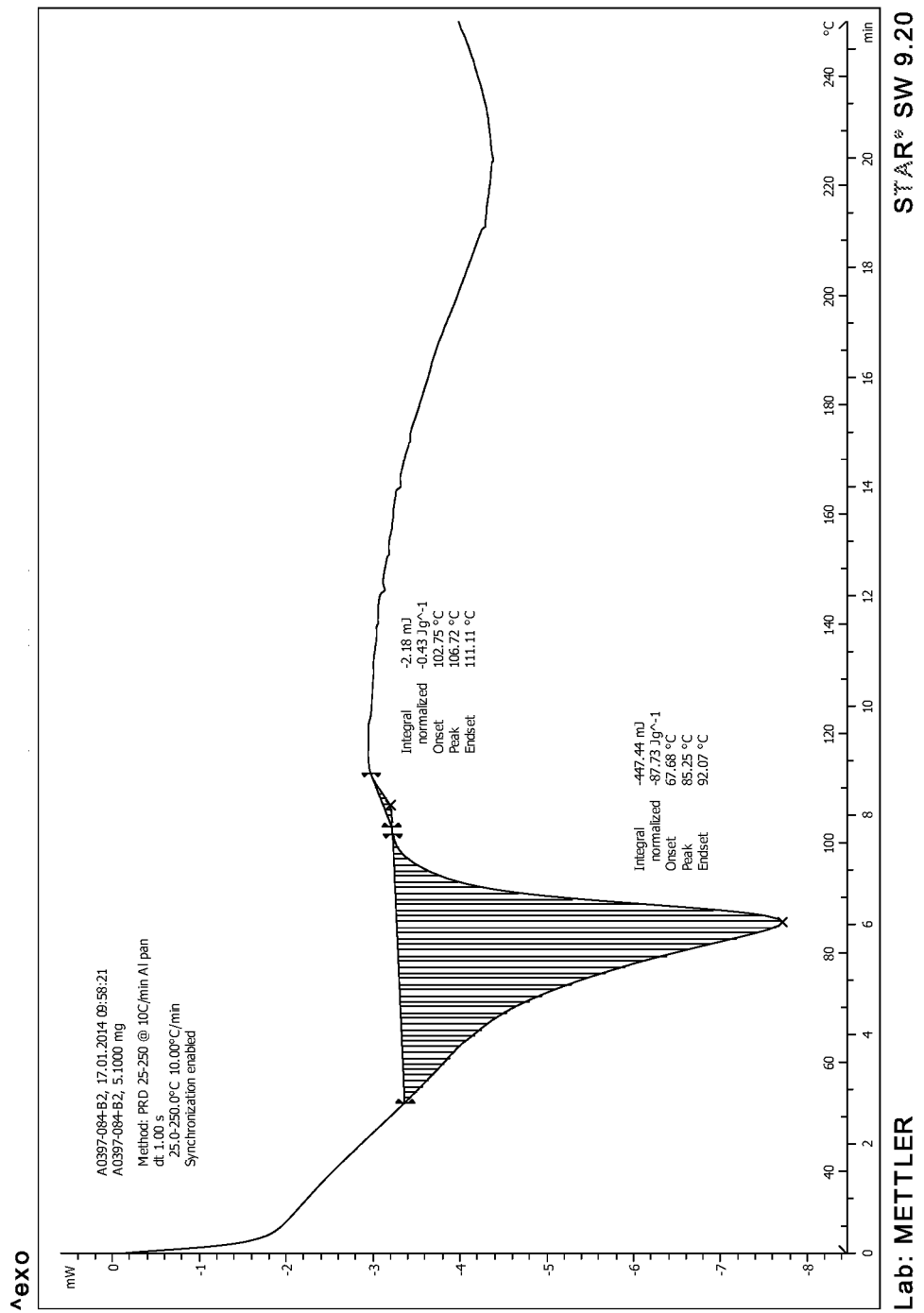
FIG. 6: DSC of Example 40.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by a DSC thermogram as depicted in FIG. 6.

In a further embodiment, the compound of formula (I) comprises the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate. This compound may be prepared as defined herein in Example 41.

Figure 7:
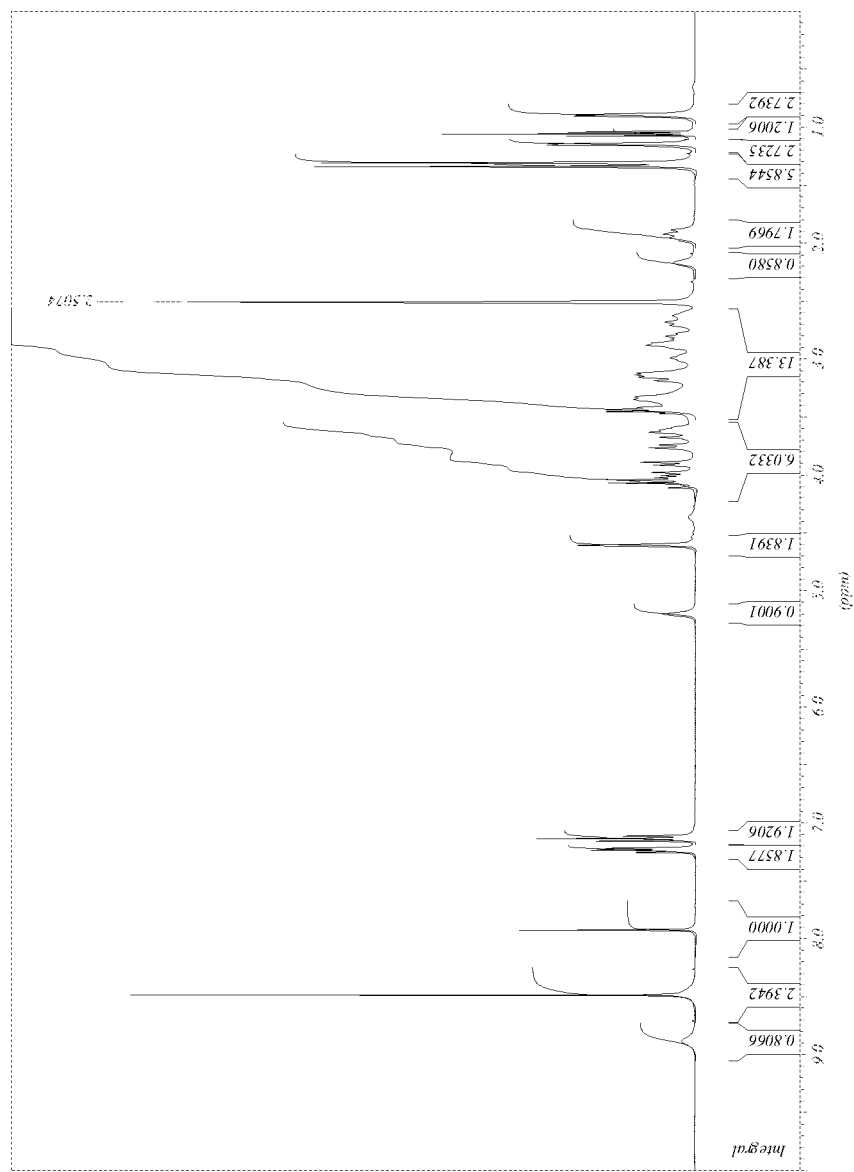
FIG. 7: $^1$H NMR of Example 41. Sample acquired in DMSO-$D_6$ and calibrated to the non-deuterated solvent residual of DMSO at 2.50 ppm.

In a yet further embodiment, 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by the $^1$H NMR spectrum depicted in FIG. 7.

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by an XRPD pattern having peaks at 8.5±0.5°, 13.5±0.5°, 13.9±0.5°, 14.3±0.5°, 16.2±0.5°, 17.3±0.5°, 20.1±0.5°, 21.3±0.5°, 23.3±0.5°, 24.4±0.5° and 27.9±0.5° (2θ, 1d.p).

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by an XRPD pattern having peaks at 8.5±0.2°, 13.5±0.2°, 13.9±0.2°, 14.3±0.2°, 16.2±0.2°, 17.3±0.2°, 20.1±0.2°, 21.3±0.2°, 23.3±0.2°, 24.4±0.2° and 27.9±0.2° (2θ, 1d.p).

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by an XRPD pattern having peaks at 8.5±0.1°, 13.5±0.1°, 13.9±0.1°, 14.3±0.1°, 16.2±0.1°, 17.3±0.1°, 20.1±0.1°, 21.3±0.1°, 23.3±0.1°, 24.4±0.1° and 27.9±0.1° (2θ, 1d.p).

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by an XRPD pattern having peaks at 8.5°, 13.5°, 13.9°, 14.3°, 16.2°, 17.3°, 20.1°, 21.3°, 23.3°, 24.4° and 27.9° (2θ, 1d.p).

Figure 8:
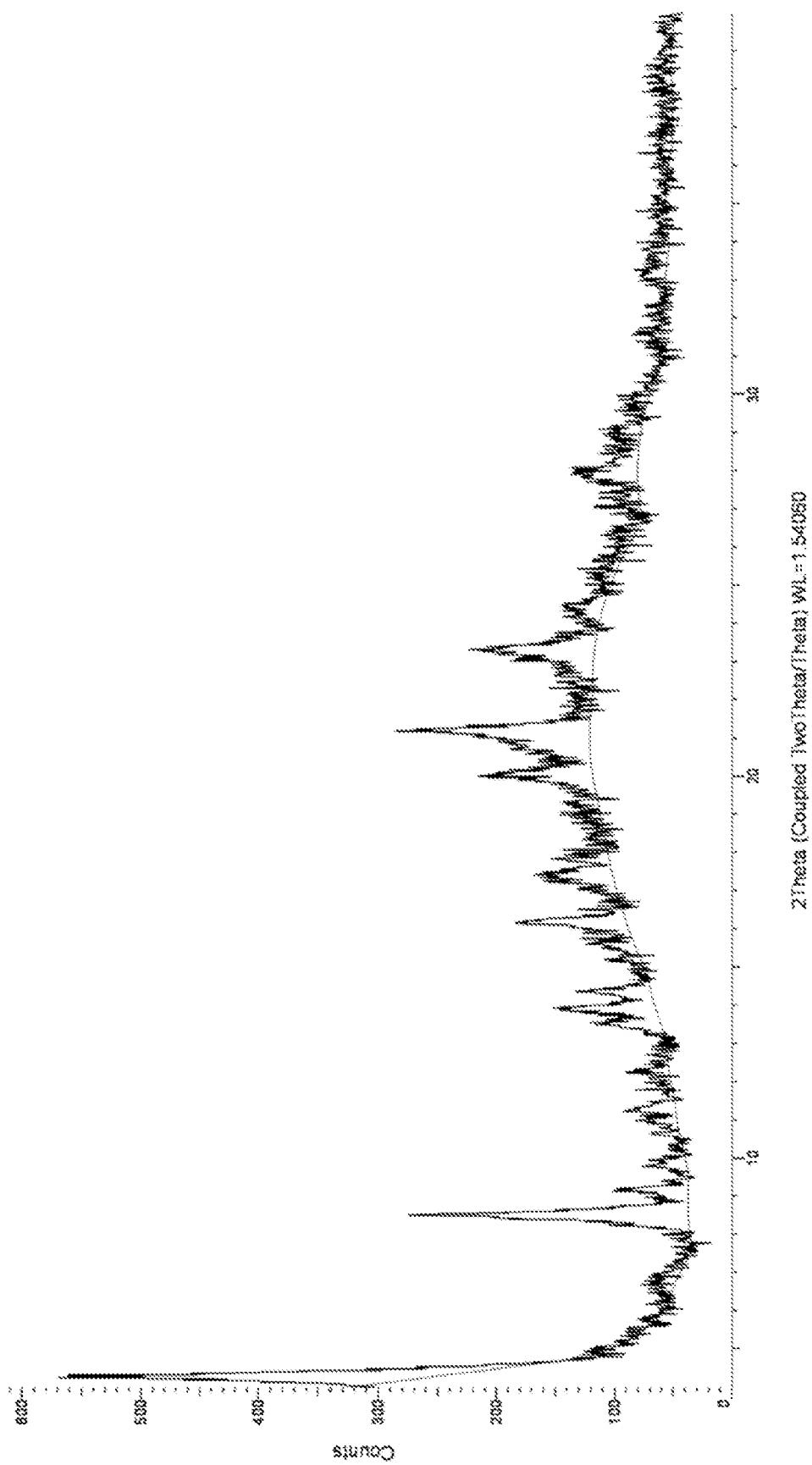
FIG. 8: XRPD of Example 41.

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by an XRPD pattern substantially as shown in FIG. 8.

In a further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by having peaks at the same diffraction angles (2θ) of the XRPD pattern shown in FIG. 8 and optionally wherein the peaks have the same relative intensity as the peaks shown in FIG. 8.

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by having major peaks at diffraction angles (2θ) and intensities as those shown in the XRPD pattern in FIG. 8.

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by interplanar spacing (d) values of 10.40±0.5 Å, 6.56±0.5 Å, 6.37±0.5 Å, 6.19±0.5 Å, 5.47±0.5 Å, 5.12±0.5 Å, 4.42±0.5 Å, 4.17±0.5 Å, 3.82±0.5 Å, 3.65±0.5 Å and 3.20±0.5 Å (d, 2d.p.).

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by interplanar spacing (d) values of 10.40±0.2 Å, 6.56±0.2 Å, 6.37±0.2 Å, 6.19±0.2 Å, 5.47±0.2 Å, 5.12±0.2 Å, 4.42±0.2 Å, 4.17±0.2 Å, 3.82±0.2 Å, 3.65±0.2 Å and 3.20±0.2 Å (d, 2d.p.).

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by interplanar spacing (d) values of 10.40±0.1 Å, 6.56±0.1 Å, 6.37±0.1 Å, 6.19±0.1 Å, 5.47±0.1 Å, 5.12±0.1 Å, 4.42±0.1 Å, 4.17±0.1 Å, 3.82±0.1 Å, 3.65±0.1 Å and 3.20±0.1 Å (d, 2d.p.).

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by interplanar spacing (d) values of 10.40 Å, 6.56 Å, 6.37 Å, 6.19 Å, 5.47 Å, 5.12 Å, 4.42 Å, 4.17 Å, 3.82 Å, 3.65 Å and 3.20 Å (d, 2d.p.).

In a further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by DSC peak temperatures of 80.31° C.±0.5° C. and/or 149.07° C.±0.5° C. (such as 80.31° C.±0.2° C. and/or 149.07° C.±0.2° C., in particular 80.31° C.±0.1° C. and/or 149.07° C.±0.1° C., more particularly 80.31° C. and/or 149.07° C.).

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by DSC onset temperatures of 51.2° C.±0.5° C. (endotherm, broad) and/or 136° C.±0.5° C. (endotherm, broad) (such as 51.2° C.±0.2° C. and/or 136° C.±0.2° C., in particular 51.2° C.±0.1° C. and/or 136° C.±0.1° C., more particularly 51.2° C. and/or 136° C.).

Figure 9:
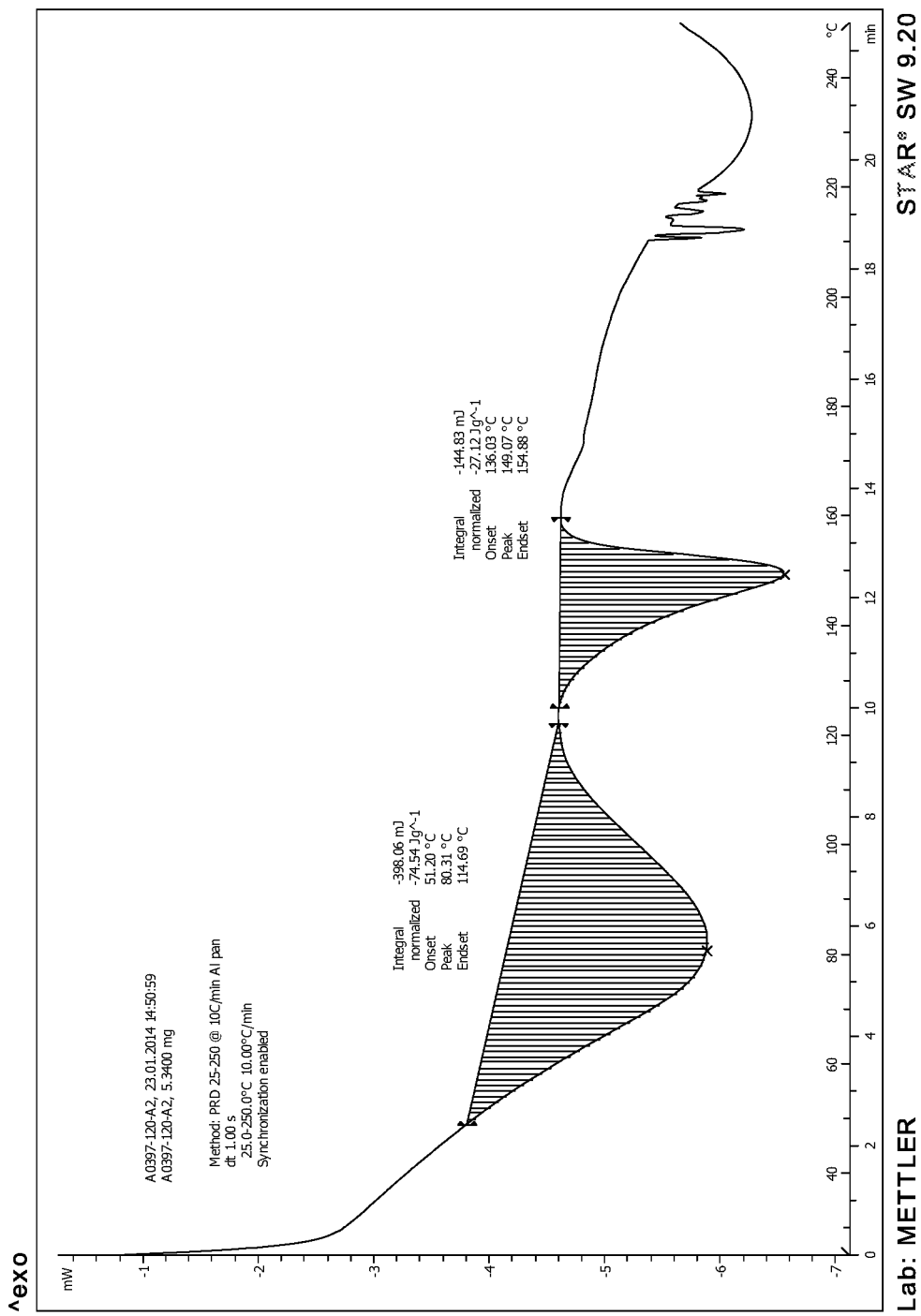
FIG. 9: DSC of Example 41.

In a yet further embodiment, the Form F polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate is characterised by a DSC thermogram as depicted in FIG. 9.

In a further embodiment, the compound of formula (I) comprises the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate. This compound may be prepared as defined herein in Example 42.

Figure 10:
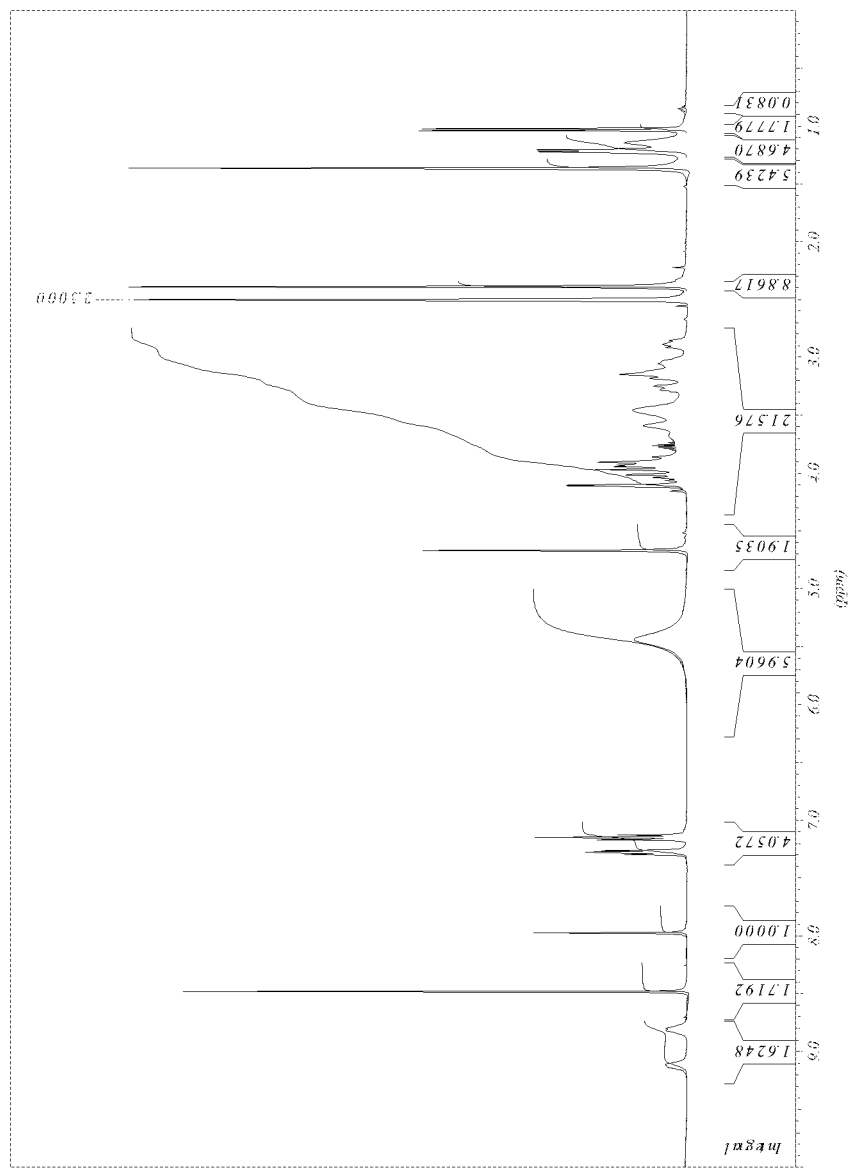
FIG. 10: $^1$H NMR of Example 42. Sample acquired in DMSO-$D_6$ and calibrated to the non-deuterated solvent residual of DMSO at 2.50 ppm.

In a yet further embodiment, 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by the $^1$H NMR spectrum depicted in FIG. 10.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by an XRPD pattern having peaks at 6.6±0.5°, 8.0±0.5°, 11.8±0.5°, 13.2±0.5°, 14.3±0.5°, 15.0±0.5°, 15.6±0.5°, 17.1±0.5°, 17.4±0.5°, 17.7±0.5°, 19.2±0.5°, 20.3±0.5°, 21.2±0.5°, 22.3±0.5°, 23.0±0.5°, 24.0±0.5°, 25.8±0.5°, 26.8±0.5° and 28.9±0.5° (2θ, 1d.p).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by an XRPD pattern having peaks at 6.6±0.2°, 8.0±0.2°, 11.8±0.2°, 13.2±0.2°, 14.3±0.2°, 15.0±0.2°, 15.6±0.2°, 17.1±0.2°, 17.4±0.2°, 17.7±0.2°, 19.2±0.2°, 20.3±0.2°, 21.2±0.2°, 22.3±0.2°, 23.0±0.2°, 24.0±0.2°, 25.8±0.2°, 26.8±0.2° and 28.9±0.2° (2θ, 1d.p).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by an XRPD pattern having peaks at 6.6±0.1°, 8.0±0.1°, 11.8±0.1°, 13.2±0.1°, 14.3±0.1°, 15.0±0.1°, 15.6±0.1°, 17.1±0.1°, 17.4±0.1°, 17.7±0.1°, 19.2±0.1°, 20.3±0.1°, 21.2±0.1°, 22.3±0.1°, 23.0±0.1°, 24.0±0.1°, 25.8±0.1°, 26.8±0.1° and 28.9±0.1° (2θ, 1d.p).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by an XRPD pattern having peaks at 6.6°, 8.0°, 11.8°, 13.2°, 14.3°, 15.0°, 15.6°, 17.1°, 17.4°, 17.7°, 19.2°, 20.3°, 21.2°, 22.3°, 23.0°, 24.0°, 25.8°, 26.8° and 28.9° (2θ, 1d.p).

Figure 11:
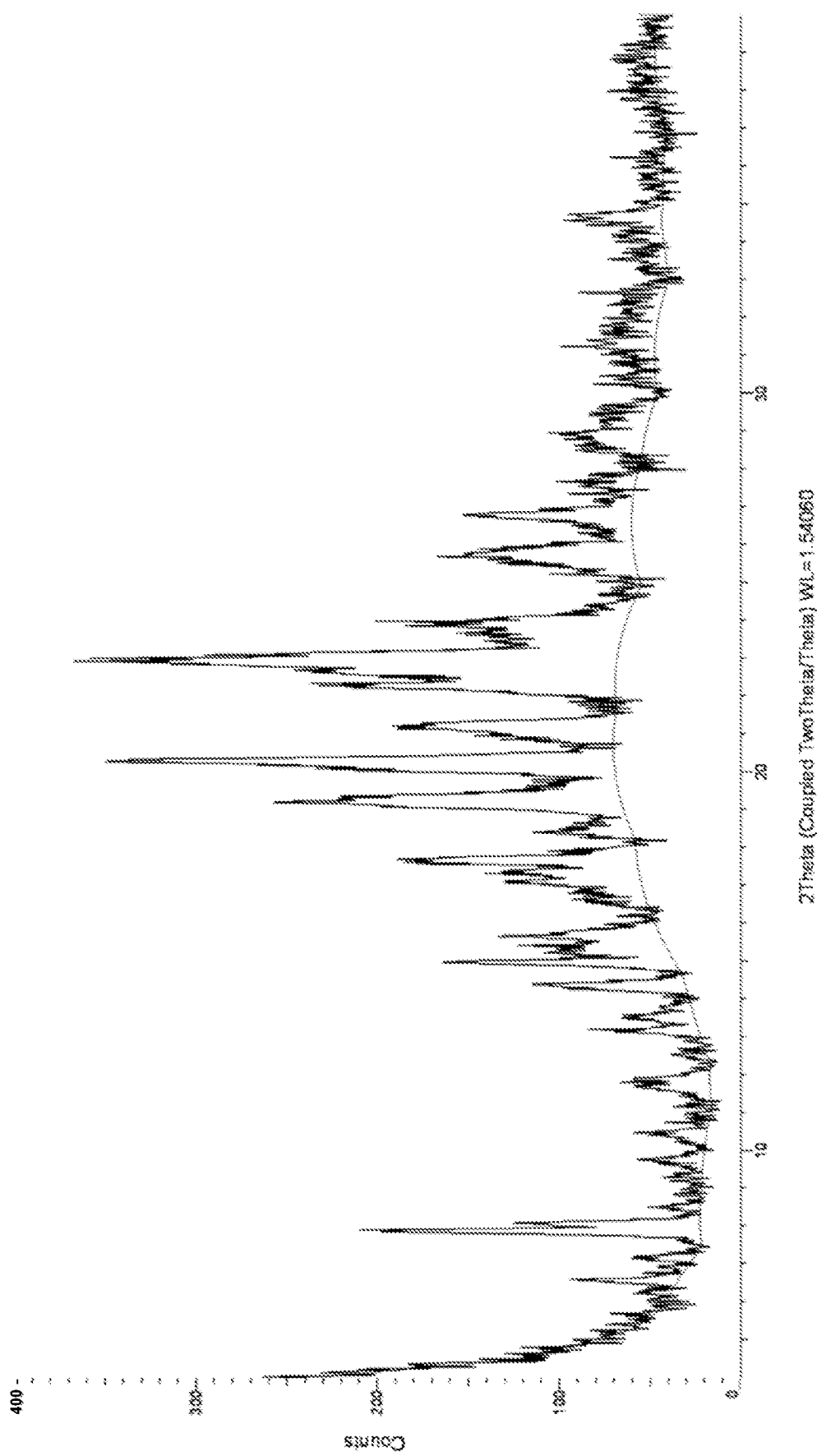
FIG. 11: XRPD of Example 42.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by an XRPD pattern substantially as shown in FIG. 11.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by having peaks at the same diffraction angles (2θ) of the XRPD pattern shown in FIG. 11 and optionally wherein the peaks have the same relative intensity as the peaks shown in FIG. 11.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by having major peaks at diffraction angles (2θ) and intensities as those shown in the XRPD pattern in FIG. 11.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by interplanar spacing (d) values of 13.39±0.5 Å, 11.05±0.5 Å, 7.50±0.5 Å, 6.70±0.5 Å, 6.19±0.5 Å, 5.90±0.5 Å, 5.68±0.5 Å, 5.18±0.5 Å, 5.09±0.5 Å, 5.01±0.5 Å, 4.62±0.5 Å, 4.37±0.5 Å, 4.19±0.5 Å, 3.98±0.5 Å, 3.86±0.5 Å, 3.71±0.5 Å, 3.45±0.5 Å, 3.32±0.5 Å and 3.09±0.5 Å (d, 2d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by interplanar spacing (d) values of 13.39±0.2 Å, 11.05±0.2 Å, 7.50±0.2 Å, 6.70±0.2 Å, 6.19±0.2 Å, 5.90±0.2 Å, 5.68±0.2 Å, 5.18±0.2 Å, 5.09±0.2 Å, 5.01±0.2 Å, 4.62±0.2 Å, 4.37±0.2 Å, 4.19±0.2 Å, 3.98±0.2 Å, 3.86±0.2 Å, 3.71±0.2 Å, 3.45±0.2 Å, 3.32±0.2 Å and 3.09±0.2 Å (d, 2d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by interplanar spacing (d) values of 13.39±0.1 Å, 11.05±0.1 Å, 7.50±0.1 Å, 6.70±0.1 Å, 6.19±0.1 Å, 5.90±0.1 Å, 5.68±0.1 Å, 5.18±0.1 Å, 5.09±0.1 Å, 5.01±0.1 Å, 4.62±0.1 Å, 4.37±0.1 Å, 4.19±0.1 Å, 3.98±0.1 Å, 3.86±0.1 Å, 3.71±0.1 Å, 3.45±0.1 Å, 3.32±0.1 Å and 3.09±0.1 Å (d, 2d.p.).

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by interplanar spacing (d) values of 13.39 Å, 11.05 Å, 7.50 Å, 6.70 Å, 6.19 Å, 5.90 Å, 5.68 Å, 5.18 Å, 5.09 Å, 5.01 Å, 4.62 Å, 4.37 Å, 4.19 Å, 3.98 Å, 3.86 Å, 3.71 Å, 3.45 Å, 3.32 Å and 3.09 Å (d, 2d.p.).

In a further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by DSC peak temperatures of 98.63° C.±0.5° C. and/or 177.11° C.±0.5° C. (such as 98.63° C.±0.2° C. and/or 177.11° C.±0.2° C., in particular 98.63° C.±0.1° C. and/or 177.11° C.±0.1° C., more particularly 98.63° C. and/or 177.11° C.).

In a further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by DSC onset temperatures of 73.3° C.±0.5° C. (endotherm, broad) and/or 160.8° C.±0.5° C. (endotherm, broad) (such as 73.3° C.±0.2° C. and/or 160.8° C.±0.2° C., in particular 73.3° C.±0.1° C. and/or 160.8° C.±0.1° C., more particularly 73.3° C. and/or 160.8° C.).

Figure 12:
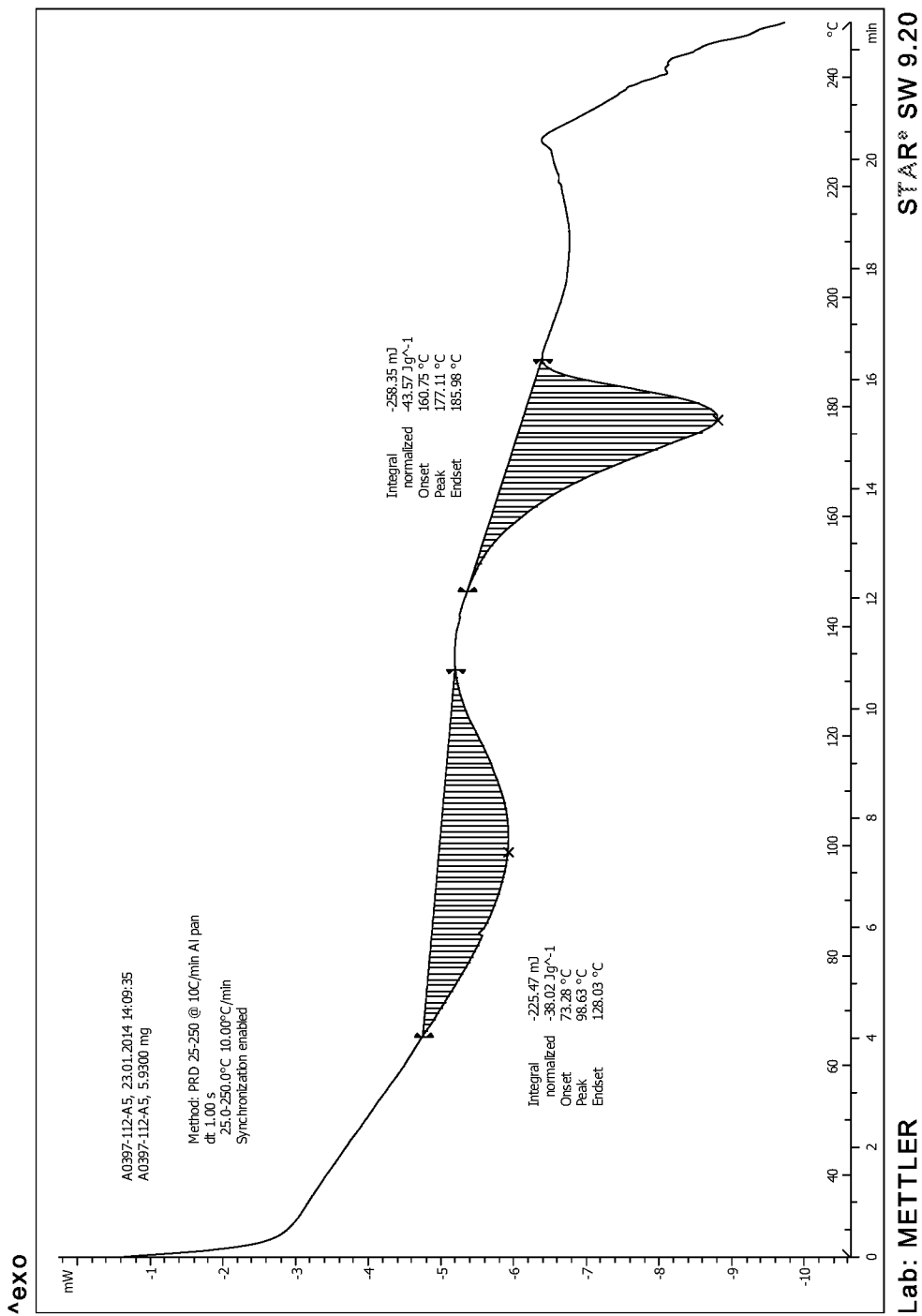
FIG. 12: DSC of Example 42.

In a yet further embodiment, the Form B polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one mesylate is characterised by a DSC thermogram as depicted in FIG. 12.

In a further embodiment, the compound of formula (I) comprises the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3- methylmorpholin-4-yl]methyl}piperazin-1-yl]ethan-1-one L-(+)-lactate. This compound may be prepared as defined herein in Example 43.

Figure 15:
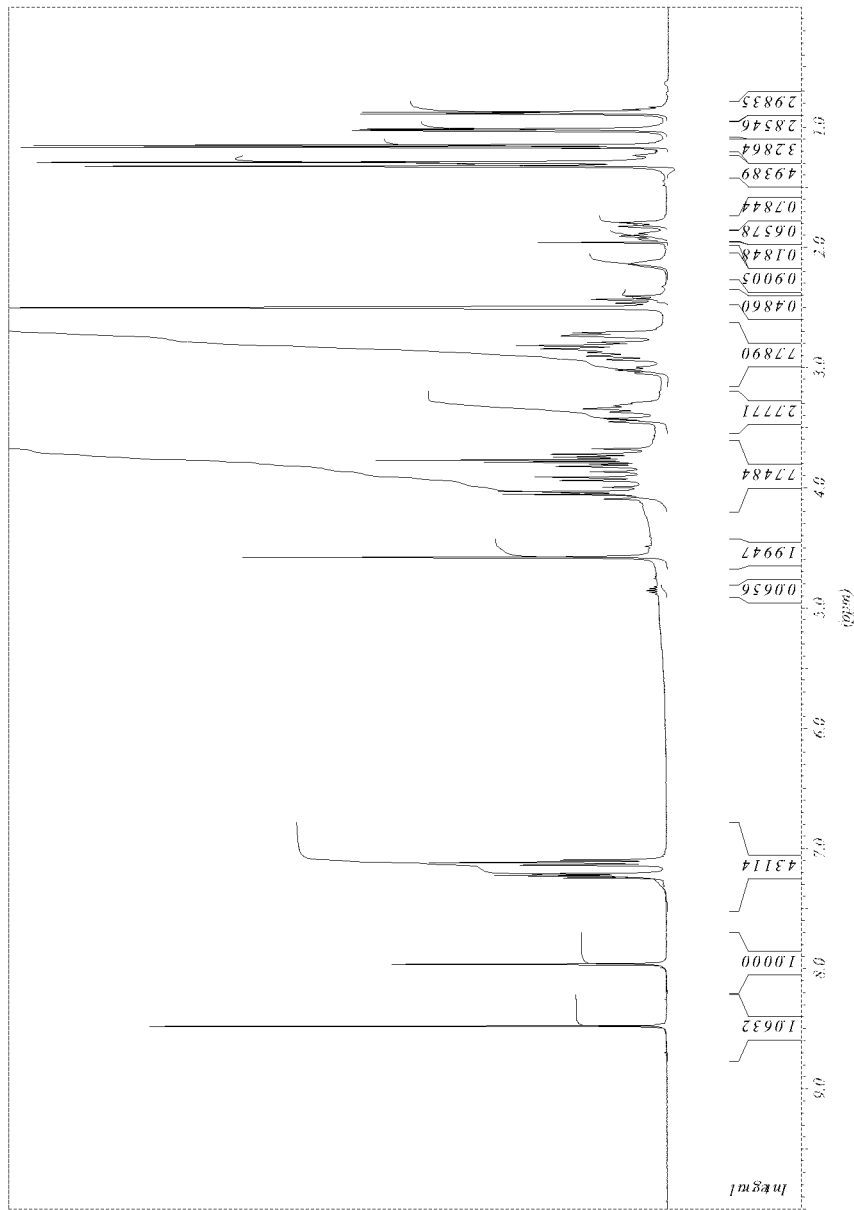
FIG. 15: $^1$H NMR of Example 43. Sample acquired in DMSO-$D_6$ and calibrated to the non-deuterated solvent residual of DMSO at δ=2.50 ppm. Contained an internal reference standard (TCNB) present as a singlet at δ=8.5 ppm.

In a yet further embodiment, 1-{6-[(4-fluorophenyl) methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin yl]methyl}piperazin-1-yl]ethan-1-one L-(+)-lactate is characterised by the $^1$H NMR spectrum depicted in FIG. 15.

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by an XRPD pattern having peaks at 7.4±0.5°, 7.9±0.5°, 8.3±0.5°, 8.7±0.5°, 9.0±0.5°, 10.4±0.5°, 11.2±0.5°, 11.6±0.5°, 12.3±0.5°, 13.1±0.5°, 13.9±0.5°, 14.7±0.5°, 15.8±0.5°, 16.5±0.5°, 17.1±0.5°, 17.9±0.5°, 18.4±0.5°, 18.9±0.5°, 19.6±0.5°, 20.4±0.5°, 21.0±0.5°, 21.8±0.5°, 22.9±0.5°, 23.3±0.5°, 23.6±0.5°, 24.0±0.5°, 24.9±0.5° and 26.4±0.5° (2θ, 1d.p).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by an
XRPD pattern having peaks at 7.4±0.2°, 7.9±0.2°, 8.3±0.2°, 8.7±0.2°, 9.0±0.2°, 10.4±0.2°, 11.2±0.2°, 11.6±0.2°, 12.3±0.2°, 13.1±0.2°, 13.9±0.2°, 14.7±0.2°, 15.8±0.2°, 16.5±0.2°, 17.1±0.2°, 17.9±0.2°, 18.4±0.2°, 18.9±0.2°, 19.6±0.2°, 20.4±0.2°, 21.0±0.2°, 21.8±0.2°, 22.9±0.2°, 23.3±0.2°, 23.6±0.2°, 24.0±0.2°, 24.9±0.2° and 26.4±0.2° (2θ, 1d.p).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by an XRPD pattern having peaks at 7.4±0.1°, 7.9±0.1°, 8.3±0.1°, 8.7±0.1°, 9.0±0.1°, 10.4±0.1°, 11.2±0.1°, 11.6±0.1°, 12.3±0.1°, 13.1±0.1°, 13.9±0.1°, 14.7±0.1°, 15.8±0.1°, 16.5±0.1°, 17.1±0.1°, 17.9±0.1°, 18.4±0.1°, 18.9±0.1°, 19.6±0.1°, 20.4±0.1°, 21.0±0.1°, 21.8±0.1°, 22.9±0.1°, 23.3±0.1°, 23.6±0.1°, 24.0±0.1°, 24.9±0.1° and 26.4±0.1° (2θ, 1d.p).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by an XRPD pattern having peaks at 7.4°, 7.9°, 8.3°, 8.7°, 9.0°, 10.4°, 11.2°, 11.6°, 12.3°, 13.1°, 13.9°, 14.7°, 15.8°, 16.5°, 17.1°, 17.9°, 18.4°, 18.9°, 19.6°, 20.4°, 21.0°, 21.8°, 22.9°, 23.3°, 23.6°, 24.0°, 24.9° and 26.4° (2θ, 1d.p).

Figure 16:
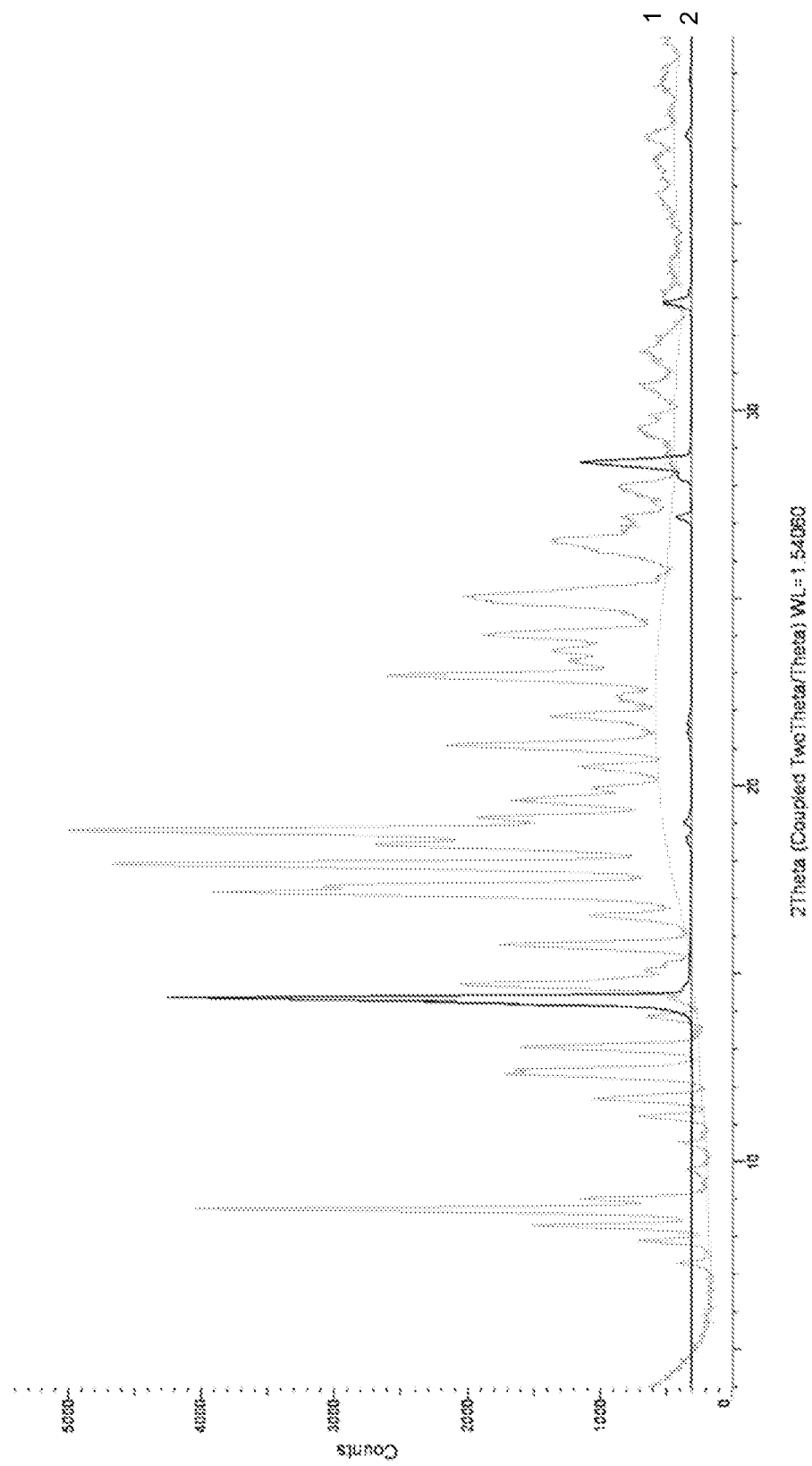
FIG. 16: XRPD of Example 43, (diffractogram labelled 1) overlaid with anhydrous L-(+)-Lactic acid (diffractogram labelled 2).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by an XRPD pattern substantially as shown in FIG. 16 labelled as 1.

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by having peaks at the same diffraction angles (2θ) of the XRPD pattern shown in FIG. 16 labelled as 1 and optionally wherein the peaks have the same relative intensity as the peaks shown in FIG. 16 labelled as 1.

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by having major peaks at diffraction angles (2θ) and intensities as those shown in the XRPD pattern in FIG. 16 labelled as 1.

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by having major peaks as measured by XRPD at 8.7±0.5°, 17.1±0.5°, 17.9±0.5° and 18.9±0.5° (2θ, 1d.p).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by having major peaks as measured by XRPD at 8.7±0.2°, 17.1±0.2°, 17.9±0.2° and 18.9±0.2° (2θ, 1d.p).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by having major peaks as measured by XRPD at 8.7±0.1°, 17.1±0.1°, 17.9±0.1° and 18.9±0.1° (2θ, 1d.p).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by having major peaks as measured by XRPD at 8.7°, 17.1°, 17.9° and 18.9° (2θ, 1d.p).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by interplanar spacing (d) values of 11.94±0.5 Å, 11.19±0.5 Å, 10.65±0.5 Å, 10.16±0.5 Å, 9.82±0.5 Å, 8.50±0.5 Å, 7.90±0.5 Å, 7.62±0.5 Å, 7.19±0.5 Å, 6.75±0.5 Å, 6.37±0.5 Å, 6.02±0.5 Å, 5.61±0.5 Å, 5.37±0.5 Å, 5.18±0.5 Å, 4.95±0.5 Å, 4.82±0.5 Å, 4.69±0.5 Å, 4.53±0.5 Å, 4.35±0.5 Å, 4.23±0.5 Å, 4.07±0.5 Å, 3.88±0.5 Å, 3.82±0.5 Å, 3.77±0.5 Å, 3.71±0.5 Å, 3.57±0.5 Å and 3.37±0.5 Å (d, 2d.p.).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl] methyl}piperazin-1-yl]ethan-1-one L-(+)-lactate is characterised by interplanar spacing (d) values of 11.94±0.2 Å, 11.19±0.2 Å, 10.65±0.2 Å, 10.16±0.2 Å, 9.82±0.2 Å, 8.50±0.2 Å, 7.90±0.2 Å, 7.62±0.2 Å, 7.19±0.2 Å, 6.75±0.2 Å, 6.37±0.2 Å, 6.02±0.2 Å, 5.61±0.2 Å, 5.37±0.2 Å, 5.18±0.2 Å, 4.95±0.2 Å, 4.82±0.2 Å, 4.69±0.2 Å, 4.53±0.2 Å, 4.35±0.2 Å, 4.23±0.2 Å, 4.07±0.2 Å, 3.88±0.2 Å, 3.82±0.2 Å, 3.77±0.2 Å, 3.71±0.2 Å, 3.57±0.2 Å and 3.37±0.2 Å (d, 2d.p.).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 11.94±0.1 Å, 11.19±0.1 Å, 10.65±0.1 Å, 10.16±0.1 Å, 9.82±0.1 Å, 8.50±0.1 Å, 7.90±0.1 Å, 7.62±0.1 Å, 7.19±0.1 Å, 6.75±0.1 Å, 6.37±0.1 Å, 6.02±0.1 Å, 5.61±0.1 Å, 5.37±0.1 Å, 5.18±0.1 Å, 4.95±0.1 Å, 4.82±0.1 Å, 4.69±0.1 Å, 4.53±0.1 Å, 4.35±0.1 Å, 4.23±0.1 Å, 4.07±0.1 Å, 3.88±0.1 Å, 3.82±0.1 Å, 3.77±0.1 Å, 3.71±0.1 Å, 3.57±0.1 Å and 3.37±0.1 Å (d, 2d.p.).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by interplanar spacing (d) values of 11.94 Å, 11.19 Å, 10.65 Å, 10.16 Å, 9.82 Å, 8.50 Å, 7.90 Å, 7.62 Å, 7.19 Å, 6.75 Å, 6.37 Å, 6.02 Å, 5.61 Å, 5.37 Å, 5.18 Å, 4.95 Å, 4.82 Å, 4.69 Å, 4.53 Å, 4.35 Å, 4.23 Å, 4.07 Å, 3.88 Å, 3.82 Å, 3.77 Å, 3.71 Å, 3.57 Å and 3.37 Å (d, 2d.p.).

In a further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by a DSC peak temperature of 174.37° C.±0.5° C. (such as 174.37° C.±0.2° C., in particular 174.37° C.±0.1° C., more particularly 174.37° C.).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by a DSC onset temperature of 171.6° C.±0.5° C. (endotherm, sharp) (such as 171.6° C.±0.2° C., in particular 171.6° C.±0.1° C., more particularly 171.6° C.).

Figure 17:
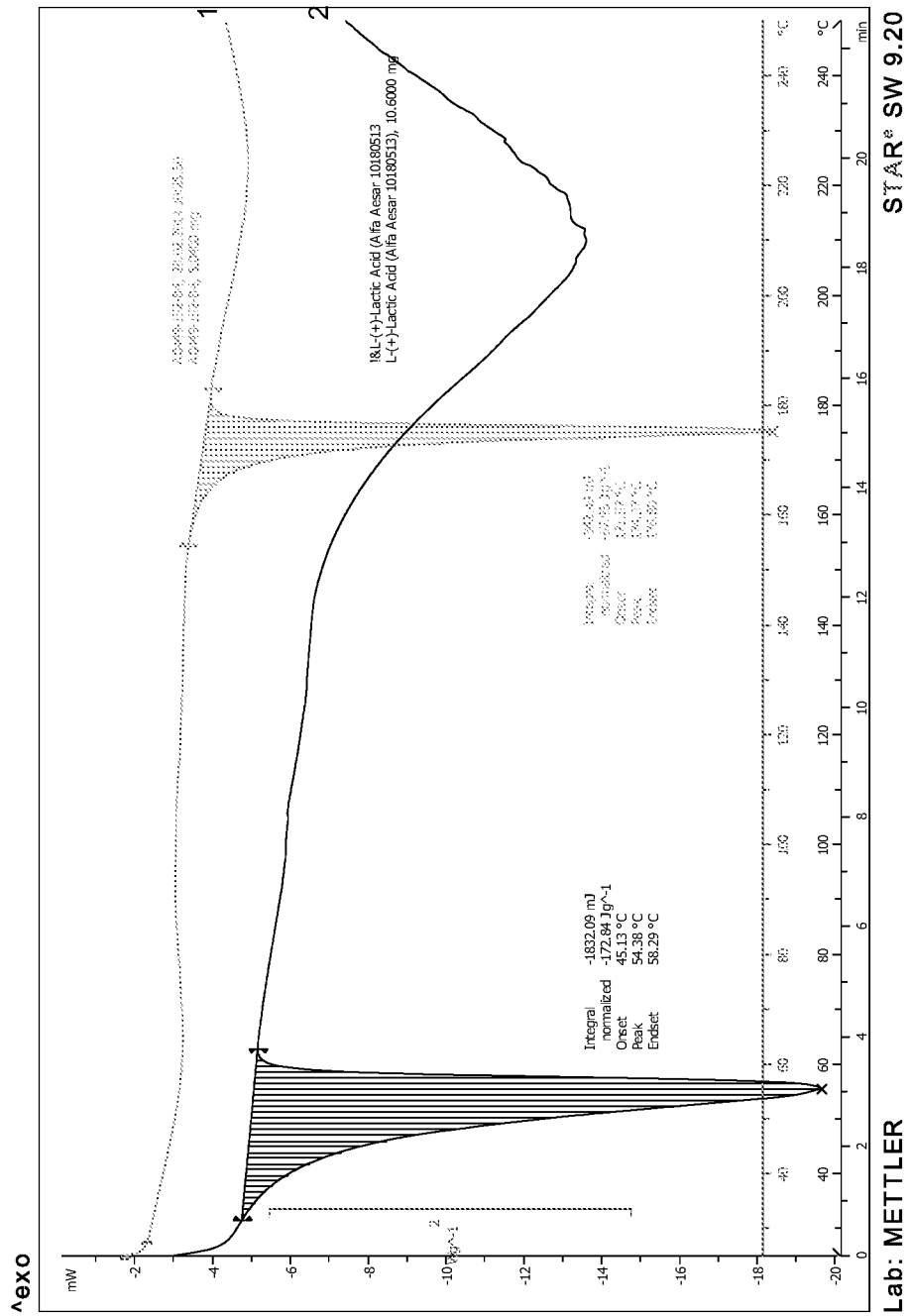
FIG. 17: DSC of Example 43, (thermogram labelled 1) overlaid with anhydrous L-(+)-Lactic acid (thermogram labelled 2).

In a yet further embodiment, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate is characterised by a
DSC thermogram as depicted in FIG. 17 labelled as 1.

In one embodiment, a lactate (e.g. L-(+)-lactate) salt of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one which is crystalline and is characterised by one or more (in any combination) or all of the following parameters:

(a) the $^1$H NMR spectrum depicted in FIG. 15; and/or
(b) an XRPD pattern having peaks at 7.4±0.5°, 7.9±0.5°, 8.3±0.5°, 8.7±0.5°, 9.0±0.5°, 10.4±0.5°, 11.2±0.5°, 11.6±0.5°, 12.3±0.5°, 13.1±0.5°, 13.9±0.5°, 14.7±0.5°, 15.8±0.5°, 16.5±0.5°, 17.1±0.5°, 17.9±0.5°, 18.4±0.5°, 18.9±0.5°, 19.6±0.5°, 20.4±0.5°, 21.0±0.5°, 21.8±0.5°, 22.9±0.5°, 23.3±0.5°, 23.6±0.5°, 24.0±0.5°, 24.9±0.5° and 26.4±0.5° (2θ, 1d.p); and/or
(c) an XRPD pattern substantially as shown in FIG. 16 labelled as 1; and/or
(d) having peaks at the same diffraction angles (2θ) of the XRPD pattern shown in FIG. 16 labelled as 1 and optionally wherein the peaks have the same relative intensity as the peaks shown in FIG. 16 labelled as 1; and/or
(e) having major peaks at diffraction angles (2θ) and intensities as those shown in the XRPD pattern in FIG. 16 labelled as 1; and/or
(f) having major peaks as measured by XRPD at 8.7±0.5°, 17.1±0.5°, 17.9±0.5° and 18.9±0.5° (2θ, 1d.p); and/or
(g) interplanar spacing (d) values of 11.94±0.5 Å, 11.19±0.5 Å, 10.65±0.5 Å, 10.16±0.5 Å, 9.82±0.5 Å, 8.50±0.5 Å, 7.90±0.5 Å, 7.62±0.5 Å, 7.19±0.5 Å, 6.75±0.5 Å, 6.37±0.5 Å, 6.02±0.5 Å, 5.61±0.5 Å, 5.37±0.5 Å, 5.18±0.5 Å, 4.95±0.5 Å, 4.82±0.5 Å, 4.69±0.5 Å, 4.53±0.5 Å, 4.35±0.5 Å, 4.23±0.5 Å, 4.07±0.5 Å, 3.88±0.5 Å, 3.82±0.5 Å, 3.77±0.5 Å, 3.71±0.5 Å, 3.57±0.5 Å and 3.37±0.5 Å (d, 2d.p.); and/or
(h) a DSC peak temperature of 174.37° C.±0.5° C. (such as 174.37° C.±0.2° C., in particular 174.37° C.±0.1° C., more particularly 174.37° C.); and/or
(i) a DSC onset temperature of 171.6° C.±0.5° C. (endotherm, sharp) (such as 171.6° C.±0.2° C., in particular 171.6° C.±0.1° C., more particularly 171.6° C.); and/or
(j) a DSC thermogram as depicted in FIG. 17 labelled as 1.

In particular, the Form C polymorph of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate provides advantages with respect to stability and crystallinity.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);
$C_{1-7}$aminoalkyl (e.g., aminoethyl; 2-(N,N-diethylamino) ethyl; 2-(4-morpholino)ethyl); and
acyloxy-$C_{1-7}$ alkyl (e.g., acyloxymethyl; acyloxyethyl; pivaloyloxymethyl; acetoxymethyl;
1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl;
1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl) carbonyloxymethyl; and 1-(4-tetrahydropyranyl) carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LI DEPT), etc.). For example, the prodrug may be a sugar derivative or other glycoside conjugate, or may be an amino acid ester derivative. In one embodiment formula (I) does not include pro-drugs of the compounds of the formula (I) within its scope.

Advantages of Compounds of the Invention

The compounds of the formula (I) may have a number of advantages over prior art compounds.

Compounds of the invention may have particular advantage in one or more of the following aspects:
(i) Superior selectivity versus the IKr (hERG) cardiac ion channel;
(ii) Superior metabolic stability;
(iii) Lower P450 inhibitory liability;
(iv) Superior oral bioavailabilty; and/or
(v) Superior in vivo efficacy.

Superior Selectivity Versus the IKr (hERG) Cardiac Ion Channel

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345 (6277):672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family. Science, 269:92-95. Therefore, elimination of hERG blocking activity remains an important consideration in the development of any new drug.

It has been found that many compounds of the formula (I) have reduced hERG activity and/or a good separation between IAP activity and hERG activity (greater 'therapeutic window'). One method for measurement of hERG activity is the patch clamp electrophysiology method. Alternative methods for measurement of functional hERG activity include hERG binding assays, which can use commercially available membranes isolated from cells stably expressing the hERG channel or commercially available cell lines expressing the hERG channel.

Many compounds of the formula (I) have improved Cardiac Safety Index (CSI) [CSI=hERG IC50/Cmax(unbound)] (Shultz et al, J. Med. Chem., 2011; Redfern et al, Cardiovasc. Res., 2003). This can be due to an increase in hERG IC50 or a reduction in Cmax required for efficacy (due to better IAP potency and/or PK).

Particular compounds of formula (I) have reduced hERG ion channel blocking activity. Particular compounds of the formula (I) have mean $IC_{50}$ values against hERG that are greater than 30 times, or greater than 40 times, or greater than 50 times the $IC_{50}$ values of the compounds in cellular proliferation assays. Particular compounds of the formula (I) have mean $IC_{50}$ values against hERG that are greater than 10 µM, more particularly greater than 20 µM, and more preferably greater than 30 µM. Some compounds of the invention have mean $IC_{50}$ values against hERG that are greater than 40 µM or display % inhibition representative of such an $IC_{50}$ at concentrations of 10, 30 or 300 µM. Some compounds of the invention have mean CSI of higher than minimum recommended value (30 fold).

As can be seen from the data in Table 1 herein, the compounds of Examples 1-34 all have a lower hERG liability than the compound Example 259 (also 262 and 263) of WO 2012/143726. In particular the compounds of Examples 1-2, 11 and 34 of the invention demonstrated an $IC_{50}$ of 40 µM against hERG whereas the compound of Example 259 (also 262 and 263) of WO 2012/143726 displays 42% inhibition of hERG at 10 µM. Therefore, superior selectivity versus hERG is a key advantage of compounds of the invention over prior disclosed IAP antagonist compounds, in particular those disclosed in WO 2012/143726.

Superior Metabolic Stability

The compounds of the formula (I) may have advantageous ADMET properties for example better metabolic stability (for example as determined with mouse liver microsomes), a better P450 profile and/or beneficial clearance (e.g. low clearance). These features could confer the advantage of having more drug available in the systemic circulation to reach the appropriate site of action to exert its therapeutic effect. Increased drug concentrations to exert pharmacological action in tumours potentially leads to improved efficacy which thereby allows reduced dosages to be administered. Thus, the compounds of formula (I) should exhibit reduced dosage requirements and should be more readily formulated and administered. In addition the compound may have reduced P450 (e.g. 3A4) turnover.

Lower P450 Inhibitory Liability

Many of the compounds of the formula (I) are advantageous in that they have different susceptibilities to P450 enzymes. For example, the particular compounds of the formula (I) have $IC_{50}$ values of greater than 10 µM against each of the cytochrome P450 enzymes 1A2, 2C9, 2C19, 3A4 and 2D6 (in particular 3A4). In addition particularly the compounds are not P450 inhibitors.

Superior Oral Bioavailabilty

Potentially the compounds of the invention have physiochemical properties suitable for oral exposure (oral exposure or AUC). In particular, compounds of the formula (I) may exhibit improved oral bioavailability. Oral bioavailability can be defined as the ratio (F) of the plasma exposure of a compound when dosed by the oral route to the plasma exposure of the compound when dosed by the intravenous (i.v.) route, expressed as a percentage.

Compounds having an oral bioavailability (F value, F %) of greater than 30%, more particularly greater than 40%, are particularly advantageous in that they may be adminstered orally rather than, or as well as, by parenteral administration.

Superior In Vivo Efficacy

As a result of increased potency against XIAP and/or cIAP compounds of the invention may have increased in vivo efficacy in cancer cell lines and in vivo models.

Methods for the Preparation of Compounds of Formula (I)

In this section, as in all other sections of this application unless the context indicates otherwise, references to formula (I) also include all other sub-groups and examples thereof as defined herein.

Compounds of the formula (I) can be prepared in accordance with synthetic methods well known to the skilled person.

According to a further aspect of the invention there is provided a process for preparing a compound of formula (I) as hereinbefore defined which comprises:
(a) (i) reacting a compound of formula (II):

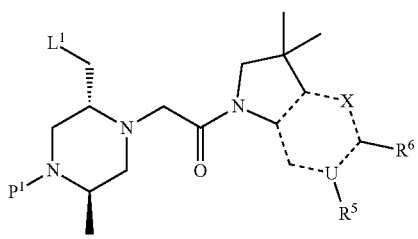

(II)

wherein $R^5$, $R^6$, U and X are as defined hereinbefore for compounds of formula (I), $L^1$ represents a suitable leaving group, such as a halogen atom (e.g. chlorine) and $P^1$ represents hydrogen or a suitable protecting group such as a tert-butyloxycarbonyl (tBoc) group, with a compound of formula (III):

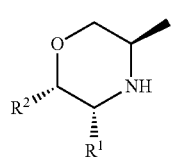

(III)

or an optionally protected derivative thereof; wherein $R^1$ and $R^2$ are as defined hereinbefore for compounds of formula (I), followed by a deprotection reaction suitable to remove the $P^1$ protecting group and any other protecting groups as necessary; or (ii) reacting a compound of formula (IV):

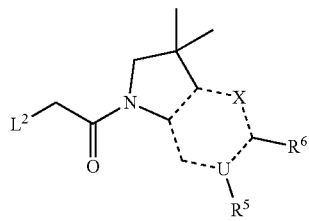

(IV)

wherein $R^5$, $R^6$, X and U are as defined hereinbefore for compounds of formula (I), and $L^2$ represents a suitable leaving group such as halogen (e.g. chlorine), with a compound of formula (V):

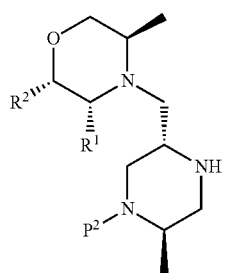

(V)

or an optionally protected derivative thereof; wherein $R^1$ and $R^2$ are as defined hereinbefore for compounds of formula (I) and $P^2$ represents hydrogen or a suitable protecting group such as a tert-butyloxycarbonyl (tBoc) group, followed by a deprotection reaction suitable to remove the $P^2$ protecting group and any other protecting groups as necessary; and/or (b) deprotection of a protected derivative of a compound of formula (I); and/or (c) interconversion of a compound of formula (I) or protected derivative thereof to a further compound of formula (I) or protected derivative thereof; and (d) optional formation of a pharmaceutically acceptable salt of a compound of formula (I).

Process (a)(i) typically comprises reacting a compound of formula (II) with a compound of formula (III), optionally in the presence of a suitable additive such as potassium iodide and a suitable base such as potassium carbonate in a suitable solvent such as acetonitrile. Such a process may be carried out at ambient temperature or at elevated temperature, e.g. 70° C.

Process (a)(ii) typically comprises reacting a compound of formula (IV) with a compound of formula (V), optionally in the presence of a suitable additive such as potassium iodide and a suitable base such as potassium carbonate in a suitable solvent such as acetonitrile.

Process (b) typically comprises any suitable deprotection reaction, the conditions of which will depend upon the nature of the protecting group. When the protecting group represents tBoc, such a deprotection reaction will typically comprise the use of a suitable acid in a suitable solvent. For example, the acid may suitably comprise trifluoroacetic acid or hydrogen chloride and the solvent may suitably comprise dichloromethane ethyl acetate, 1,4-dioxane, methanol or water. Optionally a mixture of solvents may be used, for example aqueous methanol or ethyl acetate/1,4-dioxane.

It will be appreciated that, when the protecting group represents tBoc, deprotection using a suitable acid as described above may generate a compound of formula (I) as a pharmaceutically acceptable salt, which may be isolated directly. Alternatively, the compound of formula (I) may be isolated as the free base using methods well known in the art and thereafter optionally converted to a pharmaceutically acceptable salt according to process (d).

Process (c) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor compound to a compound of formula I and are described in *Advanced Organic Chemistry* by Jerry March, 4th Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

Process (d) may be carried out by treatment of a compound of formula (I) in the free base form, dissolved in a suitable solvent, with a stoichiometric amount or an excess of a pharmaceutically acceptable organic or inorganic acid, then isolation of the resulting salt by methods well known in the art, e.g. evaporation of solvent or crystallisation.

If appropriate, the reactions previously described in processes (a), (b) and (c) are followed or preceded by one or more reactions known to the skilled of the art and are performed in an appropriate order to achieve the requisite substitutions on $R^1$, $R^2$, $R^5$ and $R^6$ defined above to afford other compounds of formula (I). Non-limiting examples of such reactions whose conditions can be found in the literature include:

- protection of reactive functions,
- deprotection of reactive functions,
- halogenation,
- dehalogenation,
- dealkylation,
- alkylation and arylation of amine, aniline, alcohol and phenol,
- Mitsunobu reaction on hydroxyl groups,
- cycloaddition reactions on appropriate groups,
- reduction of nitro, esters, cyano, aldehydes,
- transition metal-catalyzed coupling reactions,
- acylation,
- sulfonylation/introduction of sulfonyl groups,
- saponification/hydrolysis of ester groups,
- amidification or transesterification of ester groups,
- esterification or amidification of carboxylic groups,
- halogen exchange,
- nucleophilic substitution with amine, thiol or alcohol,
- reductive amination,
- oxime formation on carbonyl and hydroxylamine groups,
- S-oxidation,
- N-oxidation,
- salification.

Compounds of formula (II) may be prepared from compounds of formula (IV) in accordance with the following Scheme 1:

Scheme 1

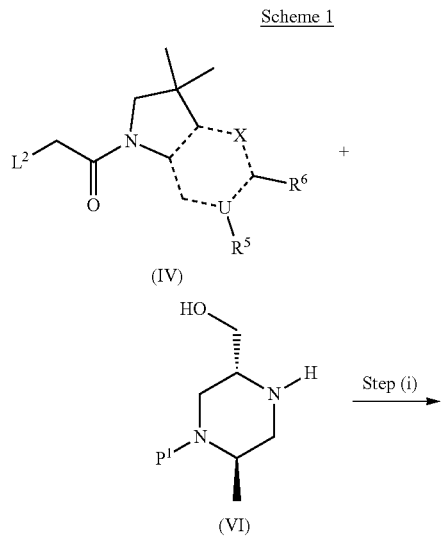

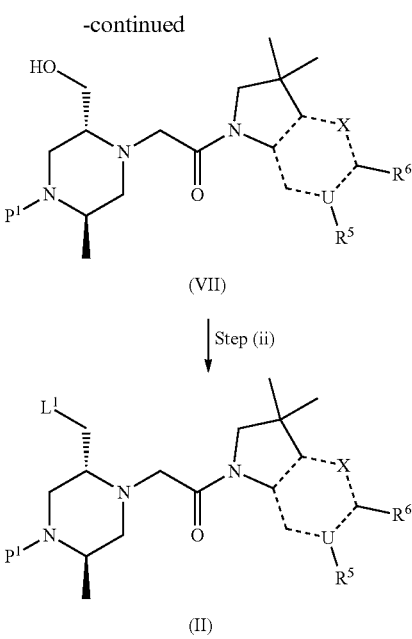

wherein X, U, $R^5$, $R^6$, $L^1$, $L^2$ and $P^1$ are as defined hereinbefore.

Step (i) of Scheme 1 typically comprises reacting the compounds of formulae (IV) and (VI), optionally in the presence of a suitable additive such as potassium iodide and a suitable base such as potassium carbonate in a suitable solvent such as acetonitrile.

When $L^1$ represents chlorine, step (ii) of Scheme 1 typically comprises reacting the compound of formula (VII) with a reagent capable of converting a hydroxyl group into a good leaving group, e.g. methylsulfonyl chloride, in the presence of a base such as triethylamine.

Compounds of formula (IV) where X represents N, U represents carbon and $R^6$ represents hydroxymethyl may be prepared in accordance with the following Scheme 2:

Scheme 2

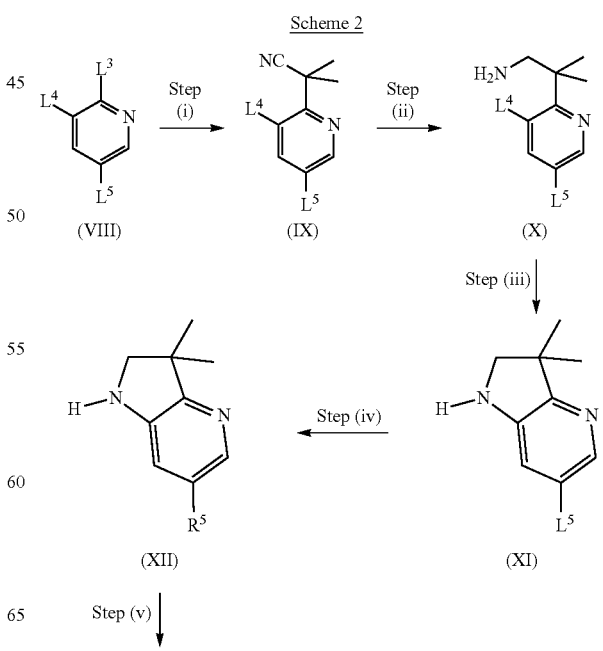

-continued

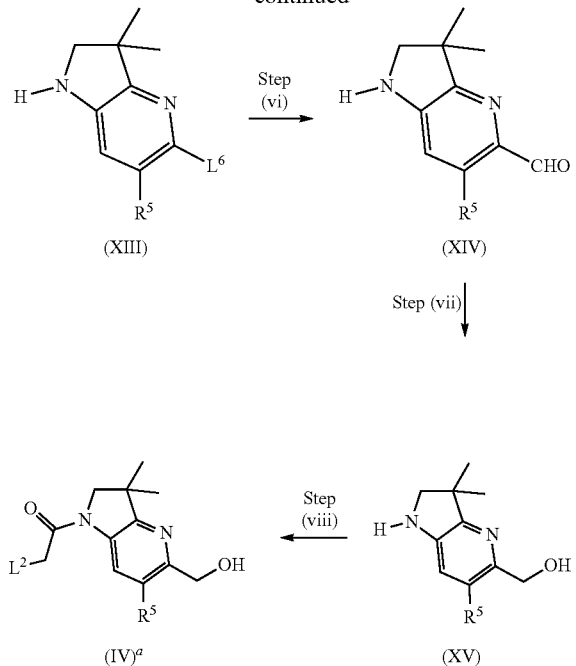

wherein $L^3$, $L^4$, $L^5$ and $L^6$ represent suitable leaving groups, such as a halogen atom (i.e. fluorine, bromine or chlorine) and $R^5$ and $L^2$ are as defined hereinbefore.

When $L^3$ and $L^4$ both represent fluorine, step (i) of Scheme 2 typically comprises reacting a compound of formula (VIII) with a base such as sodium bis(trimethylsilyl) amide in the presence of tetrahydrofuran and isobutronitrile in a suitable solvent such as toluene. An example of such a reaction is shown in Preparation 11.

Step (ii) of Scheme 2 involves reaction with a suitable reducing agent and typically comprises reacting the compound of formula (IX) with a borane-tetrahydrofuran complex in the presence of a suitable solvent such as tetrahydrofuran. An example of such a reaction is shown herein in Preparation 12. Step (ii) of Scheme 2 may also typically comprise reacting the compound of formula (IX) with nickel(II) chloride hexahydrate followed by addition of sodium borohydride. An example of such a reaction is shown in Preparation 12, alternative procedure.

Step (iii) of Scheme 2 typically comprises cyclisation of the compound of formula (X) using a suitable base e.g. potassium carbonate and an appropriate solvent such as NMP. An example of such a reaction is shown herein in Preparation 13.

Step (iv) of Scheme 2 typically comprises reacting the compound of formula (XI) with a compound of formula $R^5$-M, wherein $R^5$ is as defined hereinbefore and M represents the residue of an organometallic species such that $R^5$-M represents a nucleophilic organometallic reagent such as an organozinc halide. Step (iv) typically also comprises the use of lithium bromide, a catalyst, such as [1,3-bis(2,6-diisopropylphenyl)imidazol-2-ylidene](3-chloropyridyl)palladium(II) dichloride, in a suitable solvent system e.g. tetrahydrofuran and NMP. An example of such a reaction is shown herein in Preparation 15.

Step (v) of Scheme 2 typically comprises halogenation of the compound of formula (XII) for example using N-bromosuccinimide in dimethylformamide. An example of such a reaction is shown herein in Preparation 16.

Step (vi) of Scheme 2 involves lithiation and reaction with a suitable electrophile for introduction of the formyl group, and typically comprises reacting the compound of formula (XIII) with MeLi in THF followed by addition of tBuLi in hexane followed by addition of dimethylformamide. An example of such a reaction is shown herein in Preparation 17.

Step (vii) of Scheme 2 involves reduction of the formyl group with a suitable reducing agent and typically comprises reacting the compound of formula (XIV) with sodium borohydride in methanol. An example of such a reaction is shown herein in Preparation 17.

When $L^2$ represents a halogen such as chlorine, step (viii) of Scheme 2 typically comprises reacting the compound of formula (XV) with a haloacetyl halide such as chloroacetyl chloride in MeCN followed by addition of potassium carbonate in methanol. An example of such a reaction is shown herein in Preparation 18. Alternatively, compounds of formula (XIII) may be converted to compounds of formula (XV) by following a sequence analogous to that described in Preparations 25-29 inclusive.

It will be appreciated that compounds of formula (XV) where $R^6$ represents $CH(OR^x)CH_2OR^z$ may be prepared in an analogous manner to Scheme 2 above by varying steps (v) onwards of Scheme 2. Examples of suitable reaction sequences are shown herein in Preparations 38-42.

Compounds where X represents $NR^3$, U represents carbon and $R^6$ is =O can be synthesised using functional group interconversions on appropriate intermediates of Scheme 2 or protected derivatives thereof, for example as demonstrated in Preparations 22-24, 30-35 and 50.

It will also be appreciated that compounds of formula (IV) where $R^5$ represents unsubstituted n-butyl or alternatively substituted benzyl groups may be prepared in an analogous manner to Scheme 2 above by varying the organometallic reagent used in step (iv) of Scheme 2. An example of such a reaction is shown in Preparations 15 A, 15B and 15C.

Compounds where X represents $CR^4$, U represents nitrogen and $R^6$ represents oxo can be synthesised using analogous sequences to those described in preparations 43-49 and 51-58.

Compounds of formula (V), or optionally protected derivatives thereof, may be prepared in accordance with the following Scheme 3:

Scheme 3

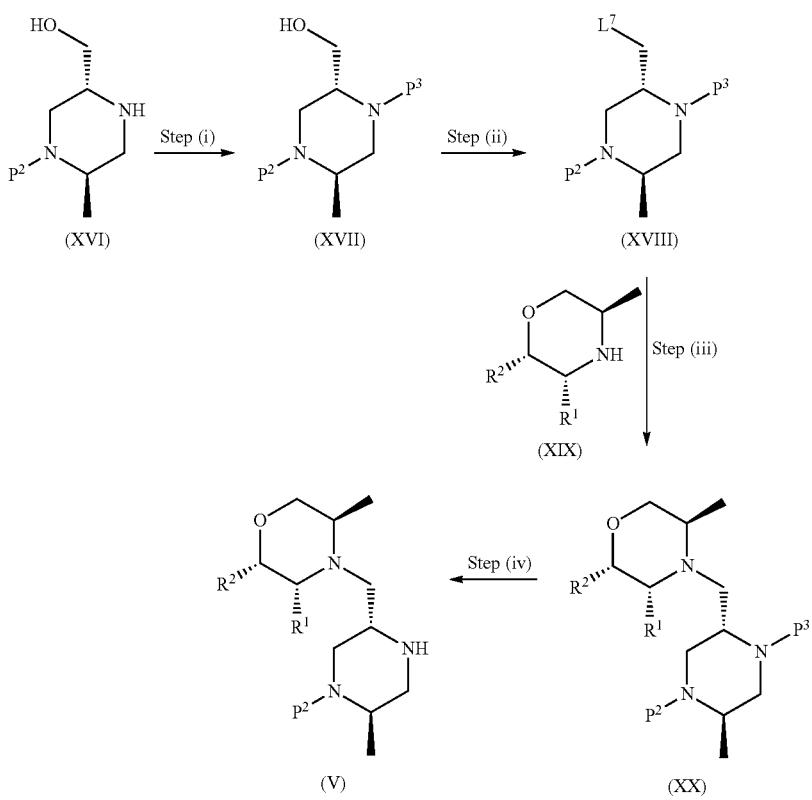

wherein $R^1$, $R^2$ and $P^2$ are as defined hereinbefore for compounds of formula (V), $L^7$ represents a suitable leaving group such as a halogen atom (e.g. chlorine) and $P^3$ represents a suitable protecting group, such as benzyl.

When $P^3$ represents benzyl, step (i) of Scheme 3 typically comprises reacting a compound of formula (XVI) with benzaldehyde in the presence of a suitable reducing agent such as sodium triacetoxyborohydride and 1,2-dichloroethane. An example of such a reaction is shown herein in Preparation 5.

When $L^7$ represents chlorine, step (ii) of Scheme 3 typically comprises reacting a compound of formula (XVII) with methanesulfonyl chloride in the presence of triethylamine and dichloromethane. An example of such a reaction is shown herein in Preparation 6.

Step (iii) of Scheme 3 typically comprises reacting the compounds of formulae (XVIII) and (XIX) in the presence of a base such as potassium carbonate, an additive such as potassium iodide in a suitable solvent such as acetonitrile. An example of such a reaction is shown herein in Preparation 7.

Step (iv) of Scheme 3 typically comprises a deprotection reaction. For example, when $P^3$ represents benzyl, step (iv) typically comprises hydrogenation of the compound of formula (XX) in the presence of a suitable catalyst such as palladium on carbon in a suitable solvent system such as ethanol or a mixture of acetic acid and ethanol. An example of such a reaction is shown herein in Preparation 8.

Alternatively compounds of formula (I) can be synthesised by reacting a compound of formula (XXI):

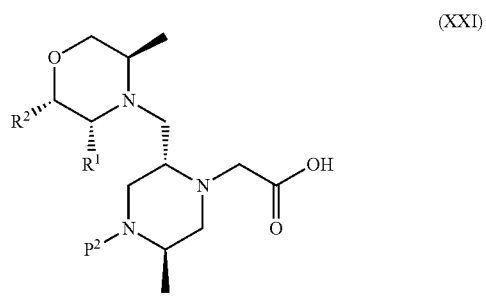

(XXI)

or an optionally protected derivative thereof, wherein $R^1$ and $R^2$ are as defined hereinbefore for compounds of formula (I) and $P^2$ represents a suitable protecting group such as a tert-butyloxycarbonyl (tBoc) group, with a compound of formula (XXII):

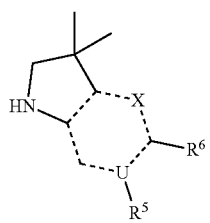

(XXII)

wherein X, U, R$^5$ and R$^6$ are as defined hereinbefore followed by a deprotection reaction suitable to remove the protecting group P$^2$ and any additional protecting groups.

One example of a suitable compound of formula (XXII) includes a compound of formula (XV) as defined hereinbefore.

This reaction typically comprises reacting a compound of formula (XXI) with a compound of formula (XXII), such as a compound of formula (XV), in a suitable solvent and at a suitable temperature e.g. ambient temperature, in the presence of a suitable base and a reagent capable of activating the carboxylic acid group present in the compound of formula (XXI). A suitable solvent should be inert toward the reagents used, for example dichloromethane. Examples of suitable bases are triethylamine and N,N-diisopropylethylamine (DIPEA). Examples of suitable activating reagents are bromo-tris-pyrrolidino-phosphonium hexofluorophosphate (PyBrop), O-benzotriazole-N,N,N',N'-tetramethyluronium-hexafluoro-phosphate (HBTU), 1,1'-carbonyldiimidazole, 1-ethyl-3-(3'-dimethylaminopropyl)-carbodiimide hydrochloride (EDC) and 2-(7-aza-1H-benzotriazol-1-yl)-1,1,3,3-tetramethyluronium hexafluorophosphate) (HATU). This process may optionally be carried out in the presence of a catalytic or stoichiometric amount of a suitable co-activating reagent such as 1-hydroxybenzotriazole (HOBt) or 1-hydroxyazabenzotriazole (HOAt).

Compounds of formula (XXI) or optionally protected derivatives thereof may be prepared from compounds of formula (V) or optionally protected derivatives thereof as defined above by methods well known in the art, for example by reaction with an ester of a monohaloacetic acid such as benzyl bromoacetate in the presence of a suitable base such as potassium carbonate in a suitable solvent such as acetonitrile; and subsequent ester hydrolysis (or optionally hydrogenolysis in the case of a benzyl ester). Compounds of formula (I) may be prepared following an analogous sequence to that described in Preparations 1-5.

Compounds of formula (XXII) may be prepared by using analogous sequences to those described in Scheme 2 or the following preparations: 38-42; 22-24, 30-35 and 50; or 43-49 and 51-58.

It will be appreciated that certain compounds e.g. compounds of formulae (I), (II), (III), (V), (VI), (VII), (XVI), (XVII), (XVIII), (XIX), (XX), (XXI) and (XXII) can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid; or enantiomer separation of a diastereomeric derivative formed by covalently linking a enantiomerically pure chiral auxiliary onto the compound, followed by separation using conventional methods such as chiral chromatography. The aforementioned covalent linkage is then cleaved to generate the appropriate enantiomerically pure product.

The required intermediates, for example compounds of formula (III), (VI), (VIII), R$^5$-M, (XVI) and (XIX) are either commercially available, known in the literature, prepared by methods analogous to those in the literature or prepared by methods analogous to those described in the example experimental procedures below. Other compounds may be prepared by functional group interconversion of the groups R$^1$, R$^2$, R$^5$ and R$^6$ using methods well known in the art.

In a further embodiment the invention provides a novel intermediate. In one embodiment the invention provides a novel intermediate of formula (II) or (IV) or (V) or (VII) or (XX). In an alternative embodiment the invention provides a novel intermediate of formula (XXI) or (XXII).

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

In particular the groups R$^1$ and R$^2$ may be synthesised in protected forms and the protecting groups removed to generate a compound of formula (I).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$Cl$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Bpoc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl) ethyl carbamate (—NH-Psec).

For example, in compounds of formula II contains an amino group, the amino group can be protected by means of a protecting group as hereinbefore defined, one particular group being the tert-butyloxycarbonyl (Boc) group while the additional funactionalisation is introduced.

Where no subsequent modification of the amino group is required, the protecting group can be carried through the reaction sequence to give an N-protected form of a compound of the formula (I) which can then be de-protected by standard methods (e.g. treatment with acid in the case of the Boc group) to give the compound of formula (I).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9. An example of such a system for purifying compounds via preparative LC-MS is described below in the Examples section of this application (under the heading "Mass Directed Purification LC-MS System").

Methods of recrystallisation of compounds of formula (I) and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes an heating step under vacuum for example using a cold finger, and crystallization from melt (Crystallization Technology Handbook 2nd Edition, edited by A. Mersmann, 2001).

Biological Effects

The compounds of the invention, subgroups and examples thereof, are antagonists of inhibitor of apoptosis protein (IAP), and which may be useful in preventing or treating disease states or conditions described herein. In addition the compounds of the invention, and subgroups thereof, will be useful in preventing or treating diseases or condition mediated by IAP. References to the preventing or prophylaxis or treatment of a disease state or condition such as cancer include within their scope alleviating or reducing the incidence of cancer.

Thus, for example, it is envisaged that the compounds of the invention will be useful in alleviating or reducing the incidence of cancer.

The compounds of the present invention may be useful for the treatment of the adult population.

The compounds of the present invention may be useful for the treatment of the pediatric population.

More particularly, the compounds of the formula (I) and sub-groups thereof are antagonists of IAP. For example, compounds of the invention have affinity against XIAP, cIAP1 and/or cIAP2, and in particular an IAP selected from XIAP and cIAP1.

Particular compounds are compounds that have affinity for one or more IAP selected from XIAP, cIAP1 and cIAP2. Particular compounds of the invention are those having $IC_{50}$ values of less than 0.1 µM.

The antagonist compounds of formula (I) are capable of binding to IAP and exhibiting potency for IAP. In one embodiment the antagonist compounds of formula (I) exhibit selectivity for one or more IAP over other IAP family members, and may be capable of binding to and/or exhibiting affinity for XIAP and/or cIAP in preference to binding to and/or exhibiting affinity for other of the IAP family members.

In addition many of the compounds of the invention exhibit selectivity for the XIAP compared to cIAP or vice versa, selectivity for the cIAP compared to XIAP (in particular cIAP1), and such compounds represent one embodiment of the invention. In particular compounds of the invention may have at least 10 times greater affinity against one or more IAP family member in particular XIAP, cIAP1 and/or cIAP2 than other IAP family members. This can be determined using the methods described herein. In a further embodiment compounds of the invention may have equivalent affinity for XIAP, cIAP1 and/or cIAP2, in particular equivalent affinity (i.e. less than 10-fold difference in affinity) for XIAP and cIAP1.

Activity against XIAP and cIAP1 may be particularly advantageous. Antagonising XIAP and cIAP1 with equipotency should enable triggering of apoptosis via activation of caspase-8 and the switch away from pro-survival NF-κB signalling towards apoptosis; and potent antagonism of XIAP will ensure that apoptosis is achieved before any inherent resistance mechanism is upregulated to block the process. On depletion of cIAP1 via autoubiquitination and proteasomal degradation there is a temporary upregulation of NF-κB signalling that is responsible for expression of TNF-alpha in sensitive cell lines—this is also responsible for upregulation of anti-apoptotic factors such as cIAP2 and c-FLIP. Hence the need for potent XIAP antagonism to potentiate effector caspase activation and cell death, rather than allowing cIAP2-mediated resistance to build up. It is generally believed that toxicities that arise on dosing these compounds in vivo will arise from the temporary induction of NF-κB signalling and resultant upregulation of pro-inflammatory cytokines, which is mediated solely by cIAP1/2 antagonism. Therefore dual potency should enable a therapeutic window to be achieved before dose-limiting toxicities are encountered.

IAP function in controlling programmed cell death has also been implicated in many diseases, including disorders associated with cell accumulation (e.g. cancer, autoimmune disorders, inflammation and restenosis), disorders where excessive apoptosis results in cell loss (e.g. stroke, heart failure, neurodegeneration such as Alzheimers' disease, Parkinson's disease, Huntington's disease, amyotrophic lateral sclerosis, AIDS, ischemia (stroke, myocardial infarction) and osteoporosis or treating autoimmune diseases such as multiple sclerosis (MS).

Therefore, it is also envisaged that the compounds of the invention may be useful in treating other conditions such as inflammation (for example arthritis including rheumatoid arthrirts), hepatitis, ulcerative colitis, gastritis, autoimmunity, restenosis, stroke, heart failure, neurodegenerative conditions such as Alzheimers' disease, Parkinson's disease, Huntington's disease, myotonic dystrophy, and amyotrophic lateral sclerosis, AIDS, ischemia such as traumatic brain injury, spinal cord injury, cerebral ischemia, cerebral ischemia/reperfusion (I/R) injury, acute and chronic CNS injury ischemia, stroke or myocardial infarction, degenerative diseases of the musculoskeletal system such as osteoporosis, autoimmune diseases such as multiple sclerosis (MS) and Type I diabetes, and eye diseases such as retinal degeneration which result from loss of control of programmed cell death. In one embodiment the compounds of the invention may be useful in treating viral infections such as herpes virus, pox virus, Epstein-Barr virus, Sindbis virus, adenovirus, HIV, HPV, hepititis for example hepatitis B (HBV) or hepatitis C (HCV) and HCMV or in mycobacterial infections such as tuberculosis (TB).

As a consequence of their affinity for IAP, the compounds will be useful in providing a means of controlling programmed cell death. It is therefore anticipated that the compounds may prove useful in treating or preventing proliferative disorders such as cancers. In addition, the compounds of the invention may be useful in the treatment of diseases in which there is a disorder associated with cell accumulation or where excessive apoptosis results in cell loss.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and pre-malignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AMU], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer. Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

In one embodiment the haematological malignancies is leukaemia. In another embodiment the haematological malignancies is lymphoma.

In one embodiment the disease to be treated is leukaemia, such as acute and chronic leukaemias, acute myeloid leukaemia (AML), and chronic lymphocytic leukaemia (CLL). In one embodiment the leukaemia is refractory DLBCL.

In one embodiment the lymphoma is MALT lymphoma. In one embodiment the leukemia is AML.

In one embodiment the haematological malignancy is multiple myeloma.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis. In particular, the compounds of the invention may be useful in the treatment of metastasis and metastatic cancers.

Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body.

Particular cancers include hepatocellular carcinoma, melanoma, oesophageal, renal, colon, colorectal, lung e.g. mesothelioma or lung adenocarcinoma, breast, bladder, gastrointestinal, ovarian and prostate cancers.

Particular cancers include renal, melanoma, colon, lung, breast, ovarian and prostate cancers.

In one embodiment the cancer is selected from melanoma, colon, breast and ovarian. In one embodiment the cancer is melanoma. In one embodiment the cancer is inflammatory breast cancer.

In one embodiment the cancer is lung cancer, for example mesothelioma including malignant peritoneal mesothelioma or malignant pleural mesothelioma.

In one embodiment the cancer is breast cancer, in particular triple negative (triple -ve) breast cancer.

In one embodiment the cancer is colorectal cancer.

A further aspect of the invention includes a compound of the invention for use in the prophylaxis or treatment of cancer in a patient selected from a sub-population possessing cancers with a high inflammatory component. Such cancers are also known as "inflammatory phenotype" and include tumours with elevated cytokine signalling (e.g. TNF). In one embodiment the cancer is an inflammatory tumour, for example, melanoma, colon, breast and ovarian, in particular, melanoma.

In one embodiment the melanoma is ras mutant melanoma.

Certain cancers are resistant to treatment with particular drugs. This can be due to the type of the tumour (most common epithelial malignancies are inherently chemoresistant) or resistance can arise spontaneously as the disease progresses or as a result of treatment. In this regard, references to mesothelioma includes mesothelioma with resistance towards topoisomerase poisons, alkylating agents, antitubulines, antifolates, platinum compounds and radiation therapy, in particular cisplatin-resistant mesothelioma. Similarly references to multiple myeloma includes bortezomib-sensitive multiple myeloma or refractory multiple myeloma and references to chronic myelogenous leukemia includes imitanib-sensitive chronic myelogenous leukemia and refractory chronic myelogenous leukemia.

The cancers may be cancers which are sensitive to antagonism of any one or more IAP selected from XIAP, cIAP1, cIAP2, NAIP, ILP2, ML-IAP, survivin and BRUCE, more particularly XIAP, cIAP1, cIAP2, ML-IAP, most particularly XIAP.

It is further envisaged that the compounds of the invention, and in particular those compounds having IAP affinity will be particularly useful in the treatment or prevention of cancers of a type associated with or characterised by the presence of elevated levels of IAP or amplification of 11q22 for example the cancers referred to in this context in the introductory section of this application.

Elevated levels of IAP due to overexpression of IAP is found in many cancers and is associated with a poor prognosis. In addition, cancers with the 11q22 amplification may also be sensitive to an IAP antagonist. The elevated levels of IAP and amplification of 11q22 can be identified by the techniques outlined herein. Whether a particular cancer is one which is sensitive to IAP function, may be determined by a method as set out in the section headed "Methods of Diagnosis".

A further aspect provides the use of a compound for the manufacture of a medicament for the treatment of a disease or condition as described herein, in particular cancer.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. In mitigating the deleterious effects of such stresses, IAPs are directly implicated in resisting the effects of cancer drugs and treatment regimens. Thus, antagonists of IAP represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

As a consequence of their affinity for IAP, the compounds will be useful in providing a means of controlling programmed cell death. Therefore, it is also envisaged that the compounds of the invention may be useful in treating other conditions such as inflammatory disorders such as hepatitis, ulcerative colitis, and gastritis; neurodegenerative conditions such as Alzheimers' disease, Parkinson's disease, Huntington's disease, myotonic dystrophy, and amyotrophic lateral sclerosis; AIDS, ischemia such as restenosis, traumatic brain injury, spinal cord injury, cerebral ischemia, cerebral ischemia/reperfusion (I/R) injury, acute and chronic CNS injury ischemia, stroke or myocardial infarction; degenerative diseases of the musculoskeletal system such as osteoporosis; autoimmune diseases such as multiple sclerosis (MS) and Type I diabetes, and eye diseases such as retinal degeneration.

The affinity of the compounds of the invention as antagonists of IAP can be measured using the biological and biophysical assays set forth in the examples herein and the level of affinity exhibited by a given compound can be defined in terms of the $IC_{50}$ value. Particular compounds of the present invention are compounds having an $IC_{50}$ value of less than 1 µM, more particularly less than 0.1 µM.

In one embodiment the invention provides a compound for use in the treatment of a disease or condition which is mediated by IAP (e.g. XIAP and/or cIAP e.g. cIAP1). In a further embodiment the invention provides a compound for use in the treatment of a disease or condition which over-expresses IAP (e.g. XIAP and/or cIAP e.g. cIAP1).

In one embodiment the invention provides a compound for use in the treatment of a disease or condition which is mediated by IAP, wherein the compound is an antagonist of IAP having an $IC_{50}$ of less than 50 µM in at least one assay (e.g. a displacement binding) against an IAP. In particular the IAP is XIAP, cIAP1 and/or cIAP2. In a further embodiment the disease or condition which is mediated by IAP is a cancer which is characterised by overexpression of at least one IAP and/or amplification of 11q22.

In one embodiment the invention provides a compound for use in the treatment of a disease or condition which is mediated by IAP, wherein the compound has an $IC_{50}$ of less than 10 µM against at least one IAP in an assay (e.g. displacement binding) against IAP.

A further aspect provides the use of a compound for the manufacture of a medicament for the treatment of a disease or condition which is mediated by IAP, wherein the compound is an antagonist of IAP having an $IC_{50}$ of less than 50 µM against at least one IAP in an assay (e.g. a displacement binding).

Methods of Diagnosis

Prior to administration of a compound of the formula (I), a patient may be screened to determine whether a disease or condition from which the patient is or may be suffering is one which would be susceptible to treatment with a compound having affinity for IAP. The term 'patient' includes human and veterinary subjects.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of IAP or to sensitisation of a pathway to normal IAP function or to upregulation of a biochemical pathway downstream of IAP activation.

Examples of such abnormalities that result in activation or sensitisation of the IAP, loss of, or inhibition of apoptotic pathways, up-regulation of the receptors or ligands, cytogenetic aberrations or presence of mutant variants of the receptors or ligands. Tumours with up-regulation of IAP, in particular over-expression of IAP, may be particularly sensitive to IAP antagonists. For example, overexpression of XIAP and cIAP has been identified in a range of cancers as discussion in the Background section.

Amplification of chromosome 11q22 has been detected in cell lines and primary tumours from squamous cell carcinomas of the esophagus (Imoto et al., 2001) and cervix (Imoto et al., 2002) as well as in primary lung cancers/cell lines (Dai et al., 2003). Immunohistochemistry and western blot analysis have identified cIAP1 and cIAP2 as potential oncogenes in this region as both are overexpressed in cancers in which this rare amplification arises.

The term up-regulation includes elevated expression or over-expression, including gene amplification (i.e. multiple gene copies), cytogenetic aberration and increased expression by a transcriptional effect. Thus, the patient may be subjected to a diagnostic test to detect a marker characteristic of up-regulation of IAP. The term diagnosis includes screening. By marker we include genetic markers including, for example, the measurement of DNA composition to identify presence of mutations of IAP or 11q22 amplification. The term marker also includes markers which are characteristic of up regulation of IAP, including protein levels, protein state and mRNA levels of the aforementioned proteins.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal spears, skin biopsy or urine.

Methods of identification and analysis of cytogenetic aberration, genetic amplification, mutations and up-regulation of proteins are known to a person skilled in the art. Screening methods could include, but are not limited to, standard methods such as reverse-transcriptase polymerase chain reaction (RT-PCR) or in situ hybridization such as fluorescence in situ hybridization (FISH).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3rd Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in situ hybridisation technique for assessing mRNA expression would be fluorescence in situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Particular probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA using a (dT) 24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, CA, USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of IAP, detection of IAP variants or mutants, or detection of 11q22 amplification could be applicable in the present case.

Abnormal levels of proteins such as IAP can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured.

Alternative methods for the measurement of the over expression or elevation of IAPs including the isoforms thereof, include the measurement of microvessel density. This can for example be measured using methods described by Orre and Rogers (Int J Cancer (1999), 84(2), 101-8). Assay methods also include the use of markers.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having affinity for IAP (i.e. an IAP antagonist).

A further embodiment provides a method of treating a patient having, or at risk of having a disease or condition described herein (e.g. cancer) comprising administering an effective amount of a compound of formula (I).

Another aspect of the invention includes a compound of the invention for use in the prophylaxis or treatment of cancer in a patient selected from a sub-population possessing overexpression of one or more of the IAP family members (e.g. cIAP and/or XIAP).

Another aspect of the invention includes a compound of the invention for use in the prophylaxis or treatment of cancer in a patient selected as possessing a cytogenetic abherration that results in overexpression of IAPs, for example, a patient selected as possessing the 11q22 amplification.

MRI determination of vessel normalization (e.g. using MRI gradient echo, spin echo, and contrast enhancement to measure blood volume, relative vessel size, and vascular permeability) in combination with circulating biomarkers may also be used to identify for treatment with a compound of the invention.

Thus a further aspect of the invention is a method for the diagnosis and treatment of a disease state or condition mediated by a IAP, which method comprises (i) screening a patient to determine whether a disease or condition from which the patient is or may be suffering is one which would be susceptible to treatment with a compound having affinity for IAP; and (ii) where it is indicated that the disease or condition from which the patient is thus susceptible, thereafter administering to the patient a compound of formula (I) and sub-groups or examples thereof as defined herein.

Pharmaceutical Formulations

While it is possible for the active compound to be administered alone, it is preferable to present it as a pharmaceutical composition (e.g. formulation). In one embodiment this is a sterile pharmaceutical composition.

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one particular embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another particular embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch.

Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13th March 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Particularly, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, particularly from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by IAP. Thus, according to a further aspect of the invention there is provided a method of treating a disease state or condition mediated by IAP, such as an XIAP and/or cIAP (e.g. cancer) which comprises administering to a subject in need thereof a compound of formula (I) as described herein. According to a further aspect of the invention there is provided a method of treating a disease state or condition (e.g. cancer) which overexpresses IAP, such as an XIAP and/or cIAP which comprises administering to a subject in need thereof a compound of formula (I) as described herein. Examples of such disease states and conditions are set out above, and in particular include cancer.

The compounds are generally administered to a subject in need of such administration, for example a human or animal patient, particularly a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

In another particular dosing schedule, a patient is given the compound orally once a week.

In another particular dosing schedule, a patient is given the compound orally once-daily for between 7 and 28 days such as 7, 14 or 28 days.

In another particular dosing schedule, a patient is given the compound orally once-daily for 1 day, 2 days, 3 days, 5 days or 1 week followed by the required amount of days off to complete a one or two week cycle.

In another particular dosing schedule, a patient is given the compound orally once-daily for 2 weeks followed by 2 weeks off.

In another particular dosing schedule, a patient is given the compound orally once-daily for 2 weeks followed by 1 week off.

In another particular dosing schedule, a patient is given the compound orally once-daily for 1 week followed by 1 week off.

Ultimately, however, the quantity of compound administered and the type of composition used will be commensurate with the nature of the disease or physiological condition being treated and will be at the discretion of the physician.

It has been discovered that IAP antagonists can be used as a single agent or in combination with other anticancer agents. For example, it may be beneficial to combine an antagonist that induces apoptosis with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (I) include but are not limited to:

Topoisomerase I inhibitors;
Antimetabolites;
Tubulin targeting agents;
DNA binder and topoisomerase II inhibitors;
Alkylating Agents;
Monoclonal Antibodies;
Anti-Hormones;
Signal Transduction Inhibitors;
Proteasome Inhibitors;
DNA methyl transferase inhibitors;
Cytokines and retinoids;

Chromatin targeted therapies;
Radiotherapy; and
Other therapeutic or prophylactic agents.

Particular examples of anti-cancer agents or adjuvants (or salts thereof), include but are not limited to any of the agents selected from groups (i)-(xlvi), and optionally group (xlvii), below:

(i) Platinum compounds, for example cisplatin (optionally combined with amifostine), carboplatin or oxaliplatin;

(ii) Taxane compounds, for example paclitaxel, paclitaxel protein bound particles (Abraxane™), docetaxel, cabazitaxel or larotaxel;

(iii) Topoisomerase I inhibitors, for example camptothecin compounds, for example camptothecin, irinotecan (CPT11), SN-38, or topotecan;

(iv) Topoisomerase II inhibitors, for example anti-tumour epipodophyllotoxins or podophyllotoxin derivatives for example etoposide, or teniposide;

(v) Vinca alkaloids, for example vinblastine, vincristine, liposomal vincristine (Onco-TCS), vinorelbine, vindesine, vinflunine or vinvesir;

(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;

(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);

(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine or decitabine, or SGI-110;

(xii) Antifolates, for example methotrexate, pemetrexed disodium, or raltitrexed;

(xiii) Cytotoxic antibiotics, for example antinomycin D, bleomycin, mitomycin C, dactinomycin, carminomycin, daunomycin, levamisole, plicamycin, or mithramycin;

(xiv) Tubulin-binding agents, for example combrestatin, colchicines or nocodazole;

(xv) Signal Transduction inhibitors such as Kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032/RG7204), dabrafenib, encorafenib or an IκB kinase inhibitor such as SAR-113945, bardoxolone, BMS-066, BMS-345541, IMD-0354, IMD-2560, or IMD-1041, or MEK inhibitors such as Selumetinib (AZD6244) and Trametinib (GSK121120212);

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;

(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, PD332991, ZK-304709, or AZD-5438;

(xviii) PKA/B inhibitors and PKB (akt) pathway inhibitors for example AKT inhibitors such as KRx-0401 (perifosine/NSC 639966), ipatasertib (GDC-0068; RG-7440), afuresertib (GSK-2110183; 2110183), MK-2206, MK-8156, AT13148, AZD-5363, triciribine phosphate (VQD-002; triciribine phosphate monohydrate (API-2; TCN-P; TCN-PM; VD-0002), RX-0201, NL-71-101, SR-13668, PX-316, AT13148, AZ-5363, Semaphore, SF1126, or Enzastaurin HCl (LY317615) or MTOR inhibitors such as rapamycin analogues such as RAD 001 (everolimus), CCI 779 (temsirolemus), AP23573 and ridaforolimus, sirolimus (originally known as rapamycin), AP23841 and AP23573, calmodulin inhibitors e.g. CBP-501 (forkhead translocation inhibitors), enzastaurin HCl (LY317615) or PI3K Inhibitors such as dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, or sonolisib (PX-866);

(xix) Hsp90 inhibitors for example AT13387, herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BUB-021 an oral purine), ganetespib (STA-9090), SNX-5422 (SC-102112) or IPI-504;

(xx) Monoclonal Antibodies (unconjugated or conjugated to radioisotopes, toxins or other agents), antibody derivatives and related agents, such as anti-CD, anti-VEGFR, anti-HER2, anti-CTLA4, anti-PD-1 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), siltuximab (IL6), or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (anti-PD-1), BMS-936559 (anti-PD-L1), MPDL320A, AMP-514 or MED14736 (anti-PD-L1), or tremelimumab (formerly ticilimumab, CP-675,206, anti-CTLA-4);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17, 20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAM BA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example panobinostat, resminostat, abexinostat, vorinostat, romidepsin, belinostat, entinostat, quisinostat, pracinostat, tefinostat, mocetinostat, givinostat, CUDC-907, CUDC-101, ACY-1215, MGCD-290, EVP-0334, RG-2833, 4SC-202, romidepsin, AR-42 (Ohio State University), CG-200745, valproic acid, CKD-581, sodium butyrate, suberoylanilide hydroxamide acid (SAHA), depsipeptide (FR 901228), dacinostat (NVP-LAQ824), R306465/JNJ-16241199, JNJ-26481585, trichostatin A, chlamydocin, A-173, JNJ-MGCD-0103, PXD-101, or apicidin;

(xxxii) Proteasome Inhibitors for example bortezomib, carfilzomib, delanzomib (CEP-18770), ixazomib (MLN-9708), oprozomib (ONX-0912) or marizomib;

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ONO-2231;

(xlvi) Agonists of Death receptor (e.g. TNF-related apoptosis inducing ligand (TRAIL) receptor), such as mapatumumab (formerly HGS-ETR1), conatumumab (formerly AMG 655), PRO95780, lexatumumab, dulanermin, CS-1008, apomab or recombinant TRAIL ligands such as recombinant Human TRAIL/Apo2 Ligand;

(xlvii) Prophylactic agents (adjuncts); i.e. agents that reduce or alleviate some of the side effects associated with chemotherapy agents, for example anti-emetic agents, agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim), agents that inhibit bone resorption such as denosumab or bisphosphonates e.g. zoledronate, zoledronic acid, pamidronate and ibandronate, agents that suppress inflammatory responses such as dexamethasone, prednisone, and prednisolone, agents used to reduce blood levels of growth hormone and IGF-I (and other hormones) in patients with acromegaly or other rare hormone-producing tumours, such as synthetic forms of the hormone somatostatin e.g. octreotide acetate, antidote to drugs that decrease levels of folic acid such as leucovorin, or folinic acid, agents for pain e.g. opiates such as morphine, diamorphine and fentanyl, non-steroidal anti-inflammatory drugs (NSAID) such as COX-2 inhibitors for example celecoxib, etoricoxib and lumiracoxib, agents for mucositis e.g. palifermin, agents for the treatment of side-effects including anorexia, cachexia, oedema or thromoembolic episodes, such as megestrol acetate.

In one embodiment the anticancer is selected from recombinant interferons (such as interferon-γ and interferon α) and interleukins (e.g. interleukin 2), for example aldesleukin, denileukin diftitox, interferon alfa 2a, interferon alfa 2b, or peginterferon alfa 2b; interferon-α2 (500 μ/ml) in particular interferon-β; and signal transduction inhibitors such as kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032/RG7204), dabrafenib, encorafenib or an IκB kinase inhibitor such as SAR-113945, bardoxolone, BMS-066, BMS-345541, IMD-0354, IMD-2560, or IMD-1041, or MEK inhibitors such as Selumetinib (AZD6244) and Trametinib (GSK121120212), in particular Raf inhibitors (e.g. vemurafenib) or MEK inhibitors (e.g. trametinib).

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, particularly 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment.

Where the compound of the formula (I) is administered in combination therapy with one, two, three, four or more other therapeutic agents (particularly one or two, more particularly one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

In one embodiment is provided a compound of formula (I) for the manufacture of a medicament for use in therapy wherein said compound is used in combination with one, two, three, or four other therapeutic agents. In another embodiment is provided a medicament for treating cancer which comprises a compound of formula (I) wherein said medicament is used in combination with one, two, three, or four other therapeutic agents. The invention further provides use of a compound of formula (I) for the manufacture of a medicament for enhancing or potentiating the response rate in a patient suffering from a cancer where the patient is being treated with one, two, three, or four other therapeutic agents.

It will be appreciated that the particular method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as a chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

In one embodiment the compound of the invention is administered with a "radiosensitizer" and/or "chemosensitizer". In one embodiment the compound of the invention is administered with an "immune sensitizer".

The term "immune sensitizer" is defined as a molecule administered to patients in therapeutically effective amounts to increase the sensitivity of cells to an IAP antagonist for example, by promoting or increasing the immune response for example by triggering release of TNF.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds of the invention; compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds of the invention; compounds which promote the incorporation of chemosensitizers to the target cells; compounds which control the flow of therapeutics, nutrients, and/or oxygen to the target cells;

chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

Examples of immune sensitizers include the following, but are not limited to: immunomodulating agents, for example monoclonal antibodies such as immune checkpoint antibodies [e.g. CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (anti-PD-1), BMS-936559 (anti-PD-L1), MPDL320A, AMP-514 or MED14736 (anti-PD-L1), or tremelimumab (formerly ticilimumab, CP-675,206, anti-CTLA-4)]; or Signal Transduction inhibitors; or cytokines (such as recombinant interferons); or oncolytic viruses; or immune adjuvants (e.g. BCG).

Immune sensitizers may be administered in conjunction with a therapeutically effective amount of one or more other compounds, including but not limited to: compounds of the invention; compounds which promote the incorporation of immune sensitizers to the target cells; compounds which control the flow of therapeutics, nutrients, and/or oxygen to the target cells; therapeutic agents which act on the tumour or other therapeutically effective compounds for treating cancer or other disease.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all agents. In an alternative embodiment, the individual therapeutic agents may be formulated separately and presented together in the form of a kit, optionally with instructions for their use.

In one embodiment is provided a combination of a compound of formula (I) with one or more (e.g. 1 or 2) other therapeutic agents (e.g. anticancer agents as described above). In a further embodiment is provided a combination of an IAP antagonist as described herein and a PI3K/AKT pathway inhibitor selected from: apitolisib, buparlisib, Copanlisib, pictilisib, ZSTK-474, CUDC-907, GSK-2636771, LY-3023414, ipatasertib, afuresertib, MK-2206, MK-8156, Idelalisib, BEZ235 (dactolisib), BYL719, GDC-0980, GDC-0941, GDC-0032 and GDC-0068.

In another embodiment is provided a compound of formula (I) in combination with one or more (e.g. 1 or 2) other therapeutic agents (e.g. anticancer agents) for use in therapy, such as in the prophylaxis or treatment of cancer.

In one embodiment the pharmaceutical composition comprises a compound of formula (I) together with a pharmaceutically acceptable carrier and optionally one or more therapeutic agent(s).

In another embodiment the invention relates to the use of a combination according to the invention in the manufacture of a pharmaceutical composition for inhibiting the growth of tumour cells.

In a further embodiment the invention relates to a product containing a compound of formula (I) and one or more anticancer agent, as a combined preparation for simultaneous, separate or sequential use in the treatment of patients suffering from cancer.

EXAMPLES

The invention will now be illustrated, but not limited, by reference to the specific embodiments described in the following examples. Compounds are named using an automated naming package such as AutoNom (MDL) or are as named by the chemical supplier.

The following synthetic procedures are provided for illustration of the methods used; for a given preparation or step the precursor used may not necessarily derive from the individual batch synthesised according to the step in the description given. In the examples, the following abbreviations are used.

$Ac_2O$ acetic anhydride
AcOH acetic acid
Boc tert-butyloxycarbonyl
Boc-Abu-OH (S)-2-(Boc-amino)butyric acid
BuLi butyllithium
CDI 1,1-carbonyldiimidazole
mCPBA m-chloroperbenzoic acid
DCM dichloromethane
DI PEA N-ethyl-N-(1-methylethyl)-2-propylamine
DMC dimethyl carbonate
DMF N,N-dimethylformamide
DMSO dimethyl sulfoxide
EDC 1-ethyl-3-(3'-dimethylaminopropyl)-carbodiimide hydrochloride
$Et_3N$ triethylamine
EtOAc ethyl acetate
EtOH ethanol
$Et_2O$ diethyl ether
HATU 2-(7-aza-1H-benzotriazole-1-yl)-1,1,3,3-tetramethyluronium hexafluorophosphate
HBTU O-benzotriazole-N,N,N',N'-tetramethyl-uronium-hexafluoro-phosphate
HCl hydrochloric acid
HOAt 1-hydroxyazabenzotriazole
HOBt 1-hydroxybenzotriazole
HPLC high pressure liquid chromatography
IPA isopropyl alcohol
KHMDS potassium hexamethyldisilazide
LiHMDS lithium bis(trimethylsilyl)amide
MeCN acetonitrile
MeOH methanol
mins. minutes
MS mass spectrometry
$NaBH(OAc)_3$ sodium triacetoxyborohydride
NaOtBu potassium tert-butoxide
NMP N-methyl-2-pyrrolidinone
NMR nuclear magnetic resonance spectroscopy
oasfb on an anhydrous solvent free basis
$Pd_2(dba)_3$ tris(dibenzylideneacetone)dipalladium (0)
$Pd(OAc)_2$ palladium (2) acetate
$Pd(PPh_3)_4$ tetrakis(triphenylphosphine)palladium (0)
petrol petroleum ether fraction with boiling point range 40-60° C.
PyBrop bromo-tris-pyrrolidino-phosphonium hexafluorophosphate
RT room temperature
$SiO_2$ silica
TBABr tetrabutylammonium bromide
TBAF tetrabutylammonium fluoride
TBME t-butylmethyl ether
TBTU N,N,N',N'-tetramethyl-O-(benzotriazol-1-yl)uronium tetrafluoroborate
TCNB 2,3,5,6-tetrachloronitrobenzene
TEA triethylamine
TFA trifluoroacetic acid
THF tetrahydrofuran
TMEDA N,N,N,N-tetramethylethylenediamine NMR Data: Unless indicated, $^1H$ NMR spectra were recorded at 25° C. on a Bruker Avance I spectrometer operating at 400 MHz. The data were processed and analysed using Topspin 2.1 software. For NMR data, where the number of protons assigned is less than the theoretical number of protons in the molecule, it is assumed that the apparently missing signal(s) is/are obscured by solvent and/or water peaks. In addition, where spectra were obtained in protic NMR solvents, exchange of NH and/or OH protons with solvent occurs and hence such signals are normally not observed.

Analytical and Preparative LC-MS Systems
Analytical LC-MS System and Method Description In the following examples, compounds were characterised by mass spectroscopy using the systems and operating conditions set out below. Where atoms with different isotopes are present and a single mass quoted, the mass quoted for the compound is the monoisotopic mass (i.e. $^{35}Cl$; $^{79}Br$ etc.).

Waters Platform LC-MS System:
  HPLC System: Waters 2795
  Mass Spec Detector: Micromass Platform LC
  PDA Detector: Waters 2996 PDA
  Platform MS conditions:
  Capillary voltage: 3.6 kV (3.40 kV on ES negative)
  Cone voltage: 30 V
  Source Temperature: 120° C.
  Scan Range: 125-800 amu
  Ionisation Mode: ElectroSpray Positive or
  ElectroSpray Negative or
  ElectroSpray Positive & Negative
Waters Fractionlynx LC-MS System:
  HPLC System: 2767 autosampler –2525 binary gradient pump
  Mass Spec Detector: Waters ZQ
  PDA Detector: Waters 2996 PDA
  Fractionlynx MS conditions:
  Capillary voltage: 3.5 kV (3.25 kV on ES negative)
  Cone voltage: 40 V (25 V on ES negative)
  Source Temperature: 120° C.
  Scan Range: 125-800 amu
  Ionisation Mode: ElectroSpray Positive or
  ElectroSpray Negative or
  ElectroSpray Positive & Negative Agilent 1200SL-6140 LC-MS System—RAPID:
  HPLC System: Agilent 1200 series SL
  Mass Spec Detector: Agilent 6140 single quadrupole
Second Detector: Agilent 1200 MWD SL
  Agilent MS conditions:
  Capillary voltage: 4000V on ES pos (3500V on ES Neg)
  Fragmentor/Gain: 100
  Gain: 1
  Drying gas flow: 7.0 L/min
  Gas Temperature: 345° C.
  Nebuliser Pressure: 35 psig
  Scan Range: 125-800 amu
  Ionisation Mode: ElectroSpray Positive-Negative switching Preparative LC-MS System and Method Description Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Several systems for purifying compounds via preparative LC-MS are described below although a person skilled in the art will appreciate that alternative systems and methods to those described could be used. From the information provided herein, or employing alternative chromatographic systems, a person skilled in the art could purify the compounds described herein by preparative LC-MS.

Waters Fractionlynx system:
  Hardware:
  2767 Dual Loop Autosampler/Fraction Collector
  2525 preparative pump
  CFO (column fluidic organiser) for column selection
  RMA (Waters reagent manager) as make up pump
  Waters ZQ Mass Spectrometer
  Waters 2996 Photo Diode Array detector
  Waters ZQ Mass Spectrometer
  Waters MS running conditions:
  Capillary voltage: 3.5 kV (3.2 kV on ES Negative)
  Cone voltage: 25 V
  Source Temperature: 120° C.
  Scan Range: 125-800 amu
  Ionisation Mode: ElectroSpray Positive or ElectroSpray Negative
Agilent 1100 LC-MS Preparative System:
  Hardware:
  Autosampler: 1100 series "prepALS"
  Pump: 1100 series "PrepPump" for preparative flow gradient and 1100 series "QuatPump"
    for pumping modifier in prep flow
  UV detector: 1100 series "MWD" Multi Wavelength Detector
  MS detector: 1100 series "LC-MSD VL"
  Fraction Collector: 2x "Prep-FC"
  Make Up pump: "Waters RMA"
  Agilent Active Splitter
  Agilent MS running conditions:
  Capillary voltage: 4000 V (3500 V on ES Negative)
  Fragmentor/Gain: 150/1
  Drying gas flow: 12.0 L/min
  Gas Temperature: 350° C.
  Nebuliser Pressure: 50 psig
  Scan Range: 125-800 amu
  Ionisation Mode: ElectroSpray Positive or ElectroSpray Negative
Columns:
  A range of commercially available columns—both achiral and chiral—may be used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge™ Prep OBD™ C18 and Phenyl, Atlantis® Prep T3 OBD™ and Sunfire™ Prep OBD C18 5 μm 19×100 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.
Eluents:
  Mobile phase eluent was chosen in conjunction with column manufacturers recommended stationary phase limitations in order to optimise a columns separation performance.
Methods:
Achiral Preparative Chromatography The compound examples described have undergone HPLC purification, where indicated, using methods developed following recommendations as described in Snyder L. R., Dolan J. W., High-Performance Gradient Elution The Practical Application of the Linear-Solvent-Strength Model, Wiley, Hoboken, 2007.

Chiral Preparative Chromatography

Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

The values of salt stoichiometry or acid content in the compounds as provided herein, are those obtained experimentally and may vary dependent on the analytical method used. In case no salt form is indicated, the compound was obtained as a free base.

Preparation 1: (R)-2-((S)-2-Benzyloxycarbonylamino-3-hydroxy-propionyl-amino)-propionic Acid Methyl Ester Diisopropylethylamine (375 mL) was added dropwise to a cooled mixture of (R)-2-amino-propionic acid methyl ester hydrochloride (100 g, 0.716 mol), EDC (165 g, 0.86 mol), carbobenzyloxy-L-serine (171.4 g, 0.716 mol) and DCM (3.6 L). The resulting mixture was stirred under nitrogen at ambient temperature for 16 h. After removing solvent in vacuo at 40° C., the residue was diluted with saturated sodium carbonate (1 L), water (1 L) and extracted with EtOAc (2 L, 2×1 L). The combined organic phases were washed with 2 M hydrochloric acid (1 L), saturated brine solution (1 L), dried over magnesium sulfate and concentrated in vacuo at 40° C., to give the title compound (172 g) as a colourless solid. $^1$H NMR (Me-d3-OD): 7.44-7.28 (6H, m), 5.13 (2H, s), 4.46 (1H, d), 4.43 (1H, d), 4.25 (1H, t), 3.82-3.68 (5H, m), 1.39 (3H, d).

Preparation 2: (3S,6R)-3-Hydroxymethyl-6-methyl-piperazine-2,5-dione

To (R)-2-((S)-2-benzyloxycarbonylamino-3-hydroxy-propionyl-amino)-propionic acid methyl ester (which may be prepared as described in Preparation 1) (172 g, 0.53 mol) was added 10% palladium on carbon (8.6 g), MeOH (530 mL) and cyclohexene (344 mL) under nitrogen. The mixture was heated to reflux for 17 h. MeOH (500 mL) was added and the reflux continued for 1 h. The hot reaction mixture was filtered through a pad of celite, cake washing with hot MeOH (2×500 mL). The combined filtrates were concentrated. The resulting solid was slurried in 2-butanone (400 mL) and petrol (400 mL) was added gradually over 10 min. After stirring for 30 min, the solids were filtered, cake washed with 2:1 petrol/2-butanone (300 mL). The filter cake was dried in vacuo at 40° C., to give the title compound (68.3 g) as an off white solid. $^1$H NMR (DMSO-d6): 8.08 (1H, s), 7.90 (1H, s), 5.11 (1H, t), 3.92 (1H, q), 3.80-3.71 (1H, m), 3.71-3.60 (1H, m), 3.58-3.47 (1H, m), 1.24 (3H, d).

Preparation 3: ((2R,5R)-5-Methyl-piperazin-2-yl)-methanol Hydrochloride

To (3S,6R)-3-hydroxymethyl-6-methyl-piperazine-2,5-dione (which may be prepared as described in Preparation 2) (34 g, 0.215 mol) was added a solution of borane in THF (1 M, 1.6 L, 1.6 mol) and the mixture was heated to 70° C. for 18 h. The solution was cooled in ice, then MeOH (425 mL) was gradually added, followed by 5 M hydrochloric acid (113 mL). The mixture was heated to 70° C. for 2 h and then cooled to ambient temperature. The resulting solid was filtered, cake washed with THF (200 mL) and dried in vacuo at 40° C., to give the title compound (39.3 g) as a colourless solid. $^1$H NMR (DMSO-d6): 9.79 (3H, s), 5.59 (1H, s), 3.76-3.40 (5H, m), 3.19-2.94 (2H, m), 1.28 (3H, d).

Preparation 4: (2R,5R)-5-Hydroxymethyl-2-methyl-piperazine-1-carboxylic acid tert-butyl ester To ((2R,5R)-5-methyl-piperazin-2-yl)-methanol hydrochloride (which may be prepared as described in Preparation 3) (20 g, 119 mmol) in MeOH (96 mL) at 0° C. (ice bath) was added triethylamine (48.7 mL, 357 mmol). tert-Butyl dicarbonate (61 g, 280 mmol) in MeOH (145 mL) was added over 30 min. The reaction temperature was maintained at <10° C. for 1 h, warmed to ambient temperature over 1 h and then heated to 50° C. for 18 h. The reaction was concentrated and the residue dissolved in ethanol (397 mL). A solution of NaOH (23.8 g, 595 mmol) in water (397 mL) was added and the reaction heated to 100° C. for 18 h, then cooled to ambient temperature. Mixture was neutralised with 1 M HCl (~300 mL) to pH 9 (using a pH meter), then extracted with chloroform (3×700 mL), dried over sodium sulfate, filtered and concentrated. The residue was redissolved in MeOH and concentrated, then dried in vacuo at 40° C., to give the title compound (21 g, 75%) as a colourless solid. $^1$H NMR (Me-d3-OD): 4.20-4.07 (1H, m), 3.79 (1H, dd), 3.71-3.58 (2H, m), 3.54 (1H, dd), 3.24 (1H, dd), 3.18-3.01 (1H, m), 3.01-2.89 (1H, m), 2.55 (1H, dd), 1.48 (9H, s), 1.25 (3H, s).

Preparation 5: (2R,5R)-4-Benzyl-5-hydroxymethyl-2-methyl-piperazine-1-carboxylic Acid Tert-Butyl Ester A mixture of (2R,5R)-5-hydroxymethyl-2-methyl-piperazine-1-carboxylic acid tert-butyl ester (which may be prepared as described in Preparation 4) (3.48 g, 15.1 mmol), benzaldehyde (1.76 g, 16.6 mmol), sodium triacetoxyborohydride (3.84 g, 18.1 mmol) and 1,2-dichloroethane (30 mL) was stirred at 20° C. for 18 h, then partitioned between saturated aqueous NaHCO$_3$ (150 mL) and DCM (3×50 mL). Combined organic extracts were dried (Na$_2$SO$_4$) then evaporated in vacuo to give an oil. Chromatography (SiO$_2$, 0-30% EtOAc in petrol) gave the title compound (4.588 g, 74%) as a colourless solid. MS: [M+H]$^+$=321.

Preparation 6: (2R,5R)-4-Benzyl-5-chloromethyl-2-methyl-piperazine-1-carboxylic Acid Tert-Butyl Ester Methanesulfonyl chloride (570 μL, 7.35 mmol) was added to a solution of (2R,5R)-4-benzyl-5-hydroxymethyl-2-methyl-piperazine-1-carboxylic acid tert-butyl ester (which may be prepared as described in Preparation 5) (1.9 g, 6.12 mmol) containing TEA (2.6 mL, 18.4 mmol) in DCM (30 mL) at 0° C. The solution was stirred at room temperature for 18 h. The reaction was partitioned between aqueous NH$_4$Cl and DCM. The organic phase was collected, dried over MgSO$_4$, filtered and concentrated in vacuo. Chromatography (30% EtOAc in petrol) gave the title compound (1.6 g) as a white solid. MS: [M+H]$^+$=339.

Preparation 7: (2R,5S)-4-Benzyl-2-methyl-5-((R)-3-methyl-morpholin-4-ylmethyl)-piperazine-1-carboxylic Acid Tert-Butyl Ester K$_2$CO$_3$ (81.6 g, 591 mmol) and KI (73.6 g, 443 mmol) were added to a solution of (2R,5R)-4-benzyl-5-chloromethyl-2-methyl-piperazine-1-carboxylic acid tert-butyl ester (which may be prepared as described in Preparation 6) (50 g, 147.9 mmol) in acetonitrile (400 mL) followed by (R)-3-methyl-morpholine hydrochloride (26.4 g, 192 mmol). The reaction was stirred at 70° C. for 18 h. The solid was then removed by filtration and the solvent removed in vacuo. The crude material was purified by chromatography using a pad of silica (20% EtOAc in Petrol) to give the title compound (41.3 g) as a white solid. MS: [M+H]$^+$=404.

Preparation 8: (2R,5S)-2-Methyl-5-((R)-3-methyl-morpholin-4-ylmethyl)-piperazine carboxylic Acid Tert-Butyl Ester Palladium on carbon (10%) (33 g) and acetic acid (220 mL) were added to a solution of (2R,5S)-4-benzyl-2-methyl-5-((R)-3-methyl-morpholin-4-ylmethyl)-piperazine-1-carboxylic acid tert-butyl ester (which may be prepared as described in Preparation 7) (41.3 g, 102 mmol) in EtOH (300 mL). The mixture was stirred under H$_2$ (1 atmosphere) at room temperature for 18 h. The reaction mixture was then filtered through a pad of Celite to remove the catalyst and the solvent was removed in vacuo. The crude material was partitioned between saturated aqueous NaHCO$_3$ and DCM and the product extracted with DCM (3×). The organic phase was dried over MgSO$_4$, filtered and concentrated in vacuo to give the title compound (30.5 g) as a pale yellow oil. $^1$H NMR (400 MHz, CDCl$_3$): 4.43-3.87 (1H, m), 3.78 (1H, d), 3.73-3.55 (3H, m), 3.32 (1H, dd), 3.22 (1H, dd), 3.16-2.93 (3H, m), 2.93-2.72 (1H, m), 2.55-2.35 (2H, m), 2.35-2.15 (2H, m), 1.89 (1H, dd), 1.45 (9H, s), 1.26 (3H, d), 0.96 (3H, d).

Alternative Procedure:

To a tightly sealed 10 L flange flask fitted with a stirrer bar was added (2R,5S)-4-benzyl-2-methyl-5-((R)-3-methyl-morpholin-4-ylmethyl)-piperazine-1-carboxylic acid tert-butyl ester (500 g, 1.24 mol, 1.0 eq) (which may be prepared as described in Preparation 7) and ethanol (Stock, 5 L). The flask was placed under nitrogen and 10% Pd/C (Aldrich, 50 g, 0.124 mol, 0.1 eq) was added as a paste in ethanol. The flask was purged several times with a di-vac pump and placed under a hydrogen atmosphere using 4 balloons. The reaction was warmed to 30° C. overnight after which time NMR confirmed complete consumption of starting material. The reaction mixture was cooled to room temperature and filtered through a pad of celite under nitrogen. The filtrates were evaporated to dryness to afford the title product as a colourless oil.

$^1$H NMR (MeOD): 1.00 (3H, d), 1.25 (3H, d), 1.48 (9H, s), 2.08-2.14 (1H, m), 2.28-2.35 (1H, m), 2.42-2.48 (1H, m), 2.49-2.55 (1H, dd), 2.80-3.06 (4H, m), 3.22-3.28 (2H, m), 3.61-3.78 (4H, m), 4.12-4.16 (1H, m).

$^{13}$C NMR (MeOD): 14.6, 15.7, 28.8, 40.8, 44.8, 48.3, 50.3, 53.2, 54.3, 57.5, 68.5, 73.9, 81.1, 157.0.

Preparation 9: (2R,5S)-4-Benzyl-5-((3R,5R)-3,5-dimethyl-morpholin-4-ylmethyl)-2-methyl-piperazine-1-carboxylic Acid Tert-Butyl Ester K$_2$CO$_3$ (2.7 g, 19.5 mmol) and KI (1.83 g, 11.05 mmol) were added to a solution of (2R,5R) benzyl-5-chloromethyl-2-methyl-piperazine-1-carboxylic acid tert-butyl ester (which may be prepared as described in Preparation 6) (2.2 g, 6.5 mmol) in acetonitrile (30 mL) followed by (3R,5R)-3,5-dimethyl-morpholine (0.80 g, 7.0 mmol). The reaction was stirred at 70° C. for 18 h. The solid was then removed by filtration and the solvent removed in vacuo. The residue was partitioned between water and dichloromethane. The organic phase was dried, filtered and the solvent evaporated. The crude material was purified by chromatography on silica (0-40% EtOAc in Petrol) to give the title compound (2.56 g, 94%) as a white solid. MS: [M+H]$^+$=418.

Preparation 10: (2R,5S)-5-((3R,5R)-3,5-Dimethyl-morpholin-4-ylmethyl)-2-methyl-piperazine-1-carboxylic Acid Tert-Butyl Ester Palladium on carbon (10%) (1.6 g) and acetic acid (10 mL) were added to a solution of (2R,5S)-4-benzyl-5-((3R,5R)-3,5-dimethyl-morpholin-4-ylmethyl)-2-methyl-piperazine-1-carboxylic acid tert-butyl ester (which may be prepared as described in Preparation 9) (2.5 g, 6.0 mmol) in EtOH (70 mL). The mixture was stirred under H$_2$ (1 atmosphere) at room temperature for 3 h. The reaction mixture was then filtered through a pad of Celite to remove the catalyst and the solvent was removed in vacuo. The crude material was partitioned between saturated aqueous NaHCO$_3$ and DCM and the product extracted with DCM (3×). The organic phase was dried over MgSO$_4$, filtered and concentrated in vacuo to give the title compound (1.53 g, 78%) as a pale yellow oil. $^1$H NMR (400 MHz, CDCl$_3$): 4.16 (1H, s), 3.79-3.59 (3H, m), 3.44-3.19 (3H, m), 3.08 (1H, dd), 2.99-2.69 (4H, m), 2.52 (1H, dd), 2.29 (1H, dd), 1.47 (9H, s), 1.27 (3H, d), 1.00 (6H, d).

The following compound was made following an analogous procedure to that described in Preparations 9 and 10:

10A: (2R,5S)-5-((2S,5R)-2,5-Dimethyl-morpholin-4-ylmethyl)-2-methyl-piperazine-1-carboxylic acid tert-butyl ester, MS: [M+H]$^+$=328.

Preparation 11: 2-(5-Chloro-3-fluoro-pyridin-2-yl)-2-methyl-propionitrile

A solution of sodium bis(trimethylsilyl)amide (610 mL, 40% in tetrahydrofuran, 1.326 mole) was added to an ice-cooled solution of 5-chloro-2,3-difluoropyridine (198.2 g, 1.326 mole) and isobutyronitrile (238 mL, 2.65 mole) in toluene (2 L). The mixture was stirred under nitrogen at RT overnight before addition of saturated aqueous ammonium chloride (1 L). Phases were separated and the aqueous extracted with ethyl acetate (2×1 L). Combined organic extracts were dried (MgSO$_4$) and concentrated in vacuo at 40° C. to give the title compound (259.8 g, 95%)$^1$H NMR (400 MHz, DMSO-d6): 8.57 (1H, dd), 8.24 (1H, dd), 1.74 (6H, broad).

Preparation 12: 2-(5-Chloro-3-fluoropyridin-2-yl)-2-methylpropylamine

Borane-tetrahydrofuran complex (1 M, 1.37 L, 1.365 mole) was added to a cooled solution of 2-(5-chloro-3-fluoro-pyridin-2-yl)-2-methyl-propionitrile (which may be prepared as described in Preparation 11) (135.6 g, 0.683 mole) in tetrahydrofuran (670 mL). The mixture was stirred under nitrogen at room temperature overnight before cooling in ice. The mixture was quenched by the addition of 5 M hydrochloric acid (335 mL). The resulting mixture was basified with 40% aqueous potassium hydroxide (460 mL) and the phases were separated. The basic aqueous phase was extracted with ethyl acetate (2×670 mL) and the combined organic extracts were washed with brine (670 mL), dried (MgSO$_4$) and concentrated in vacuo at 40° C. to give the title compound (102.9 g, 74%)$^1$H NMR (400 MHz, DMSO-d6): 8.44 (1H, t), 7.95 (1H, dd), 2.85 (2H, d), 1.29 (6H, d).

Preparation 12, alternative procedure: 2-(5-Chloro-3-fluoropyridin-2-yl)-2-methylpropylamine To a 10 L flange flask was added 2-(5-chloro-3-fluoro-pyridin-2-yl)-2-methyl-propionitrile (which may be prepared as described in Preparation 11) (200 g, 1.00 mol), nickel(II) chloride hexahydrate (239.4 g, 1.00 mol) and ethanol (3.0 L). The resulting green solution was cooled to 0° C. using a dry ice/acetone bath under an atmosphere of nitrogen. Sodium borohydride (114.3 g, 3.02 mol) was added portionwise at such a rate that the reaction temperature remained below 6° C. (addition time=1% h) to give a black suspension. Once the addition was complete, the cold bath was replaced with an ice/water bath, then the reaction was allowed to warm to RT overnight. The reaction mixture was cooled to 0-4° C. in an ice bath. 25% Aqueous ammonia solution (2680 mL) was added from a dropping funnel such that the reaction temperature remained below 10° C. (addition time=1 h). Once addition was complete, stirring was continued at ca 0° C. for 30 min then the mixture was filtered through celite, and the residues washed with ethanol (2×750 mL). (Care! Don't let the filter pad dry up. Total filtration time ca 2 h.) The pale yellow/brown filtrate was transferred to a large rotary evaporator and concentrated until all ethanol had been removed. The resulting green oil was transferred to a 5 L separating funnel and 25% aqueous ammonia solution added until the oil turned yellow (200 mL). The oil was separated and the aqueous phase extracted with toluene (2×300 mL). The combined organic extracts were washed with 1:1 25% aqueous ammonia solution/brine (300 mL), dried over sodium sulfate, filtered and concentrated on the rotary evaporator (bath temperature up to 70° C.) to give the crude product as a yellow oil (161 g), data consistent with those given above. This was used in the next step without purification.

Preparation 13: 6-Chloro-3,3-dimethyl-2,3-dihydro-1H-pyrrolo[3,2-b]pyridine

A mixture of 2-(5-chloro-3-fluoropyridin-2-yl)-2-methylpropylamine (which may be prepared as described in Preparation 12 and Preparation 12, alternative procedure) (33 g, 0.163 mole), potassium carbonate (122 g, 0.884 mole) and NMP (100 mL) was heated to 150° C. for 4 hours. The cooled mixture was diluted with water (330 mL) and extracted with toluene (3×300 mL) The combined organic extracts were washed with brine (160 mL), dried (MgSO$_4$) and concentrated in vacuo at 40° C. to give crude material (24.8 g). Chromatography on silica eluting with 5-30% ethyl acetate/petrol gave the title compound (21 g, 71%) $^1$H NMR (400 MHz, DMSO-d6): 7.61 (1H, d), 6.75 (1H, d), 6.06 (1H, bs), 3.31 (2H, s), 1.21 (6H, s).

Preparation 14: 6-Chloro-3,3-dimethyl-2,3-dihydro-pyrrolo[3,2-b]pyridine-1-carboxylic Acid Tert-Butyl Ester Di-tertbutyldicarbonate (3.7 g, 17.1 mmol) was added to a mixture of 6-chloro-3,3-dimethyl-2,3-dihydro-1H-pyrrolo[3,2-b]pyridine (which may be prepared as described in Preparation 13) (2.6 g, 14.2 mmol), tetrahydrofuran (26 mL) and 2 M sodium hydroxide (11.4 mL, 22.8 mmol) with stirring over 2 days. The biphasic mixture was diluted with water (20 mL) and extracted with ethyl acetate (2×20 mL). The combined organic extracts were dried (MgSO$_4$) and concentrated in vacuo at 40° C. to give crude material (6.02 g). Chromatography on silica eluting with 5-30% ethyl acetate/petrol gave the title compound (2.23 g, 55%); $^1$H NMR (400 MHz, DMSO-d6): 8.11 (1H, d), 7.85 (1H, bs), 3.77 (2H, s), 1.52 (9H, s), 1.28 (6H, s).

Preparation 15: 6-(4-Fluorobenzyl)-3,3-dimethyl-2,3-dihydro-1H-pyrrolo[3,2-b]pyridine A solution of 4-fluorobenzylzinc chloride (2 L of 0.5 M solution in THF, 1 mol) was added to a degassed mixture of 6-chloro-3,3-dimethyl-2,3-dihydro-1H-pyrrolo[3,2-b]pyridine (which may be prepared as described in Preparation 13) (91.3 g, 0.5 mol), lithium bromide (130.3 g, 1.5 mol) and [1,3-bis(2,6-diisopropylphenyl)imidazol-2-ylidene](3-chloropyridyl)palladium(II) dichloride (6.8 g, 0.01 mol) in THF (685 mL) and NMP (910 mL) at 20° C. with exotherm. The resulting dark mixture was stirred under nitrogen at room temperature for 18 h. The reaction was quenched with 2.5% aqueous citric acid (900 mL) and extracted with toluene (2×900 mL). The combined organic phases were washed with water (3×900 mL), brine (900 mL), dried over MgSO$_4$, filtered and concentrated in vacuo. The resulting solid was slurried in petrol (450 mL) and toluene (100 mL). After stirring for 30 min, the solids were filtered, cake washed with petrol (2×90 mL). The filter cake was dried in vacuo at 40° C., to give the title compound (107.3 g) as a grey solid. $^1$H NMR (DMSO-d6): 7.60 (1H, d), 7.30-7.22 (2H, m), 7.15-7.06 (2H, m), 6.53 (1H, d), 5.64 (1H, s), 3.78 (2H, s), 3.22 (2H, d), 1.19 (6H, s).

The following compounds were prepared in a similar manner to that described in Preparation 15:

15A: tert-Butyl 6-[(4-fluorophenyl)methyl]-3,3-dimethyl-1H,2H,3H-pyrrolo[3,2-b]pyridine-1-carboxylate, MS: [M+H]$^+$=357.

15B: 6-(3-Fluorobenzyl)-3,3-dimethyl-2,3-dihydro-1H-pyrrolo[3,2-b]pyridine, MS: [M+H]$^+$=257.

15C: 6-Butyl-3,3-dimethyl-2,3-dihydro-1H-pyrrolo[3,2-b]pyridine, MS: [M+H]$^+$=205.

15D: 6-(2-Fluorobenzyl)-3,3-dimethyl-2,3-dihydro-1H-pyrrolo[3,2-b]pyridine, MS: [M+H]$^+$=257.

15E: 6-(2,4-Difluorobenzyl)-3,3-dimethyl-2,3-dihydro-1H-pyrrolo[3,2-b]pyridine

Preparation 16: 5-Bromo-6-(4-fluorobenzyl)-3,3-dimethyl-2,3-dihydro-1H-pyrrolo[3,2-b]pyridine A solution of 6-(4-fluorobenzyl)-3,3-dimethyl-2,3-dihydro-1H-pyrrolo[3,2-b]pyridine (which may be prepared as described in Preparation 15) (88.5 g, 0.345 mol) in DMF (1.67 L) was cooled to −5° C. Solid N-bromosuccinimide (61.5 g, 0.345 mol) was added in portions with exotherm. The mixture was stirred for 1 h warming to room temperature. Water (2.66 L) was added with exotherm and the resulting mixture was stirred for 18 h at room temperature The solids were filtered and cake washed with water (270 mL). The filter cake was dissolved in THF (1.5 L), dried over MgSO$_4$, filtered and concentrated in vacuo to give the title compound (109.7 g) as a yellow solid. $^1$H NMR (DMSO-d6): 7.29-7.20 (2H, m), 7.20-7.03 (2H, m), 6.64 (1H, s), 5.88 (1H, s), 3.89 (2H, s), 3.26 (2H, d), 1.20 (6H, s).

The following compounds were prepared in a similar manner to Preparation 16:

16A: 5-Bromo-6-(3-fluorobenzyl)-3,3-dimethyl-2,3-dihydro-1H-pyrrolo[3,2-b]pyridine, MS: [M+H]$^+$=335, 337.

16B: 5-Bromo-6-(2-fluorobenzyl)-3,3-dimethyl-2,3-dihydro-1H-pyrrolo[3,2-b]pyridine, MS: [M+H]$^+$=335, 337.

16C: 5-Bromo-6-Butyl-3,3-dimethyl-2,3-dihydro-1H-pyrrolo[3,2-b]pyridine, MS: [M+H]$^+$=283, 285.

16D: 5-Bromo-6-(2,4-difluorobenzyl)-3,3-dimethyl-2,3-dihydro-1H-pyrrolo[3,2-b]pyridine Preparation 17: [6-(4-Fluoro-benzyl)-3,3-dimethyl-2,3-dihydro-1H-pyrrolo[3,2-b]pyridin-5-yl]-methanol To 5-bromo-6-(4-fluorobenzyl)-3,3-dimethyl-2,3-dihydro-1H-pyrrolo[3,2-b]pyridine (which may be prepared as described in Preparation 16) (22.8 g, 68.2 mmol) in THF (300 mL), cooled to −78° C., was added MeLi (1.6 M in Et$_2$O; 51.1 mL, 91.8 mmol) over 15 minutes. tert-Butyllithium (1.7 M in hexane; 96 mL, 164 mmol) was then added over 30 minutes. After 15 minutes, DMF (26 mL) was added and the mixture stirred at −78° C. for a further 50 minutes. Saturated aqueous NH$_4$Cl (450 mL) was added and the mixture was stirred for 10 minutes at RT. The organic layer was isolated and the aqueous layer extracted with EtOAc (2×150 mL). The combined organic fractions were washed with brine (200 mL), dried (MgSO$_4$) and evaporated to give 6-(4-fluoro-benzyl)-3,3-dimethyl-2,3-dihydro-1H-pyrrolo

[3,2-b]pyridine-5-carbaldehyde as a yellow solid which was used without any further purification. MS: m/z=285 (M+H$^+$)$^+$. This product (~68 mmol) was suspended in MeOH (250 mL) and cooled in an ice bath. NaBH$_4$ (3.4 g, 81.8 mmol) was added portion-wise over 5 minutes. Cooling was removed and the mixture stirred for a further 20 minutes. The mixture was cooled in an ice bath followed by careful addition of 10% aqueous KHSO$_4$ over 10 minutes (care: effervescence). After stirring for 5 minutes at RT the mixture was re-cooled using an ice bath. The mixture was basified by addition of 50% aqueous NaOH (~18 mL) and then concentrated in vacuo to ~ one third volume. The resulting aqueous mixture was extracted with CH$_2$Cl$_2$ (1×200 mL, 2×100 mL) and the combined CH$_2$Cl$_2$ layers were dried (MgSO$_4$). The CH$_2$Cl$_2$ solution was concentrated in vacuo to ~30 mL and then diluted with toluene (70 mL) to initiate crystallisation of the product. Collection by filtration gave the product as a colourless crystalline solid (10.6 g). A second crop (2.1 g) was collected from the filtrate. The filtrate was concentrated and the remaining material was purified by SiO$_2$ chromatography (eluting with 25-50% EtOAc/hexanes) to give a third batch of material (2.1 g); giving the title compound in an overall yield of 14.8 g (76% over 2 steps), MS: [M+H]$^+$=287. An alternative procedure involves subsequent recrystallization from isopropyl alcohol.

The following compound was prepared in a similar manner to Preparation 17:
(6-Butyl-3,3-dimethyl-2,3-dihydro-1H-pyrrolo[3,2-b]pyridin-5-yl)-methanol, MS: [M+H]$^+$=235.

Preparation 18: 2-Chloro-1-{6-[(4-fluorophenyl)methyl]-5-(hydroxymethyl)-3,3-dimethyl-1H,2H,3H-pyrrolo[3,2-b]pyridin-1-yl}ethan-1-one To a cooled (~5° C.) suspension of [6-(4-fluoro-benzyl)-3,3-dimethyl-2,3-dihydro-1H-pyrrolo[3,2-b]pyridin-5-yl]-methanol (which may be prepared as described in Preparation 17) (11.8 g, 41.3 mmol) in MeCN (175 mL) was added chloroacetyl chloride (6.9 mL, 86.7 mmol). Cooling was removed and the mixture stirred for 30 minutes at RT. The mixture was then evaporated in vacuo and dissolved in MeOH (200 mL). K$_2$CO$_3$ solution (12 g in 100 mL H$_2$O) was added and the mixture stirred at RT for 20 minutes after which the mixture was concentrated in vacuo to one quarter volume. The aqueous mixture was extracted with CH$_2$Cl$_2$ (1×100 mL, 2×30 mL) and the combined CH$_2$Cl$_2$ layers were dried (MgSO$_4$). Evaporation in vacuo gave the product as colourless crystalline solid (12.1 g, ~100%), MS: [M+H]$^+$=363.

The following compounds were prepared following a method analogous or similar to that of Preparation 18:
18A: 1-(2-Chloroacetyl)-6-[(4-fluorophenyl)methyl]-3,3-dimethyl-1H,2H,3H,4H,5H-pyrrolo[3,2-b]pyridin-5-one, MS: [M+H]$^+$=349.
18B: 2-Chloro-1-{6-[(2-fluorophenyl)methyl]-5-(hydroxymethyl)-3,3-dimethyl-1H,2H,3H-pyrrolo[3,2-b]pyridin-1-yl}ethan-1-one, MS: [M+H]$^+$=363.
18C: 1-(2-Chloroacetyl)-6-[(4-fluorophenyl)methyl]-3,3,4-trimethyl-1H,2H,3H,4H,5H-pyrrolo[3,2-b]pyridin-5-one, MS: [M+H]$^+$=363.
18D: 1-(2-Chloroacetyl)-6-[(2,4-fluorophenyl)methyl]-3,3-dimethyl-1H,2H,3H,4H,5H-pyrrolo[3,2-b]pyridin-5-one, MS: [M+H]$^+$=367.
18E: 1-(2-Chloroacetyl)-6-[(2-fluorophenyl)methyl]-3,3,4-trimethyl-1H,2H,3H,4H,5H-pyrrolo[3,2-b]pyridin-5-one, MS: [M+H]$^+$=363.
18F: 2-Chloro-1-{6-[(2,4-difluorophenyl)methyl]-5-(hydroxymethyl)-3,3-dimethyl-1H,2H,3H-pyrrolo[3,2-b]pyridin-1-yl}ethan-1-one, MS: [M+H]$^+$=381.
18G: 2-Chloro-1-[5-(1,2-dihydroxyethyl)-6-[(4-fluorophenyl)methyl]-3,3-dimethyl-1H,2H,3H-pyrrolo[3,2-b]pyridin-1-yl]ethan-1-one, MS: [M+H]$^+$=393.
18H: 2-Chloro-1-{6-[(3-fluorophenyl)methyl]-5-(hydroxymethyl)-3,3-dimethyl-1H,2H,3H-pyrrolo[3,2-b]pyridin-1-yl}ethan-1-one, MS: [M+H]$^+$=363.
18I: 1-(2-Chloro-acetyl)-6-(4-fluoro-benzyl)-3,3-dimethyl-1,2,3,6-tetrahydro-pyrrolo[2,3-c]pyridin-5-one, MS: [M+H]$^+$=349.
18J: 1-(2-Chloro-acetyl)-6-(2,4-difluoro-benzyl)-3,3-dimethyl-1,2,3,6-tetrahydro-pyrrolo[2,3-c]pyridin-5-one, MS: [M+H]$^+$=367.
18K: 2-Chloro-1-[5-((R or S)-1,2-dihydroxyethyl)-6-[(4-fluorophenyl)methyl]-3,3-dimethyl-1H,2H,3H-pyrrolo[3,2-b]pyridin-1-yl]ethan-1-one, from slower eluting precursor. MS: [M+H]$^+$=393.
18L: 1-(2-Chloroacetyl)-6-[(2,4-fluorophenyl)methyl]-3,3,4-trimethyl-1H,2H,3H,4H,5H-pyrrolo[3,2-b]pyridin-5-one, MS: [M+H]$^+$=381.
18M: 2-Chloro-1-{6-[(4-fluorophenyl)methyl]-5-(R or S)-1-hydroxy-2-methoxyethyl)-3,3-dimethyl-1H,2H,3H-pyrrolo[3,2-b]pyridin-1-yl}ethan-1-one, from faster eluting precursor, MS: [M+H]$^+$=407.
18N: 2-Chloro-1-{6-[(4-fluorophenyl)methyl]-5-(R or S)-1-methoxy-2-hydroxyethyl)-3,3-dimethyl-1H,2H,3H-pyrrolo[3,2-b]pyridin-1-yl}ethan-1-one, from faster eluting precursor, MS: [M+H]$^+$=407.
18O: 2-Chloro-1-{6-[(4-fluorophenyl)methyl]-5-(R or S)-1-hydroxy-2-methoxyethyl)-3,3-dimethyl-1H,2H,3H-pyrrolo[3,2-b]pyridin-1-yl}ethan-1-one, from slower eluting precursor, MS: [M+H]$^+$=407.
18P: 2-Chloro-1-{6-[(4-fluorophenyl)methyl]-5-(R or S)-1-methoxy-2-hydroxyethyl)-3,3-dimethyl-1H,2H,3H-pyrrolo[3,2-b]pyridin-1-yl}ethan-1-one, from slower eluting precursor, MS: [M+H]$^+$=407.
18Q: 1-(2-Chloro-acetyl)-6-(2,4-difluoro-benzyl)-3,3,4-trimethyl-1,2,3,6-tetrahydro-pyrrolo[2,3-c]pyridin-5-one, MS: [M+H]$^+$=381.
18R: 6-Butyl-1-(2-chloro-acetyl)-3,3-dimethyl-1,2,3,4-tetrahydro-pyrrolo[3,2-b]pyridin-5-one, MS: [M+H]$^+$=297.
18S: 1-[6-Butyl-5-(hydroxymethyl)-3,3-dimethyl-1H,2H,3H-pyrrolo[3,2-b]pyridin-1-yl]-2-chloroethan-1-one, MS: [M+H]$^+$=311.
18T: 6-Butyl-1-(2-chloro-acetyl)-3,3-dimethyl-1,2,3,6-tetrahydro-pyrrolo[2,3-c]pyridin-5-one, MS: [M+H]$^+$=297.

Preparation 19: tert-Butyl (2R,5S)-4-(2-{6-[(4-fluorophenyl)methyl]-5-(hydroxymethyl)-3,3-dimethyl-1H,2H,3H-pyrrolo[3,2-b]pyridin-1-yl}-2-oxoethyl)-2-methyl-5-{[(3R) methylmorpholin-4-yl]methyl}piperazine-1-carboxylate (2R,5S)-2-Methyl-5-((R)-3-methyl-morpholin-4-ylmethyl)-piperazine-1-carboxylic acid tert-butyl ester (which may be prepared as described in Preparation 8) (15.5 g, 46.4 mmol), KI (12.8 g, 77.4 mmol) and K$_2$CO$_3$ (21.4 g, 155 mmol) were stirred in MeCN (70 mL) and cooled in an ice bath. 2-Chloro-1-{6-[(4-fluorophenyl)methyl]-5-(hydroxymethyl)-3,3-dimethyl-1H,2H,3H-pyrrolo[3,2-b]pyridin-1-yl}ethan-1-one (which may be prepared as described in Preparation 18) (14.0 g, 38.7 mmol) was then added as a solution in MeCN (100 mL). The mixture was stirred at RT for 2 hours and then concentrated in vacuo to ~ one quarter volume. The mixture was partitioned between EtOAc (150 mL) and H₂O (150 mL) and then the aqueous layer extracted with further EtOAc (1×75 mL). The combined EtOAc layers were washed with 10% aqueous KH₂PO₄ (4×100 mL) and then brine (70 mL). The organic layer was dried (MgSO₄) and evaporated to give the product as a colourless solid (25.8 g, 98%), MS: [M+H]⁺=640.

The following compounds were prepared following a method analogous to that of Preparation 19:

tert-Butyl (2R,5S)-5-{[(3R,5R)-3,5-dimethylmorpholin-4-yl]methyl}-4-(2-{6-[(4-fluorophenyl)methyl]-5-(hydroxymethyl)-3,3-dimethyl-1H,2H,3H-pyrrolo[3,2-b]pyridin-1-yl}-2-oxoethyl)-2-methylpiperazine-1-carboxylate, MS: [M+H]⁺=654.

tert-Butyl (2R,5S)-5-{[(3R,5R)-3,5-dimethylmorpholin-4-yl]methyl}-4-(2-{6-[(4-fluorophenyl)methyl]-3,3-dimethyl-5-oxo-1H,2H,3H,4H,5H-pyrrolo[3,2-b]pyridin-1-yl}-2-oxoethyl)-2-methylpiperazine-1-carboxylate, MS: [M+H]⁺=640.

tert-Butyl (2R,5S)-4-(2-{6-[(2-fluorophenyl)methyl]-5-(hydroxymethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate, MS: [M+H]⁺=640.

tert-Butyl (2R,5S)-4-(2-{6-[(4-fluorophenyl)methyl]-3,3-dimethyl-5-oxo-1H,2H,3H,4H,5H-pyrrolo[3,2-b]pyridin-1-yl}-2-oxoethyl)-2-methyl-5-{[(3R)-3-methylmorpholin-4-yl]methyl}piperazine-1-carboxylate, MS: [M+H]⁺=626.

tert-Butyl (2R,5S)-4-(2-{6-[(4-fluorophenyl)methyl]-3,3,4-trimethyl-5-oxo-1H,2H,3H,4H,5H-pyrrolo[3,2-b]pyridin-1-yl}-2-oxoethyl)-2-methyl-5-{[(3R)-3-methylmorpholin-4-yl]methyl}piperazine-1-carboxylate, MS: [M+H]⁺=640.

tert-Butyl (2R,5S)-4-(2-{6-[(2,4-difluorophenyl)methyl]-3,3-dimethyl-5-oxo-1H,2H,3H,4H,5H-pyrrolo[3,2-b]pyridin-1-yl}-2-oxoethyl)-5-{[(3R,5R)-3,5-dimethylmorpholin-4-yl]methyl}-2-methylpiperazine-1-carboxylate, MS: [M+H]⁺=658.

tert-Butyl (2R,5S)-4-(2-{6-[(2,4-difluorophenyl)methyl]-3,3-dimethyl-5-oxo-1H,2H,3H,4H,5H-pyrrolo[3,2-b]pyridin-1-yl}-2-oxoethyl)-2-methyl-5-{[(3R)-3-methylmorpholin yl]methyl}piperazine-1-carboxylate, MS: [M+H]⁺=644.

tert-Butyl (2R,5S)-4-(2-{6-[(2-fluorophenyl)methyl]-3,3,4-trimethyl-5-oxo-1H,2H,3H,4H,5H-pyrrolo[3,2-b]pyridin-1-yl}-2-oxoethyl)-2-methyl-5-{[(3R)-3-methylmorpholin yl]methyl}piperazine-1-carboxylate, MS: [M+H]⁺=640.

tert-Butyl (2R,5S)-5-{[(3R,5R)-3,5-dimethylmorpholin-4-yl]methyl}-4-(2-{6-[(4-fluorophenyl)methyl]-3,3,4-trimethyl-5-oxo-1H,2H,3H,4H,5H-pyrrolo[3,2-b]pyridin-1-yl}-2-oxoethyl)-2-methylpiperazine-1-carboxylate, MS: [M+H]⁺=654.

tert-Butyl (2R,5S)-4-(2-{6-[(2,4-difluorophenyl)methyl]-5-(hydroxymethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate, 1H NMR (400 MHz, Me-d3-OD): 8.12 (1H, s), 7.27-7.16 (1H, m), 7.06-6.86 (2H, m), 4.76 (2H, s), 4.17 (1H, s), 4.10-4.07 (2H, m), 3.99 (1H, d), 3.74-3.49 (5H, m), 3.30-3.22 (2H, m), 2.97-2.77 (4H, m), 2.59-2.43 (2H, m), 2.43-2.32 (1H, m), 2.32-2.21 (1H, m), 1.47 (9H, s), 1.43 (6H, s), 1.22 (3H, d), 1.00 (3H, d).

tert-Butyl (2R,5S)-4-{2-[5-(1,2-dihydroxyethyl)-6-[(4-fluorophenyl)methyl]-3,3-dimethyl-1H,2H,3H-pyrrolo[3,2-b]pyridin-1-yl]-2-oxoethyl}-2-methyl-5-{[(3R)-3-methylmorpholin-4-yl]methyl}piperazine-1-carboxylate MS: [M+H]⁺=670; chiral HPLC (heptane/ethanol, 80:20, 0.2% DEA, chiralPAk-IC column) gave faster eluting diastereoisomer A, MS: [M+H]⁺=670 and slower eluting diastereoisomer B, MS: [M+H]⁺=670.

tert-Butyl (2R,5S)-4-(2-{6-[(3-fluorophenyl)methyl]-5-(hydroxymethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate, MS: [M+H]⁺=640.

tert-Butyl (2R,5S)-5-{[(3R,5R)-3,5-dimethylmorpholin-4-yl]methyl}-4-(2-{6-[(4-fluorophenyl)methyl]-3,3-dimethyl-5-oxo-1H,2H,3H,5H,6H-pyrrolo[2,3-c]pyridin-1-yl}-2-oxoethyl)-2-methylpiperazine-1-carboxylate, MS: [M+H]⁺=640.

tert-Butyl (2R,5S)-4-(2-{6-[(4-fluorophenyl)methyl]-3,3-dimethyl-5-oxo-1H,2H,3H,5H,6H-pyrrolo[2,3-c]pyridin-1-yl}-2-oxoethyl)-2-methyl-5-{[(3R)-3-methylmorpholin-4-yl]methyl}piperazine-1-carboxylate, MS: [M+H]⁺=626.

tert-Butyl (2R,5S)-5-{[(2S,5R)-2,5-dimethylmorpholin-4-yl]methyl}-4-(2-{6-[(4-fluorophenyl)methyl]-3,3,4-trimethyl-5-oxo-1H,2H,3H,4H,5H-pyrrolo[3,2-b]pyridin-1-yl}-2-oxoethyl)-2-methylpiperazine-1-carboxylate, MS: [M+H]⁺=654.

tert-Butyl (2R,5S)-4-(2-{6-[(2,4-difluorophenyl)methyl]-3,3-dimethyl-5-oxo-1H,2H,3H,5H,6H-pyrrolo[2,3-c]pyridin-1-yl}-2-oxoethyl)-5-{[(3R,5R)-3,5-dimethylmorpholin-4-yl]methyl}-2-methylpiperazine-1-carboxylate, MS: [M+H]⁺=658.

tert-Butyl (2R,5S)-4-{2-[5-((R or S)-1,2-dihydroxyethyl)-6-[(4-fluorophenyl)methyl]-3,3-dimethyl-1H,2H,3H-pyrrolo[3,2-b]pyridin-1-yl]-2-oxoethyl}-5-{[(3R,5R)-3,5-dimethylmorpholin-4-yl]methyl}-2-methylpiperazine-1-carboxylate, MS: [M+H]⁺=684.

tert-Butyl (2R,5S)-4-(2-{6-[(2,4-difluorophenyl)methyl]-3,3-dimethyl-5-oxo-1H,2H,3H,5H,6H-pyrrolo[2,3-c]pyridin-1-yl}-2-oxoethyl)-5-{[(2S,5R)-2,5-dimethylmorpholin-4-yl]methyl}-2-methylpiperazine-1-carboxylate, MS: [M+H]⁺=658.

tert-Butyl (2R,5S)-4-(2-{4-amino-6-[(2,4-difluorophenyl)methyl]-3,3-dimethyl-5-oxo-1H,2H,3H,4H,5H-pyrrolo[3,2-b]pyridin-1-yl}-2-oxoethyl)-2-methyl-5-{[(3R)-3-methylmorpholin yl]methyl}piperazine-1-carboxylate, MS: [M+H]⁺=659.

tert-Butyl (2R,5S)-4-(2-{4-amino-6-[(4-fluorophenyl)methyl]-3,3-dimethyl-5-oxo-1H,2H,3H,4H,5H-pyrrolo[3,2-b]pyridin-1-yl}-2-oxoethyl)-2-methyl-5-{[(3R)-3-methylmorpholin-4-yl]methyl}piperazine-1-carboxylate, MS: [M+H]⁺=641.

tert-Butyl (2R,5S)-4-(2-{6-[(2,4-difluorophenyl)methyl]-3,3,4-trimethyl-5-oxo-1H,2H,3H,4H,5H-pyrrolo[3,2-b]pyridin-1-yl}-2-oxoethyl)-5-{[(2S,5R)-2,5-dimethylmorpholin-4-yl]methyl}-2-methylpiperazine-1-carboxylate, MS: [M+H]⁺=672.

tert-Butyl (2R,5S)-4-(2-{6-[(4-fluorophenyl)methyl]-5-((R or S)1-hydroxy-2-methoxyethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate (from faster eluting isomer), MS: [M+H]⁺=684.

tert-Butyl (2R,5S)-4-(2-{6-[(4-fluorophenyl)methyl]-5-((R or S)1-hydroxy-2-methoxyethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate (from slower eluting isomer), MS: [M+H]⁺=684.

tert-Butyl (2R,5S)-4-(2-{6-[(4-fluorophenyl)methyl]-5-((R or S)1-methoxy-2-hydroxyethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate (from faster eluting isomer), MS: [M+H]$^+$ =684.
tert-Butyl (2R,5S)-4-(2-{6-[(4-fluorophenyl)methyl]-5-((R or S)1-methoxy-2-hydroxyethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate (from slower eluting isomer), MS: [M+H]$^+$ =684.
tert-Butyl (2R,5S)-4-(2-{4-amino-6-butyl-3,3-dimethyl-5-oxo-1H,2H,3H,4H,5H-pyrrolo[3,2-b]pyridin-1-yl}-2-oxoethyl)-5-{[(3R,5R)-3,5-dimethylmorpholin-4-yl]methyl}-2-methylpiperazine-1-carboxylate, MS: [M+H]$^+$ =603.
tert-Butyl (2R,5S)-4-(2-{6-[(2,4-difluorophenyl)methyl]-3,3,4-trimethyl-5-oxo-1H,2H,3H,5H,6H-pyrrolo[2,3-c]pyridin-1-yl}-2-oxoethyl)-2-methyl-5-{[(3R)-3-methylmorpholin-4-yl]methyl}piperazine-1-carboxylate, MS: [M+H]$^+$=658.
tert-Butyl (2R,5S)-4-(2-{6-butyl-3,3-dimethyl-5-oxo-1H,2H,3H,4H,5H-pyrrolo[3,2-b]pyridin-1-yl}-2-oxoethyl)-5-{[(3R,5R)-3,5-dimethylmorpholin-4-yl]methyl}-2-methylpiperazine-1-carboxylate, MS: [M+H]$^+$=588.
tert-Butyl (2R,5S)-4-(2-{6-butyl-3,3,4-trimethyl-5-oxo-1H,2H,3H,4H,5H-pyrrolo[3,2-b]pyridin-1-yl}-2-oxoethyl)-5-{[(3R,5R)-3,5-dimethylmorpholin-4-yl]methyl}-2-methylpiperazine-1-carboxylate, MS: [M+H]$^+$=602.
tert-Butyl (2R,5S)-4-{2-[6-butyl-5-(hydroxymethyl)-3,3-dimethyl-1H,2H,3H-pyrrolo[3,2-b]pyridin-1-yl]-2-oxoethyl}-5-{[(3R,5R)-3,5-dimethylmorpholin-4-yl]methyl}-2-methylpiperazine carboxylate, MS: [M+H]$^+$=602.
tert-Butyl (2R,5S)-4-(2-{6-butyl-3,3-dimethyl-5-oxo-1H,2H,5H,6H-pyrrolo[2,3-c]pyridin-1-yl}-2-oxoethyl)-5-{[(3R,5R)-3,5-dimethylmorpholin-4-yl]methyl}-2-methylpiperazine-1-carboxylate, MS: [M+H]$^+$=588.
tert-Butyl (2R,5S)-5-{[(3R,5R)-3,5-dimethylmorpholin-4-yl]methyl}-4-(2-{6-[(4-fluorophenyl)methyl]-5-((R or S)-2-hydroxy-1-methoxyethyl)-3,3-dimethyl-1H,2H,3H-pyrrolo[3,2-b]pyridin-1-yl}-2-oxoethyl)-2-methylpiperazine-1-carboxylate, MS: [M+H]$^+$=698.
tert-Butyl (2R,5S)-4-(2-{6-butyl-3,3-dimethyl-5-oxo-1H,2H,3H,4H,5H-pyrrolo[3,2-b]pyridin-1-yl}-2-oxoethyl)-5-{[(2S,5R)-2,5-dimethylmorpholin-4-yl]methyl}-2-methylpiperazine-1-carboxylate, MS: [M+H]$^+$=588.

Preparation 20: (2R,5S)-4-{2-[6-(2,4-Difluoro-benzyl)-3,3,4-trimethyl-5-oxo-2,3,4,5-tetrahydro-pyrrolo[3,2-b]pyridin-1-yl]-2-oxo-ethyl}-5-((3R,5R)-3,5-dimethyl-morpholin-4-ylmethyl)-2-methyl-piperazine-1-carboxylic acid tert-butyl ester (2R,5S)-4-{2-[6-(2,4-Difluoro-benzyl)-3,3-dimethyl-5-oxo-2,3,4,5-tetrahydro-pyrrolo[3,2-b]pyridin-1-yl]-2-oxoethyl}-5-((3R,5R)-3,5-dimethyl-morpholin-4-ylmethyl)-2-methyl-piperazine-1-carboxylic acid tert-butyl ester (146 mg, 0.22 mmol) was dissolved in DMF (3 mL). Sodium hydride (60%, 11 mg, 0.27 mmol) was added and the reaction mixture was stirred for 30 mins. Iodomethane (0.017 mL, 0.27 mmol) was added and the reaction was stirred for 30 mins at room temperature before being partitioned between water (10 mL) and EtOAc (2×10 mL). The organic fractions were washed with brine, dried over magnesium sulfate and concentrated. The residue was purified by column chromatography, eluting with 0-10% MeOH in EtOAc and then by preparative HPLC to give the title compound (17.6 mg). MS: [M+H]$^+$=672.

Preparation 21: (2R,5S)-4-{2-[6-(2,4-Difluoro-benzyl)-3,3,4-trimethyl-5-oxo-2,3,4,5-tetrahydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester (2R,5S)-4-{2-[6-(2,4-Difluoro-benzyl)-3,3-dimethyl-5-oxo-2,3,4,5-tetrahydro-pyrrolo[3,2-b]pyridin-1-yl]-2-oxoethyl}-2-methyl-5-((R)-3-methyl-morpholin-4-ylmethyl)-piperazine-1-carboxylic acid tert-butyl ester (670 mg, 1.04 mmol) was dissolved in THF (20 mL). Lithium tert-butoxide (170 mg, 2.08 mmol) was added, followed by iodomethane (0.16 mL, 2.60 mmol). The reaction was stirred overnight at room temperature before being partitioned between water (30 mL) and EtOAc (2×30 mL). The organic fractions were washed with brine, dried over magnesium sulfate and concentrated. The residue was purified by column chromatography, eluting with 0-10% MeOH in DCM to give the title compound (350 mg). MS: [M+H]$^+$=658.

The following compound was prepared in an analogous method to Preparation 21:

21A: (2R,5S)-4-[2-(6-Butyl-3,3,4-trimethyl-5-oxo-2,3,4,5-tetrahydro-pyrrolo[3,2-b]pyridin-1-yl) oxo-ethyl]-5-((3R,5R)-3,5-dimethyl-morpholin-4-ylmethyl)-2-methyl-piperazine-1-carboxylic acid tert-butyl ester, MS: [M+H]$^+$=602.

Preparation 22: tert-Butyl 6-[(4-fluorophenyl)methyl]-3,3-dimethyl-4-oxy-1H,2H,3H-pyrrolo[3,2-b]pyridine-1-carboxylate To a stirred solution of tert-butyl 6-[(4-fluorophenyl)methyl]-3,3-dimethyl-1H,2H,3H-pyrrolo[3,2-b]pyridine-1-carboxylate (which may be prepared as described in Preparation 15A) (3.88 g, 10.9 mmol) in DCM (30 mL) at ambient temperature was added, portionwise over 0.1 h, 3-chloroperbenzoic acid (77%, 2.7 g, 12.0 mmol). The mixture was stirred for 3 h then partitioned between saturated aqueous NaHCO$_3$ (150 mL) and DCM (3×30 mL). Combined organic extracts were dried (Na$_2$SO$_4$) and evaporated in vacuo. Residue was crystallised from ether-petrol to give the title compound (2.62 g). 1H NMR (400 MHz, Me-d3-OD): 7.74 (1H, s), 7.35-7.24 (2H, m), 7.13-7.02 (2H, m), 3.96 (2H, s), 3.79 (2H, s), 1.57 (6H, s), 1.53 (9H, s).

Preparation 23: tert-Butyl 6-[(4-fluorophenyl)methyl]-3,3-dimethyl-5-oxo-1H,2H,3H,4H,5H-pyrrolo[3,2-b]pyridine-1-carboxylate A mixture of tert-butyl 6-[(4-fluorophenyl)methyl]-3,3-dimethyl-4-oxy-1H,2H,3H-pyrrolo[3,2-b]pyridine-1-carboxylate (which may be prepared as described in Preparation 22) (0.6 g, 1.6 mmol) and acetic anhydride (4 mL) was heated at 105° C. for 2 h then at 140° C. for 3 h, cooled then resulting solution poured into ice-water (~100 g). Resulting colourless solid was collected by filtration, then was suspended in methanol (15 mL). Aqueous NaOH (1 M, 1.8 mL) was added and mixture stirred for 0.25 h. The solution was concentrated to 12 mL in vacuo then diluted with water (20 mL) and resulting solid collected by filtration to give the title compound (0.6 g). MS: [M+H]$^+$=373.

The following compound was prepared in a similar manner to Preparation 23:

23A: tert-Butyl 6-[(2-fluorophenyl)methyl]-3,3-dimethyl-5-oxo-1H,2H,3H,4H,5H-pyrrolo[3,2-b]pyridine-1-carboxylate Preparation 24: 6-[(4-Fluorophenyl)methyl]-3,3-dimethyl-5-oxo-1H,2H,3H,4H,5H-pyrrolo[3,2-b]pyridine A mixture of tert-butyl 6-[(4-fluorophenyl)methyl]-3,3-dimethyl-5-oxo-1H,2H,3H,4H,5H-pyrrolo[3,2-b]pyridine-1-carboxylate (which may be prepared as described in Preparation 23) (0.6 g, 1.6 mmol), methanol (20 mL) and 5 M aqueous HCl (20 mL) was heated at reflux for 16 h, cooled then treated with water. Resulting solid was collected by filtration to give the title compound (0.255 g). MS: [M+H]$^+$=273.

Preparation 25: 1-[5-Bromo-6-(3-fluoro-benzyl)-3,3-dimethyl-2,3-dihydro-pyrrolo[3,2-b]pyridin-1-yl]-ethanone To a solution of 5-bromo-6-(3-fluoro-benzyl)-3,3-dimethyl-2,3-dihydro-1H-pyrrolo[3,2-b]pyridine (which may be prepared as described in Preparation 16A) (4.5 g, 13.43 mmol) in toluene (50 mL) was added acetyl chloride (1.05 mL, 14.78 mmol) and the reaction mixture was stirred at room temperature overnight. Saturated NaHCO$_3$ solution (50 mL) was added and the product was extracted with EtOAc (2×40 mL). The organic phase was washed with brine, dried, filtered and the solvent evaporated to afford the title compound (4.99 g). MS: [M+H]$^+$=377.

The following compound was prepared in a similar manner to that described in Preparation 25:
25A: 1-[5-Bromo-6-(4-fluoro-benzyl)-3,3-dimethyl-2,3-dihydro-pyrrolo[3,2-b]pyridin-1-yl]-ethanone, MS: [M+H]$^+$=377.

Preparation 26: 1-[6-(3-Fluoro-benzyl)-3,3,5-trimethyl-2,3-dihydro-pyrrolo[3,2-b]pyridin-1-yl]-ethanone To a degassed solution of 1-[5-bromo-6-(3-fluoro-benzyl)-3,3-dimethyl-2,3-dihydro-pyrrolo[3,2-b]pyridin-1-yl]-ethanone (which may be prepared as described in Preparation 25) (4.9 g, 13.0 mmol), LiBr (3.35 g, 39.0 mmol) and [1,3-bis(2,6-diisopropylphenyl)imidazol-2-ylidene](3-chloropyridyl)palladium(II) dichloride (180 mg, 0.26 mmol) in THF (30 mL) and NMP (30 mL) was added methylzinc chloride (2M in THF, 10 mL, 20 mmol) and the reaction mixture was stirred at room temperature overnight. The reaction mixture was poured into water (20 mL) and 5% aqueous citric acid (3 mL) and the product was extracted with toluene—EtOAc (1:1, 2×40 mL). The organic phase was washed with brine, dried, filtered and the solvent evaporated to afford the title compound (4.05 g). MS: [M+H]$^+$=313.

Preparation 27: 1-[6-(3-Fluoro-benzyl)-3,3,5-trimethyl-4-oxy-2,3-dihydro-pyrrolo[3,2-b]pyridin-1-yl]-ethanone To a solution of 1-[6-(3-fluoro-benzyl)-3,3,5-trimethyl-2,3-dihydro-pyrrolo[3,2-b]pyridin-1-yl]-ethanone (which may be prepared as described in Preparation 26) (4.05 g, 13.0 mmol) in DCM (50 mL) was added m-chloro-perbenzoic acid (77%, 4.4 g, 19.5 mmol) in small portions and the reaction mixture was stirred at room temperature for 2 h. Na$_2$S$_2$O$_3$ (10%, 50 mL) was added and stirred for 30 mins. The product was extracted with DCM (3×40 mL), the combined organic layers were washed with 1M NaOH, dried, filtered and the solvent evaporated to afford the title compound (4.22 g). MS: [M+H]$^+$=329.

Preparation 28: Acetic acid 1-acetyl-6-(3-fluoro-benzyl)-3,3-dimethyl-2,3-dihydro-1H-pyrrolo[3,2-b]pyridin-5-ylmethyl ester A solution of 1-[6-(3-fluoro-benzyl)-3,3,5-trimethyl-4-oxy-2,3-dihydro-pyrrolo[3,2-b]pyridin-1-yl]-ethanone (which may be prepared as described in Preparation 27) (4.22 g, 12.86 mmol) in acetic anhydride (25 mL) was heated at 110° C. for 2 h. The reaction mixture was cooled, poured onto ice and stirred for 2 h. The mixture was neutralized with Na$_2$CO$_3$ and the product extracted with DCM (3×30 mL). The organic phase was dried, filtered and the solvent evaporated. The crude product was purified on Silica, eluted with petrol —EtOAc 0-50% to afford the title compound (3.49 g). MS: [M+H]$^+$=371.

Preparation 29: [6-(3-Fluoro-benzyl)-3,3-dimethyl-2,3-dihydro-1H-pyrrolo[3,2-b]pyridin-5-yl]-methanol A solution of acetic acid 1-acetyl-6-(3-fluoro-benzyl)-3,3-dimethyl-2,3-dihydro-1H-pyrrolo[3,2-b]pyridin-5-ylmethyl ester (which may be prepared as described in Preparation 28) (3.49 g, 9.43 mmol) and NaOH (6.0 g, 150 mmol) in EtOH (60 mL) and water (60 mL) was heated at reflux overnight. The EtOH was evaporated, the pH was adjusted to pH=8 with 5 M HCl and the product was extracted with DCM (3×30 mL). The organic phase was dried, filtered and the solvent evaporated. The crude product was purified on Silica, eluted with petrol —EtOAc 0-100% to afford the title compound (2.04 g). MS: [M+H]$^+$=287.

The following compounds were prepared using a similar sequence to that described in Preparations 25-29 inclusive:
[6-(2-Fluoro-benzyl)-3,3-dimethyl-2,3-dihydro-1H-pyrrolo[3,2-b]pyridin-5-yl]-methanol, [M+H]$^+$=287.
[6-(4-Fluoro-benzyl)-3,3-dimethyl-2,3-dihydro-1H-pyrrolo[3,2-b]pyridin-5-yl]-methanol, [M+H]$^+$=287.
[6-(2,4-Difluoro-benzyl)-3,3-dimethyl-2,3-dihydro-1H-pyrrolo[3,2-b]pyridin-5-yl]-methanol, $^1$H NMR (400 MHz, Me-d3-OD): 7.22-7.12 (1H, m), 7.00-6.82 (2H, m), 6.67-6.59 (1H, m), 4.72-4.61 (2H, m), 4.04 (2H, s), 1.34 (6H, s).

Preparation 30: 1-[6-(4-Fluoro-benzyl)-3,3-dimethyl-2,3-dihydro-pyrrolo[3,2-b]pyridin-1-yl]-ethanone To a solution of 6-(4-fluoro-benzyl)-3,3-dimethyl-2,3-dihydro-1H-pyrrolo[3,2-b]pyridine (which may be prepared as described in Preparation 15) (10.1 g, 39 mmol) in MeCN (130 mL), at ~10° C., was added acetyl chloride (3.6 mL, 51 mmol). The mixture was stirred overnight at RT and then evaporated in vacuo. The residue was partitioned between CH$_2$Cl$_2$ and 1N aqueous NaOH. CH$_2$Cl$_2$ layer was dried (MgSO$_4$) and evaporated to give the title compound (12.3 g) as a crystalline solid. MS: m/z=299 (M+H$^+$)$^+$.

Preparation 31: 1-[6-(4-Fluoro-benzyl)-3,3-dimethyl-4-oxy-2,3-dihydro-pyrrolo[3,2-b]pyridin-1-yl]-ethanone 1-[6-(4-Fluoro-benzyl)-3,3-dimethyl-2,3-dihydro-pyrrolo[3,2-b]pyridin-1-yl]-ethanone (which may be prepared as described in Preparation 30) (12.2 g, 41 mmol) and mCPBA (77%, 12 g, ~53 mmol) were dissolved in $CH_2Cl_2$ (150 mL) and stirred for 3 hours. 20% aqueous $Na_2S_2O_3$ was then added and the mixture stirred for 25 minutes. The aqueous layer was extracted with a further batch of $CH_2Cl_2$ and then the combined $CH_2Cl_2$ layers were washed with 2×1N aqueous NaOH. The organic layer was dried ($MgSO_4$) and evaporated in vacuo to give the title compound (12 g) as a yellow crystalline solid. MS: m/z=315 $(M+H^+)^+$.

Preparation 32: Acetic acid 1-acetyl-6-(4-fluoro-benzyl)-3,3-dimethyl-2,3-dihydro-1H-pyrrolo[3,2-b]pyridin-5-yl ester 1-[6-(4-Fluoro-benzyl)-3,3-dimethyl-4-oxy-2,3-dihydro-pyrrolo[3,2-b]pyridin-1-yl]-ethanone (which may be prepared as described in Preparation 31) (11.55 g, 37 mmol) was heated in $Ac_2O$ (70 mL) for 5 hours. The mixture was then cooled and poured into ice/water (500 g). The mixture was stirred for 1 hour and the resulting precipitate collected by filtration to give the title compound (12.1 g, 92%) as a grey solid. MS: m/z=357 $(M+H^+)^+$.

Preparation 33: 1-Acetyl-6-(4-fluoro-benzyl)-3,3-dimethyl-1,2,3,4-tetrahydro-pyrrolo[3,2-b]pyridin-5-one Acetic acid 1-acetyl-6-(4-fluoro-benzyl)-3,3-dimethyl-2,3-dihydro-1H-pyrrolo[3,2-b]pyridin-5-yl ester (which may be prepared as described in Preparation 32) (6 g, 19 mmol) was suspended in EtOH (60 mL) and treated with 2N aqueous NaOH (42 mL). The mixture was stirred overnight and then acidified with 5N aqueous HCl. The product was extracted with $CH_2Cl_2$ and the organic layer dried ($MgSO_4$). Purification by $SiO_2$ chromatography (eluting with 50-100% EtOAc/hexanes) gave a yellow solid. This was triturated with toluene and the solid collected to give the title compound (2.4 g, 44%). MS: m/z=315 $(M+H^+)^+$.

The following compounds were prepared in a similar manner to that described in Preparations 30-33:
1-Acetyl-6-(2,4-difluoro-benzyl)-3,3-dimethyl-1,2,3,4-tetrahydro-pyrrolo[3,2-b]pyridin-5-one, MS: $[M+H]^+$=333.
1-Acetyl-6-butyl-3,3-dimethyl-1,2,3,4-tetrahydro-pyrrolo[3,2-b]pyridin-5-one, MS: $[M+H]^+$=263.

Preparation 34: 1-Acetyl-6-(4-fluoro-benzyl)-3,3,4-trimethyl-1,2,3,4-tetrahydro-pyrrolo[3,2-b]pyridin-5-one To a mixture of 1-acetyl-6-(4-fluoro-benzyl)-3,3-dimethyl-1,2,3,4-tetrahydro-pyrrolo[3,2-b]pyridin-5-one (which may be prepared as described in Preparation 33) (3.1 g, 9.9 mmol) and $K_2CO_3$ (2.7 g, 20 mmol) in DMF (30 mL), at 0° C., was added iodomethane (0.74 mL, 11.9 mmol). The mixture was allowed to stir at RT for 5 h after which the mixture was partitioned between EtOAc and water. The EtOAc layer was washed with brine and dried ($MgSO_4$). Purification by $SiO_2$ chromatography (eluting with 0-10% MeOH/EtOAc) gave the title compound (960 mg, 29%) as a colourless crystalline solid. MS: $[M+H]^+$=329.

Preparation 35: 6-(4-Fluoro-benzyl)-3,3,4-trimethyl-1,2,3,4-tetrahydro-pyrrolo[3,2-b]pyridin-5-one 1-Acetyl-6-(4-fluoro-benzyl)-3,3,4-trimethyl-1,2,3,4-tetrahydro-pyrrolo[3,2-b]pyridin-5-one (which may be prepared as described in Preparation 34) (960 mg, 2.9 mmol) was dissolved in a mixture of EtOH (10 mL) and 5N aqueous HCl (10 mL) and heated at 95° C. for 1 hour under $N_2$. The mixture was then cooled and concentrated in vacuo. Ice and conc. aqueous $NH_3$ were added and the resulting aqueous mixture was extracted with $CH_2Cl_2$. The $CH_2Cl_2$ solution was dried ($MgSO_4$) and evaporated to give the title compound which was used immediately. MS: $[M+H]^+$=287.

The following compound was prepared in a similar manner to that described in Preparations 30-35:
6-(2,4-Difluoro-benzyl)-3,3,4-trimethyl-1,2,3,4-tetrahydro-pyrrolo[3,2-b]pyridin-5-one, MS: $[M+H]^+$=269.

The following compounds were prepared in a similar manner to that described in Preparation 35:
6-(4-Fluoro-benzyl)-3,3,-dimethyl-1,2,3,4-tetrahydro-pyrrolo[3,2-b]pyridin-5-one, MS: $[M+H]^+$=273.
6-Butyl-3,3-dimethyl-1,2,3,4-tetrahydro-pyrrolo[3,2-b]pyridin-5-one, MS: $[M+H]^+$=221.
6-[(2,4-Difluorophenyl)methyl]-3,3-dimethyl-5-oxo-1H,2H,3H,4H,5H-pyrrolo[3,2-b]pyridine, MS: $[M+H]^+$=291.

Preparation 36: 6-(2-Fluoro-benzyl)-3,3,4-trimethyl-5-oxo-2,3,4,5-tetrahydro-pyrrolo[3,2-b]pyridine-1-carboxylic acid tert-butyl ester Prepared from tert-butyl 6-[(2-fluorophenyl)methyl]-3,3-dimethyl-5-oxo-1H,2H,3H,4H,5H-pyrrolo[3,2-b]pyridine-1-carboxylate using a similar method to that described in Preparation 34. MS: $[M+H]^+$=387.

Preparation 37: 6-(2-Fluoro-benzyl)-3,3,4-trimethyl-1,2,3,4-tetrahydro-pyrrolo[3,2-b]pyridin-5-one Prepared from 6-(2-fluoro-benzyl)-3,3,4-trimethyl-5-oxo-2,3,4,5-tetrahydro-pyrrolo[3,2-b]pyridine-1-carboxylic acid tert-butyl ester (which may be prepared as described in Preparation 36) using a similar method to that described in Preparation 24. MS: $[M+H]^+$=287.

Preparation 38: 1-[6-(4-Fluoro-benzyl)-3,3-dimethyl-5-vinyl-2,3-dihydro-pyrrolo[3,2-b]pyridin-1-yl]-ethanone 1-[5-Bromo-6-(4-fluoro-benzyl)-3,3-dimethyl-2,3-dihydro-pyrrolo[3,2-b]pyridin-1-yl]-ethanone (which may be prepared as described in Preparation 25A) (7.64 g, 20.27 mmol), tributylvinyltin (6.22 mL, 21.28 mmol) and bis(tri-tert-butylphosphine)palladium(0) (0.104 g, 0.20 mmol) were dissolved in toluene (39 mL). After being degassed with nitrogen, the reaction was heated to 85° C. for 2h. The reaction was concentrated in vacuo and the crude product was purified by column chromatography on silica gel (gradient elution, 0-100%, ethyl acetate/petrol 40-60° C.), to give the title compound (3.64 g). MS: $[M+H]^+$=325.

Preparation 39: (RS)-1-[5-(1,2-Di hydroxy-ethyl)-6-(4-fluoro-benzyl)-3,3-dimethyl-2,3-dihydro-pyrrolo[3,2-b]pyridin-1-yl]-ethanone To 1-[6-(4-fluoro-benzyl)-3,3-dimethyl-5-vinyl-2,3-dihydro-pyrrolo[3,2-b]pyridin-1-yl]-ethanone (which may be prepared as described in Preparation 38) (3.64 g, 11.23 mmol) in acetone (76 mL) and water (8.5 mL) was added aqueous sodium hydroxide (2.5 M, 13.48 mL, 11.23 mmol) and the reaction cooled to 0° C. (ice bath). Potassium permanganate (1.78 g, 11.23 mol) was added to the reaction and stirred for 1 h. The reaction was warmed to room temperature and stirred for 20 h. Additional potassium permanganate was added (1.77 g, 33.7 mmol) and after 1h the reaction was filtered through celite washing with acetone and water. The filtrate was concentrated to give an aqueous mixture which was extracted with ethyl acetate (3×). The combined organics were dried over sodium sulfate, filtered and concentrated in vacuo. The crude product was purified by column chromatography on silica gel (gradient elution, 0-100%, ethyl acetate/petrol 40-60° C.), to give the title compound (1.5 g). MS: $[M+H]^+=359$.

Chiral Purification (RS)-1-[5-(1,2-Dihydroxy-ethyl)-6-(4-fluoro-benzyl)-3,3-dimethyl-2,3-dihydro-pyrrolo[3,2-b]pyridin-1-yl]-ethanone (which may be prepared as described in Preparation 39) (1.5 g) was purified by chiral preparative HPLC (ChiralPAK AD-H, heptane/ethanol), to give 39 Å (R or S)-1-[5-(1,2-dihydroxy-ethyl)-6-(4-fluoro-benzyl)-3,3-dimethyl-2,3-dihydro-pyrrolo[3,2-b]pyridin-1-yl]-ethanone (fast running isomer) (0.5 g) and 39B (R or S)-1-[5-(1,2-Dihydroxy-ethyl)-6-(4-fluoro-benzyl)-3,3-dimethyl-2,3-dihydro-pyrrolo[3,2-b]pyridin-1-yl]-ethanone (slower running isomer) (0.6 g).

Preparation 40: (RS)-1-[6-(4-Fluoro-benzyl)-3,3-dimethyl-2,3-dihydro-1H-pyrrolo[3,2-b]pyridin-5-yl]-ethane-1,2-diol (RS)-1-[5-(1,2-Dihydroxy-ethyl)-6-(4-fluoro-benzyl)-3,3-dimethyl-2,3-dihydro-pyrrolo[3,2-b]pyridin-1-yl]-ethanone (which may be prepared as described in Preparation 39) (0.250 mg, 0.70 mmol) was dissolved in ethanol (4.37 mL) and water (4.37 mL). Sodium hydroxide (0.447 g, 11.2 mmol) was added and the reaction was heated to reflux for 4 h. After cooling to room temperature, the reaction was concentrated. Water was added and the aqueous was extracted with ethyl acetate (3×). The combined organic extracts were dried over sodium sulfate, filtered and concentrated, to give the title compound, (171 mg). MS: $[M+H]^+=317$.

The following compounds were prepared in a similar manner to that described in Preparation 40:

40A: (R or S)-1-[6-(4-Fluoro-benzyl)-3,3-dimethyl-2,3-dihydro-1H-pyrrolo[3,2-b]pyridin-5-yl]-ethane-1,2-diol, from slower eluting isomer 39B. MS: $[M+H]^+=317$.

40B: (R or S)-1-[6-(4-Fluoro-benzyl)-3,3-dimethyl-2,3-dihydro-1H-pyrrolo[3,2-b]pyridin-5-yl]-2-methoxy-ethanol, from faster eluting precursor, MS: $[M+H]^+=331$.

40C: (R or S)-1-[6-(4-Fluoro-benzyl)-3,3-dimethyl-2,3-dihydro-1H-pyrrolo[3,2-b]pyridin-5-yl]-2-methoxy-ethanol, from slower eluting precursor, MS: $[M+H]^+=331$.

40D: (R or S)-2-[6-(4-Fluoro-benzyl)-3,3-dimethyl-2,3-dihydro-1H-pyrrolo[3,2-b]pyridin-5-yl]-2-methoxy-ethanol from faster eluting precursor, MS: $[M+H]^+=331$.

40E: (R or S)-2-[6-(4-Fluoro-benzyl)-3,3-dimethyl-2,3-dihydro-1H-pyrrolo[3,2-b]pyridin-5-yl]-2-methoxy-ethanol from slower eluting precursor, MS: $[M+H]^+=331$.

Preparation 41: (RS)-Methanesulfonic acid 2-[1-acetyl-6-(4-fluoro-benzyl)-3,3-dimethyl-2,3-dihydro-1H-pyrrolo[3,2-b]pyridin-5-yl]-2-hydroxy-ethyl ester To (RS)-1-[5-(1,2-dihydroxy-ethyl)-6-(4-fluoro-benzyl)-3,3-dimethyl-2,3-dihydro-pyrrolo[3,2-b]pyridin-1-yl]-ethanone (which may be prepared as described in Preparation 39) (1.48 g, 4.13 mol) in dichloromethane (20.7 mL) cooled to 0° C. was added triethylamine (0.502 g, 4.96 mmol) and methane sulfonyl chloride (0.34 mL, 4.34 mmol). The reaction was warmed to room temperature and stirred for 2h. The reaction was poured into water and extracted with DCM (3×). The combined organic extracts were dried over sodium sulfate, filtered and concentrated in vacuo. The crude product was purified by column chromatography on silica gel (gradient elution, 0-100%, ethyl acetate/petrol 40-60° C.), to give the title compound (1.25 g) MS: $[M+H]^+=437$.

Preparation 42: 1-[6-(4-Fluoro-benzyl)-5-(1-hydroxy-2-methoxy-ethyl)-3,3-dimethyl-2,3-dihydro-pyrrolo[3,2-b]pyridin-1-yl]-ethanone (42A) and 1-[6-(4-fluoro-benzyl)-5-(2-hydroxy-1-methoxy-ethyl)-3,3-dimethyl-2,3-dihydro-pyrrolo[3,2-b]pyridin-1-yl]-ethanone (42B)

To (RS)-methanesulfonic acid 2-[1-acetyl-6-(4-fluoro-benzyl)-3,3-dimethyl-2,3-dihydro-1H-pyrrolo[3,2-b]pyridin-5-yl]-2-hydroxy-ethyl ester (which may be prepared as described in Preparation 41) (1.24 g, 2.84 mmol) in methanol (9.48 mL), was added sodium methoxide (25%) in methanol (1.23 mL, 5.69 mmol). After stirring for 6 h additional sodium methoxide (25%) in methanol (1.23 mL) was added. Mixture was stirred for 18 h, then sodium methoxide (25%) in methanol (1.23 mL) was added. After stirring for a further 22 h, water was added and the reaction was extracted with ethyl acetate (3×). The combined organic extracts were concentrated in vacuo and the crude product was purified by column chromatography on silica gel (gradient elution, 0-100%, ethyl acetate/petrol 40-60° C.), to give, separately, the two title compounds as racemic mixtures. Chiral HPLC separation was carried out as follows:

42A: ADH column, 80/20 heptane ethanol, 0.2% DEA gave faster eluting 42A1 and slower eluting 42A2

42B: LUX-2 column, 80/20 heptane ethanol, 0.2% DEA gave faster eluting 42B1 [1H NMR (400 MHz, Me-d3-OD): 8.18 (1H, s), 7.19 (2H, dd), 7.03 (2H, t), 4.66 (1H, dd), 4.21-4.05 (2H, m), 4.05-3.82 (3H, m), 3.63 (1H, dd), 3.13 (3H, s), 2.24 (3H, s), 1.42 (6H, s)] and slower eluting 42B2

Preparation 43: (6-Methoxy-4-methyl-pyridin-3-yl)-carbamic Acid Tert-Butyl Ester To a solution of 5-amino-2-methoxy-4-picoline (5.0 g, 36.2 mmol) in THF (80 mL) and saturated aqueous $Na_2CO_3$ (20 mL) was added di-tert-butyl-dicarbonate (7.9 g, 36.2 mmol) and the reaction mixture was stirred overnight. The reaction mixture was concentrated, extracted with DCM, washed with brine, dried, filtered and the solvent evaporated to afford the title compound (8.8 g). MS: $[M+H]^+=239$.

Preparation 44: (5-tert-Butoxycarbonylamino-2-methoxy-pyridin-4-yl)-acetic Acid

To a solution of (6-methoxy-4-methyl-pyridin-3-yl)-carbamic acid tert-butyl ester (which may be prepared as described in Preparation 43) (2.8 g, 11.9 mmol) in THF (100 mL) was added sec-butyl lithium (1.4 M in cyclohexane, 28 mL, 39.3 mmol) at −78° C. The reaction mixture was stirred for 10 mins, then $CO_2$ gas was bubbled into it via cannula for 1 h. The reaction mixture was left to warm to room temperature, quenched with 2N HCl. The pH was adjusted to pH=4 with 1 N NaOH and the product extracted with EtOAc. The organic layer was washed with brine, dried, filtered and the solvent was evaporated to afford the title compound (4.4 g). MS: [M+H]$^+$=283.

Preparation 45: 5-Methoxy-2-oxo-2,3-dihydro-pyrrolo[2,3-c]pyridine-1-carboxylic Acid Tert-Butyl Ester A mixture of (5-tert-butoxycarbonylamino-2-methoxy-pyridin-4-yl)-acetic acid (which may be prepared as described in Preparation 44) (3.4 g, 11.9 mmol), diisopropyl-ethyl-amine (4.6 mL, 26.18 mmol), EDC (2.5 g, 13.09 mmol) and HOAt (1.78 g, 13.09 mmol) in DCM (50 mL) was stirred for 3 h. The reaction mixture was washed with saturated NaHCO$_3$, water, brine, then dried, filtered and the solvent was evaporated. The crude product was purified on silica, eluted with petrol —EtOAc 0-50% to afford the title compound (2.2 g). MS: [M+H]$^+$=265.

Preparation 46: 5-Methoxy-3,3-dimethyl-2-oxo-2,3-dihydro-pyrrolo[2,3-c]pyridine-1-carboxylic Acid Tert-Butyl Ester A mixture of 5-methoxy-2-oxo-2,3-dihydro-pyrrolo[2,3-c]pyridine-1-carboxylic acid tert-butyl ester (which may be prepared as described in Preparation 45) (1.94 g, 7.35 mmol), K$_2$CO$_3$ (2.33 g, 18.57 mmol) and iodomethane (1.14 mL, 18.57 mmol) in acetone (25 mL) was heated at reflux for 3 h. The reaction mixture was cooled, the solvent evaporated, the residue was partitioned between water and DCM. The organic phase was dried, filtered and the solvent evaporated. The crude product was purified on silica, eluted with petrol —EtOAc 0-20% to afford the title compound (1.47 g). MS: [M+H]$^+$=293.

Preparation 47: 6-(4-Fluoro-benzyl)-3,3-dimethyl-2,5-dioxo-2,3,5,6-tetrahydro-pyrrolo[2,3-c]pyridine-1-carboxylic Acid Tert-Butyl Ester A mixture of 5-methoxy-3,3-dimethyl-2-oxo-2,3-dihydro-pyrrolo[2,3-c]pyridine-1-carboxylic acid tert-butyl ester (which may be prepared as described in Preparation 46) (1.43 g, 4.9 mmol), NaI (1.47 g, 9.8 mmol) and 4-fluorobenzyl bromide (0.67 mL, 5.4 mmol) in acetonitrile (50 mL) was heated at reflux for 5 h, stirred at room temperature overnight and heated at reflux again for further 6 h. The reaction mixture was cooled, poured into 10% aqueous Na$_2$S$_2$O$_3$, extracted with DCM, the organic phase was dried, filtered and the solvent evaporated. The crude product was purified on silica, eluted with petrol —EtOAc 0-100% to afford the title compound (910 mg). MS: [M+H]$^+$=387.

The following compound was prepared following an analogous procedure to that described in Preparation 47:
47A: 6-(2,4-Difluoro-benzyl)-3,3-dimethyl-2,5-dioxo-2,3,5,6-tetrahydro-pyrrolo[2,3-c]pyridine-1-carboxylic acid tert-butyl ester, MS: [M+H]$^+$=405.

Preparation 48: 6-(4-Fluoro-benzyl)-3,3-dimethyl-1,6-dihydro-3H-pyrrolo[2,3-c]pyridine-2,5-dione A solution of 6-(4-fluoro-benzyl)-3,3-dimethyl-2,5-dioxo-2,3,5,6-tetrahydro-pyrrolo[2,3-c]pyridine-1-carboxylic acid tert-butyl ester (which may be prepared as described in Preparation 47) (910 mg, 2.36 mmol) in TFA (5 mL) and DCM (5 mL) was stirred for 1 h. The solvent was evaporated, the residue was partitioned between DCM and saturated NaHCO$_3$, the organic phase was dried, the solvent evaporated to afford the title compound (0.67 g). MS: [M+H]$^+$=287.

Preparation 49: 6-(4-Fluoro-benzyl)-3,3-dimethyl-1,2,3,6-tetrahydro-pyrrolo[2,3-c]pyridin-5-one To a solution of 6-(4-fluoro-benzyl)-3,3-dimethyl-1,6-dihydro-3H-pyrrolo[2,3-c]pyridine-2,5-dione (which may be prepared as described in Preparation 48) (526 mg, 1.84 mmol) in THF (30 mL) was added a solution of BH$_3$·Me$_2$S (2M, 9.7 mL, 18.4 mmol) and the mixture was heated at reflux for 3 h. Cooled, MeOH (10 mL) was added carefully and heated at reflux for 2 h. The solvent was evaporated, the residue was partitioned between DCM and saturated NaHCO$_3$. The organic phase was dried, filtered and the solvent evaporated to give the title compound (494 mg). Used without purification. MS: [M+H]$^+$=273.

The following compound was prepared following an analogous procedure to that described in Preparation 49:
49A: 6-(2,4-Difluoro-benzyl)-3,3,4-trimethyl-1,2,3,6-tetrahydro-pyrrolo[2,3-c]pyridin-5-one, MS: [M+H]$^+$=305.

The following compound was prepared following an analogous procedure to that described in Preparations 47-49 inclusive:
49B: 6-(2,4-Difluoro-benzyl)-3,3-dimethyl-1,2,3,6-tetrahydro-pyrrolo[2,3-c]pyridin-5-one, MS: [M+H]$^+$=291.

Preparation 50: 4-Amino-1-(2-chloro-acetyl)-6-(2,4-difluoro-benzyl)-3,3-dimethyl-1,2,3,4-tetrahydro-pyrrolo[3,2-b]pyridin-5-one To a solution of 1-(2-chloro-acetyl)-6-(2,4-difluoro-benzyl)-3,3-dimethyl-1,2,3,4-tetrahydro-pyrrolo[3,2-b]pyridin-5-one (which may be prepared as described in Preparation 18D) (117 mg, 0.32 mmol) in DMF (2 mL) was added potassium carbonate (88 mg, 0.64 mmol)) and O-(2,4-dinitrophenyl)-hydroxylamine (95 mg, 0.48 mmol). The resulting mixture was stirred for 2h at room temperature. 1 M aqueous sodium hydroxide (5 mL) was added and the mixture was extracted with EtOAc (2×10 mL). The organic fractions were washed with water, dried over MgSO$_4$ and concentrated. The residue was purified by column chromatography, eluting with 20-65% EtOAc in petrol to give the title compound (79 mg) as an orange solid. MS: [M+H]$^+$=382.

The following compounds were prepared following an analogous procedure to that described in Preparation 50:
50A: 4-Amino-1-(2-chloro-acetyl)-6-(4-fluoro-benzyl)-3,3-dimethyl-1,2,3,4-tetrahydro-pyrrolo[3,2-b]pyridin-5-one, MS: [M+H]$^+$=364.
50B: 4-Amino-1-(2-chloro-acetyl)-6-butyl-3,3-dimethyl-1,2,3,4-tetrahydro-pyrrolo[3,2-b]pyridin one, MS: [M+H]$^+$=312.

Preparation 51: 4-Bromo-6-(2,4-difluoro-benzyl)-3,3-dimethyl-2,5-dioxo-2,3,5,6-tetrahydro-pyrrolo[2,3-c]pyridine-1-carboxylic Acid Tert-Butyl Ester N-Bromosuccinimide (529 mg, 2.97 mmol) was added to a solution of 6-(2,4-difluoro-benzyl)-3,3-dimethyl-2,5-dioxo-2,3,5,6-tetrahydro-pyrrolo[2,3-c]pyridine-1-carboxylic acid tert-butyl ester (which may be prepared as described in Preparation 47A) (1.0 g, 2.47 mmol) in DMF. The solution was stirred for 1.5 hours at 60° C. The reaction mixture was cooled to room temperature, water was added and the product was extracted with DCM (3×). The organic phases were collected, dried over Na$_2$SO$_4$, filtered and concentrated in vacuo. The residue was purified by flash chromatography to give 1.1 g of the title compound as a yellow solid. MS: [M+H]$^+$=484.

Preparation 52: 6-(2,4-Difluoro-benzyl)-3,3,4-trimethyl-1,6-dihydro-3H-pyrrolo[2,3-c]pyridine-2,5-dione Me$_2$Zn solution in heptane (1M, 5.8 mL, 5.8 mmol) was slowly added to a solution of 4-bromo-6-(2,4-difluoro-benzyl)-3,3-dimethyl-2,5-dioxo-2,3,5,6-tetrahydro-pyrrolo[2,3-c]pyridine-1-carboxylic acid tert-butyl ester (which may be prepared as described in Preparation 51) (935 mg, 1.93 mmol) and Pd(dppf)$_2$Cl$_2$ (282 mg, 0.38 mmol) in dioxane (10 mL). The reaction mixture was stirred at 70° C. under N$_2$ in a sealed vessel for 1 hour. Then a second aliquot of Me$_2$Zn (5.8 mL, 5.8 mmol) was added and the stirring was maintained for 2 hours. The reaction mixture was cooled to room temperature, quenched with sat. NaHCO$_3$ and extracted with DCM. The organic phase was dried over Na$_2$SO$_4$, filtered and concentrated in vacuo. The crude material was purified by flash chromatography to give 200 mg of the title compound as a yellow semi-solid. MS: [M+H]$^+$=319.

Preparation 53: 5-Methoxy-3,3-dimethyl-1,3-dihydro-pyrrolo[2,3-c]pyridin-2-one Prepared from 5-methoxy-3,3-dimethyl-2-oxo-2,3-dihydro-pyrrolo[2,3-c]pyridine-1-carboxylic acid tert-butyl ester using a similar procedure to that described in Preparation 48. MS: [M+H]$^+$=193.

Preparation 54: 5-Methoxy-3,3-dimethyl-2,3-dihydro-1H-pyrrolo[2,3-c]pyridine To a solution of 5-methoxy-3,3-dimethyl-1,3-dihydro-pyrrolo[2,3-c]pyridin-2-one (which may be prepared as described in Preparation 53) (2.8 g, 14.6 mmol) in THF (60 mL) was added a solution of BH$_3$·THF (1M, 150 mL, 150 mmol) and the mixture was stirred at room temperature overnight. MeOH (50 mL) was added carefully and heated at reflux for 1 h. The solvent was evaporated, the residue was partitioned between DCM and saturated NaHCO$_3$. The organic phase was dried, filtered and the solvent evaporated. The crude product was purified on silica, eluted with petrol —EtOAc 0-60% to afford the title compound (2.27 g). MS: [M+H]$^+$=179.

Preparation 55: 5-Methoxy-3,3-dimethyl-2,3-dihydro-pyrrolo[2,3-c]pyridine-1-carboxylic acid tert-butyl ester To a solution of 5-methoxy-3,3-dimethyl-2,3-dihydro-1H-pyrrolo[2,3-c]pyridine (which may be prepared as described in Preparation 54) (534 mg, 3.0 mmol) in THF (10 mL) and saturated aqueous Na$_2$CO$_3$ (4 mL) was added di-tert-butyl-dicarbonate (780 mg, 3.6 mmol) and the reaction mixture was stirred overnight, then it was diluted with water, extracted with EtOAc, washed with brine, dried, filtered and the solvent evaporated to afford the title compound (760 mg). MS: [M+H]$^+$=279.

Preparation 56: 6-((E)-But-2-enyl)-3,3-dimethyl-5-oxo-2,3,5,6-tetrahydro-pyrrolo[2,3-c]pyridine-1-carboxylic acid tert-butyl ester A mixture of 5-methoxy-3,3-dimethyl-2,3-dihydro-pyrrolo[2,3-c]pyridine-1-carboxylic acid tert-butyl ester (which may be prepared as described in Preparation 55) (760 mg, 2.7 mmol), NaI (410 mg, 2.7 mmol) and crotyl bromide (0.33 mL, 3.24 mmol) in acetonitrile (25 mL) was heated at reflux for 5 h. The reaction mixture was cooled, poured on 10% Na$_2$S$_2$O$_3$, extracted with DCM, the organic phase was dried, filtered and the solvent evaporated. The crude product was purified on silica, eluted with petrol —EtOAc 0-70% to afford the title compound (433 mg). MS: [M+H]$^+$=319.

Preparation 57: 6-Butyl-3,3-dimethyl-5-oxo-2,3,5,6-tetrahydro-pyrrolo[2,3-c]pyridine-1-carboxylic Acid Tert-Butyl Ester A mixture of 6-((E)-but-2-enyl)-3,3-dimethyl-5-oxo-2,3,5,6-tetrahydro-pyrrolo[2,3-c]pyridine-1-carboxylic acid tert-butyl ester (which may be prepared as described in Preparation 56) (433 mg, 1.36 mmol) and Pd/C (10%, 100 mg) in EtOH (15 mL) was hydrogenated for 1 h. The catalyst was filtered, the filtrate evaporated and the residue was purified on silica, eluted with petrol —EtOAc 0-50% to afford the title compound (387 mg). MS: [M+H]$^+$=321.

Preparation 58: 6-Butyl-3,3-dimethyl-1,2,3,6-tetrahydro-pyrrolo[2,3-c]pyridin-5-one A solution of 6-butyl-3,3-dimethyl-5-oxo-2,3,5,6-tetrahydro-pyrrolo[2,3-c]pyridine-1-carboxylic acid tert-butyl ester (380 mg, 1.19 mmol) in TFA (5 mL) and DCM (5 mL) was stirred for 1 h. The solvent was evaporated, the residue was partitioned between DCM and saturated NaHCO$_3$, the organic phase was dried, the solvent evaporated and the residue was purified on silica, eluted with petrol —EtOAc 0-100% to afford the title compound (170 mg). MS: [M+H]$^+$=221.

Examples 1-37

The following procedure is illustrative for the preparation of Examples 1-37 listed in the table below.

A mixture of tert-butyl (2R,5S)-4-(2-{6-[(4-fluorophenyl)methyl]-5-(hydroxymethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate (0.47 g), ethyl acetate (10 mL) and HCl—dioxane (4 M; 10 mL) was stirred at 20° C. for 18 h and resulting solid was collected by filtration to give 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one dihydrochloride (Example 2, 0.43 g).

By following methods similar and/or analogous to that described above, the compounds set out in the table below were prepared from the corresponding N-Boc protected derivatives, with any significant variations indicated below. Precursors for the N-Boc protected derivatives are identified (by preparation number or name) in the table below. The title compounds were either isolated directly as the free base or appropriate salt without further purification, or purified for example using mass-directed preparative HPLC, crystallization or trituration.

1H NMR is generated at 400 MHz, in Me-d3-OD unless indicated.

| Eg. | Structure | Name | Method | Comment | 1H NMR Data | [M + H]+ |
|---|---|---|---|---|---|---|
| 1 | 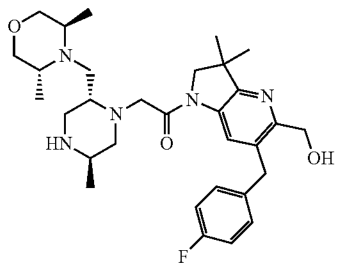 [SMILES: C[C@@H]1CN(CC(=O)N2CC(C)(C)c3nc(CO)c(Cc4ccc(F)cc4)cc32)[C@@H](CN2[C@H](C)COC[C@H]2C)CN1] | 2-[(2R,5R)-2-{[(3R,5R)-3,5-Dimethylmorpholin-4-yl]methyl}-5-methylpiperazin-1-yl]-1-{6-[(4-fluorophenyl)methyl]-5-(hydroxymethyl)-3,3-dimethyl-1H,2H,3H-pyrrolo[3,2-b]pyridin-1-yl}ethan-1-one dihydrochloride | 10 + 18 | | 8.53 (1H, s), 7.39-7.29 (2H, m), 7.21-7.11 (2H, m), 5.01 (2H, s), 4.33-4.12 (5H, m), 4.12-3.56 (10H, m), 3.38-3.34 (2H, m), 3.24-3.05 (2H, m), 1.65 (6H, s), 1.50 (3H, d), 1.39 (3H, d), 1.13 (3H, d). | 554 |
| 2 | 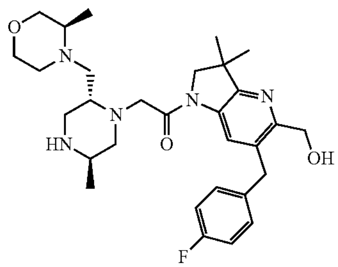 [SMILES: C[C@@H]1CN(CC(=O)N2CC(C)(C)c3nc(CO)c(Cc4ccc(F)cc4)cc32)[C@@H](CN2CCOC[C@H]2C)CN1] | 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one dihydrochloride | 8 + 18 | | 8.56 (1H, s), 7.34 (2H, dd), 7.15 (2H, dd), 5.00 (2H, s), 4.33-4.19 (4H, m), 4.18-3.92 (5H, m), 3.83-3.38 (8H, m), 3.16 (4H, m), 1.65 (6H, s), 1.46 (3H, d), 1.38-1.25 (3H, m). | 540 |
| 3 | 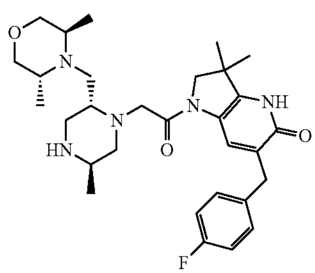 [SMILES: C[C@@H]1CN(CC(=O)N2CC(C)(C)c3[nH]c(=O)c(Cc4ccc(F)cc4)cc32)[C@@H](CN2[C@H](C)COC[C@H]2C)CN1] | 1-{2-[(2R,5R)-2-{[(3R,5R)-3,5-Dimethylmorpholin-4-yl]methyl}-5-methylpiperazin-1-yl]acetyl}-6-[(4-fluorophenyl)methyl]-3,3-dimethyl-1H,2H,3H,4H,5H-pyrrolo[3,2-b]pyridin-5-one dihydrochloride | 10 + 18A | | 7.96 (1H, s), 7.32-7.23 (2H, m), 7.14-7.05 (2H, m), 4.09-3.93 (4H, m), 3.93-3.69 (7H, m), 3.59 (4H, m), 3.28-3.21 (3H, m), 3.18-3.12 (1H, m), 3.12-3.02 (1H, m), 1.49 (3H, d), 1.46 (3H, s), 1.44 (3H, s), 1.35 (3H, d), 1.09 (3H, d). | 540 |
| 4 | 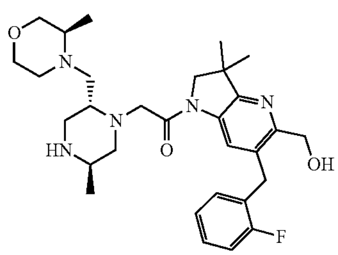 [SMILES: C[C@@H]1CN(CC(=O)N2CC(C)(C)c3nc(CO)c(Cc4ccccc4F)cc32)[C@@H](CN2CCOC[C@H]2C)CN1] | 1-{6-[(2-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one dihydrochloride | 8 + 18B | | 8.59 (1H, s), 7.47-7.34 (2H, m), 7.30-7.16 (2H, m), 5.05 (2H, s), 4.40-3.90 (10H, m), 3.90-2.94 (11H, m), 1.65 (6H, s), 1.45 (3H, m), 1.31-1.23 (3H, m). | 540 |
| 5 | 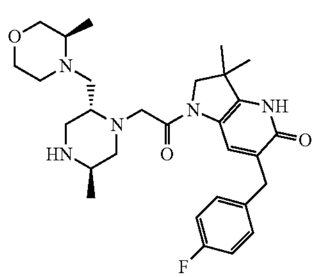 [SMILES: C[C@@H]1CN(CC(=O)N2CC(C)(C)c3[nH]c(=O)c(Cc4ccc(F)cc4)cc32)[C@@H](CN2CCOC[C@H]2C)CN1] | 6-[(4-Fluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride | 8 + 18A | | 8.02 (1H, s), 7.28 (2H, dd), 7.10 (2H, t), 4.10-3.78 (9H, m), 3.74-3.54 (4H, m), 3.42 (s), 3.31-2.93 (6H, m), 1.46 (6H, d), 1.39 (3H, m), 1.28-1.13 (3H, m). | 526 |
| 6 | 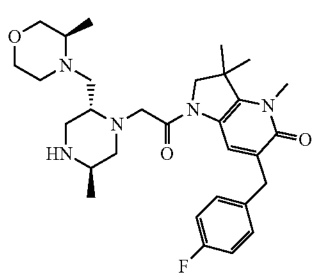 [SMILES: C[C@@H]1CN(CC(=O)N2CC(C)(C)c3c2cc(Cc2ccc(F)cc2)c(=O)n3C)[C@@H](CN2CCOC[C@H]2C)CN1] | 6-[(4-Fluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride | 8 + 18C | | 8.06 (1H, s), 7.27 (2H, dd), 7.09 (2H, t), 4.22-3.52 (18H, m), 3.52-2.87 (6H, m), 1.58 (6H, d), 1.40 (3H, m), 1.24-1.16 (3H, m). | 540 |

-continued

| Eg. | Structure | Name | Method | Comment | 1H NMR Data | [M + H]+ |
|---|---|---|---|---|---|---|
| 7 | 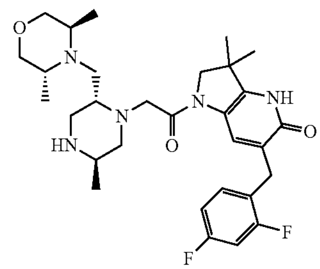 [SMILES: C[C@@H]1CN(CC(=O)N2CC(C)(C)c3[nH]c(=O)c(Cc4ccc(F)cc4F)cc32)[C@@H](CN2[C@H](C)COC[C@H]2C)CN1] | 6-[(2,4-Difluorophenyl)methyl]-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one dihydrochloride | 10 + 18D | | 8.04 (1H, s), 7.45-7.35 (1H, m), 7.06-6.94 (2H, m), 4.27-3.91 (6H, m), 3.91-3.80 (4H, m), 3.80-3.47 (6H, m), 3.21-3.03 (2H, m), 1.50 (3H, d), 1.46 (6H, d), 1.35 (3H, d), 1.12 (3H, d). | 558 |
| 8 | 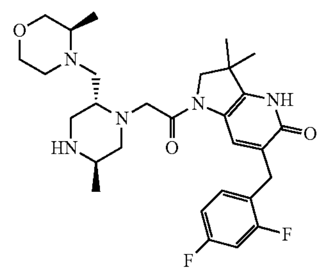 [SMILES: C[C@@H]1CN(CC(=O)N2CC(C)(C)c3[nH]c(=O)c(Cc4ccc(F)cc4F)cc32)[C@@H](CN2CCOC[C@H]2C)CN1] | 6-[(2,4-Difluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride | 8 + 18D | | 8.03 (1H, s), 7.44-7.35 (1H, m), 7.05-6.94 (2H, m), 4.18-3.89 (6H, m), 3.89-3.76 (4H, m), 3.76-3.65 (3H, m), 3.65-3.52 (2H, m), 3.25-3.14 (2H, m), 3.05 (2H, d), 1.50-1.38 (9H, m), 1.31-1.16 (3H, m). | 544 |
| 9 | 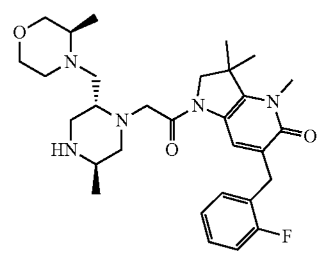 [SMILES: C[C@@H]1CN(CC(=O)N2CC(C)(C)c3c2cc(Cc2ccccc2F)c(=O)n3C)[C@@H](CN2CCOC[C@H]2C)CN1] | 6-[(2-Fluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride | 8 + 18E | | 8.09 (1H, s), 7.35 (2H, m), 7.23-7.10 (2H, m), 4.08-3.78 (9H, m), 3.71-3.53 (4H, m), 3.49-3.36 (4H, m), 3.29-3.13 (4H, m), 3.04 (2H, d), 1.58 (6H, d), 1.52-1.38 (3H, m), 1.35-1.18 (3H, m). | 540 |
| 10 | 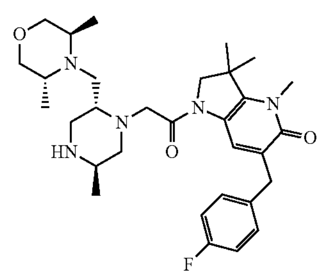 [SMILES: C[C@@H]1CN(CC(=O)N2CC(C)(C)c3c2cc(Cc2ccc(F)cc2)c(=O)n3C)[C@@H](CN2[C@H](C)COC[C@H]2C)CN1] | 1-{2-[(2R,5R)-2-{[(3R,5R)-3,5-Dimethylmorpholin-4-yl]methyl}-5-methylpiperazin-1-yl]acetyl}-6-[(4-fluorophenyl)methyl]-3,3,4-trimethyl-1H,2H,3H,4H,5H-pyrrolo[3,2-b]pyridin-5-one dihydrochloride | 10 + 18C | | 8.04 (1H, s), 7.32-7.23 (2H, m), 7.15-7.02 (2H, m), 4.10-3.52 (17H, m), 3.30-3.04 (6H, m), 1.58 (6H, d), 1.48 (3H, d), 1.35 (3H, d), 1.09 (3H, d). | 554 |
| 11 | 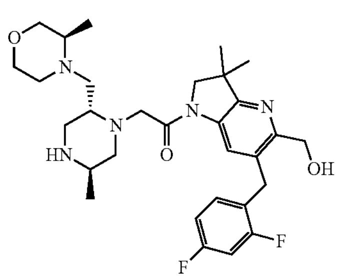 [SMILES: C[C@@H]1CN(CC(=O)N2CC(C)(C)c3nc(CO)c(Cc4ccc(F)cc4F)cc32)[C@@H](CN2CCOC[C@H]2C)CN1] | 1-{6-[(2,4-Difluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one dihydrochloride | 8 + 18F | | 8.55 (1H, s), 7.50-7.41 (1H, m), 7.13-7.01 (2H, m), 5.03 (2H, s), 4.26 (4H, m), 4.13-3.97 (4H, m), 3.85-3.66 (3H, m), 3.51 (5H, m), 3.24 (2H, m), 3.18-2.98 (2H, m), 1.64 (6H, s), 1.47 (3H, m), 1.39-1.28 (3H, m). | 558 |

-continued

| Eg. | Structure | Name | Method | Comment | 1H NMR Data | [M + H]+ |
|---|---|---|---|---|---|---|
| 12 | 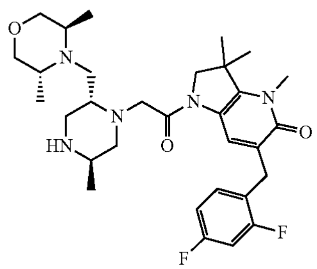 [SMILES: C[C@@H]1CN(CC(=O)N2CC(C)(C)c3c2cc(Cc2ccc(F)cc2F)c(=O)n3C)[C@@H](CN2[C@H](C)COC[C@H]2C)CN1] | 6-[(2,4-Difluorophenyl)methyl]-1-{2-[(2R,5R)-2-{[(3R,5R)-3,5-dimethylmorpholin-4-yl]methyl}-5-methylpiperazin-1-yl]acetyl}-3,3,4-trimethyl-1H,2H,3H,4H,5H-pyrrolo[3,2-b]pyridin-5-one dihydrochloride | 20 | | 7.98 (1H, s), 7.33-7.23 (1H, m), 6.93-6.78 (2H, m), 3.99-3.69 (9H, m), 3.65-3.52 (8H, m), 3.09-2.93 (2H, m), 1.46 (6H, d), 1.38 (3H, d), 1.23 (3H, d), 1.01 (3H, d). | 572 |
| 13 | 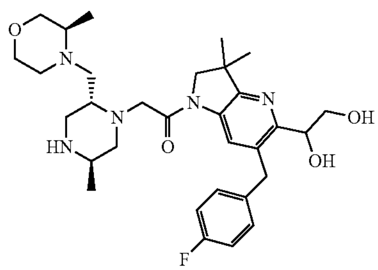 [SMILES: C[C@@H]1CN(CC(=O)N2CC(C)(C)c3nc(C(O)CO)c(Cc4ccc(F)cc4)cc32)[C@@H](CN2CCOC[C@H]2C)CN1] | 1-[5-((R or S)-1,2-Dihydroxyethyl)-6-[(4-fluorophenyl)methyl]-3,3-dimethyl-1H,2H,3H-pyrrolo[3,2-b]pyridin-1-yl]-2-[(2R,5R)-5-methyl-2-{[(3R)-3-methylmorpholin-4-yl]methyl}piperazin-1-yl]ethan-1-one dihydrochloride | 8 + 18G then prep. HPLC, slower eluting isomer | | 8.56-8.41 (1H, m), 7.32 (2H, m), 7.14 (2H, t), 5.35 (1H, s), 4.24 (5H, m), 4.06 (3H, m), 4.01-3.94 (1H, m), 3.91 (2H, d), 3.74 (3H, m), 3.60 (2H, d), 3.43 (2H, d), 3.23 (2H, m), 3.06 (2H, s), 1.64 (6H, s), 1.60-1.20 (6H, m). | 570 |
| 14 | 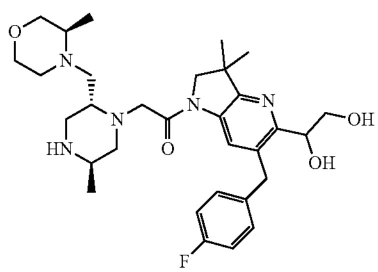 [SMILES: C[C@@H]1CN(CC(=O)N2CC(C)(C)c3nc(C(O)CO)c(Cc4ccc(F)cc4)cc32)[C@@H](CN2CCOC[C@H]2C)CN1] | 1-[5-((R or S)-1,2-Dihydroxyethyl)-6-[(4-fluorophenyl)methyl]-3,3-dimethyl-1H,2H,3H-pyrrolo[3,2-b]pyridin-1-yl]-2-[(2R,5R)-5-methyl-2-{[(3R)-3-methylmorpholin-4-yl]methyl}piperazin-1-yl]ethan-1-one dihydrochloride | 8 + 18G then prep. HPLC, slower eluting isomer | | 8.51 (1H, s), 7.37-7.27 (2H, m), 7.14 (2H, t), 5.36 (1H, dd), 4.32-3.93 (9H, m), 3.91 (2H, d), 3.85-3.39 (8H, m), 3.15 (4H, m), 1.64 (6H, s), 1.51-1.41 (3H, m), 1.29 (3H, s). | 570 |
| 15 | 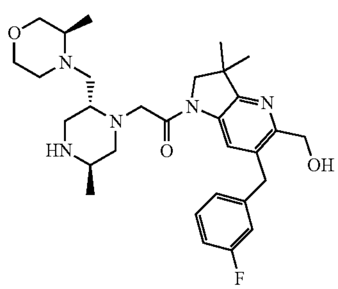 [SMILES: C[C@@H]1CN(CC(=O)N2CC(C)(C)c3nc(CO)c(Cc4cccc(F)c4)cc32)[C@@H](CN2CCOC[C@H]2C)CN1] | 1-{6-[(3-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one dihydrochloride | 8 + 18H | | 8.62 (1H, s), 7.49-7.39 (1H, m), 7.17 (1H, d), 7.13-7.02 (2H, m), 5.01 (2H, s), 4.28 (4H, d), 4.18-3.92 (5H, m), 3.77 (3H, m), 3.60 (2H, m), 3.45 (4H, m), 3.14 (2H, m), 1.67 (6H, s), 1.50-1.36 (3H, m), 1.31-1.22 (3H, m). | 540 |
| 16 | 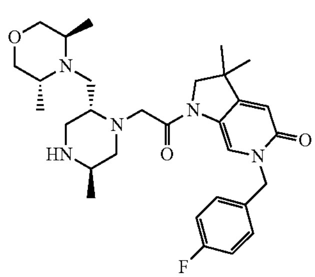 [SMILES: C[C@@H]1CN(CC(=O)N2CC(C)(C)c3cc(=O)n(Cc4ccc(F)cc4)cc32)[C@@H](CN2[C@H](C)COC[C@H]2C)CN1] | 1-{2-[(2R,5R)-2-{[(3R,5R)-3,5-Dimethylmorpholin-4-yl]methyl}-5-methylpiperazin-1-yl]acetyl}-6-[(4-fluorophenyl)methyl]-3,3-dimethyl-1H,2H,3H,5H,6H-pyrrolo[2,3-c]pyridin-5-one dihydrochloride | 10 + 18I | | 8.34 (1H, s), 7.46-7.37 (2H, m), 7.19-7.09 (2H, m), 6.58 (1H, s), 5.42 (1H, d), 5.10 (1H, d), 4.07-3.88 (7H, m), 3.83 (1H, m), 3.67-3.55 (3H, m), 3.51 (1H, dd), 3.22-3.08 (2H, m), 1.51 (3H, d), 1.44 (6H, d), 1.36 (3H, d), 1.08 (3H, d). | 540 |

| Eg. | Structure | Name | Method | Comment | 1H NMR Data | [M + H]+ |
| --- | --- | --- | --- | --- | --- | --- |
| 17 | 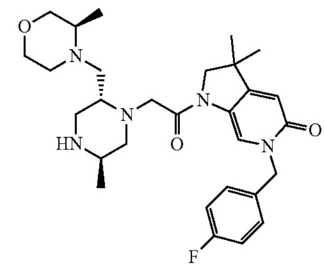 [SMILES: C[C@@H]1CN(CC(=O)N2CC(C)(C)c3cc(=O)n(Cc4ccc(F)cc4)cc32)[C@@H](CN2CCOC[C@H]2C)CN1] | 6-[(4-Fluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,5H,6H-pyrrolo[2,3-c]pyridin-5-one dihydrochloride | 8 + 18I | | 8.35 (1H, s), 7.46-7.36 (2H, m), 7.18-7.08 (2H, m), 6.60 (1H, s), 5.34 (1H, d), 5.19 (1H, d), 4.10-3.70 (10H, m), 3.64-3.52 (2H, m), 3.14 (4H, m), 1.43 (9H, m), 1.31-1.09 (3H, m). | 526 |
| 18 | 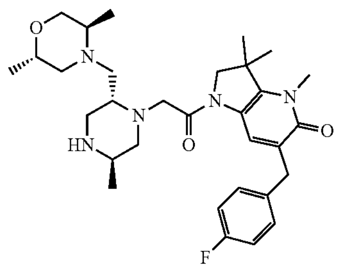 [SMILES: C[C@@H]1CN(CC(=O)N2CC(C)(C)c3c2cc(Cc2ccc(F)cc2)c(=O)n3C)[C@@H](CN2C[C@H](C)OC[C@H]2C)CN1] | 1-{2-[(2R,5R)-2-{[(2S,5R)-2,5-Dimethylmorpholin-4-yl]methyl}-5-methylpiperazin-1-yl]acetyl}-6-[(4-fluorophenyl)methyl]-3,3,4-trimethyl-1H,2H,3H,4H,5H-pyrrolo[3,2-b]pyridin-5-one trihydrochloride | 10A + 18C | | 8.04 (1H, s), 7.32-7.23 (2H, m), 7.15-7.03 (2H, m), 4.06-3.51 (17H, m), 3.25-3.13 (1H, m), 3.08-2.98 (2H, m), 2.82 (1H, t), 2.76-2.76 (1H, m), 1.57 (6H, d), 1.40 (3H, d), 1.29 (3H, d), 1.18 (3H, d). | 554 |
| 19 | 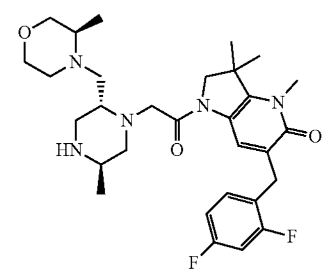 [SMILES: C[C@@H]1CN(CC(=O)N2CC(C)(C)c3c2cc(Cc2ccc(F)cc2F)c(=O)n3C)[C@@H](CN2CCOC[C@H]2C)CN1] | 6-[(2,4-Difluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride | 21 | | 8.11 (1H, s), 7.45-7.35 (1H, m), 7.04-6.94 (2H, m), 4.20-3.76 (10H, m), 3.71 (3H, s), 3.64-3.53 (2H, m), 3.21 (2H, s), 3.05 (2H, s), 1.58 (6H, d), 1.45-1.18 (6H, m). | 558 |
| 20 | 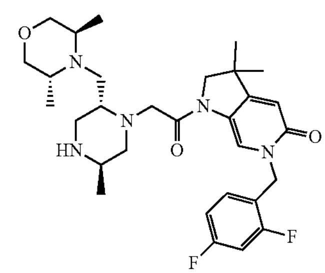 [SMILES: C[C@@H]1CN(CC(=O)N2CC(C)(C)c3cc(=O)n(Cc4ccc(F)cc4F)cc32)[C@@H](CN2[C@H](C)COC[C@H]2C)CN1] | 6-[(2,4-Difluorophenyl)methyl]-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,5H,6H-pyrrolo[2,3-c]pyridin-5-one dihydrochloride | 10 + 18J | | 8.48 (1H, s), 7.63-7.53 (1H, m), 7.12-6.98 (2H, m), 6.57 (1H, s), 5.35 (1H, d), 5.23 (1H, d), 4.17-3.93 (7H, m), 3.91-3.82 (1H, m), 3.82-3.56 (8H, m), 3.27-3.11 (2H, m), 1.54 (3H, d), 1.44 (6H, d), 1.37 (3H, d), 1.19 (3H, d). | 558 |
| 21 | 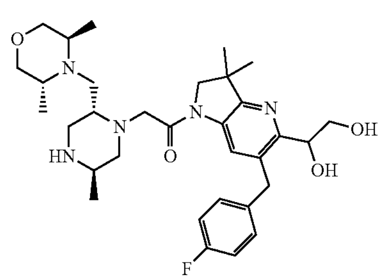 [SMILES: C[C@@H]1CN(CC(=O)N2CC(C)(C)c3nc(C(O)CO)c(Cc4ccc(F)cc4)cc32)[C@@H](CN2[C@H](C)COC[C@H]2C)CN1] | 1-[5-((R or S)-1,2-Dihydroxyethyl)-6-[(4-fluorophenyl)methyl]-3,3-dimethyl-1H,2H,3H-pyrrolo[3,2-b]pyridin-1-yl]-2-[(2R,5R)-2-{[(3R,5R)-3,5-dimethylmorpholin-4-yl]methyl}-5-methylpiperazin-1-yl]ethan-1-one dihydrochloride | 10 + 18K (from slower eluting precursor) | | 8.38 (1H, s), 7.35-7.27 (2H, m), 7.14 (2H, t), 5.34-5.26 (1H, m), 4.37-3.76 (14H, m), 3.76-3.55 (5H, m), 3.25-3.05 (2H, m), 1.63-1.58 (6H, m), 1.50 (3H, d), 1.38 (3H, d), 1.10 (3H, d). | 584 |

| Eg. | Structure | Name | Method | Comment | 1H NMR Data | [M + H]+ |
|---|---|---|---|---|---|---|
| 22 | 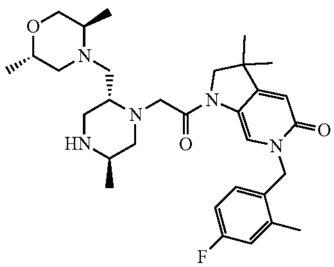 [SMILES: Cc1cc(F)ccc1Cn1cc2c(cc1=O)C(C)(C)CN2C(=O)CN1C[C@@H](C)NC[C@@H]1CN1C[C@H](C)OC[C@H]1C] | 6-[(2,4-Difluorophenyl)methyl]-1-{2-[(2R,5R)-2-{[(2S,5R)-2,5-dimethylmorpholin-4-yl]methyl}-5-methylpiperazin-1-yl]acetyl}-3,3-dimethyl-1H,2H,3H,5H,6H-pyrrolo[2,3-c]pyridin-5-one dihydrochloride | 10A + 18J | | 8.46 (1H, s), 7.61-7.52 (1H, m), 7.11-6.98 (2H, m), 6.61 (1H, s), 5.34 (1H, d), 5.26 (1H, d), 4.18-3.89 (7H, m), 3.84-3.71 (2H, m), 3.71-3.57 (2H, m), 3.53-3.36 (3H, m), 3.24 (1H, dd), 3.14-3.01 (2H, m), 2.97-2.86 (1H, m), 1.46-1.41 (9H, m), 1.31 (3H, d), 1.28 (3H, d). | 558 |
| 23 | 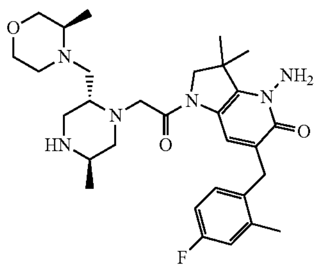 [SMILES: Cc1cc(F)ccc1Cc1cc2c(n(N)c1=O)C(C)(C)CN2C(=O)CN1C[C@@H](C)NC[C@@H]1CN1CCOC[C@H]1C] | 4-Amino-6-[(2,4-difluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride | 8 + 50 | | 8.06 (1H, s), 7.44-7.38 (1H, m), 7.04-6.95 (2H, m), 4.14-3.73 (14H, m), 3.63-3.53 (3H, m), 3.21 (2H, d), 3.10-2.98 (2H, m), 1.63 (6H, d), 1.54-1.30 (3H, m), 1.24 (3H, d). | 559 |
| 24 | 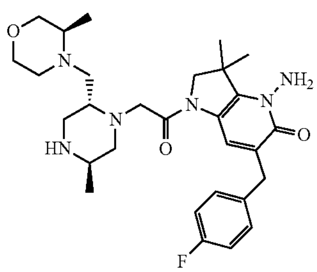 [SMILES: C[C@@H]1CN(CC(=O)N2CC(C)(C)c3c2cc(Cc2ccc(F)cc2)c(=O)n3N)[C@@H](CN2CCOC[C@H]2C)CN1] | 4-Amino-6-[(4-fluorophenyl)methyl]-3,3-dimethyl-1-{2-[(2R,5R)-5-methyl-2-{[(3R)-3-methylmorpholin-4-yl]methyl}piperazin-1-yl]acetyl}-1H,2H,3H,4H,5H-pyrrolo[3,2-b]pyridin-5-one dihydrochloride | 8 + 50A | | 8.01 (1H, s), 7.32-7.24 (2H, m), 7.13-7.05 (2H, m), 4.08-3.74 (9H, m), 3.59 (8H, m), 3.22-2.97 (4H, m), 1.63 (6H, d), 1.44-1.16 (6H, m). | 541 |
| 25 | 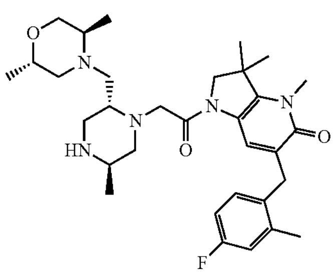 [SMILES: Cc1cc(F)ccc1Cc1cc2c(n(C)c1=O)C(C)(C)CN2C(=O)CN1C[C@@H](C)NC[C@@H]1CN1C[C@H](C)OC[C@H]1C] | 6-[(2,4-Difluorophenyl)methyl]-1-{2-[(2R,5R)-2-{[(2S,5R)-2,5-dimethylmorpholin-4-yl]methyl}-5-methylpiperazin-1-yl]acetyl}-3,3,4-trimethyl-1H,2H,3H,4H,5H-pyrrolo[3,2-b]pyridin-5-one dihydrochloride | 10 A + 18L | | 8.09 (1H, s), 7.44-7.35 (1H, m), 7.05-6.93 (2H, m), 4.15-3.91 (5H, m), 3.91-3.55 (11H, m), 3.40-3.34 (3H, m), 3.25-3.13 (1H, m), 3.13-2.97 (2H, m), 2.94-2.79 (1H, m), 1.63-1.55 (6H, m), 1.41 (3H, d), 1.31 (3H, d), 1.24-1.16 (3H, m). | 572 |
| 26 | 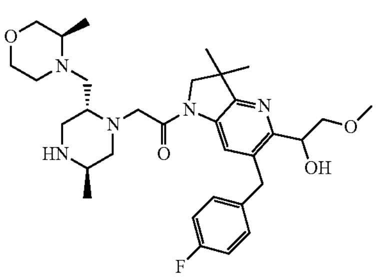 [SMILES: COCC(O)c1nc2c(cc1Cc1ccc(F)cc1)N(C(=O)CN1C[C@@H](C)NC[C@@H]1CN1CCOC[C@H]1C)CC2(C)C] | 1-{6-[(4-Fluorophenyl)methyl]-5-((R or S)-1-hydroxy-2-methoxyethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one trihydrochloride | 8 + 18M | | 8.55 (1H, s), 7.31 (2H, dd), 7.19-7.08 (2H, m), 5.47 (1H, t), 4.37-4.18 (4H, m), 4.18-3.91 (5H, m), 3.84-3.66 (5H, m), 3.64-3.57 (1H, m), 3.56-3.35 (7H, m), 3.16 (4H, m), 1.65 (6H, s), 1.50-1.25 (6H, m). | 584 |

-continued

| Eg. | Structure | Name | Method | Comment | 1H NMR Data | [M + H]+ |
|---|---|---|---|---|---|---|
| 27 | 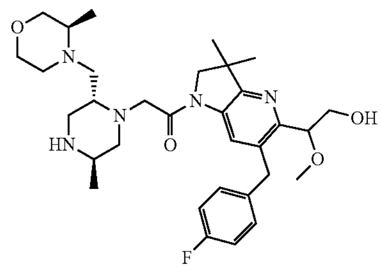 [SMILES: COC(CO)c1nc2c(cc1Cc1ccc(F)cc1)N(C(=O)CN1C[C@@H](C)NC[C@@H]1CN1CCOC[C@H]1C)CC2(C)C] | 1-{6-[(4-Fluorophenyl)methyl]-5-((R or S)-2-hydroxy-1-methoxyethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one trihydrochloride | 8 + 18N | | 8.57 (1H, s), 7.32 (2H, dd), 7.15 (2H, t), 5.01 (1H, t), 4.28 (4H, m), 4.19-3.85 (8H, m), 3.76 (3H, m), 3.68 (3H, s), 3.66-3.57 (1H, m), 3.56-3.42 (3H, m), 3.17 (4H, m), 1.65 (6H, d), 1.45 (3H, s), 1.32 (3H, s). | 584 |
| 28 | 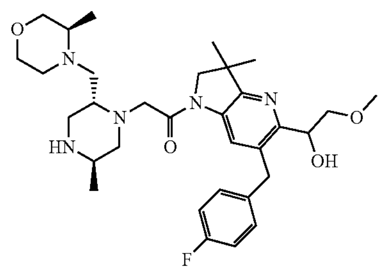 [SMILES: COCC(O)c1nc2c(cc1Cc1ccc(F)cc1)N(C(=O)CN1C[C@@H](C)NC[C@@H]1CN1CCOC[C@H]1C)CC2(C)C] | 1-{6-[(4-Fluorophenyl)methyl]-5-((R or S)-1-hydroxy-2-methoxyethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one trihydrochloride | 8 + 18O | | 8.46 (1H, s), 7.30 (2H, dd), 7.14 (2H, t), 5.48-5.39 (1H, m), 4.37-4.12 (5H, m), 4.01 (4H, m), 3.83-3.68 (4H, m), 3.68-3.54 (2H, m), 3.45 (3H, d), 3.37 (3H, s), 3.16 (4H, s), 1.63 (6H, s), 1.43 (3H, s), 1.26 (3H, s). | 584 |
| 29 | 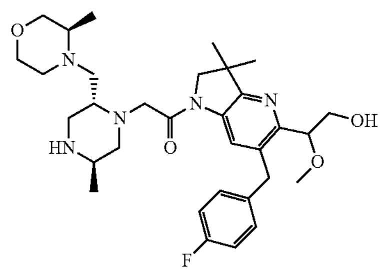 [SMILES: COC(CO)c1nc2c(cc1Cc1ccc(F)cc1)N(C(=O)CN1C[C@@H](C)NC[C@@H]1CN1CCOC[C@H]1C)CC2(C)C] | 1-{6-[(4-Fluorophenyl)methyl]-5-((R or S)-2-hydroxy-1-methoxyethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one | 8 + 18P | | 8.17 (1H, s), 7.19 (2H, dd), 7.03 (2H, t), 4.68 (1H, dd), 4.22-4.04 (3H, m), 4.01-3.86 (3H, m), 3.77 (1H, d), 3.68 (1H, dd), 3.59 (2H, d), 3.17 (3H, s), 3.16-3.11 (1H, m), 3.11-2.78 (7H, m), 2.65-2.48 (2H, m), 2.28 (1H, d), 1.89 (1H, d), 1.45 (3H, s), 1.42 (3H, s), 1.07 (3H, d), 0.98 (3H, d). | 584 |
| 30 | 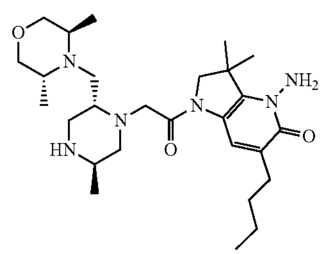 [SMILES: CCCCc1cc2c(n(N)c1=O)C(C)(C)CN2C(=O)CN1C[C@@H](C)NC[C@@H]1CN1[C@H](C)COC[C@H]1C] | 4-Amino-6-butyl-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one dihydrochloride | 10 + 50B | | 8.38 (1H, s), 4.11-3.96 (7H, m), 3.86 (2H, m), 3.70 (4H, m), 3.66-3.56 (3H, m), 3.21 (1H, dd), 3.14-3.08 (1H, m), 2.65-2.54 (2H, m), 1.64 (6H, d), 1.63-1.57 (2H, m), 1.54 (3H, d), 1.47-1.41 (2H, m), 1.37 (3H, d), 1.23 (3H, d), 0.98 (3H, t). | 503 |
| 31 | 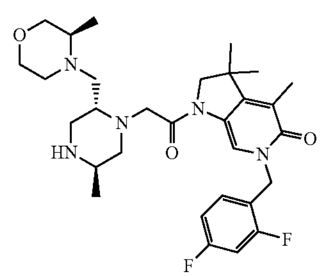 | 6-[(2,4-Difluorophenyl)methyl]-3,3,4-trimethyl-1-{2-[(2R,5R)-5-methyl-2-{[(3R)-3-methylmorpholin-4-yl]methyl}piperazin-1-yl]acetyl}-1H,2H,3H,5H,6H-pyrrolo[2,3-c]pyridin-5-one dihydrochloride | 8 + 18Q | | 8.38 (1H, s), 7.60-7.51 (1H, m), 7.09-6.93 (2H, m), 5.28 (1H, d), 5.20 (1H, d), 4.25-3.88 (8H, m), 3.69 (5H, m), 3.56-3.46 (1H, m), 3.41 (1H, m), 3.17 (4H, m), 2.23 (3H, s), 1.52 (6H, d), 1.41 (3H, s), 1.36-1.26 (3H, m). | 558 |
| 32 | 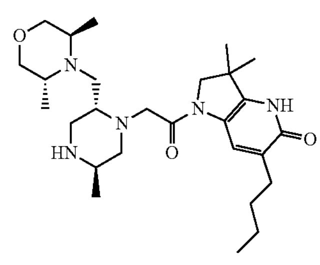 [SMILES: CCCCc1cc2c([nH]c1=O)C(C)(C)CN2C(=O)CN1C[C@@H](C)NC[C@@H]1CN1[C@H](C)COC[C@H]1C] | 6-Butyl-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one dihydrochloride | 10 + 18R | | 8.58 (1H, s), 4.18 (2H, s), 4.16-4.06 (3H, m), 4.06-3.96 (2H, m), 3.91 (1H, d), 3.80 (1H, s), 3.76-3.56 (3H, m), 3.45-3.36 (3H, m), 3.27-3.01 (2H, m), 2.75-2.59 (2H, m), 1.72-1.58 (2H, m), 1.55 (3H, d), 1.52 (6H, s), 1.47-1.41 (2H, m), 1.38 (3H, d), 1.27-1.24 (3H, m), 1.00 (3H, t). | 488 |

-continued

| Eg. | Structure | Name | Method | Comment | 1H NMR Data | [M + H]⁺ |
|---|---|---|---|---|---|---|
| 33 | 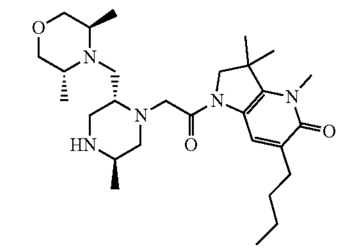 [SMILES: CCCCc1cc2c(n(C)c1=O)C(C)(C)CN2C(=O)CN1C[C@@H](C)NC[C@@H]1CN1[C@H](C)COC[C@H]1C] | 6-Butyl-1-{2-[(2R,5R)-2-{[(3R,5R)-3,5-dimethylmorpholin-4-yl]methyl}-5-methylpiperazin-1-yl]acetyl}-3,3,4-trimethyl-1H,2H,3H,4H,5H-pyrrolo[3,2-b]pyridin-5-one dihydrochloride | 21A | | 8.46-8.38 (1H, m), 4.22-4.04 (5H, m), 4.04-3.94 (3H, m), 3.94-3.84 (2H, m), 3.72 (2H, m), 3.69 (2H, s), 3.68 (3H, s), 3.66-3.60 (2H, m), 3.24-3.12 (2H, m), 2.69-2.49 (2H, m), 1.59 (6H, d), 1.54 (3H, d), 1.49- 1.39 (4H, m), 1.38 (3H, d), 1.27-1.16 (3H, m), 1.01-0.95 (3H, m). | 502 |
| 34 | 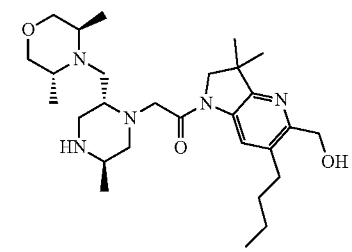 [SMILES: CCCCc1cc2c(nc1CO)C(C)(C)CN2C(=O)CN1C[C@@H](C)NC[C@@H]1CN1[C@H](C)COC[C@H]1C] | 1-[6-Butyl-5-(hydroxymethyl)-3,3-dimethyl-1H,2H,3H-pyrrolo[3,2-b]pyridin-1-yl]-2-[(2R,5R)-2-{[(3R,5R)-3,5-dimethylmorpholin-4-yl]methyl}-5-methylpiperazin-1-yl]ethan-1-one dihydrochloride | 10 + 18S | | 8.95 (1H, s), 4.97-4.90 (2H, m), 4.41-4.21 (3H, m), 4.21-4.12 (3H, m), 4.06-3.86 (3H, m), 3.86-3.69 (4H, m), 3.67-3.55 (1H, m), 3.47-3.37 (2H, m), 3.30-3.22 (1H, m), 3.16 (1H, dd), 2.97-2.81 (2H, m), 1.70-1.65 (6H, m), 1.56 (3H, d), 1.53-1.44 (4H, m), 1.41 (3H, d), 1.32-1.29 (3H, m), 1.05-1.00 (3H, m). | 502 |
| 35 | 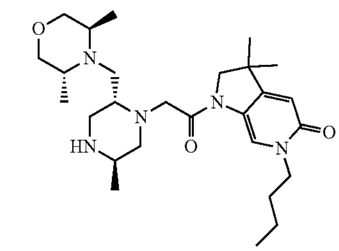 | 6-Butyl-1-{2-[(2R,5R)-2-{[(3R,5R)-3,5-dimethylmorpholin-4-yl]methyl}-5-methylpiperazin-1-yl]acetyl}-3,3-dimethyl-1H,2H,3H,5H,6H-pyrrolo[2,3-c]pyridin-5-one dihydrochloride | 10 + 18T | | 8.50 (1H, s), 6.65 (1H, s), 4.40-3.96 (10H, m), 3.91 (2H, m), 3.82-3.69 (4H, m), 3.67-3.49 (2H, m), 3.27-3.11 (2H, m), 1.86-1.67 (2H, m), 1.55 (3H, d), 1.46 (6H, s), 1.45-1.40 (2H, m), 1.38 (3H, d), 1.25 (3H, d), 1.00 (3H, t). | 488 |
| 36 | 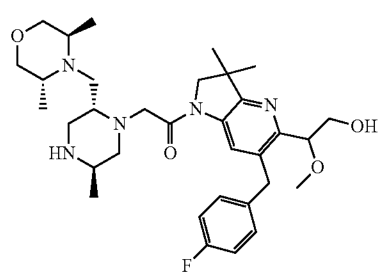 [SMILES: COC(CO)c1nc2c(cc1Cc1ccc(F)cc1)N(C(=O)CN1C[C@@H](C)NC[C@@H]1CN1[C@H](C)COC[C@H]1C)CC2(C)C] | 2-[(2R,5R)-2-{[(3R,5R)-3,5-Dimethylmorpholin-4-yl]methyl}-5-methylpiperazin-1-yl]-1-{6-[(4-fluorophenyl)methyl]-5-((R or S)-2-hydroxy-1-methoxyethyl)-3,3-dimethyl-1H,2H,3H-pyrrolo[3,2-b]pyridin-1-yl}ethan-1-one | 10 + 18N | Purified by HPLC as free base | 8.18 (1H, s), 7.24-7.16 (2H, m), 7.08-6.99 (2H, m), 4.69 (1H, dd), 4.21-3.97 (4H, m), 3.97-3.86 (2H, m), 3.72-3.59 (2H, m), 3.59-3.47 (2H, m), 3.30-3.20 (2H, m), 3.16 (3H, s), 3.08-2.77 (7H, m), 2.55-2.41 (2H, m), 2.19 (1H, m), 1.43 (6H, d), 1.05 (3H, d), 0.97 (6H, d). | 598 |
| 37 | 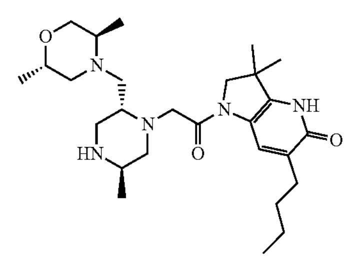 [SMILES: CCCCc1cc2c([nH]c1=O)C(C)(C)CN2C(=O)CN1C[C@@H](C)NC[C@@H]1CN1C[C@H](C)OC[C@H]1C] | 6-Butyl-1-{2-[(2R,5R)-2-{[(2S,5R)-2,5-dimethylmorpholin-4-yl]methyl}-5-methylpiperazin-1-yl]acetyl}-3,3-dimethyl-1H,2H,3H,4H,5H-pyrrolo[3,2-b]pyridin-5-one dihydrochloride | 10A + 18R | | 8.74 (1H, s), 4.50-4.16 (4H, m), 4.16-4.05 (4H, m), 3.95 (1H, m), 3.89-3.73 (2H, m), 3.69-3.62 (2H, m), 3.57-3.49 (2H, m), 3.22-3.05 (2H, m), 3.05-2.80 (1H, m), 2.74 (2H, t), 1.70-1.60 (2H, m), 1.56 (6H, d), 1.50-1.41 (5H, m), 1.37 (3H, d), 1.31 (3H, d), 1.01 (3H, t). | 488 |

Example 38: 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin yl]methyl}piperazin-1-yl]ethan-1-one (Free Base)

1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one dihydrochloride (1.00 g, 1.0 eq., 1.00 wt.) (which may be prepared as described in Example 2) was charged to a RB flask, dissolved in water (10.0 mL, 10.0 vol, 10.00 wt.) and stirred under nitrogen at 18 to 23° C. to give a straw coloured solution (pH=4.73, T=19.3° C.). To the aqueous solution was added ethyl acetate (10.0 mL, 10.0 vol) and the biphasic mixture was stirred at 18 to 23° C. for 5 minutes. The layers were separated and the aqueous layer (pH=4.58, 19.6° C.) was returned to the flask. Sodium hydrogen carbonate (388.2 mg, 3×1.05 eq., 0.4 wt.) was added (cautiously) and effervescence was observed. The mixture was stirred for 20 minutes (pH=7.51, 18.2° C.), dichloromethane (5.0 mL, 5.0 vol) was added and the mixture was stirred under the same conditions, for a further 5 minutes. The layers were separated, the dichloromethane layer was retained and the aqueous layer (pH=7.66, T=17.7° C.) was returned to the flask. Two further extractions with dichloromethane (2×5.0 mL, 2×5.0 vol) were performed (pH=8.25, T=18.5° C. & pH=8.47, T=18.3° C.) and the combined organic layers were dried over sodium sulfate (1.0 g, 1.0 wt.), filtered and concentrated to dryness under reduced pressure at 40° C. (400 mbar). The concentrate was then dried at 40° C. (<20 mbar) over 2 hours to give a white foam (850.2 mg, 102% th., 100% corr. for input and output w/w assays), 94.3% w/w osfb (against TCNB), that contained ethyl acetate (3.4% w/w) and dichloromethane (0.8% w/w).

Example 39: 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate (Form A)

The free base of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one (500.0 mg, 1.0 wt) (which may be prepared as described in Example 38) was charged to a 25 mL vessel and dissolved in ethanol (1.0 mL, 2.0 vol). L-(+)-Lactic acid (106.2 mg, 1.0 eq) was added and the contents of the vessel were stirred for 1 hour at 18 to 23° C. to give a yellow solution. After this time, TBME (9.0 mL, 18.0 vol) was charged to the vessel and the mixture was left to stir at 18 to 23° C. The progress of the salt crystallisation was monitored by XRPD. The lactate salt remained in solution after stirring for 16 hours at 18 to 23° C. After this time, the solution was concentrated to approximately ¼ the original volume and TBME (9.0 mL, 18.0 vol) was added to give a gummy solid and clear supernatant that changed into a finely divided suspension after sonication and further stirring (ca. 20 hours at 18 to 23° C.). The solid was isolated by filtration, dried under a stream of nitrogen to give 365 mg of a white solid that was identified as Form B by XRPD. The solid was oven dried at 40 to 45° C. for 67 hours to give a white solid (325 mg, 56% th.), 98.8% w/w oasfb (against TCNB) that contained TBME (1.0% w/w) and water (0.6% w/w) and was indicated as Form A by XRPD. Detailed characterising data ($^1$H NMR, XRPD and DSC) for Example 39 is shown in FIGS. 1-3.

Example 40: 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate (Form B)

The reaction was performed according to the procedure described for Example 39, but without oven drying to afford a white solid (529.1 mg, 90% th.), 96.1% w/w oasfb (against TCNB) that contained TBME (5.9% w/w) and water (3.8% w/w) and was indicated as Form B by XRPD. An alternative procedure to Example 40 was also used which avoided the use of ethanol. Detailed characterising data ($^1$H NMR, XRPD and DSC) for Example 40 is shown in FIGS. 4-6.

Example 41: 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one sulfate (Form F)

The free base of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one (500.0 mg, 1.0 wt) (which may be prepared as described in Example 38) was charged to a 10 mL vessel and dissolved in ethanol (1.0 mL, 2.0 vol). Sulfuric acid (103.2 mg, 1.0 eq.) solution in ethanol (4.0 mL, 8.0 vol) was added over 10 minutes with stirring at 18 to 23° C. to give a clear gel. The contents of the vessel were stirred for 1 hour at the same temperature, during which time the gel dissolved to give a yellow solution. Stirring was continued for 16 hours and a white suspension was generated. The progress of the salt crystallisation was monitored by XRPD. Ethanol (2.0 mL, 4.0 vol) was then added to properly mobilise the suspension and the product was isolated by filtration and dried under a stream of nitrogen to give a white solid (465.2 mg, 79% th.), 94.9% w/w oasfb (against TCNB) that contained ethanol (2.9% w/w) and water (3.6% w/w) and was indicated as Form F by XRPD. Detailed characterising data ($^1$H NMR, XRPD and DSC) for Example 41 is shown in FIGS. 7-9.

Example 42: 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin yl]methyl}piperazin-1-yl]ethan-1-one mesylate (Form B)

The free base of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one (500.0 mg, 1.0 wt) (which may be prepared as described in Example 38) was charged to a 25 mL vessel and dissolved in 2-propanol (2.5 mL, 5.0 vol). Methanesulfonic acid (276.0 mg, 3.0 eq.) was added (small exotherm was observed) and the resulting oily-gummy mixture was stirred for 1 hour at 18 to 23° C. n-Heptane (10.0 mL, 20.0 vol) was added slowly over 10 minutes to give a white suspension and a small quantity of gummy solid. The progress of the salt crystallisation was monitored by XRPD. The salt did not crystallise under mild conditions (stirring at 18 to 23° C. for 3 days), therefore the temperature was increased to 40 to 45° C. to give a sticky gummy solid and clear supernatant. This mixture was cooled to 18 to 23° C., mobilised with a spatula and sonicated for 20 minutes to provide a white suspension that contained some gummy solids. The suspension was stirred for 20 hours at the same temperature, filtered and dried under a stream of nitrogen to give a beige solid (402.9 mg, 63% th.), 99.0% w/w oasfb (against TCNB), that contained 2-propanol (2.3% w/w), n-heptane (0.2% w/w), water (1.9% w/w) and was indicated as Form B by XRPD. Detailed characterising data ($^1$H NMR, XRPD and DSC) for Example 42 is shown in FIGS. 10-12.

Example 43: 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate (Form C)

First Batch

Figure 13:
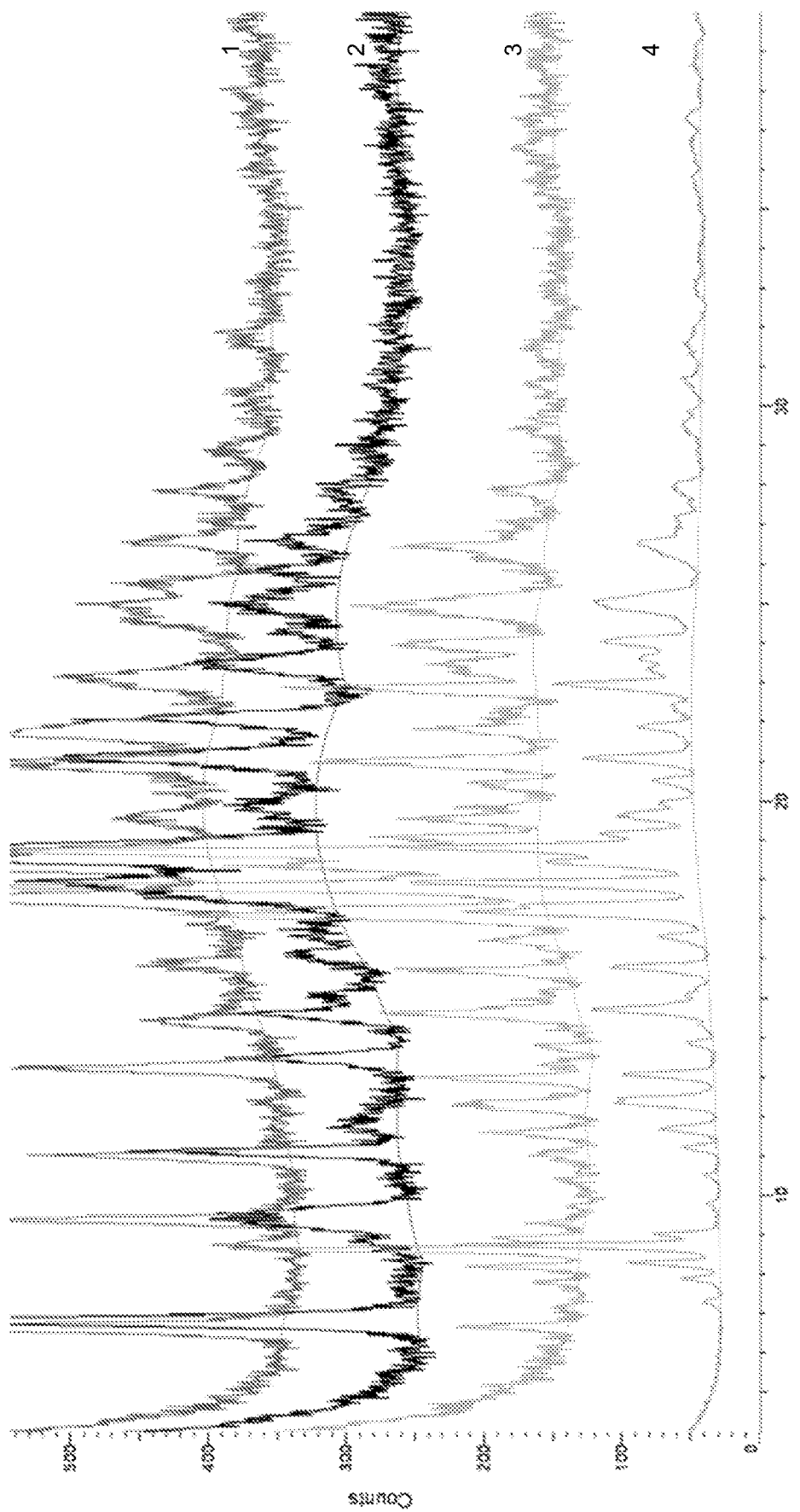
FIG. 13: XRPD L-(+)-lactate Form B (diffractogram labelled 1) product of Example 40, reaction mixture at t=0h (diffractogram labelled 2), after 4 days (diffractogram labelled 3) compared with L-(+)-lactate Form C (diffractogram labelled 4) Example 43.
Figure 14:
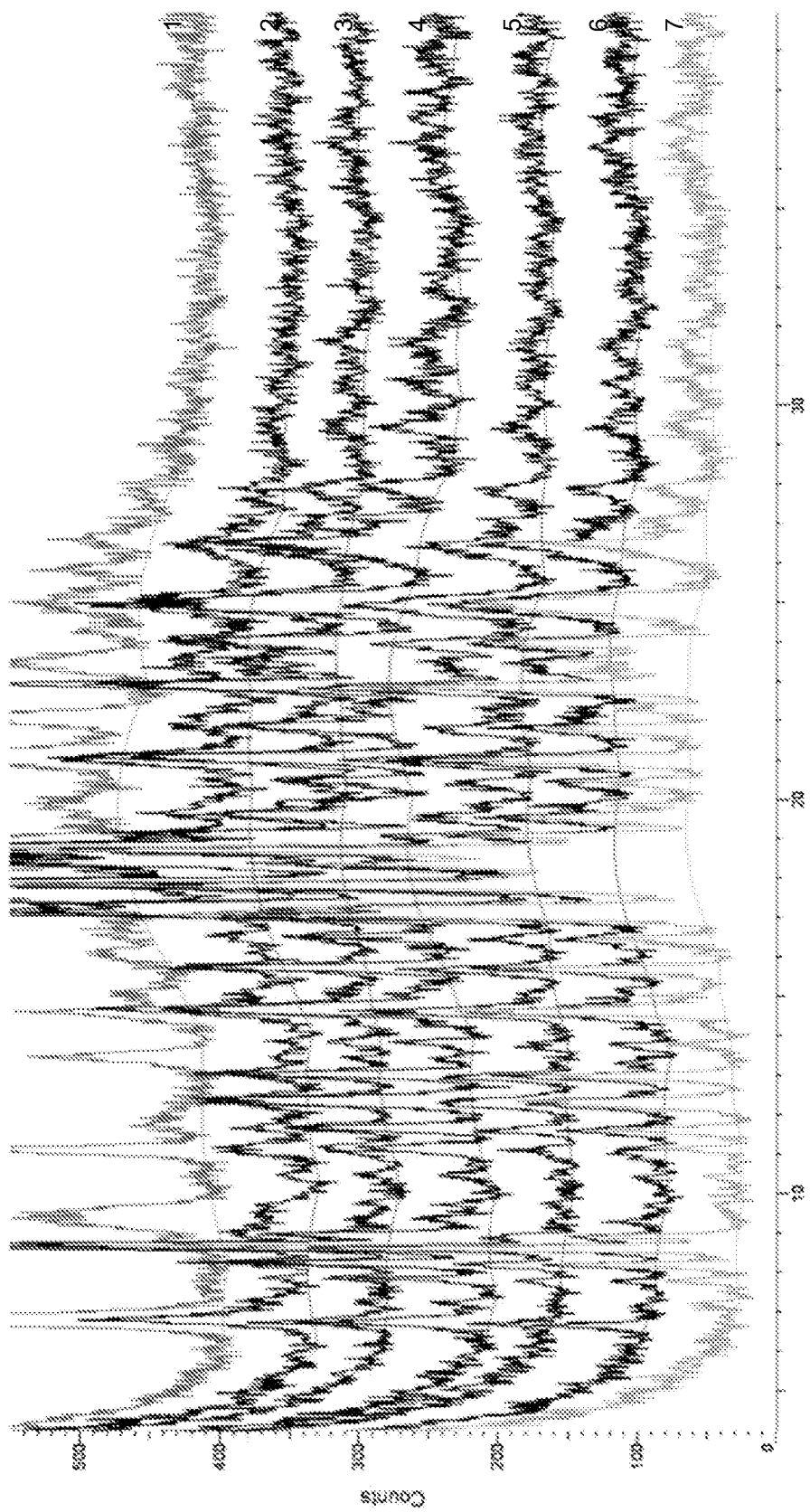
FIG. 14: XRPD of Example 43 iso-structural with Form B at t=0h (diffractogram labelled 1), progress of the reaction mixtures (diffractograms labelled 2-6), inter-conversion completed after heating for t=5 days to give Form C (diffractogram labelled 7).

The free base of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one (10.0 g, corr.) (which may be prepared as described in Example 38) was dissolved in isopropyl acetate (80.0 mL, 8.0 vol) to give a pale yellow solution. Solid, anhydrous L-(+)-lactic acid (1.67 g, 1.0 eq.) was charged in one portion to the same flask and a small quantity of gum was evident at the base of the flask. The mixture was then stirred rapidly to mobilise the gum and the solution spontaneously nucleated and solid was precipitated. A specimen of solid precipitant was analysed by XRPD and was consistent with Form B. n-Heptane (12.0 vol) was added and the mixture was stirred at 40° C. under nitrogen for 4 days to demonstrate that the mixture would convert into Form C, the progress of which was monitored by XRPD (FIG. 13). The temperature of the mixture was raised to 55° C. and stirring was continued for 24h to complete the transformation (FIG. 14). The product was isolated by filtration (rapid <0.5 minute), washed with isopropyl acetate/n-heptane (2.0/3.0, v/v, 5.0 vol) and dried under a stream of nitrogen for 20h to give the title compound as a white powder (8.89 g, 79% th.), 91.6% w/w (osfb), Form C, m.p. 172° C.

Second Batch

The free base of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one (10.0 g, corr.) (which may be prepared as described in Example 38) was dissolved in isopropyl acetate (60.0 mL, 6.0 vol) to give a pale yellow solution. To which was added anhydrous L-(+)-lactic acid (1.67 g, 1.0 eq.) dissolved in isopropyl acetate (10.0 mL, 1.0 vol). A line rinse of isopropyl acetate (10.0 mL, 1.0 vol) was applied and the mixture was stirred at 18-23° C. to give a pale yellow solution. n-Heptane (120 mL, 12.0 vol) was added drop wise over 40 min and gum was formed on the bottom of the flask. After stirring for 1 h 40 min the appearance of the mixture had improved but the gum was still present on the base of the flask.

The mixture was stirred for 16 h at 18-23° C. during which time the gum had mobilised and a granular, finely divided suspension had formed. The suspension was filtered under nitrogen (filtration was rapid) and the cake was sampled and analysed by XRPD (Form C). The cake was washed with isopropyl acetate/n-heptane (2.0/3.0, v/v, 5.0 vol), sampled and analysed by XRPD (Form C) and left to pull dry on the filter under a stream of nitrogen over 16 h. The product consisted of a slightly off-white powdery solid (11.36 g, 91% corr.) Form C, 94.3% w/w (oasfb), Form C, m.p. 172° C. and contained isopropyl acetate (1.0% ww).

Detailed characterising data ($^1$H NMR, XRPD, and DSC) for Example 43 is shown in FIGS. 15-17.

Example 44: 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate (Form C)

Step 1

To a solution of tert-butyl (2R,5S)-4-(2-{6-[(4-fluorophenyl)methyl]-5-(hydroxymethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate (1.0 wt) (which may be prepared as described in Preparation 19) in methanol (10 vol) cooled to <10° C. is slowly added 4M HCl in 1,4-dioxane (3 vol), followed by a line rinse of methanol (0.5 vol). The mixture is warmed to 15 to 25° C. and stirred at this temperature for at least 12 h. The reaction mixture is then warmed to 30 to 40° C. and stirred until the reaction is deemed complete by HPLC (typically >2 h). On completion the reaction solution is concentrated to dryness at up to 40° C. The residue is dissolved in purified water (8 vol) and washed with ethyl acetate (2×4 vol). The pH of the aqueous phase is adjusted to pH 12 to 13 using 4M NaOH (as required) prior to extraction with ethyl acetate (3×5 vol). The combined organic phases are washed with a sodium chloride solution (5 vol) and dried over magnesium sulfate (1.0 wt) for at least 10 minutes. The solid is removed by filtration and the filter cake washed with ethyl acetate (2×2 vol). The filtrates are concentrated on a rotary evaporator at up to 40° C., the resulting concentrate is dissolved in methyl acetate (5 vol) and the solution concentrated as above to yield the free base of 1-{6-[(4-Fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one.

Step 2

To a solution of the free base of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one (1.0 wt) (which may be prepared as described in Step 1) in methyl acetate (3 vol) is added a solution of L-(+)-lactic acid (0.085 wt) in methyl acetate (0.75 vol). A seed slurry of 1-{6-[(4-fluorophenyl)methyl]-5-(hydroxymethyl)-3,3-dimethyl-1H,2H,3H-pyrrolo[3,2-b]pyridin-1-yl}-2-[(2R,5R)-5-methyl-2-{[(3R)-3-methylmorpholin-4-yl]methyl}piperazin-1-yl]ethan-1-one L-(+)-lactate (Form C) (0.01 wt) in methyl acetate (0.08 vol) is then charged followed by a solution of L-(+)-lactic acid (0.085 wt) in methyl acetate (0.75 vol) and a line rinse of methyl acetate (0.5 vol). The suspension is stirred for ca. 30 minutes prior to the addition of n-heptane (12.0 vol) over at least 1 h maintaining 15 to 25° C. The mixture is held at 15 to 25° C. and stirred for at least 2 h. The solid is removed by filtration and the filter cake washed with 2:3 methyl acetate/n-heptane (5 vol). The material is dried on the filter until suitable for handling and then dried in an oven at up to 80° C. until the methyl acetate content is 0.5% w/w, to give the title compound as an off-white to beige solid.

Example 45: Examples of Pharmaceutical Formulations (i) Tablet Formulation

A tablet composition containing a compound of formula (I) is prepared by mixing an appropriate amount of the compound (for example 50-250 mg) with an appropriate diluent, disintegrant, compression agent and/or glidant. One possible tablet comprises 50 mg of the compound with 197 mg of lactose (BP) as diluent, and 3 mg magnesium stearate as a lubricant and compressing to form a tablet in known manner. The compressed tablet may be film coated.

(ii) Capsule Formulation

A capsule formulation is prepared by mixing 100-250 mg of a compound of formula (I) with an equivalent amount of lactose and filling the resulting mixture into standard hard gelatin capsules. An appropriate disintegrant and/or glidant can be included in appropriate amounts as required.

(iii) Injectable Formulation I

A parenteral composition for administration by injection can be prepared by dissolving a compound of formula (I) (e.g. in a salt form) in water containing 10% propylene glycol to give a concentration of active compound of 1.5% by weight. The solution is then made isotonic, sterilised by filtration or by terminal sterilisation, filled into an ampoule or vial or pre-filled syringe, and sealed.

(iv) Injectable Formulation II

A parenteral composition for injection is prepared by dissolving in water a compound of formula (I) (e.g. in salt form) (2 mg/ml) and mannitol (50 mg/ml), sterile filtering the solution or by terminal sterilisation, and filling into sealable 1 ml vials or ampoules or pre-filled syringe.

(v) Injectable Formulation III

A formulation for i.v. delivery by injection or infusion can be prepared by dissolving the compound of formula (I) (e.g. in a salt form) in water at 20 mg/ml and then adjusted for isotonicity. The vial is then sealed and sterilised by autoclaving or filled into an ampoule or vial or pre-filled syringe, sterilised by filtration and sealed.

(vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial, ampoule or pre-filled syringe is then sealed and sterilised by autoclaving or sterilized by filtration and sealed.

(vii) Subcutaneous or Intramuscular Injection Formulation

A composition for sub-cutaneous administration is prepared by mixing a compound of the formula (I) with pharmaceutical grade corn oil to give a concentration of 5-50 mg/ml. The composition is sterilised and filled into a suitable container.

(viii) Lyophilised Formulation I

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation II

Aliquots of formulated compound of formula (I) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(x) Lyophilised Formulation for Use in i.v. Administration III

An aqueous buffered solution is prepared by dissolving a compound of formula (I) in a buffer. The buffered solution is filled, with filtration to remove particulate matter, into a container (such as a Type 1 glass vial) which is then partially sealed (e.g. by means of a Fluorotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle. On completion of the freeze drying cycle the vials are back filled with nitrogen to atmospheric pressure, stoppered and secured (e.g. with an aluminium crimp). For intravenous administration, the freeze dried solid can be reconstituted with a pharmaceutically acceptable diluent, such as 0.9% saline or 5% dextrose. The solution can be dosed as is, or can be diluted further into an infusion bag (containing a pharmaceutically acceptable diluent, such as 0.9% saline or 5% dextrose), before administration.

(xi) Active Pharmaceutical Ingredient in a Bottle

A composition for oral administration is prepared by filling a bottle or vial with a compound of formula (I). The composition is then reconstituted with a suitable diluent for example water, fruit juice, or commercially available vehicle such as OraSweet or Syrspend. The reconstituted solution may be dispensed into dosing cups or oral syringes for administration.

Biological Assays

Expression and Purification of XIAP, cIAP-1 and cIAP-2 BI R3 Domains

The recombinant BI R3 domain of human XIAP (residues 252-350) fused to a His-tag, human cIAP-1 (residues 267-363) fused to a GST-tag and human cIAP-2 (residues 244-337) fused to a His-tag were overexpressed from *Escherichia coli* cells grown in TB medium. Protein was isolated from lysates using Ni-NTA affinity chromatography (XIAP/cIAP-2) or glutathione sepharase 4B affinity chromatography (cIAP-1). Affinity tags for XIAP and cIAP-1 were cleaved with thrombin in 25 mM HEPES pH 7.5, 100 mM NaCl, 50 µM $Zn(OAc)_2$ and 1 mM $Ca(OAc)_2$ followed by purification of BI R3 domains by size-exclusion chromatography. The His-tag was uncleaved for cIAP-2 and the protein was not concentrated above 3 mg/mL due to aggregation induced covalent self-oligomerization issues. The purified protein was stored in 25 mM Tris pH 7.5, 100 mM NaCl at −80° C.

XIAP, cIAP-1 and cIAP-2 In Vitro Competitive Displacement Binding Assays

Modified SMAC peptides and compounds were tested for their ability to displace the fluorescent tracer from either XIAP, cIAP-1 or cIAP-2. BI R3 domains of cIAP-1, cIAP-2 and XIAP were incubated with test compounds or SMAC based peptides and their respective peptide probes (Peptide Protein Research) in assay buffer (50 mM Hepes pH 7.5, 0.025% Tween-20, 0.01% BSA, and 1 mM DTT). Positive controls consisted of BIR3 proteins and tracer (no inhibition) and negative controls contained tracer only (100% inhibition). The samples were incubated at room temperature for 1 hr (XIAP and cIAP-2) or 3 hrs (cIAP-1) prior to being read in the BMG Pherastar in Fluorescence Polarization mode (FP 485 nm, 520 nm, 520 nm). $IC_{50}$ values were determined from dose-response plots using nonlinear least-squares analysis.

Final Conditions for XIAP, cIAP-1 and cIAP-2 Assays

| Protein | Protein Conc | Peptide Probe | Peptide Conc |
|---------|--------------|---------------|--------------|
| XIAP    | 20 nM        | AbuRPFK(5&6FAM)-amide | 5 nM |
| cIAP-1  | 4 nM         | AbuRPFK(5&6FAM)-amide | 2 nM |
| cIAP-2  | 20 nM        | AVPWK(5&6FAM)-amide   | 2 nM |

Anti-Proliferative Activity

Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds (in 0.1% DMSO v/v) for a further 72 hours.

At the end of the incubation period 10% (v/v) Alamar Blue is added and incubated for a further 6 hours prior to determination of fluorescent product at 535 nM ex/590 nM em. The anti-proliferative activities of compounds of the invention can be determined by measuring the ability of the compounds to inhibit growth in 3 cancer cell lines:

EVSA-T (human breast carcinoma) DSMZ cat. no. ACC 433

MDA-MB-231 (human breast carcinoma) ECACC cat. no. 92020424

HCT116 (human colon carcinoma) ECACC cat. no. 91091005 (insensitive cell line used as a control for non-specific cytoxicity)

In an assay using the cell line EVSA-T, Examples 1-34 have an $EC_{50}$ of less than 0.01 µM. In particular, Examples 1-3, 5-8, 10-14, 16, 18-25, 27-28 and 30-32 have an $EC_{50}$ of less than 0.001 µM. In an assay using the cell line MDA-MB-231, Examples 1-34 have an $EC_{50}$ of less than 0.1 µM. In particular, Examples 1-8, 10-14 and 18-32 have an $EC_{50}$ of less than 0.01 µM. More particularly, Examples 7-8 have an $EC_{50}$ of less than 0.001 µM. Data for the compounds of the invention in these assays is provided in Table 1.

Apoptosis Induction

The table below summarises the sensitivity of a panel of nine human melanoma cell lines that were evaluated for apoptosis induction in the presence of 1 ng/ml TNF-α added at the same time as 1 µM Example 2 for 24 hours. A range of sensitivities were observed with 3 cell lines (SK-MEL-24, WM-266-4 and WM-115) appearing the least sensitive (<20% cells apoptotic after 24 h). The table details the percentage of total cells positive for cleaved-caspase-3 activity after 24 hour treatment with 1 µM Example 2 plus 1 ng/ml TNF-α by cytometry using a fluorogenic caspase-3 substrate (NucView488—Biotium).

| Melanoma Cell Line | % CleavedCaspase-3 | SD |
|---|---|---|
| SK-MEL-28 | 63.2 | 3.3 |
| SK-MEL-5 | 52.8 | 2.9 |
| SK-MEL-2 | 49.5 | 2.9 |
| RPMI-7951 | 44.0 | 5.7 |
| MALME-3M | 29.5 | 2.8 |
| A375 | 26.5 | 0.2 |
| WM-115 | 16.7 | 1.1 |
| WM-266-4 | 13.2 | 1.3 |
| SK-MEL-24 | 2.1 | 0.5 |

HEK293-XIAP-Caspase-9 Immunoprecipitation (IP) MSD Assay Protocol

Stable HEK293-XIAP-Caspase-9 cells were plated out into 96-well plates [200 µl/well at 1×10⁶ cells/mL in cultured complete medium (DMEM+10% FBS+0.5 mg/mL Geneticin (Invitrogen)] and left overnight at 37° C. to recover. Compounds were added to duplicate wells in 0.1% DMSO for 2 h at 37° C. Cells were lysed in 50 µl 1×MSD lysis buffer (1% Triton X-100 in 20 mM Tris·Cl (pH 7.6), 150 mM NaCl including protease inhibitors) for 20 min rocking at room temperature. Streptavidin high bind MSD plate (L15SB-2) were coated with biotinylated anti-FLAG M2 antibody (Sigma F9291) at 25 µl/well with a 5 µg/mL dilution of antibody in PBS for 1 h, shaking; followed by blocking for 1 h with 150 µl 3% BSA/TBST. Cell lysate (25 µl) was added to the 96-well anti-FLAG coated MSD plate and placed on shaker for 4 h at room temperature. After washing 4 times with 150 µl TBST (20 mM Tris·Cl (pH 7.6), 150 mM NaCl, 0.1% Tween-20), anti-Caspase-9 [CST #9505] diluted to 5 µl/mL in MSD blocking buffer (3% BSA/TBST) was added overnight at 4° C. After washing plates 4 times with 150 µl TBST, anti-rabbit-sulfo tag (MSD cat no. R32AB-1), diluted to 2 µg/mL in MSD blocking buffer, was added for 2 hours at RT. Plates were washed 4 times with 150 µl TBST, and 150 µl/well 1×MSD read buffer (R92TC-2) added before reading each plate.

$EC_{50}$ values were determined from dose-response plots using nonlinear least-squares analysis. Examples 1-37 have an $EC_{50}$ of less than 0.1 µM. In particular, Examples 1-13, 15, 18-25, 27-28, 30-34 and 36-37 have an $EC_{50}$ of less than 0.01 µM. More particularly, Examples 10, 12, 23-24 and 31 have an $EC_{50}$ of less than 0.001 µM. Data for the compounds of the invention in this assay is provided in Table 1.

Protocol for cIAP1 Degradation MSD Assay in MDA-MB-231 Cells

MDA-MB-231 cells were plated out into 96-well plates [200 µl/well at 4×10⁵ cells/mL in cultured complete medium (DMEM+10% FBS) and left overnight at 37° C. to recover. Compounds were added to duplicate wells in 0.1% DMSO for 2 h at 37° C. Cells were lysed in 50 µl 1×MSD lysis buffer (1% Triton X-100 in 20 mM Tris·Cl (pH 7.6), 150 mM NaCl including protease inhibitors) for 20 min rocking at room temperature. Streptavidin high bind MSD plate (L15SB-2) were coated with biotinylated anti-cIAP1 antibody (R&D Systems cat no. AF8181—biotinylated in house) at 25 µl/well with a 5 µg/mL dilution of antibody in PBS for 1 h, shaking; followed by blocking for 1 h with 150 µl 3% BSA/TBST. Cell lysate (25 µl) was added to the 96-well anti-cIAP1-coated MSD plate and placed at 4° C. overnight. After washing 4 times with 150 µl TBST (20 mM Tris·Cl (pH 7.6), 150 mM NaCl, 0.1% Tween-20), anti-cIAP1-sulfo tag detection antibody (R&D Systems cat no. AF8181—sulfo-tagged in house), diluted to 6 µg/mL in MSD blocking buffer, was added for 2 hours at RT. Plates were washed 4 times with 150 µl TBST, and 150 µl/well 1×MSD read buffer (R92TC-2) added before reading each plate.

$EC_{50}$ values were determined from dose-response plots using nonlinear least-squares analysis. Examples 1-37 have an $EC_{50}$ of less than 0.01 µM. In particular, Examples 1-8, 10-14, 16, 18-27, 30-34 and 37 have an $EC_{50}$ of less than 0.001 µM. More particularly, Example 7 has an $EC_{50}$ of less than 0.0001 µM. Data for the compounds of the invention in this assay is provided in Table 1.

Population Patch Clamp (PPC) Assay Protocol

Inhibition of the hERG channel was measured by automated patch clamp assay in CHO K1 cells, stably transfected with the hERG ion channel. PPC measurements were performed using an IonWorks Quattro instrument (Molecular Devices Corporation, Union City, CA) using a 384 well PatchPlate (Molecular Devices Corporation) with 64 apertures per well. Each concentration of test compound was tested in duplicate wells. Amphotericin B was used to obtain electrical access to the cell interior at a final concentration of 200 µg/mL. Human ether-à-gogo related gene (hERG) currents were measured with a prepulse to +40 mV (2 s) from the holding potential of −80 mV, followed by a step to −50 mV (2 s) to elicit the deactivating tail currents, before returning to the holding potential for 1s. Compounds were incubated for 600s between the pre- and post-compound reads. The external recording solution used was 130 mM Na Gluconate, 20 mM NaCl, 4 mM KCl, 1 mM $MgCl_2$, 1.8 mM $CaCl_2$, 10 mM Hepes, 5 mM Glucose, pH to 7.3 with NaOH. All data were filtered for seal quality, seal drop, and current amplitude. The maximum current amplitude of the 3rd pulse tail current was calculated before (Pre) and after (Post) compound addition and the amount of block assessed by dividing the Post-compound current amplitude by the Pre-compound current amplitude. Data generated using this assay is detailed in Table 1.

Manual Patch Clamp (MPC) Assay Protocol

Inhibition of the hERG channel was measured by Manual Patch Clamp assay in HEK293 cells stably transfected with the hERG ion channel. A HEKA EPC10 amplifier and PatchMaster software were used to collect and analyze the data for this project. Cells were plated out onto a glass cover slip, mounted on an inverted microscope and continuously bathed in control solution (137 mM NaCl, 4 mM KCl, 1 mm $MgCl_2$, 1.8 mM $CaCl_2$, 10 mM Hepes, 10 mM Glucose, pH7.35).

After the cells had been electronically clamped and left to equilibrate, the pulse protocol was applied. The pulse protocol involved stepping from a holding potential of −80 mV to +40 mV for 4s to inactivate hERG channels, the membrane voltage was then stepped back to −50 mV for 4s to evoke a tail current prior to returning to the holding potential. This sequence was repeated with an inter-pulse interval of 20s. The voltage protocol was applied throughout the experiment starting prior to drug (0.33% DMSO control) and after cumulative additions of ascending compound concentrations. Evoked peak current amplitudes were continuously monitored throughout the experiment.

Test compounds were applied for 5 minutes or until steady state was reached, which ever occurred earlier, before measuring the compound effect. The peak tail current was measured before and after each compound addition. Individual cell results were normalized to their respective vehicle control and the results were averaged. Each concentration of compound was measured in duplicate. 0.1 μM Cisapride was used as a reference inhibitor.

TABLE 1

| E.g. No. | EVSA-T prolif (μM) | HEK293-X-C9 IP (μM) | MDA MB 231 (μM) | MDA-MB-231 cIAP1 level (μM) | hERG PPC (IC50 or PI, μM) |
|---|---|---|---|---|---|
| 1 | 0.00024 (n = 2) | 0.0016 (n = 3) | 0.0018 (n = 2) | 0.0001 (n = 4) | 40 |
| 2 | 0.00043 (n = 4) | 0.0028 (n = 5) | 0.0018 (n = 4) | 0.00022 (n = 7) | 85% @ 69 (n = 2) |
| 3 | 0.00023 (n = 3) | 0.0054 (n = 3) | 0.0021 (n = 3) | 0.00013 (n = 3) | 39% @ 100 |
| 4 | 0.002 | 0.0026 | 0.0036 | 0.00080 | 47% @ 30 |
| 5 | 0.00031 | 0.0053 | 0.0025 | 0.00026 | 42% @ 300 |
| 6 | 0.00055 (n = 3) | 0.0020 (n = 3) | 0.0050 (n = 3) | 0.00042 (n = 4) | 56% @ 250 |
| 7 | 0.00013 (n = 2) | 0.0012 (n = 2) | 0.00045 (n = 2) | 0.000098 (n = 2) | 33% @ 100 |
| 8 | 0.00019 | 0.0054 | 0.00075 | 0.00012 | 39% @ 300 |
| 9 | 0.0042 | 0.0030 | 0.016 | 0.0024 | 50% @ 300 |
| 10 | 0.00018 | 0.00083 (n = 2) | 0.0024 | 0.00018 (n = 2) | 35% @ 62.5 |
| 11 | 0.00031 | 0.0011 | 0.0019 | 0.00020 | 51 |
| 12 | 0.00024 | 0.00069 | 0.0021 | 0.00017 | 41% @ 100 |
| 13 | 0.00079 | 0.0044 | 0.0036 | 0.00026 | 46% @ 300 |
| 14 | 0.00091 | 0.013 | 0.0050 | 0.00053 | 58% @ 300 |
| 15 | 0.0078 | 0.0049 | 0.019 | 0.0023 | 55% @ 100 |
| 16 | 0.00095 | 0.014 (n = 2) | 0.018 | 0.00070 (n = 2) | 31% @ 100 |
| 17 | 0.0026 | 0.028 (n = 2) | 0.039 | 0.0050 (n = 2) | 59% @ 300 |
| 18 | 0.00019 | 0.0012 | 0.0031 | 0.00056 | 44% @ 75 |
| 19 | 0.00030 (n = 2) | 0.0012 (n = 2) | 0.0046 (n = 2) | 0.00057 (n = 2) | 42% @ 100 |
| 20 | 0.00049 (n = 2) | 0.0063 (n = 2) | 0.0040 (n = 2) | 0.00013 (n = 2) | 44% @ 100 |
| 21 | 0.00042 | 0.0021 | 0.0015 | 0.00018 | 35% @ 100 |
| 22 | 0.00056 (n = 2) | 0.0039 (n = 3) | 0.0044 (n = 2) | 0.00025 (n = 2) | 47% @ 100 |
| | | | | 0.00028 (n = 3) | |
| 23 | 0.00035 | 0.00077 | 0.0016 | 0.00033 | 63% @ 100 |
| 24 | 0.00035 (n = 2) | 0.00058 (n = 2) | 0.0032 (n = 2) | 0.00022 (n = 2) | 40% @ 100 |
| | 0.00039 (n = 3) | 0.0011 (n = 3) | 0.0034 (n = 3) | 0.00019 (n = 3) | |
| 25 | 0.00033 | 0.0027 | 0.0017 | 0.00018 | 47% @ 62.5 |
| 26 | 0.0012 | 0.012 (n = 2) | 0.0079 | 0.00053 (n = 2) | 41% @ 31.3 |
| 27 | 0.00084 | 0.0060 (n = 2) | 0.0052 | 0.00072 (n = 3) | 55% @ 1000 |
| | 0.00074 (n = 2) | 0.0099 (n = 3) | 0.0049 (n = 2) | 0.00055 (n = 4) | |
| 28 | 0.00082 | 0.0044 | 0.0062 | 0.0010 | 45% @ 125 |
| 29 | 0.0019 | 0.013 | 0.0063 | 0.0017 | 53% @ 500 |
| 30 | 0.00069 (n = 2) | 0.0012 (n = 3) | 0.0081 (n = 2) | 0.00084 (n = 3) | 230 |
| | 0.0010 (n = 3) | 0.0014 (n = 4) | 0.0087 (n = 3) | 0.00079 (n = 4) | |
| 31 | 0.00042 | 0.00094 | 0.0046 | 0.00014 | 140 |
| | 0.00051 (n = 2) | 0.0022 (n = 3) | 0.0043 (n = 2) | 0.00020 (n = 3) | |
| 32 | 0.00057 | 0.0015 (n = 2) | 0.0063 | 0.00019 (n = 2) | 55% @ 500 |
| 33 | 0.0014 | 0.0024 (n = 2) | 0.036 | 0.0018 (n = 2) | 33% @ 31.3 |
| 34 | 0.0034 | 0.0038 | 0.026 | 0.0013 | 55 |
| 35 | 0.016 | 0.013 (n = 2) | 0.13 | 0.0022 (n = 2) | 53% @ 1000 |
| 36 | 0.00038 | 0.0026 | 0.0025 | 0.0022 | 420 |
| | 0.00048 (n = 2) | 0.0042 (n = 2) | 0.0027 (n = 2) | 0.00061 (n = 2) | |
| 37 | 0.0032 | 0.0074 | 0.018 | 0.00055 | 63% @ 500 |
| Example 259, (262 and 263) of WO2012/143726 | 0.00082 (n = 19) 0.00083 (n = 21) | 0.0052 (n = 41) 0.0051 (n = 43) | 0.0042 (n = 19) 0.0044 (n = 21) | 0.00032 (n = 25) 0.00032 (n = 27) | 42% @ 10 (n = 2) 38% @ 10 (n = 3) |

Unless indicated above the data is a result of a single experiment. Where more than one data point has been obtained, the table above shows an average (e.g. geometric or arithmetic mean) of these data points (n) to 2 significant figures.

Combination Protocol for Apoptosis

Melanoma cell lines were plated out in duplicate wells of 24-well plates at 0.5×106 cells/ml the day before treatment to allow them to adhere. After incubation of the cells with compound(s) with or without 1 ng/ml TNF-α (R&D Systems) for 24 h in a $CO_2$ incubator at 37° C., cells were harvested by trypsinisation. The cell pellet from the 24-well plate was resuspended in 100 µl FACS buffer (PBS+1% fetal bovine serum). NucView488 reagent (from Biotium) was added to a final concentration of 2 µM. The plate was incubated in the dark for 30 minutes before measuring fluorescent stained cells in a Guava easyCyte HT cytometer (Millipore). Cleaved caspase-3 staining was recorded in the FL1 channel, with unstained and DMSO control wells being used to set the gated stained and unstained cell populations.

Table 2 summarises the % apoptosis increases seen in either SK-MEL-28 or A375 with the indicated combination of agents included with Example 2 plus 1 ng/ml TNF-α for 24 h in culture. No increase in apoptosis was seen over this time scale with the combination agent shown in the first column of the table alone (with or without TNF-α)—data not shown.

TABLE 2

Increase in percentage cells apoptotic after incubation with the indicated combination (relative to Example 2 + TNF-α alone*)

| Combination | Cell Line | % Apoptosis Example 2 alone* | % Apoptosis Combination | Fold Increase |
|---|---|---|---|---|
| Interferon-α2 (500 u/ml) | SK-MEL-28 | 42.2 (0.1 µM) | 53.9 | 1.3 |
| Interferon-β (500 u/ml) | SK-MEL-28 | 42.2 (0.1 µM) | 70.9 | 1.7 |
| Vemurafenib (1 µM) | SK-MEL-28 | 51.9 (1 µM) | 87.3 | 1.7 |
| Vemurafenib (4 µM) | A375 | 31.2 (1 µM) | 61.3 | 2.0 |
| Trametinib (0.1 µM) | A375 | 14.4 (0.1 µM) | 52.3 | 3.6 |

Combination Protocol for Cell Proliferation

The effect of a compound of formula (I) (Compound I) in combination with an anticancer agent (Compound II) can be assessed using the following technique. Cells from human cells lines (e.g. MDA-MB-231 and EVSA-T) were seeded onto 96-well tissue culture plates at a concentration of $2.5×10^3$, $6.0×10^3$, or $4.0×10^3$ cells/well respectively. Cells were allowed to recover for 48 hours prior to addition of compound(s) or vehicle control (0.35% DMSO) as follows:

Compounds were added concurrent for 96 hours. Following a total of 96 hours compound incubation, cells were fixed with ice-cold 10% (w/v) trichloroacetic acid for 1 hour on ice and then washed four times with $dH_2O$ using a plate washer (Labsystems Wellwash Ascent) and air-dried. Cells were then stained with 0.4% (w/v) Sulforhodamine B (Sigma) in 1% acetic acid for 20 min at room temperature and then washed four times with 1% (v/v) acetic acid and air-dried before the addition of 10 mM Tris buffer to solubilise the dye. Colourmetric product was quantified by reading at Abs490 nm on a Wallac Victor² plate reader (1420 multilabel counter, Perkin Elmer Life Sciences). The $IC_{50}$ for Compound II in the presence of varying doses of Compound I was determined. Synergy was determined when the $IC_{50}$ shifted down in the presence of sub-effective doses of Compound I. Additivity was determined when the response to Compound II and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

The invention claimed is:

1. A protected form of a compound of formula (I), wherein formula (I) is:

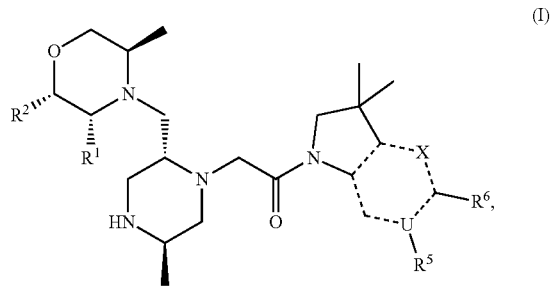

or a tautomeric or a stereochemically isomeric form, a pharmaceutically acceptable salt or a solvate thereof, wherein X is $CR^4$, N or $NR^3$;

wherein when X is $CR^4$, then U represents nitrogen and $R^6$ represents oxo; or when X is N, then U represents carbon and $R^6$ represents hydroxymethyl or —$CH(OR^x)CH_2OR^z$; or when X is $NR^3$, then U represents carbon and $R^6$ represents oxo;

dashed bond (------) represents a single or double bond wherein at least two of said dashed bonds represent a double bond;

$R^3$ represents hydrogen, methyl or —$NH_2$;

$R^4$ represents hydrogen, methyl, hydroxymethyl, —$NH_2$ or fluorine;

$R^5$ represents unsubstituted n-butyl or benzyl substituted on the phenyl group by one or two fluorines;

$R^x$ and $R^z$ independently represent hydrogen or methyl; and $R^1$ and $R^2$ independently represent hydrogen or methyl.

2. The protected form of a compound of formula (I) according to claim 1, having the formula:

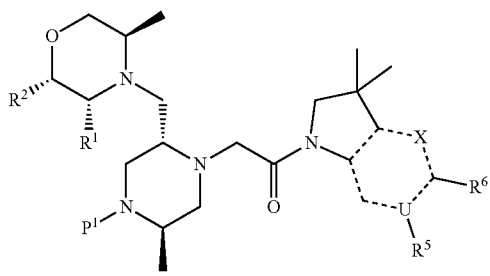

wherein, X, U, dashed bond (------), $R^1$, $R^2$, $R^5$ and $R^6$ are as defined in claim 1, and $P^1$ represents a protecting group, or a tautomeric or a stereochemically isomeric form, a pharmaceutically acceptable salt or a solvate thereof.

3. The protected form of a compound of formula (I) according to claim 2, wherein the protecting group is a tert-butyloxycarbonyl (tBoc) group, or a tautomeric or a stereochemically isomeric form, a pharmaceutically acceptable salt or a solvate thereof.

4. The protected form of a compound of formula (I) according to claim 2, wherein X is N, U represents carbon, and $R^6$ represents hydroxymethyl or —CH(OR$^x$)CH$_2$OR$^z$, or a tautomeric or a stereochemically isomeric form, a pharmaceutically acceptable salt or a solvate thereof.

5. The protected form of a compound of formula (I) according to claim 4, wherein $R^6$ represents hydroxymethyl, or a tautomeric or a stereochemically isomeric form, a pharmaceutically acceptable salt or a solvate thereof.

6. The protected form of a compound of formula (I) according to claim 4, wherein $R^1$ and $R^2$ independently represent hydrogen, or a tautomeric or a stereochemically isomeric form, a pharmaceutically acceptable salt or a solvate thereof.

7. The protected form of a compound of formula (I) according to claim 4, wherein the protecting group is a tert-butyloxycarbonyl (tBoc) group, or a tautomeric or a stereochemically isomeric form, a pharmaceutically acceptable salt or a solvate thereof.

8. The protected form of a compound of formula (I) according to claim 4, wherein $R^5$ represents benzyl substituted on the phenyl group by one or two fluorines, or a tautomeric or a stereochemically isomeric form, a pharmaceutically acceptable salt or a solvate thereof.

9. The protected form of a compound of formula (I) according to claim 8, wherein $R^5$ represents benzyl substituted on the phenyl group by one fluorine, or a tautomeric or a stereochemically isomeric form, a pharmaceutically acceptable salt or a solvate thereof.

10. The protected form of a compound of formula (I) according to claim 2, wherein $R^5$ represents benzyl substituted on the phenyl group by one or two fluorines, or a tautomeric or a stereochemically isomeric form, a pharmaceutically acceptable salt or a solvate thereof.

11. The protected form of a compound of formula (I) according to claim 10, wherein $R^5$ represents benzyl substituted on the phenyl group by one fluorine, or a tautomeric or a stereochemically isomeric form, a pharmaceutically acceptable salt or a solvate thereof.

12. The protected form of a compound of formula (I) according to claim 10, wherein $R^1$ and $R^2$ independently represent hydrogen, or a tautomeric or a stereochemically isomeric form, a pharmaceutically acceptable salt or a solvate thereof.

13. The protected form of a compound of formula (I) according to claim 10, wherein the protecting group is a tert-butyloxycarbonyl (tBoc) group, or a tautomeric or a stereochemically isomeric form, a pharmaceutically acceptable salt or a solvate thereof.

14. A compound of formula:

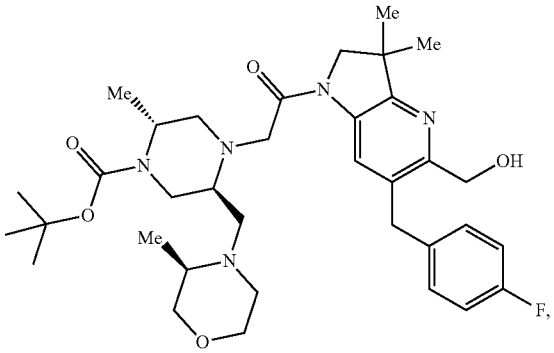 [SMILES: C[C@@H]1COCCN1C[C@H]1CN(C(=O)OC(C)(C)C)[C@H](C)CN1CC(=O)N1CC(C)(C)c2nc(CO)c(Cc3ccc(F)cc3)cc21]

or a tautomeric or a stereochemically isomeric form, a pharmaceutically acceptable salt or a solvate thereof.

15. A compound which is:

tert-Butyl (2R,5S)-5-{[(3R,5R)-3,5-dimethylmorpholin-4-yl]methyl}-4-(2-{6-[(4-fluorophenyl) methyl]-5-(hydroxymethyl)-3,3-dimethyl-1H,2H,3H-pyrrolo [3,2-b] pyridin-1-yl}-2-oxoethyl)-2-methylpiperazine-1-carboxylate;

tert-Butyl (2R,5S)-4-(2-{6-[(4-fluorophenyl) methyl]-5-(hydroxymethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-5-{[(3R,5R)-3,5-dimethylmorpholin-4-yl]methyl}-4-(2-{6-[(4-fluorophenyl) methyl]-3,3-dimethyl-5-oxo-1H,2H,3H,4H,5H-pyrrolo [3,2-b]pyridin-1-yl}-2-oxoethyl)-2-methylpiperazine-1-carboxylate;

tert-Butyl (2R,5S)-4-(2-{6-[(2-fluorophenyl) methyl]-5-(hydroxymethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(4-fluorophenyl) methyl]-3,3-dimethyl-5-oxo-1H,2H, 3H, 4H,5H-pyrrolo [3,2-b] pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(4-fluorophenyl) methyl]-3,3,4-trimethyl-5-oxo-1H,2H,3H, 4H,5H-pyrrolo [3,2-b] pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(2,4-difluorophenyl) methyl]-3,3-dimethyl-5-oxo-1H,2H, 3H,4H,5H-pyrrolo [3,2-b] pyridin-1-yl}-2-oxoethyl)-5-{[(3R,5R)-3,5-dimethylmorpholin-4-yl]methyl}-2-methylpiperazine-1-carboxylate;

tert-Butyl (2R,5S)-4-(2-{6-[(2,4-difluorophenyl) methyl]-3,3-dimethyl-5-oxo-1H,2H, 3H, 4H, 5H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(2-fluorophenyl) methyl]-3,3,4-trimethyl-5-oxo-1H,2H, 3H,4H,5H-pyrrolo [3,2-b]

pyridin-1-yl}-2-oxoethyl)-2-methyl-5-{[(3R)-3-methylmorpholin-4-yl]methyl}piperazine-1-carboxylate;

tert-Butyl (2R,5S)-5-{[(3R,5R)-3,5-dimethylmorpholin-4-yl]methyl}-4-(2-{6-[(4-fluorophenyl) methyl]-3,3,4-trimethyl-5-oxo-1H,2H, 3H,4H,5H-pyrrolo [3,2-b] pyridin-1-yl}-2-oxoethyl)-2-methylpiperazine-1-carboxylate;

tert-Butyl (2R,5S)-4-(2-{6-[(2,4-difluorophenyl) methyl]-5-(hydroxymethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-{2-[5-(1,2-dihydroxyethyl)-6-[(4-fluorophenyl) methyl]-3,3-dimethyl-1H,2H,3H-pyrrolo [3,2-b]pyridin-1-yl]-2-oxoethyl}-2-methyl-5-{[(3R)-3-methylmorpholin-4-yl]methyl}piperazine-1-carboxylate;

tert-Butyl (2R,5S)-4-(2-{6-[(3-fluorophenyl) methyl]-5-(hydroxymethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-5-{[(3R,5R)-3,5-dimethylmorpholin-4-yl]methyl}-4-(2-{6-[(4-fluorophenyl) methyl]-3,3-dimethyl-5-oxo-1H,2H, 3H, 5H, 6H-pyrrolo [2,3-c] pyridin-1-yl}-2-oxoethyl)-2-methylpiperazine-1-carboxylate;

tert-Butyl (2R,5S)-4-(2-{6-[(4-fluorophenyl) methyl]-3,3-dimethyl-5-oxo-1H,2H, 3H,5H,6H-pyrrolo [2,3-c] pyridin-1-yl}-2-oxoethyl)-2-methyl-5-{[(3R)-3-methylmorpholin-4-yl]methyl}piperazine-1-carboxylate;

tert-Butyl (2R,5S)-5-{[(2S,5R)-2,5-dimethylmorpholin-4-yl]methyl}-4-(2-{6-[(4-fluorophenyl) methyl]-3,3,4-trimethyl-5-oxo-1H, 2H,3H, 4H, 5H-pyrrolo [3,2-b] pyridin-1-yl}-2-oxoethyl)-2-methylpiperazine-1-carboxylate;

tert-Butyl (2R,5S)-4-(2-{6-[(2,4-difluorophenyl) methyl]-3,3-dimethyl-5-oxo-1H,2H, 3H,5H,6H-pyrrolo [2,3-c] pyridin-1-yl}-2-oxoethyl)-5-{[(3R,5R)-3,5-dimethyl-morpholin-4-yl]methyl}-2-methylpiperazine-1-carboxylate;

tert-Butyl (2R,5S)-4-{2-[5-((R or S)-1,2-dihydroxyethyl)-6-[(4-fluorophenyl) methyl]-3,3-dimethyl-1H, 2H,3H-pyrrolo [3,2-b]pyridin-1-yl]-2-oxoethyl}-5-{[(3R,5R)-3,5-dimethylmorpholin-4-yl]methyl}-2-methylpiperazine-1-carboxylate;

tert-Butyl (2R,5S)-4-(2-{6-[(2,4-difluorophenyl) methyl]-3,3-dimethyl-5-oxo-1H,2H, 3H,5H,6H-pyrrolo [2,3-c] pyridin-1-yl}-2-oxoethyl)-5-{[(2S,5R)-2,5-dimethyl-morpholin-4-yl]methyl}-2-methylpiperazine-1-carboxylate;

tert-Butyl (2R,5S)-4-(2-{4-amino-6-[(2,4-difluorophenyl) methyl]-3,3-dimethyl-5-oxo-1H,2H,3H,4H,5H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{4-amino-6-[(4-fluorophenyl) methyl]-3,3-dimethyl-5-oxo-1H,2H,3H,4H,5H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(2,4-difluorophenyl) methyl]-3,3,4-trimethyl-5-oxo-1H,2H,3H,4H,5H-pyrrolo [3,2-b]pyridin-1-yl}-2-oxoethyl)-5-{[(2S,5R)-2,5-dimethylmorpholin-4-yl]methyl}-2-methylpiperazine-1-carboxylate;

tert-Butyl (2R,5S)-4-(2-{6-[(4-fluorophenyl) methyl]-5-((R or S) 1-hydroxy-2-methoxyethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(4-fluorophenyl) methyl]-5-((R or S) 1-methoxy-2-hydroxyethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{4-amino-6-butyl-3,3-dimethyl-5-oxo-1H,2H,3H,4H,5H-pyrrolo [3,2-b]pyridin-1-yl}-2-oxoethyl)-5-{[(3R,5R)-3,5-dimethylmorpholin-4-yl] methyl}-2-methylpiperazine-1-carboxylate;

tert-Butyl (2R,5S)-4-(2-{6-[(2,4-difluorophenyl) methyl]-3,3,4-trimethyl-5-oxo-1H,2H,3H,5H,6H-pyrrolo [2,3-c]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-butyl-3,3-dimethyl-5-oxo-1H, 2H,3H,4H,5H-pyrrolo [3,2-b]pyridin-1-yl}-2-oxoethyl)-5-{[(3R,5R)-3,5-dimethylmorpholin-4-yl] methyl}-2-methylpiperazine-1-carboxylate;

tert-Butyl (2R,5S)-4-(2-{6-butyl-3,3,4-trimethyl-5-oxo-1H,2H,3H,4H,5H-pyrrolo [3,2-b]pyridin-1-yl}-2-oxoethyl)-5-{[(3R,5R)-3,5-dimethylmorpholin-4-yl] methyl}-2-methylpiperazine-1-carboxylate;

tert-Butyl (2R,5S)-4-{2-[6-butyl-5-(hydroxymethyl)-3,3-dimethyl-1H,2H, 3H-pyrrolo [3,2-b]pyridin-1-yl]-2-oxoethyl}-5-{[(3R,5R)-3,5-dimethylmorpholin-4-yl] methyl}-2-methylpiperazine-1-carboxylate;

tert-Butyl (2R,5S)-4-(2-{6-butyl-3,3-dimethyl-5-oxo-1H, 2H,3H,5H,6H-pyrrolo [2,3-c]pyridin-1-yl}-2-oxoethyl)-5-{[(3R,5R)-3,5-dimethylmorpholin-4-yl] methyl}-2-methylpiperazine-1-carboxylate;

tert-Butyl (2R,5S)-5-{[(3R,5R)-3,5-dimethylmorpholin-4-yl]methyl}-4-(2-{6-[(4-fluorophenyl) methyl]-5-((R or S)-2-hydroxy-1-methoxyethyl)-3,3-dimethyl-1H, 2H,3H-pyrrolo [3,2-b]pyridin-1-yl}-2-oxoethyl)-2-methylpiperazine-1-carboxylate; or tert-Butyl (2R,5S)-4-(2-{6-butyl-3,3-dimethyl-5-oxo-1H, 2H,3H, 4H,5H-pyrrolo [3,2-b]pyridin-1-yl}-2-oxoethyl)-5-{[(2S,5R)-2,5-dimethylmorpholin-4-yl] methyl}-2-methylpiperazine-1-carboxylate, or a tautomeric or a stereochemically isomeric form, a pharmaceutically acceptable salt or a solvate thereof.

16. A compound according to claim 15, which is:

tert-Butyl (2R,5S)-5-{[(3R,5R)-3,5-dimethylmorpholin-4-yl]methyl}-4-(2-{6-[(4-fluorophenyl) methyl]-5-(hydroxymethyl)-3,3-dimethyl-1H,2H,3H-pyrrolo [3,2-b] pyridin-1-yl}-2-oxoethyl)-2-methylpiperazine-1-carboxylate;

tert-Butyl (2R,5S)-4-(2-{6-[(4-fluorophenyl) methyl]-5-(hydroxymethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(2-fluorophenyl) methyl]-5-(hydroxymethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(2,4-difluorophenyl) methyl]-5-(hydroxymethyl)-3,3-dimethyl-1H,2H,3H-pyrrolo [3,2-b]pyridin-1-yl}-2-oxoethyl)-2-methyl-5-{[(3R)-3-methylmorpholin-4-yl]methyl}piperazine-1-carboxylate;

tert-Butyl (2R,5S)-4-(2-{6-[(3-fluorophenyl) methyl]-5-(hydroxymethyl)-3,3-dimethyl-1H,2H,3H-pyrrolo[3,2-b]pyridin-1-yl}-2-oxoethyl)-2-methyl-5-{[(3R)-3-methylmorpholin-4-yl]methyl}piperazine-1-carboxylate; or tert-Butyl (2R,5S)-4-{2-[6-butyl-5-(hydroxymethyl)-3,3-dimethyl-1H,2H,3H-pyrrolo [3,2-b]pyridin-1-yl]-2-oxoethyl}-5-{[(3R,5R)-3,5-dimethylmorpholin-4-yl]methyl}-2-methylpiperazine-1-carboxylate, or a tautomeric or a stereochemically isomeric form, a pharmaceutically acceptable salt or a solvate thereof.

17. A pharmaceutical composition comprising a protected form of formula (I) according to claim 1, or a tautomeric or a stereochemically isomeric form, a pharmaceutically acceptable salt or a solvate thereof.

18. A pharmaceutical composition comprising a compound according to claim 14, or a tautomeric or a stereochemically isomeric form, a pharmaceutically acceptable salt or a solvate thereof.

19. A pharmaceutical composition comprising a protected form of formula (I) according to claim 1, or a tautomeric or a stereochemically isomeric form, a pharmaceutically acceptable salt or a solvate thereof, in combination with one or more therapeutic agents.

20. A pharmaceutical composition comprising a compound according to claim 14, or a tautomeric or a stereochemically isomeric form, a pharmaceutically acceptable salt or a solvate thereof, in combination with one or more therapeutic agents.

21. A method of inhibiting the activity of inhibitor of apoptosis protein (IAP), the method comprising contacting the IAP with a protected form of a compound of formula (I) according to claim 1, or a tautomeric or a stereochemically isomeric form, a pharmaceutically acceptable salt or a solvate thereof.

22. A method of inhibiting the activity of inhibitor of apoptosis protein (IAP), the method comprising contacting the IAP with a compound according to claim 14, or a tautomeric or a stereochemically isomeric form, a pharmaceutically acceptable salt or a solvate thereof.

23. A method of treating a patient having a cancer mediated by IAP comprising administering to the patient an effective amount of a protected form of formula (I) according to claim 1, or a tautomeric or a stereochemically isomeric form, a pharmaceutically acceptable salt or a solvate thereof.

24. A method of treating a patient having a cancer mediated by IAP comprising administering to the patient an effective amount of a compound according to claim 14, or a tautomeric or a stereochemically isomeric form, a pharmaceutically acceptable salt or a solvate thereof.

25. A method of treating a patient having a disease or condition mediated by IAP comprising administering to the patient a protected form of formula (I) according to claim 1, or a tautomeric or a stereochemically isomeric form, a pharmaceutically acceptable salt or a solvate thereof, in combination with one or more other therapeutic agents.

26. A method of treating a patient having a disease or condition mediated by IAP comprising administering to the patient a compound according to claim 14, or a tautomeric or a stereochemically isomeric form, a pharmaceutically acceptable salt or a solvate thereof, in combination with one or more other therapeutic agents.

27. A method of treating a patient having a disease or condition mediated by IAP comprising administering to the patient an effective amount of a protected form of formula (I) according to claim 1, or a tautomeric or a stereochemically isomeric form, a pharmaceutically acceptable salt or a solvate thereof.

28. A method of treating a patient having a disease or condition mediated by IAP comprising administering to the patient an effective amount of a compound according to claim 14, or a tautomeric or a stereochemically isomeric form, a pharmaceutically acceptable salt or a solvate thereof.

29. A method of treating a patient having mesothelioma comprising administering to the patient an effective amount of a protected form of formula (I) according to claim 1, or a tautomeric or a stereochemically isomeric form, a pharmaceutically acceptable salt or a solvate thereof.

30. A method of treating a patient having mesothelioma comprising administering to the patient an effective amount of a compound according to claim 14, or a tautomeric or a stereochemically isomeric form, a pharmaceutically acceptable salt or a solvate thereof.

31. A method of treating a patient having a cancer mediated by IAP, wherein the cancer is selected from leukemias and lymphomas comprising administering to the patient an effective amount of a protected form of formula (I) according to claim 1, or a tautomeric or a stereochemically isomeric form, a pharmaceutically acceptable salt or a solvate thereof.

32. A method of treating a patient having a cancer mediated by IAP, wherein the cancer is selected from leukemias and lymphomas comprising administering to the patient an effective amount of a compound according to claim 14, or a tautomeric or a stereochemically isomeric form, a pharmaceutically acceptable salt or a solvate thereof.

33. A method of treating a patient having cancer selected from acute myelogenous leukemia (AML), T-cell lymphomas, B-cell lymphomas, MALT lymphoma, head and neck cancer, and cervical cancer, comprising administering to the patient an effective amount of a protected form of formula (I) according to claim 1, or a tautomeric or a stereochemically isomeric form, a pharmaceutically acceptable salt or a solvate thereof.

34. The method of claim 33, wherein the cancer is acute myelogenous leukemia (AML).

35. The method of claim 33, wherein the cancer is selected from T-cell lymphomas.

36. The method of claim 33, wherein the cancer is selected from B-cell lymphomas.

37. The method of claim 36, wherein the cancer is diffuse large B-cell lymphoma (DLBCL).

38. The method of claim 33, wherein the cancer is MALT lymphoma.

39. The method of claim 33, wherein the cancer is a head and neck cancer.

40. The method of claim 33, wherein the cancer is cervical cancer.

41. A method of treating a patient having cancer selected from acute myelogenous leukemia (AML), T-cell lymphomas, B-cell lymphomas, MALT lymphoma, head and neck cancer, and cervical cancer, comprising administering to the patient an effective amount of a compound according to claim 14, or a tautomeric or a stereochemically isomeric form, a pharmaceutically acceptable salt or a solvate thereof.

42. The method of claim 41, wherein the cancer is acute myelogenous leukemia (AML).

43. The method of claim 41, wherein the cancer is selected from T-cell lymphomas.

44. The method of claim 41, wherein the cancer is selected from B-cell lymphomas.

45. The method of claim 44, wherein the cancer is diffuse large B-cell lymphoma (DLBCL).

46. The method of claim 41, wherein the cancer is MALT lymphoma.

47. The method of claim 41, wherein the cancer is a head and neck cancer.

48. The method of claim 41, wherein the cancer is cervical cancer.

\* \* \* \* \*

UNITED STATES PATENT AND TRADEMARK OFFICE
CERTIFICATE OF CORRECTION

PATENT NO. : 12,202,828 B2
APPLICATION NO. : 18/069571
DATED : January 21, 2025
INVENTOR(S) : Chessari et al.

Page 1 of 1

It is certified that error appears in the above-identified patent and that said Letters Patent is hereby corrected as shown below:

In the Claims

Column 128, Line 50: Claim 1, Delete "or $-CH(OR^x)CH_2OR^2$; or" and insert -- or $-CH(OR^x)CH_2OR^z$; or --

Signed and Sealed this
Twenty-fourth Day of June, 2025

Coke Morgan Stewart
*Acting Director of the United States Patent and Trademark Office*